US012790312B2

(12) United States Patent
Ogawa et al.

(10) Patent No.: US 12,790,312 B2
(45) **Date of Patent: *Nov. 10, 2026**

(54) PLASMA KALLIKREIN INHIBITORS

(71) Applicant: Merck Sharp & Dohme LLC, Rahway, NJ (US)

(72) Inventors: Anthony Ken Ogawa, San Mateo, CA (US); Christopher J. Sinz, Walnut Creek, CA (US); Jacqueline D. Hicks, Watchung, NJ (US); Alan C. Cheng, San Francisco, CA (US); Song Yang, San Francisco, CA (US); Jianming Bao, Princeton, NJ (US); Donna A. A. W. Hayes, San Francisco, CA (US); Simon B. Lang, San Francisco, CA (US); Maoqun Tian, Forster, CA (US); Salman Jabri, Moraga, CA (US); Galen Paul Shearn-Nance, Tiburon, CA (US); Rongze Kuang, Green Brook, NJ (US); Zhiqiang Zhao, Little Neck, NY (US); Zhicai Wu, Montvale, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 599 days.

This patent is subject to a terminal disclaimer.

(21) Appl. No.: 18/043,357

(22) PCT Filed: Sep. 9, 2021

(86) PCT No.: PCT/US2021/049545

§ 371 (c)(1),
(2) Date: Feb. 28, 2023

(87) PCT Pub. No.: WO2022/056051

PCT Pub. Date: Mar. 17, 2022

(65) Prior Publication Data

US 2023/0416227 A1 Dec. 28, 2023

Related U.S. Application Data

(60) Provisional application No. 63/076,592, filed on Sep. 10, 2020.

(51) Int. Cl.

| | |
|---|---|
| ***C07D 401/14*** | (2006.01) |
| ***A61K 45/06*** | (2006.01) |
| ***A61P 9/10*** | (2006.01) |

(52) U.S. Cl.

CPC ............ *C07D 401/14* (2013.01); *A61K 45/06* (2013.01); *A61P 9/10* (2018.01)

(58) Field of Classification Search

CPC .......... C07D 401/14; A61K 45/06; A61P 9/10
See application file for complete search history.

(56) References Cited

U.S. PATENT DOCUMENTS

| | | | |
|---|---|---|---|
| 6,548,525 B2 * | 4/2003 | Galemmo, Jr. et al. |
| 9,284,298 B2 | 3/2016 | Casuscelli et al. |
| 12,528,786 B2 * | 1/2026 | Hicks et al. |
| 2010/0190980 A1 | 7/2010 | Umemiya et al. |
| 2012/0035168 A1 | 2/2012 | Brandl et al. |

FOREIGN PATENT DOCUMENTS

| | | |
|---|---|---|
| WO | 2012017020 A1 | 2/2012 |
| WO | 2017207983 A1 | 12/2017 |
| WO | 2021257353 A1 | 12/2021 |

OTHER PUBLICATIONS

Kumari et al.; Amide Bond Bioisosteres: Strategies, Synthesis, and Successes; J. Med. Chem., 2020, 63, 12290-12358. (Year: 2020).*

Bastiaans et al.; Factor Xa and thrombin stimulate proinflammatory and profibrotic mediator production by retinal pigment epithelial cells: a role in vitreoretinal disorders?; Graefes Arch Clin Exp Ophthalmol, 2013, 251:1723-1733. (Year: 2013).*

Funk et al.; Intraocular Concentrations of Growth Factors and Cytokines in Retinal Vein Occlusion and the Effect of Therapy with Bevacizumab; Investigative Ophthalmology & Visual Science, 2009, 50, 1025-1032. (Year: 2009).*

(Continued)

*Primary Examiner* — Sarah Pihonak
*Assistant Examiner* — Jackson J Hernandez
(74) *Attorney, Agent, or Firm* — Daniel Woods; John C. Todaro

(57) ABSTRACT

The present invention provides a compound of Formula (I) and pharmaceutical compositions comprising one or more said compounds, and methods for using said compounds for treating or preventing one or more disease states that could benefit from inhibition of plasma kallikrein, including hereditary angioedema, uveitis, posterior uveitis, wet age related macular edema, diabetic macular edema, diabetic retinopathy and retinal vein occlusion. The compounds are selective inhibitors of plasma kallikrein.

(I)

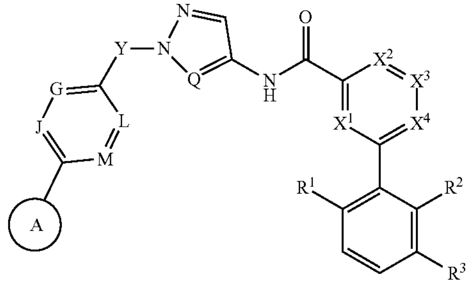

16 Claims, No Drawings

(56) References Cited

OTHER PUBLICATIONS

Chou, Ting-Chao et al., Quantitative Analysis of Dose-Effect Relationships: the Combined Effects of Multiple Drugs or Enzyme Inhibitors, Adv. Enzyme Regul., 1984, 27-55, 22.

Clermont, Allen et al., Plasma Kallikrein Mediates Retinal Vascular Dysfunction and Induces Retinal Thickening in Diabetic Rats, Diabetes, 2011, 1590-1598, 60.

Colman, Robert W., Contact Activation Pathway: Inflammatory, Fibrinolytic, Anticoagulant, Antiadhesive, and Antiangiogenic Activities, Hemostasis and Thrombosis, 2001, 103-121, Chapter 6.

Daiss, Jurgen, O. et al., Sila-venlafaxine, a Sila-Analogue of the Serotonin/Noradrenaline Reuptake Inhibitor Venlafaxine: Synthesis, Crystal Structure Analysis, and Pharmacological Characterization, Organometallics, 2006, pp. 1188-1198, vol. 25.

Pubchem-SID: 386554046 deposited Nov. 1, 2019 (01.11 .201) pp. 1-5. p. 5 (6 pages).

Schmaier, Alvin H., Contact Activation, Thrombosis and Hemorrhage, 1998, 105-127, Chapter 5.

Schneider, Lynda et al., Critical role of kallikrein in hereditary angioedema pathogenesis: a clinical trial of ecallantide, a novel kallikrein inhibitor, J Allergy Clin Immunol, 2007, 416-422, 120(2).

Showell, Graham, A. et al., (R)-Sila-venlafaxine: a selective noradrenaline reuptake inhibitor for the treatment of emesis, Bioorganic & Medicinal Chemistry Letters, 2006, pp. 2555-2558, vol. 16.

* cited by examiner

PLASMA KALLIKREIN INHIBITORS

CROSS-REFERENCE TO RELATED APPLICATIONS

This application is a National Stage application of International Patent Application No. PCT/US2021/049545, filed Sep. 9, 2021, which claims the benefit of priority to U.S. Provisional Patent Application No. 63/076,592, filed Sep. 10, 2020.

BACKGROUND OF THE INVENTION

Plasma kallikrein is a zymogen of a trypsin-like serine protease and is present in plasma. The gene structure is similar to that of factor XI. Overall, the amino acid sequence of plasma kallikrein has 58% homology to factor XI. Proteolyticactivation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and Cl-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Patients presenting genetic deficiency on Cl-esterase inhibitor suffer from hereditary angioedema (HAE), a life-long disease that results in intermittent swelling throughout the body, including the hands, feet, face, throat, genitals and gastrointestinal tract. Analysis of blisters arising from acute episodes have been shown to contain high levels of plasma kallikrein, and treatment with a protein-based reversible plasma kallikrein inhibitor, Ecallantide (Kalbitor), has been approved by the FDA for the treatment of acute attacks of HAE (Schneider, L, et al., J. Allergy Clin. Immunol., 120: p.416 (2007)).

Additionally, the plasma kallikrein-kinin system is abnormally abundant in patients diagnosed with advanced diabetic macular edema (DME). Recent publications have shown that plasma kallikrein contributes to observed retinal vascular leakage and dysfunction in diabetic rodent models (A. Clermont, et al., Diabetes, 60:1590 (2011)), and that treatment with a small molecule plasma kallikrein inhibitor ameliorated the observed retinal vascular permeability and other abnormalities related to retinal blood flow.

It would be desirable in the art to develop plasma kallikrein inhibitors having utility to treat a wide range of disorders, including hereditary angioedema, diabetic macular edema and diabetic retinopathy.

SUMMARY OF THE INVENTION

The present invention relates to compounds of Formula I:

I

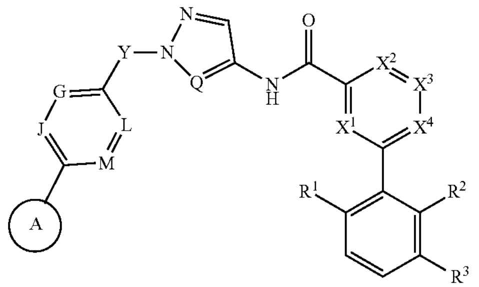

and pharmaceutically acceptable salts thereof. The compounds of Formula I are inhibitors of plasma kallikrein, and as such may be useful in the treatment, inhibition or amelioration of one or more disease states that could benefit from inhibition of plasma kallikrein, including hereditary angioedema, uveitis, posterior uveitis, wet age related macular edema, diabetic macular edema, diabetic retinopathy and retinal vein occlusion. The compounds of this invention could further be used in combination with other therapeutically effective agents, including but not limited to, other drugs useful for the treatment of hereditary angioedema, uveitis, posterior uveitis, wet age related macular edema, diabetic macular edema, diabetic retinopathy and retinal vein occlusion. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The present invention relates to compounds of Formula I:

I

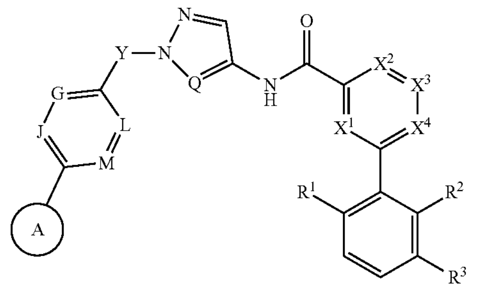

wherein

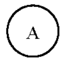

is selected from

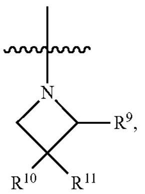 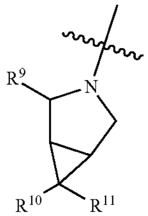, 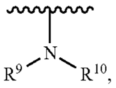 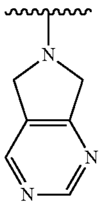,

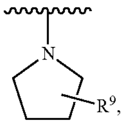 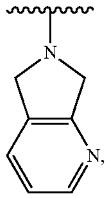 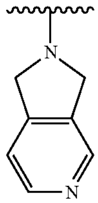, 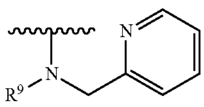,

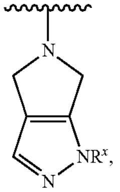 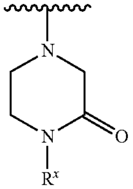, 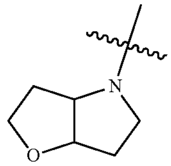,

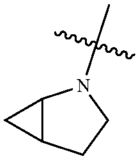, 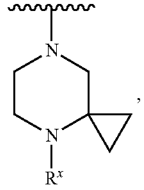, 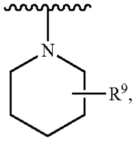

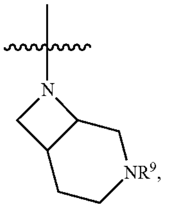 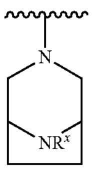, 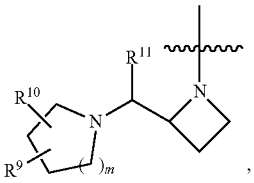,

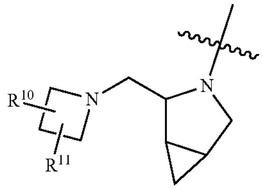 or 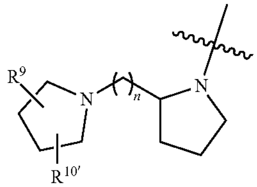;

$X^1$ is CH or N;
$X^2$ is $NR^4$ or $CR^4$;
$X^3$ is N, NO, $NR^x$ or C═O;
$X^4$ is CH or N;
Y is $CR^5R^6$ or $SO_2$;
Q is N or CH;
G is N or $CR^7$;
J is N or $CR^7$;
L is N or $CR^7$;
M is N or $CR^7$;
$R^1$ is selected from the group consisting of hydrogen, halo, cyano, $R^x$, $OR^x$, heteroaryl and $SO_2R^x$;
$R^2$ is hydrogen or halo;
$R^3$ is hydrogen, halo or $OR^x$;
$R^4$ is hydrogen, $R^x$, $OR^x$, (C═O)$OR^x$, (C═O)$NR^xR^y$, $C_{1-3}$ alkyl-$OR^x$ or $NR^xR^y$;
$R^5$ is hydrogen or $C_{1-3}$ alkyl, which is optionally substituted with one to three substituents selected from deuterium, halo and hydroxy;
$R^6$ is hydrogen, deuterium or $C_{1-3}$ alkyl;
or $R^5$ and $R^6$ can be taken together with the carbon atom between them to form a $C_{3-6}$ cycloalkyl group;
each $R^7$ is independently selected from the group consisting of halo, cyano, $R^x$, $OR^x$, cyclopropyl, (C═O)$NR^xR^y$ and $NR^xR^y$;
or $R^5$ and $R^7$ can be taken together with the atoms between them to form a $C_{3-6}$ cycloalkyl group;
each $R^9$ is independently selected from the group consisting of hydrogen, halo, hydroxy, cyano, triazolyl, cyclopropyl, (C═O)$NR^xR^y$, (C═O)$R^x$ and $C_{1-3}$ alkyl, wherein said triazolyl group is optionally substituted with $R^x$, said cyclopropyl group is optionally substituted with $R^x$ or $OR^x$, and said alkyl group is optionally substituted with one to four substituents selected from halo, hydroxy, heteroaryl, heterocyclyl, $C_{3-6}$ cycloalkyl, $C_{3-6}$ cycloalkyl($R^{10}$), $OR^x$, (C═O)$NR^xR^y$ and $NR^xR^y$;
$R^{10}$ is hydrogen, halo, hydroxy or $C_{1-3}$ alkyl, wherein said alkyl is optionally substituted with one to four substituents selected from halo and hydroxy;
$R^{11}$ is hydrogen, halo, hydroxy or $R^x$;
or $R^{10}$ and $R^{11}$ can be taken together with the atoms between them to form a $C_{3-6}$ cycloalkyl group;
each $R^x$ is independently hydrogen or $C_{1-6}$ alkyl, which is optionally substituted with one to four substituents selected from halo and hydroxy;
each $R^y$ is independently selected from the group consisting of hydrogen, $C_{1-6}$ alkyl, $C_{3-6}$ cycloalkyl, $CH_2$—$C_{3-6}$ cycloalkyl and heterocyclyl, wherein said alkyl is optionally substituted with one to four substituents selected from halo and hydroxy, said cycloalkyl is optionally substituted with one or two $R^x$ or $OR^x$ and said heterocyclyl is optionally substituted with one or two $R^{10}$;
m is an integer from zero to two;
n is an integer from zero to two;
or a pharmaceutically acceptable salt thereof.

In an embodiment of the invention,

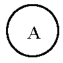 is 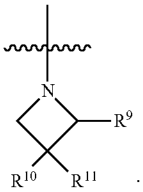.

In another embodiment of the invention,

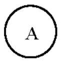 is 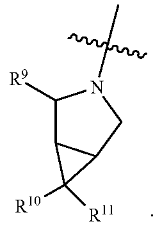.

In another embodiment of the invention,

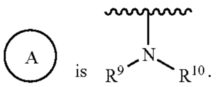

In another embodiment of the invention,

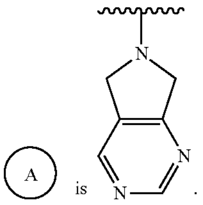

In another embodiment of the invention,

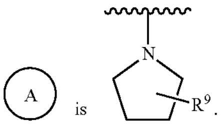

In another embodiment of the invention,

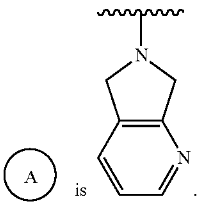

In another embodiment of the invention,

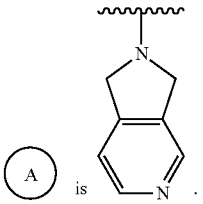

In another embodiment of the invention,

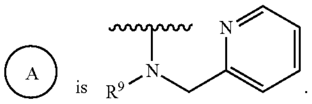

In another embodiment of the invention

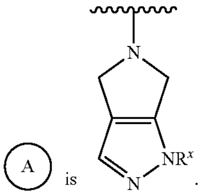

In another embodiment of the invention

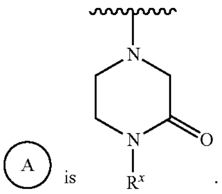

In another embodiment of the invention,

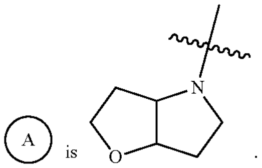

In another embodiment of the invention,

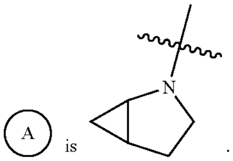

In another embodiment of the invention,

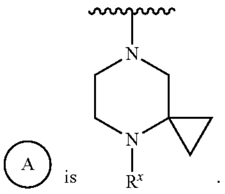

In another embodiment of the invention,

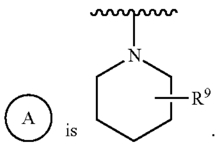

In another embodiment of the invention,

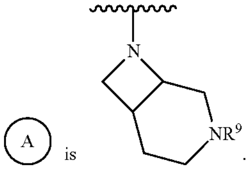

In another embodiment of the invention,

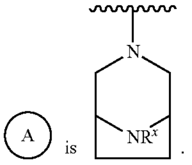

In another embodiment of the invention,

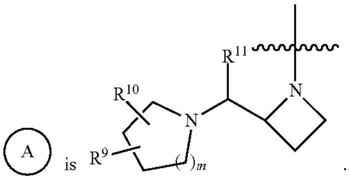

In another embodiment of the invention,

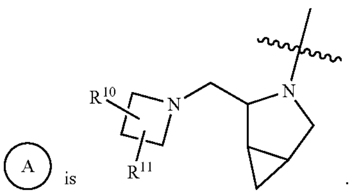

In another embodiment of the invention,

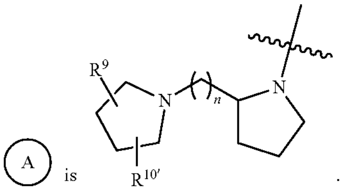

In an embodiment of the invention, $X^1$ is CH. In another embodiment of the invention, $X^1$ is N.

In an embodiment of the invention, $X^2$ is $NR^4$. In another embodiment of the invention, $X^2$ is $CR^4$.

In an embodiment of the invention, $X^3$ is N. In another embodiment of the invention, $X^3$ is NO. In another embodiment of the invention, $X^3$ is $NR^x$. In another embodiment of the invention, $X^3$ is C═O.

In an embodiment of the invention, $X^4$ is CH. In another embodiment of the invention, $X^4$ is N.

In an embodiment of the invention, $X^1$ is N; $X^2$ is $CR^4$; $X^3$ is N; $X^4$ is CH.

In an embodiment of the invention, Y is $CR^5R^6$. In a class of the invention, Y is $CH_2$. In another embodiment of the invention, Y is $SO_2$.

In an embodiment of the invention, Q is N. In another embodiment of the invention, Q is CH.

In an embodiment of the invention, G is N. In another embodiment of the invention, G is $CR^7$. In a class of the invention, G is CH.

In an embodiment of the invention, J is N. In another embodiment of the invention, J is $CR^7$. In a class of the invention, J is CH.

In an embodiment of the invention, L is N. In another embodiment of the invention, L is $CR^7$. In a class of the invention, L is CH.

In an embodiment of the invention, M is N. In another embodiment of the invention, M is $CR^7$. In a class of the invention, M is CH.

In an embodiment of the invention, J is N; M is N; G is $CR^7$; L is $CR^7$.

In an embodiment of the invention, $R^1$ is hydrogen, bromo, cyano, tetrazolyl, $CH_3$, $CHF_2$, $CF_3$, $OCHF_2$ or $SO_2CH_3$. In a class of the embodiment, $R^1$ is hydrogen. In another class of the embodiment, $R^1$ is bromo. In another class of the embodiment, $R^1$ is cyano. In another class of the embodiment, $R^1$ is tetrazolyl. In another class of the embodiment, $R^1$ is $CH_3$. In another class of the embodiment, $R^1$ is $CHF_2$. In another class of the embodiment, $R^1$ is $CF_3$. In a class of the embodiment, $R^1$ is $OCHF_2$. In a class of the embodiment, $R^1$ is $SO_2CH_3$.

In an embodiment of the invention, $R^2$ is hydrogen. In another embodiment of the invention, $R^2$ is halo. In a class of the invention, $R^2$ is fluoro.

In an embodiment of the invention, $R^3$ is hydrogen. In another embodiment of the invention, $R^3$ is halo. In a class of the invention, $R^3$ is chloro. In another embodiment of the invention, $R^3$ is $OCH_3$.

In an embodiment of the invention, $R^4$ is hydrogen, $CH_3$, $CHF_2$, $OCH_3$, $NH_2$, $N(CH_3)_2$, (C═O)OH and (C═O)$NH_2$.

In an embodiment of the invention, $R^5$ is hydrogen, $CH_3$, $CHF_2$ or $CH_2OH$. In another class of the invention, $R^5$ is $CH_3$. In another class of the invention, $R^5$ is $CHF_2$. In another class of the invention, $R^5$ is $CH_2OH$.

In an embodiment of the invention, $R^6$ is hydrogen.

In an embodiment of the invention, m is zero. In another embodiment of the invention, m is one. In another embodiment of the invention, m is two.

In an embodiment of the invention, n is zero. In another embodiment of the invention, n is one. In another embodiment of the invention, n is two.

Reference to the preferred classes and subclasses set forth above is meant to include all combinations of particular and preferred groups unless stated otherwise.

Specific embodiments of the present invention include, but are not limited to the compounds identified herein as Examples 1 to 208, or pharmaceutically acceptable salts thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention includes compositions for treating diseases or condition in which plasma kallikrein activity is implicated. Accordingly the invention includes compositions for treating impaired visual activity, diabetic retinopathy, diabetic macular edema, retinal vein occlusion, hereditary angioedema, diabetes, pancreatitis, cerebral hemorrhage, nephropathy, cardiomyopathy, neuropathy, inflammatory bowel disease, arthritis, inflammation, septic shock, hypotension, cancer, adult respiratory distress syndrome, disseminated intravascular coagulation, blood coagulation during cardiopulmonary bypass surgery, and bleeding from postoperative surgery in a mammal, comprising a compound of the invention in a pharmaceutically acceptable carrier. A class of the invention includes compositions for treating hereditary angioedema, uveitis, posterior uveitis, wet age related macular edema, diabetic macular edema, diabetic retinopathy and retinal vein occlusion. These compositions may optionally include anti-inflammatory agents, anti-VEGF agents, immunosuppressive agents, anticoagulants, antiplatelet agents, and thrombolytic agents. The compositions can be added to blood, blood products, or mammalian organs in order to effect the desired inhibitions.

The invention also includes compositions for preventing or treating retinal vascular permeability associated with diabetic retinopathy and diabetic macular edema in a mammal, comprising a compound of the invention in a pharmaceutically acceptable carrier. These compositions may optionally include anti-inflammatory agents, anti-VEGF agents, immunosuppressive agents, anticoagulants, antiplatelet agents, and thrombolytic agents.

The invention also includes compositions for treating inflammatory conditions of the eye, which includes, but is not limited to, uveitis, posterior uveitis, macular edema, acute macular degeneration, wet age related macular edema, retinal detachments, retinal vein occlusion, ocular tumors, fungal infections, viral infections, multifocal choroiditis, diabetic uveitis, diabetic macular edema, diabetic retinopathy, proliferative vitreoretinopathy, sympathetic opthalmia, Vogt Koyanagi-Harada syndrome, histoplasmosis and uveal diffusion. These compositions may optionally include anti-inflammatory agents, anti-VEGF agents, immunosuppressive agents, anticoagulants, antiplatelet agents, and thrombolytic agents.

The invention also includes compositions treating posterior eye disease, which includes, but is not limited to, uveitis, posterior uveitis, wet age related macular edema, diabetic macular edema, diabetic retinopathy and retinal vein occlusion. These compositions may optionally include anti-inflammatory agents, anti-VEGF agents, immunosuppressive agents, anticoagulants, antiplatelet agents, and thrombolytic agents.

It will be understood that the invention is directed to the compounds of structural Formula I described herein, as well as the pharmaceutically acceptable salts of the compounds of structural Formula I and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I simultaneously contain acidic and basic groups in the molecule the invention also includes, in addition to the salt forms mentioned, inner salts or betaines (zwitterions).

The present invention encompasses all stereoisomeric forms of the compounds of Formula I. Unless a specific stereochemistry is indicated, the present invention is meant to comprehend all such isomeric forms of these compounds. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both each individual enantiomer and mixtures thereof, are embraced within the Formula. When a particular configuration is depicted, that entantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

Unless a specific enationmer or diastereomer is indicated, the invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($1_H$) and deuterium ($2_H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^x$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —$COO^-$ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the terms "alkyl" and "alkylene" are intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

"  ", ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

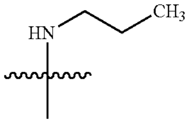

and

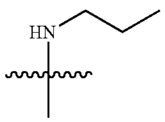

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on.

Except where noted, the term "aryl", as used herein, represents a stable monocyclic or bicyclic ring system of up to 10 carbon atoms in each ring, wherein at least one ring is aromatic. Bicyclic aryl ring systems include fused ring systems, where two rings share two atoms, and spiro ring systems, where two rings share one atom. Aryl groups within the scope of this definition include, but are not limited to: phenyl, indene, isoindene, naphthalene, and tetralin.

Except where noted, the term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzoxazolyl, carbazolyl, carbolinyl, cinnolinyl, dihydroindenyl, furanyl, indolinyl, indolyl, indolazinyl, indazolyl, isobenzofuranyl, isoindolyl, isoquinolyl, isothiazolyl, isoxazolyl, naphthalenyl, naphthpyridinyl, oxadiazolyl, oxazolyl, oxazoline, isoxazoline, pyranyl, pyrazinyl, pyrazolyl, pyrazolopyrimidinyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, dihydrobenzodioxinyl, dihydropyrazoloxazinyl, dihydropyrazolyothiazinedioxidyl, methylenedioxybenzene, benzothiazolyl, benzothienyl, quinolinyl, isoquinolinyl, oxazolyl, tetra-hydroquinoline and 3-oxo-3,4dihydro-2N-benzo[b][1,4]thiazine. If the heteroaryl contains nitrogen atoms, it is understood that the corresponding N-oxides thereof are also encompassed by this definition.

The term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: azaspirononanyl, azaspirooctanyl, azetidinyl, dioxanyl, oxadiazaspirodecenyl, oxaspirooctanyl, oxazolidinonyl, piperazinyl, piperidinyl, pyrrolidinyl, morpholinyl, thiomorpholinyl, tetrahydrofurnayl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "halogen" or "halo" means fluorine, chlorine, bromine or iodine.

"Celite®" (Fluka) diatomite is diatomaceous earth, and can be referred to as "celite".

Except where noted herein, structures containing substituent variables such as variable "R" below:

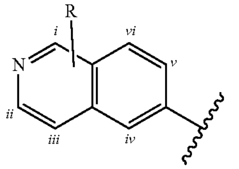

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also relates to medicaments containing at least one compound of the Formula I and/or of a pharmaceutically acceptable salt of the compound of the Formula I and/or an optionally stereoisomeric form of the compound of the Formula I or a pharmaceutically acceptable salt of the stereoisomeric form of the compound of Formula I, together with a pharmaceutically suitable and pharmaceutically acceptable vehicle, additive and/or other active substances and auxiliaries.

The term "patient" used herein is taken to mean mammals such as primates, humans, sheep, horses, cattle, pigs, dogs, cats, rats, and mice.

The medicaments according to the invention can be administered by oral, inhalative, rectal or transdermal administration or by subcutaneous, intraarticular, intraperitoneal or intravenous injection. Oral administration is preferred. Coating of stents with compounds of the Formulas I and other surfaces which come into contact with blood in the body is possible.

The invention also relates to a process for the production of a medicament, which comprises bringing at least one compound of the Formula I into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specificed otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the plasma kallikrein inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of Formula I can be administered both as a monotherapy and in combination with other therapeutic agents, including but not limited to anti-inflammatory agents, anti-VEGF agents, immunosuppressive agents, anticoagulants, antiplatelet agents, and thrombolytic agents.

An "anti-inflammatory agent" is any agent which is directly or indirectly effective in the reduction of inflammation when administered at a therapeutically effective level. "Anti-inflammatory agent" includes, but is not limited to steroidal anti-inflammatory agents and glucocorticoids. Suitable anti-inflammatory agents include, but are not limited to, cortisone, dexamethasone, hydrocortisone, methylprednisolone, prednisolone, prednisone and triamcinolone.

An "anti-VEGF agent" is any agent which is directly or indirectly effective in inhibiting the activity of VEGF (Vascular Endothelial Growth Factor). Suitable anti-VEGF agents include, but are not limited to, bevacizumab, ranibizumab and aflibercept.

An "immunosuppressant agent" is any agent which is directly or indirectly effective in suppressing, or reducing, the strength of the body's immune system. Suitable immunosuppressant agents include, but are not limited to, corticosteroids (for example, prednisone, budesonide, prednisolone), janus kinase inhibitors (for example, tofacitinib), calcineurin inhibitors (for example, cyclosporin, tacrolimus), mTOR inhibitors (for example, sirolimus, everolimus), IMDH inhibitors (for example, azathioprine, leflunomide, mycophenolate), biologics (for example, abatacept, adalimumab, anakinra, certolizumab, etanercept, golimumab, infliximab, ixekizumab, natalizumab, rituximab, secukinumab, tocilizumab, ustekinumab, vedolizumab), and monoclonal antibodies (for example, basiliximab, daclizumab).

Suitable anticoagulants include, but are not limited to, factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors.

In certain embodiments the anti-inflammatory agents, anti-VEGF agents, immunosuppressant agents, anticoagulants, antiplatelet agents, and thrombolytic agents described herein are employed in their conventional dosage ranges and regimens as reported in the art, including, for example, the dosages described in editions of the Physicians' Desk Reference, such as the 70th edition (2016) and earlier editions. In other embodiments, the anti-inflammatory agents, anti-VEGF agents, immunosuppressant agents, anticoagulants, antiplatelet agents, and thrombolytic agents described herein are employed in lower than their conventional dosage ranges.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin, remogliflozin and sotagliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of the plasma kallikrein inhibitors of the invention in combination with other suitable agents may be the same as those doses of plasma kallikrein inhibitors administered without coadministration of additional agents, or may be substantially less that those doses of plasma kallikrein inhibitors administered without coadministration of additional agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. The administration of each component does not need to be via the same route of administration; for example, one component can be administered orally, and another can be delivered into the vitreous of the eye.

The present invention is not limited in scope by the specific embodiments disclosed in the examples which are intended as illustrations of a few aspects of the invention and any embodiments that are functionally equivalent are within the scope of this invention.

Indeed, various modifications of the invention in addition to those shown and described herein will become apparent to those skilled in the relevant art and are intended to fall within the scope of the appended claims.

General Methods

Compounds of the present invention may be prepared using conventional techniques or according to the methodology outlined in the following general synthetic schemes. One skilled in the art can vary the procedures and reagents shown to arrive at similar intermediates and/or final compounds.

NMR spectra were measured on VARIAN or Bruker NMR Systems (400, 500 or 600 MHz). Chemical shifts are reported in ppm downfield and up field from tetramethylsilane (TMS) and referenced to either internal TMS or solvent resonances ($^1$H NMR: δ 7.27 for $CDCl_3$, δ 2.50 for $(CD_3)(CHD_2)SO$, and $^{13}$C NMR: δ 77.02 for $CDCl_3$, δ 39.51 for $(CD_3)_2SO$. Coupling constants (J) are expressed in hertz (Hz), and spin multiplicities are given as s (singlet), d (doublet), dd (double doublet), t (triplet), m (multiplet), and br (broad). Chiral resolutions were performed on either Waters Thar 80 SFC or Berger MG II preparative SFC systems. LC-MS data were recorded on SHIMADAZU LC-MS-2020, SHIMADAZU LC-MS-2010, or Agilent 1100 series LC-MS, Agilent Prime-1260, or Waters Acquity LC-MS instruments using C18 columns employing a MeCN gradient in water containing 0.02 to 0.1% TFA. UV detections were at 220 and/or 254 nm and ESI ionization was used for MS detection.

When chiral resolution was achieved by chromatography using chiral columns, the chiral columns used for SFC chiral resolutions are listed in tables. Some of the chiral columns used were CHIRALPAK AD, CHIRALCEL OJ, CHIRALPAK AS, CHIRALPAK AY, CHIRALPAK IA, CHIRALPAK AD-H, and CHIRALPAK AS-H. Henceforth, they will be referred by their two or three letter abbreviations. As a convention, the fast-eluting isomer from a chiral resolution is always listed first in this table followed immediately by the slower-eluting isomer from the same resolution. If more than two isomers were separated, they will be always listed in the tables in order they were eluted, such as Peak 1 followed by Peak 2, Peak 3 and so on. A * symbol near a chiral center in a structure denotes that this chiral center was resolved by chiral resolution without its stereochemical configuration unambiguously determined.

Also, TLC is thin layer chromatography; UV is ultraviolet; W is watts; wt. % is percentage by weight; ×g is times gravity; $\alpha_D$ is the specific rotation of polarized light at 589 nm; ° C. is degrees Celsius; % w/v is percentage in weight of the former agent relative to the volume of the latter agent; Hz is hertz; cpm is counts per minute; $\delta_H$ is chemical shift; d is doublet; dd is doublet of doublets; MHz is megahertz; MS is mass spectrum, and a mass spectrum obtained by ES-MS may be denoted herein by "LC-MS"; m z is mass to charge ratio; n is normal; N is normal; nm is nanometer; nM is nanomolar.

Several catalysts and ligands are used in the following procedures. "$Me_4{}^tBu$ XPhos Pd G3" is methanesulfonato (2-di-tert-butylphosphino-3,4,5,6-tetramethyl-2',4',6'-triisopropyl-1,1-biphenyl)(2'-amino-1,1'-biphenyl-2-yl) palladium(II). "$[Ir\{dFCF_3ppy\}_2(bpy)]PF_6$" is bis[2-(2,4-difluorophenyl)-5-trifluoromethylpyridine] [2-2'-bipyridyl] iridium hexafluorophosphate. These catalysts and ligands are available from Millipore Sigma.

For purposes of this specification, the following abbreviations have the indicated meanings:

Ac acetyl
ACN acetonitrile
AcOH or acetic acid
HOAc
aq. aqueous
Ar aryl
Boc or BOC tert-butoxycarbonyl
Bpin bis(pinacolato)diboron
br broad calcd. calculated
CPME cyclopentylmethyl ether
d doublet
DAST (diethylamino)sulfur trifluoride
DBAD Di-tert-buty; azodicarboxylate
DCE 1,2-dichloroethane
DCM dichloromethane
dd doublet of doublets
DEA diethanolamine
DIAD diisopropyl azodicarboxylate
DIBAL-H or diisobutylaluminum hydride
Dibal-H
DIEA or N,N-diisopropylethylamine
Hünig's base
DMA 1,2-dimethylacetamide
DMAP 4-dimethylaminopyridine
DMF dimethylformamide
DMP Dess-Martin periodinane (1,1,1-triacetoxy)-1,1-dihydro-1,2-benziodoxol-3(1H)-one
DMPU 3,4,5,6-tetrahydro-2(1H)-pyrimidinone
DMS dimethylsulfide
DMSO dimethyl sulfoxide
dpm 2,2,6,6-tetramethylheptane-3,5-dione
DTT dithiothreitol
EDC or EDCI 1-ethyl-3-(3-dimethylaminopropyl)carbodiimide
EDTA ethylenediamine tetraacetic acid
equiv equivalents
ESI electrospray ionization
Et ethyl
EtOH ethanol
EtOAc ethyl acetate
g grams
GST glutathione S-transferase
h hour
HATU N,N,N,N-tetramethyl-O-(7-azabenzotriazol-1-yl) uronium hexafluorophosphate
HOBt 1-hydroxybenzotriazole
HPLC high-performance liquid chromatography
$IC_{50}$ concentration at which 50% inhibition exists
IPA isopropanol
iPr isopropyl
J coupling constant
L liters
LAH lithium aluminum hydride
LC liquid chromatography
LCMS liquid chromatography mass spectrometry
LDA lithium diisopropylamide
LED light emitting diode
LG leaving group
M mass
M molar
m multiplet
mCPBA 3-chloroperoxybenzoic acid
Me methyl
MeOH methanol
mg milligrams
min minute
µL microliters
mL milliliters
mmol millimoles
MPLC medium pressure liquid chromatography
Ms methanesulfonyl (mesyl)
MTBE methyl tert-butyl ether
nm nanometer
NMP 1-methylpyrrolidinone
NMR nuclear magnetic resonance spectroscopy
p pentet
pH measure of acidity or basicity of aq. or other solutions
Ph phenyl
pin pinacol
PMB 4-methoxybenzyl
PMBOH 4-methoxybenzyl alcohol
Pr propyl
psi pounds per square inch
q quartet
quint quintet
rac racemic mixture
RT or rt room temperature (ambient, about 25° C.)
s singlet
satd. saturated
SEM 2-(trimethylsilyl)ethoxymethyl
SFC supercritical fluid chromatography
SNAr nucleophilic aromatic substitution
t triplet
T3P propylphosphonic anhydride
TBAF tert-butyl ammonium fluoride
TBS or tert-butyldimethyl silyl
TBDMS
TBDPS tert-butyldiphenylsilyl
TBDPSCl tert-butyldiphenylsilyl chloride
TBSCl tert-butyldimethylsilyl chloride
tBu tert-butyl
TEA triethylamine ($Et_3N$)
Tf triflate
TFA trifluoroacetic acid
TFAA trifluoroacetic anhydride
THF tetrahydrofuran
TMS trimethylsilyl
TMSOTf trimethylsilyl trifluoromethanesulfonate
Tris tris(hydroxymethyl)aminomethane
UPLC ultra performance liquid chromatography

General

Starting materials used were obtained from commercial sources, prepared in other examples, or prepared as known in the literature, unless otherwise noted.

The methods used for the preparation of the compounds of this invention are illustrated by the following schemes.

Scheme AA.

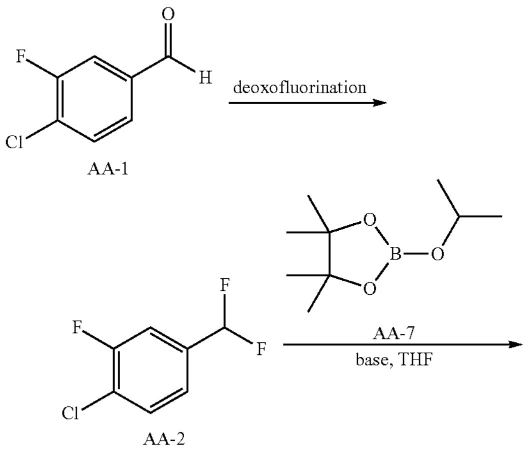

AA-1
AA-7
AA-2

-continued

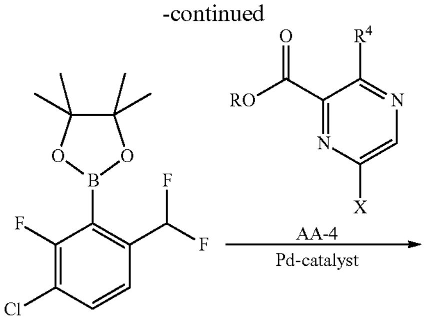

AA-3

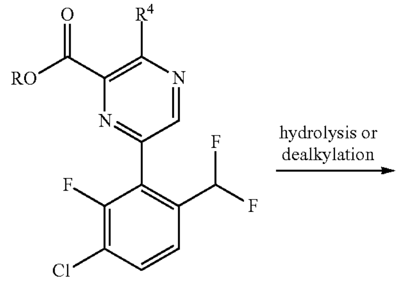

AA-5

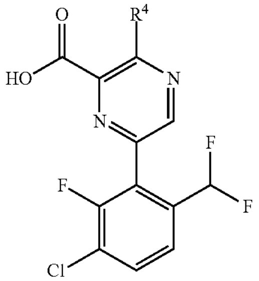

AA-6

Scheme AA illustrates a synthetic sequence for the preparation of bi-heteroaryl derivatives such as AA-6 from arene AA-1 and alkyl pyrazine-2-carboxylates such as AA-4. Deoxofluorination of aldehyde AA-1 provides AA-2. Borylation of AA-2 by treatment with a trialkoxyborane such as AA-7 and a base such as LDA furnishes boronate ester AA-3. Palladium-catalyzed cross-coupling of AA-3 with halide AA-4 affords AA-5. Base-mediated hydrolysis or dealkylation of the ester of AA-5 by treatment with reagents such as LiOH, NaOH or LiI furnishes carboxylic acid AA-6 that can be carried on to compounds of this invention.

Scheme AB.

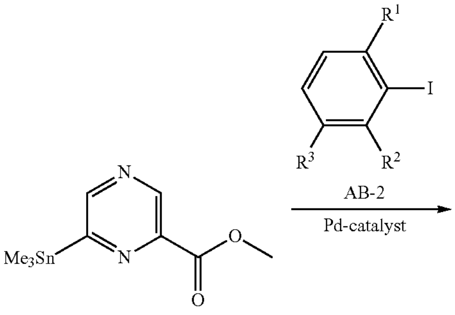

AB-1

-continued

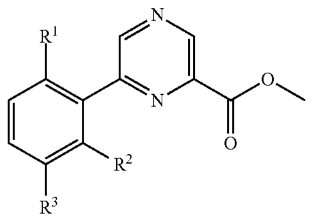

AB-3

Scheme AB illustrates the synthetic sequence for preparation of ester derivatives such as AB-3 from a stannane AB-1. Pd-catalyzed Stille coupling. of AB-1 with aryl iodide AB-2 gives the biaryl ester derivative AB-3 that can be carried on to compounds of this invention.

Scheme AC.

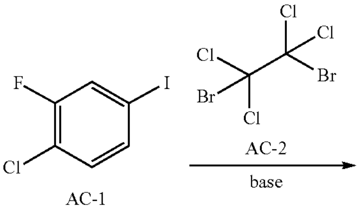

AC-1

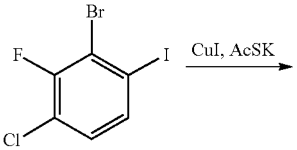

AC-3

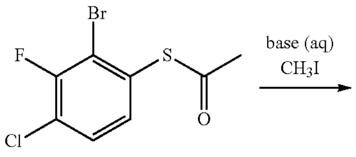

AC-4

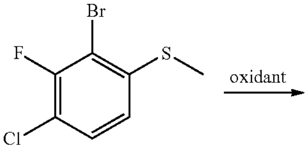

AC-5

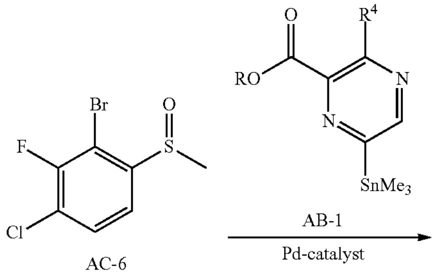

AC-6

-continued

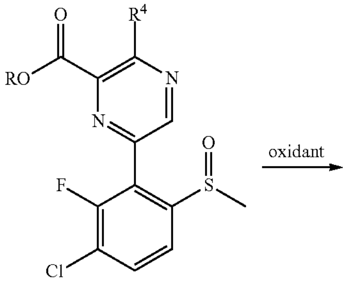

AC-7

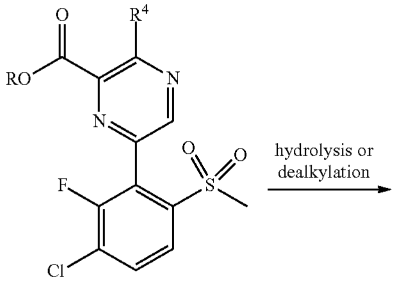

AC-8

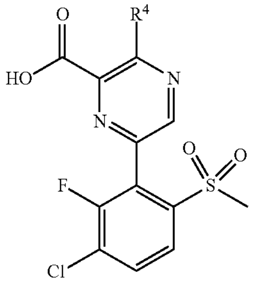

AC-9

Scheme AC illustrates a synthetic sequence for the preparation of bi-heteroaryl derivatives such as AC-9 from arene AC-1 and pyrazine AB-1. Bromination of AC-1 by treament with a base such as LDA and a brominating agent such as 1,2-dibromo-1,1,2,2-tetrachloroethane AC-2 affords AC-3. Copper-catalyzed cross-coupling of AC-3 with potassium thioacetate gives thioester AC-4. Treatment with an aqueous base such as NaOH and an alkylation agent such as methyliodide converts thioester AC-4 to thioether AC-5, which is subsequently oxidized to sulfoxide AC-6 by use of an oxidant such as mCPBA. Palladium-catalyzed cross-coupling of bromide AC-6 with stannane AB-1 affords AC-7. Oxidation of the suloxide of AC-7 using an oxidant such as Oxone® gives sulfone AC-8, and base-mediated hydrolysis or dealkylation of the ester of AC-8 furnishes carboxylic acid AC-9 that can be carried on to compounds of this invention.

Scheme AD.

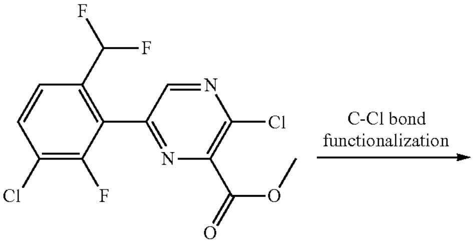

AD-1

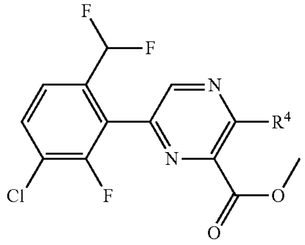

AD-2

Scheme AD illustrates the synthetic sequence for preparation of biaryl derivatives such as AD-2 by C—Cl functionalization of the aryl chloride AD-1.

Scheme BA.

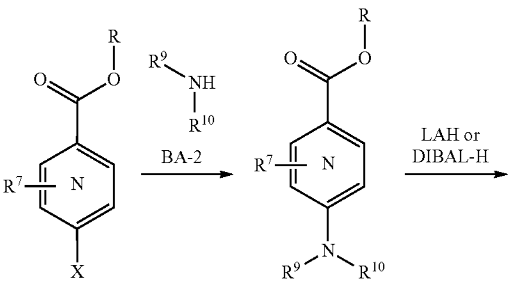

BA-1 BA-3

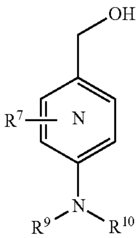

BA-4

Scheme BA illustrates the synthetic sequence for preparation of primary alcohols such as BA-4. $S_NAr$ reaction of BA-1 with aliphatic amines BA-2 gives anilines BA-3. The subsequent reduction of ester group in BA-3 using LAH or DIBAL-H, for example, gives the alcohols BA-4 that can be carried on to compounds of this invention.

Scheme BB.

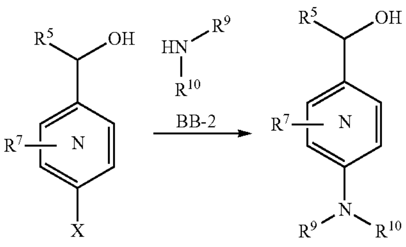

BB-1 BB-3

Scheme BB illustrates the synthetic sequence for preparation of alcohol derivatives such as BB-3. $S_NAr$ reaction of aryl halides BB-1 with aliphatic amines BB-2 gives the anilines BB-3 that can be carried on to compounds of this invention.

Scheme BC.

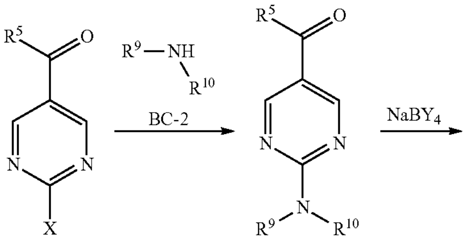

BC-1 BC-3

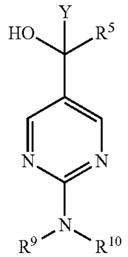

BC-4

Scheme BC illustrates the synthetic sequence for preparation of alcohols such as BC-4 from ketones such as BC-1 by $S_NAr$ of aryl halides such as BC-2, as described above, followed by reduction of ketones, such as BC-3, to afford alcohols (BC-4) that can be carried on to compounds of this invention.

Scheme BD.

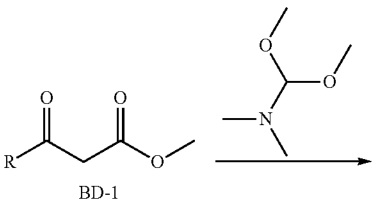

BD-1

-continued

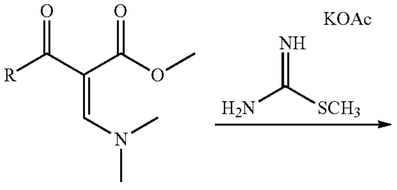

BD-2

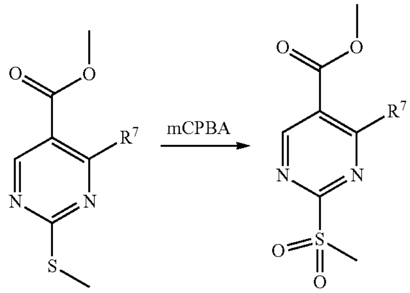

BD-3 BD-4

Scheme BD illustrates the synthetic sequence for preparation of sulfone BD-4 from condensation between 1,3-dicarbonyl derivatives (BD-1) and N,N-dimethylformamide dimethyl acetal, followed by cyclization with thiopseudourea to afford a 2-mercaptopyrimidine (BD-3) and oxidation to afford sulfones (BD-4) that can be carried on to compounds of this invention.

Scheme BE.

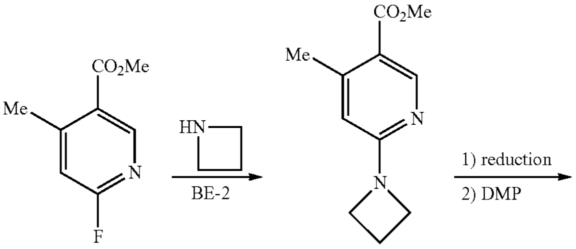

BE-1 BE-3

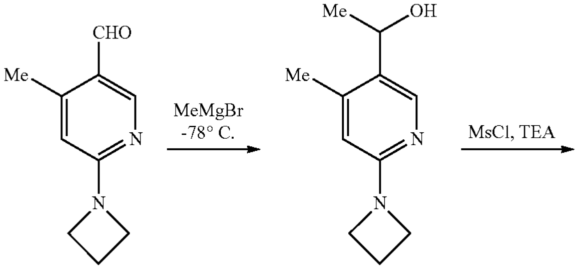

BE-4 BE-5

-continued

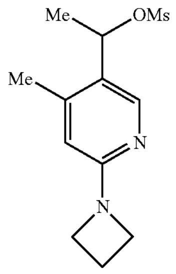

BE-6

Scheme BE illustrates the synthetic sequence for preparation of mesylate BE-6 from ester BE-1. $S_NAr$ of BE-1 with azetidine gives BE-2 affords an ester (BE-3) which can undergo reduction, followed by oxidation to give an aldehyde (BE-4). Grignard addition to BE-4 to afford a secondary alcohol BE-5, followed by mesylation can yield intermediate BE-6 that can be carried on to compounds of this invention.

Scheme BF.

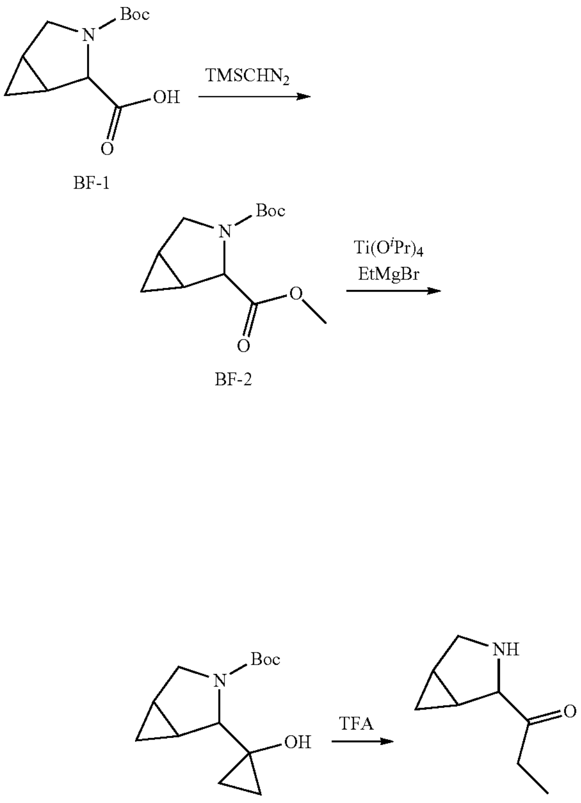

BF-1 BF-2 BF-3 BF-4

Scheme BF illustrates the synthetic sequence for preparation of ketone BF-4 from the acid derivative BF-1. Esterification of BF-1, followed by cyclopropanation can afford alcohol BF-3, which can undergo dual Boc-deprotection/rearrangement under acidic conditions to give ketone BF-4 that can be carried on to compounds of this invention.

Scheme CA.

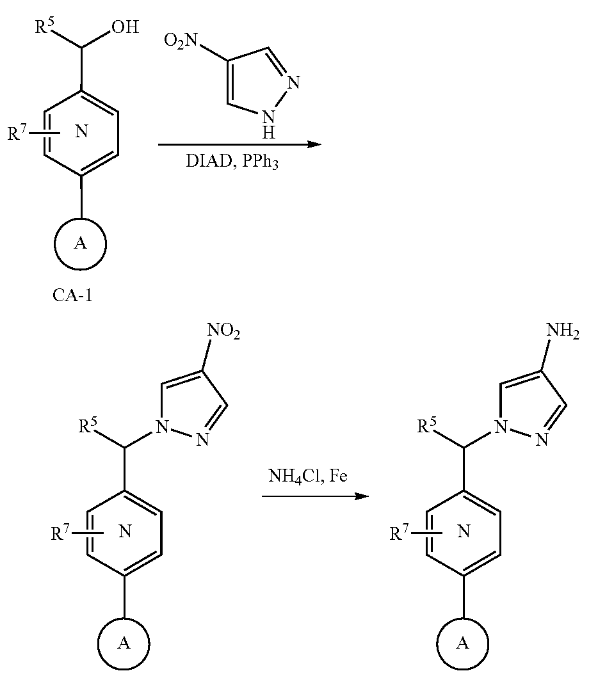

CA-1 CA-2 CA-3

Scheme CA illustrates the synthetic sequence for preparation of 4-aminopyrazole derivatives such as CA-3 from alcohols such as CA-1. Mitsunobu reaction of 4-nitropyrazole with alcohols CA-2 followed by reduction of nitro group (CA-2) can afford the aminopyrazole derivatives CA-3.

Scheme CB.

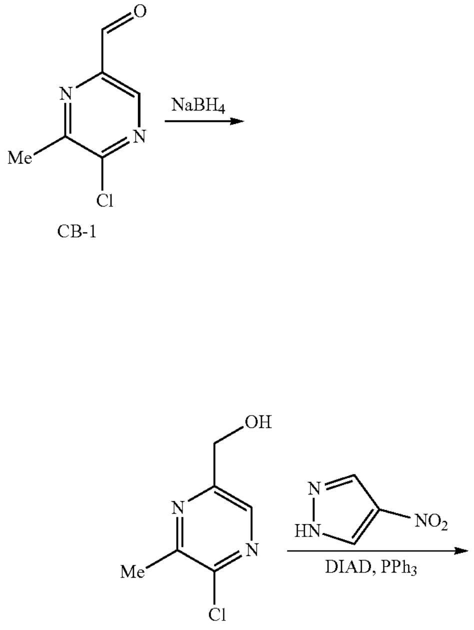

CB-1 CB-2

-continued

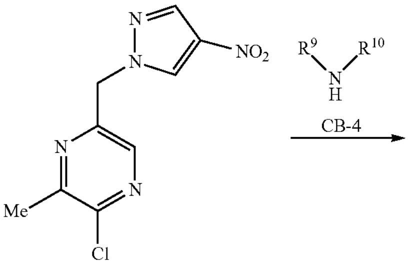

CB-3

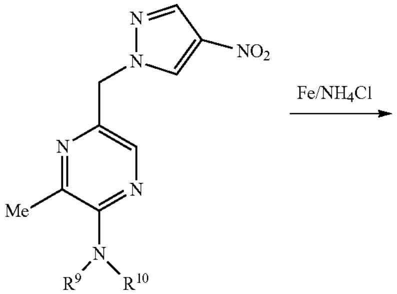

CB-5

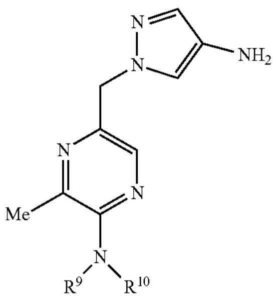

CB-6

Scheme CB illustrates the synthetic sequence for preparation of aminopyrazole derivative CB-6 from aldehyde CB-1. Reduction of CB-1, followed by Mitsunobu displacement of the alcohol moiety with nitropyrazole can give chloropyrazine CB-3. $S_NAr$ of CB-3 with an amine (CB-4), followed by reduction of nitro group in CB-5 can yield an aminopyrazole CB-6 that can be carried on to compounds of this invention.

Scheme CC.

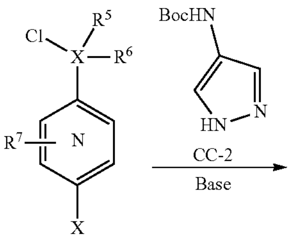

CC-1

-continued

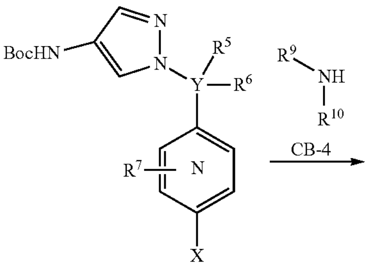

CC-3

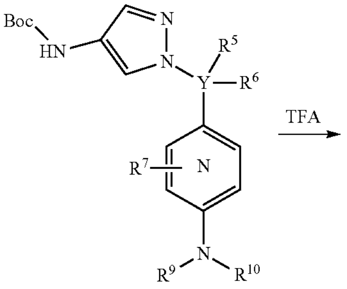

CC-4

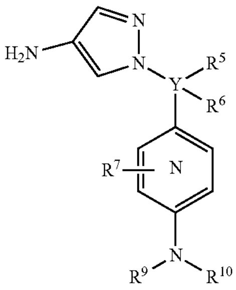

CC-5

Scheme CC illustrates the synthetic sequence for preparation of aminopyrazole derivatives such as CC-5 from compounds such as CC-1. Nucleophilic displacement of Cl from CC-1 with Boc-protected aminopyrazole CC-2 can yield an aryl halide (CC-3), which can undergo $S_NAr$ reaction with aliphatic amines CB-4 to give anilines CC-4. Boc-deprotection under acidic conditions can give the free aminopyrazole CC-5 that can be carried on to compounds of this invention.

Scheme CD.

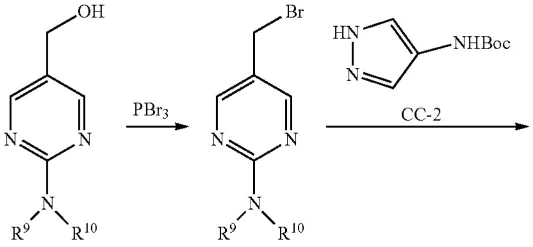

CD-1 CD-2

-continued

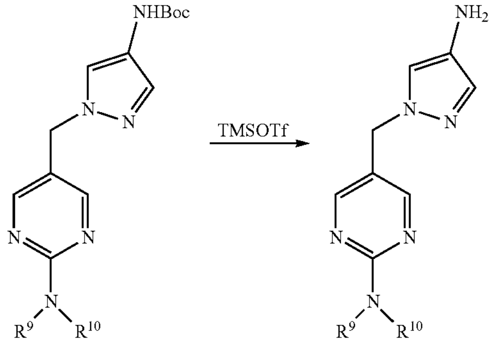

CD-3

CD-4

Scheme CD illustrates the synthetic sequence for preparation of amino pyrazole derivative CD-4 from alcohol such as CD-1. Bromine displacment of the alcohol moiety from CD-1, followed by substitution with Boc-amino pyrazole (CD-2) and deprotection (CD-3) gives amino pyrazole CD-4 that can be carried on to compounds of this invention.

-continued

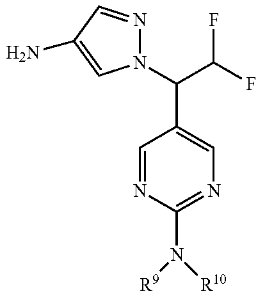

CE-5

Scheme CE illustrates the synthetic sequence for preparation of aminopyrazole derivative such as CE-5 from aldehyde CE-1. $S_NAr$ with an amine (CB-4), followed by reaction with a difluoromethyl nucleophile to the aldehyde moiety can give alcohol CE-3. Mitsunobu reaction with nitropyrazole, followed by nitro group reduction as described previously can afford an aminopyrazole derivative CE-5 that can be carried on to compounds of this invention.

Scheme CE.

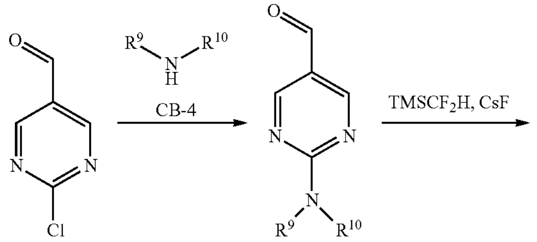

CE-1

CE-2

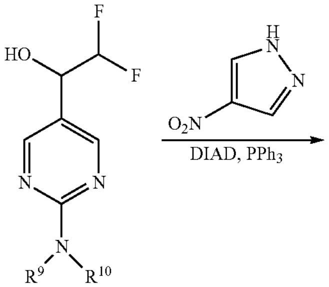

CE-3

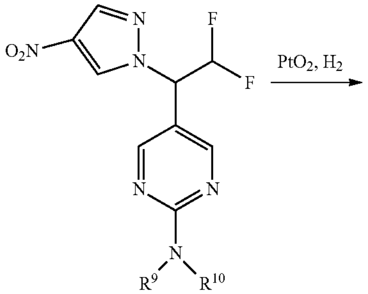

CE-4

Scheme CF.

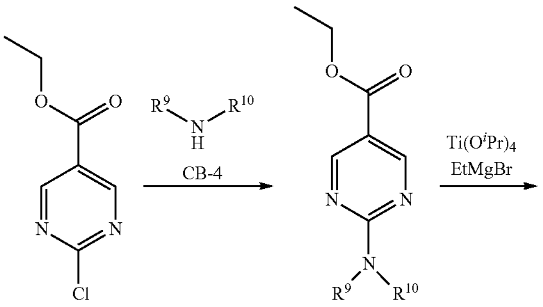

CF-1

CF-2

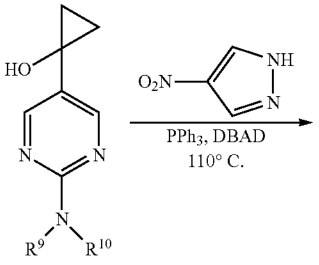

CF-3

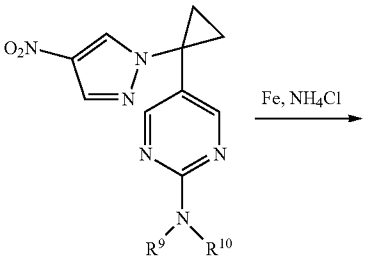

CF-4

-continued

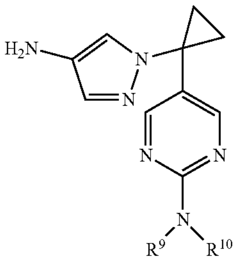

CF-5

Scheme CF illustrates the synthetic sequence for preparation of aminopyrazole CF-5 from ester CF-1. $S_NAr$ reaction of an amine (CB-4) with CF-1, followed by titanium-mediated cylcopropanation can yield alcohol CF-3. Mitsunobu reaction at elevated reaction temperature, and subsequent reduction of the nitro group, as previously described, can afford the aminopyrazole derivative CF-5 that can be carried on to compounds of this invention.

Scheme CG.

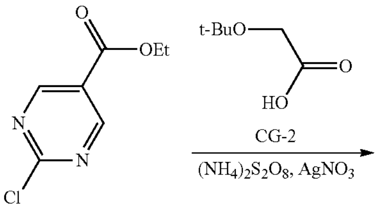

CG-1

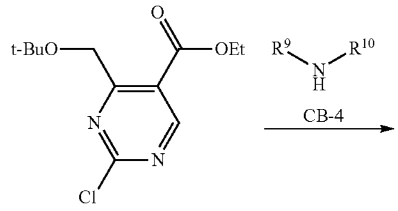

CG-3

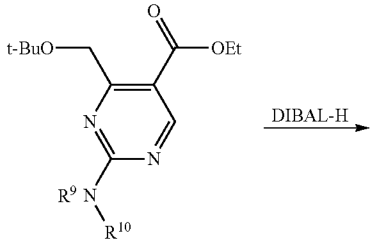

CG-4

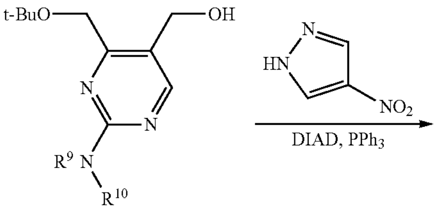

CG-5

-continued

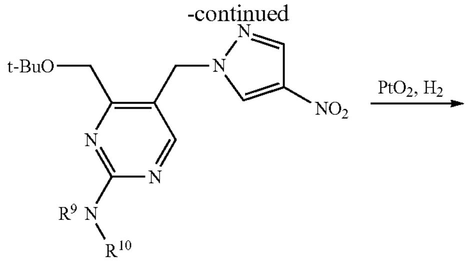

CG-6

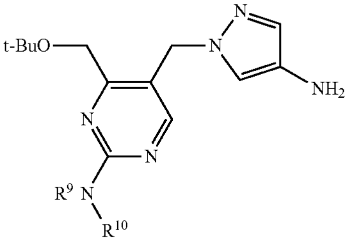

CG-7

Scheme CG illustrates the synthetic sequence for preparation of an aminopyrazole CG-6 from pyrimidine ester CG-1. Minisci reaction of CG-1 with an alkoxyacetic acid (CG-2) can give an ether derivative CG-3. $S_NAr$ reaction with an amine (CB-4), followed by reduction of the ester moiety can yield a benzylic alcohol CG-5. Mitsunobu reaction, followed by nitro group reduction, as described above, can give an aminopyrazole CG-7 that can be carried on to compounds of this invention.

Scheme CH.

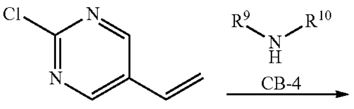

CH-1

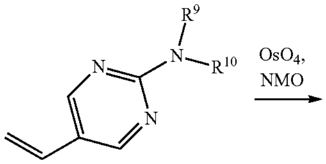

CH-2

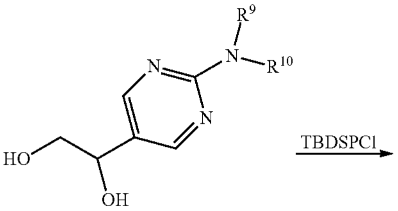

CH-3

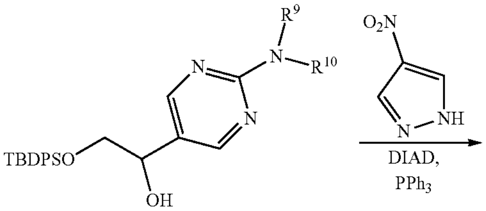

CH-4

-continued

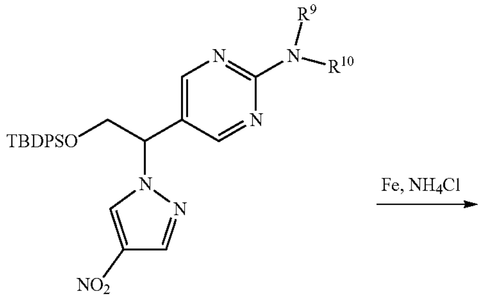

CH-5

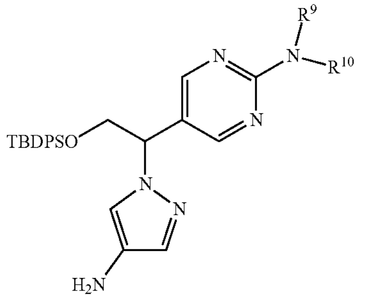
CH-6

Scheme CH illustrates the synthetic sequence for preparation of an aminopyrazole CH-7 from olefin CH-1. $S_NAr$ reaction of CH-1 with an amine (CB-4) can give aminopyrimidine CH-2, which can undergo dihydroxylation to yield afford a diol such as CH-3. Selective protection of the primary alcohol gives CH-4, which enables Mitsunobu reaction of nitropyrazole at the secondary hydroxyl group to afford adduct CH-5. Reduction can yield an aminopyrazole (CH-6) that can be carried on to compounds of this invention.

Scheme CI.

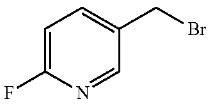
CI-1

+

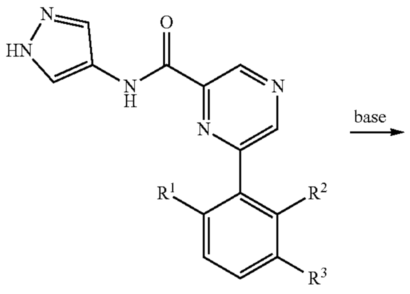

CI-2

-continued

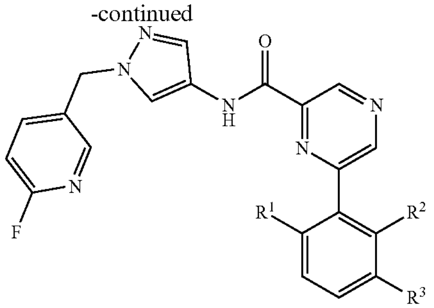
CI-3

Scheme CI illustrates the synthetic sequence for preparation of tetracyclic intermediate CI-3 by reaction of benzylic bromide CI-1 with an aminopyrazole nucleophile CI-2 in the presence of a suitable base, such as $Cs_2CO_3$ or the like. The reaction is typically performed at room temperature, but can require elevated reaction temperatures to produce CI-3, which can be carried on to compounds of this invention.

Scheme CJ.

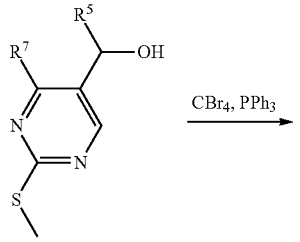

CJ-1

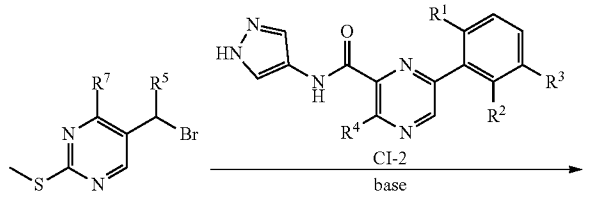

CJ-2

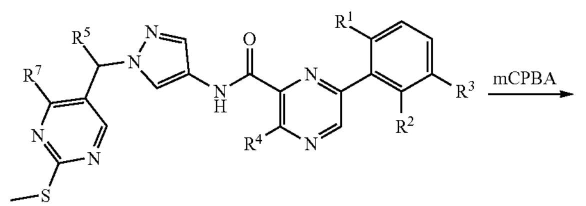

CJ-3

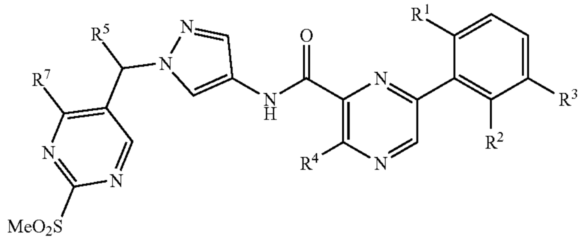
CJ4

Scheme CJ illustrates the synthetic sequence for preparation of the sulfone derivatives such as CJ-4 from benzylic alcohols such as CJ-1. Bromination of CJ-1, followed by reaction with an aminopyrazole (CI-2) in the presence of a suitable base, such as $Cs_2CO_3$ or the like, can afford a sulfide intermediate (CJ-3) that can undergo oxidation to sulfones (CJ-4) that can be carried on to compounds of this invention.

Scheme AAA.

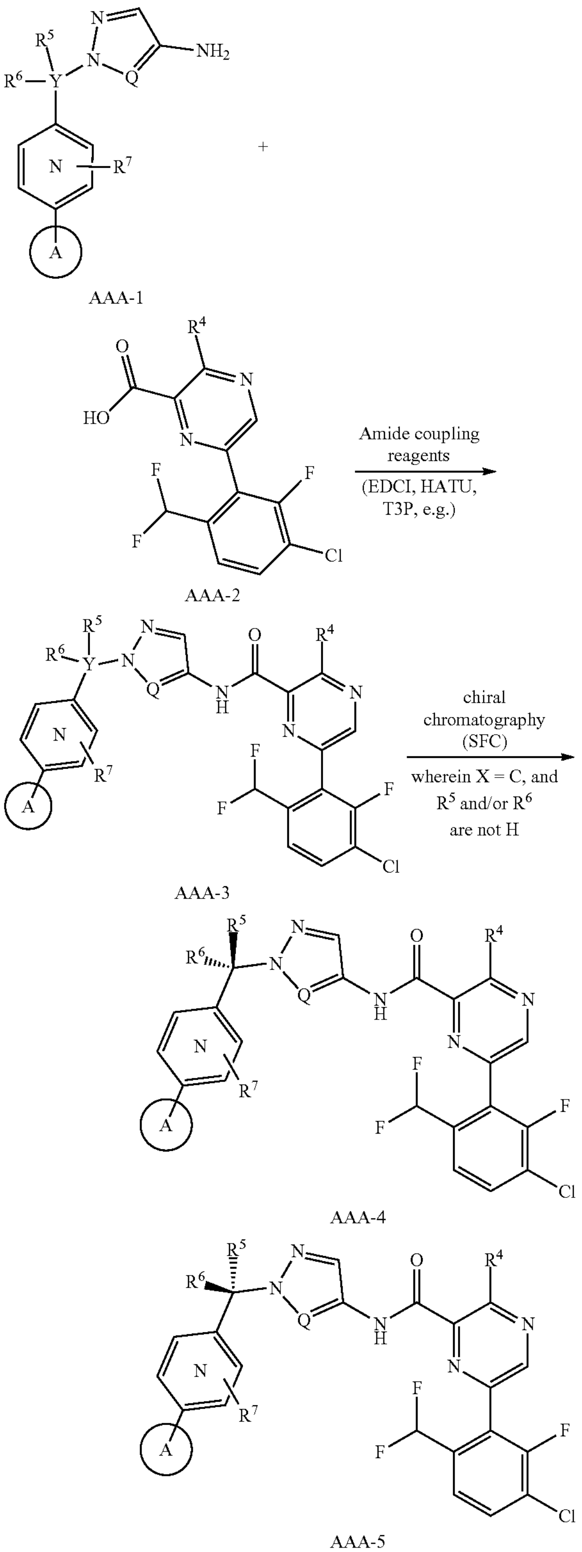

Scheme AAA illustrates the synthetic sequence for preparing amide compounds of this invention, such as AAA-3 employing amide couplings between amino pyrazole derivatives such as AAA-1 and carboxylic acid derivatives such as AAA-2. When compounds AAA-3 exist as mixtures of stereoisomers, specifically as racemic mixture, such compounds can be separated by chiral chromatography, preferably SFC, when appropriate (wherein Y═C, and $R^5$ and/or $R^6$ are not H) to yield individual stereoisomers AAA-4 and AAA-5.

Scheme AAB.

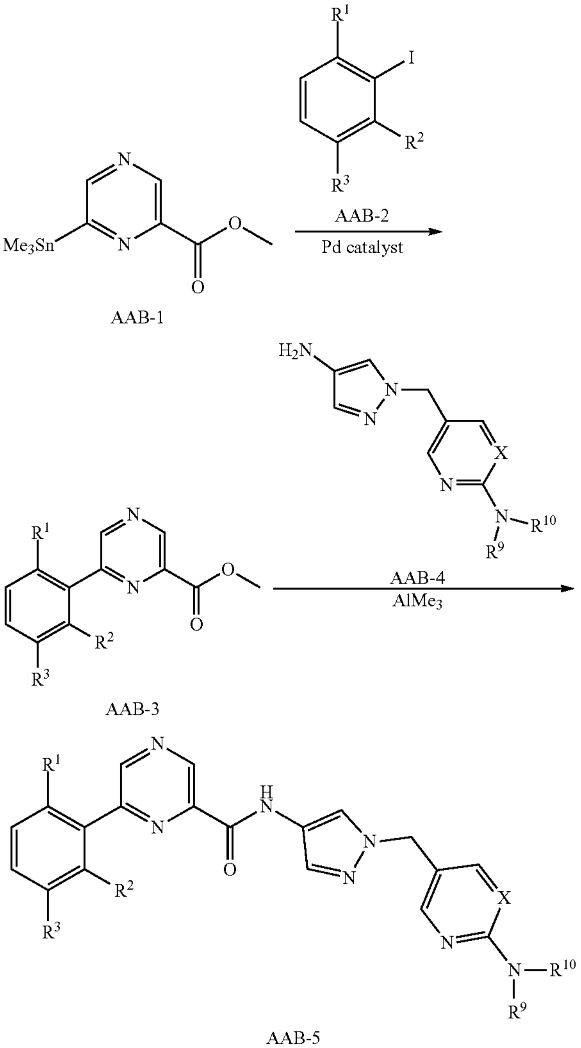

Scheme AAB illustrates a synthetic sequence for preparing amide compounds of this invention, such as AAA-5. The sequence is initiated from cross-coupling of a stanylated heteroaryl ester (AAB-1) with an aryl iodide partner (AAB-2) using a suitable palladium catalyst and ligand. The biaryl product (AAB-3) can be hydrolyzed to the corresponding carboxylic acid and coupled as described in Scheme AAA (not shown) or alternatively reacted in the presence of an amine donor like aminopyrazole AAB-4 and a carboxylate activating reagent, such as trimethylaluminum, to afford compounds of this invention (AAB-5).

Scheme AAC.

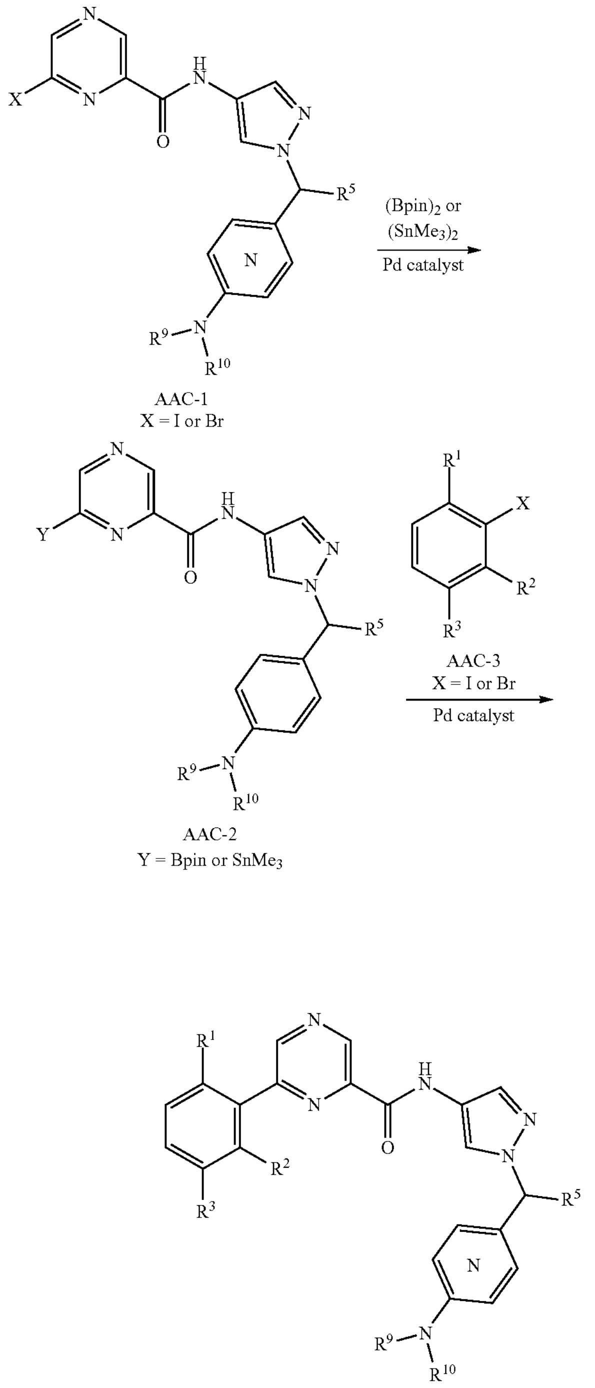

AAC-1
X = I or Br

AAC-2
Y = Bpin or $SnMe_3$

AAC-3
X = I or Br

AAC-4

Scheme AAC illustrates the synthetic sequence for an alternate preparation of biaryl compounds of this invention (AAC-4) from tricyclic heteroaryl halides (AAC-1) and aryl halide (AAC-3) inputs. Initial palladium catalyzed borylation or stannylation of AAC-1 yields an activated coupling partner (AAC-2) for AAC-3, which can be cross-coupled with a subsequent palladium catalyzed coupling reaction to give the desired biaryl compounds of this invention (AAC-4).

Scheme AAD.

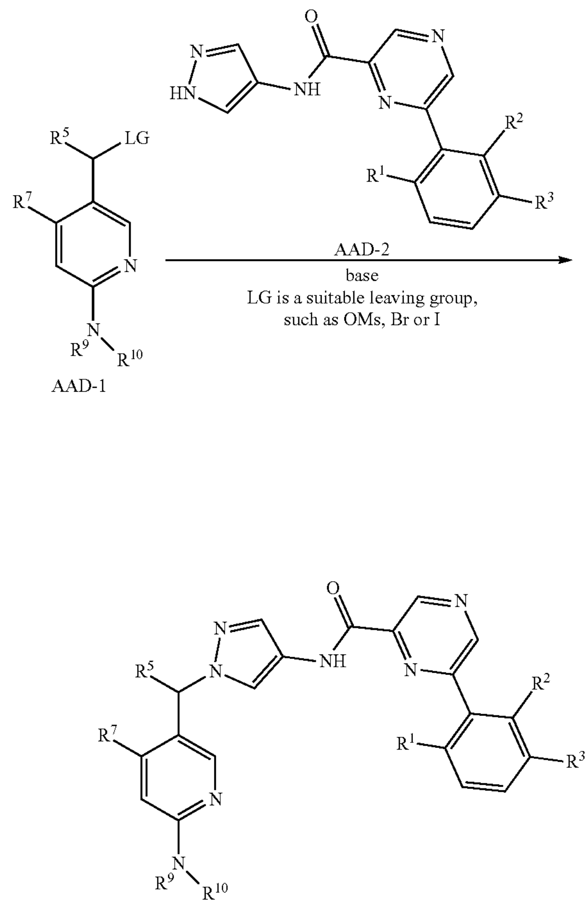

AAD-1

AAD-3

Scheme AAD illustrates an alternate synthetic sequence for preparing compounds of this invention (AAD-3). Alkylation of activated intermediate AAD-1 with a suitable heteroaryl nucleophile, such as AAD-2, in the presence of a base ($Cs_2CO_3$, or the like), can afford the desired compounds of this invention AAD-3. It should be noted that the alkylation can require elevated reaction temperatures to enable complete reaction of AAD-1 and AAD-2.

Scheme AAE.

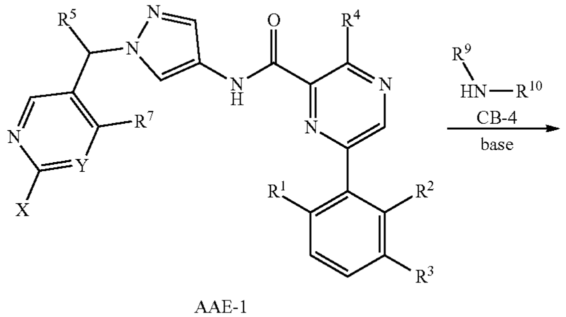

AAE-1
if X = F, then Y = CH
if X = Cl or $SO_2Me$, then Y = N

-continued

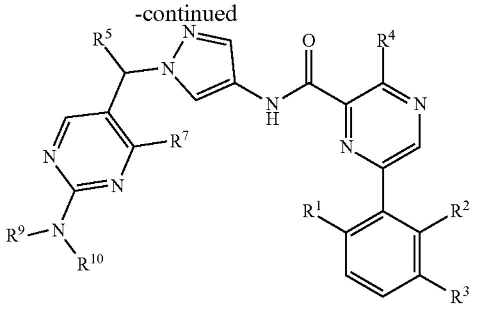

AAE-2

Scheme AAE illustrates a synthetic sequence for preparing amide compounds of this invention AAB-2. $S_NAr$ reaction of an activated heterocyclic intermediate (AAE-1) with a suitable amine nucleophile (CB-4), under reaction conditions that can require elevated temperatures to facilitate completion, can afford AAE-2.

Scheme AAF.

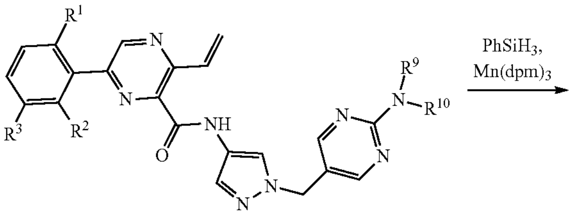

AAF-1

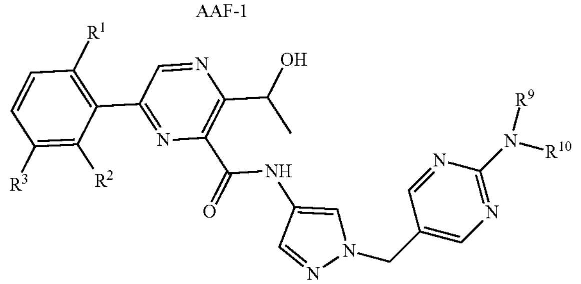

AAF-2

Scheme AAF illustrates the synthetic sequence for preparing secondary alcohols AAF-2 from Mn-catalyzed hydration of the olefin AAF-1.

Scheme AAG.

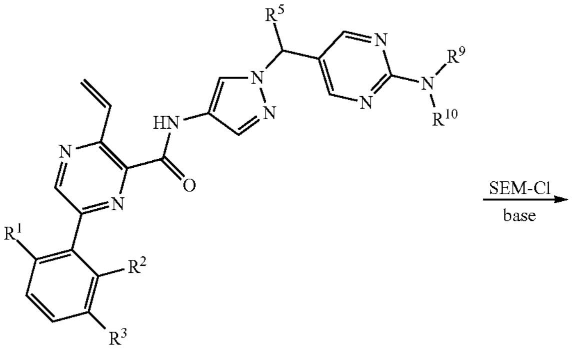

AAF-1

-continued

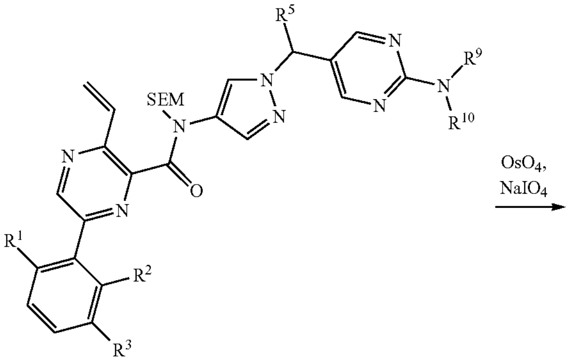

AAG-1

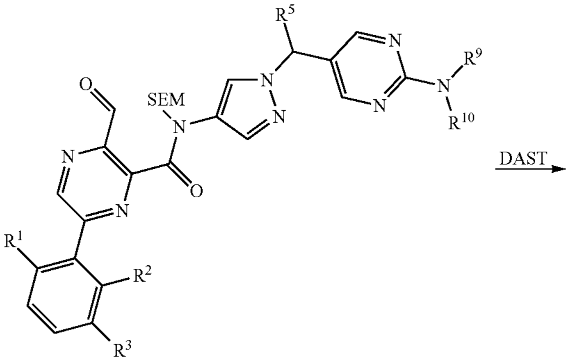

AAG-2

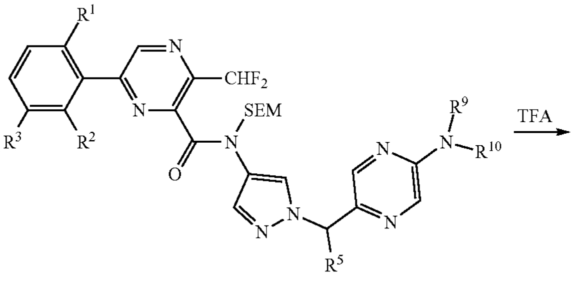

AAG-3

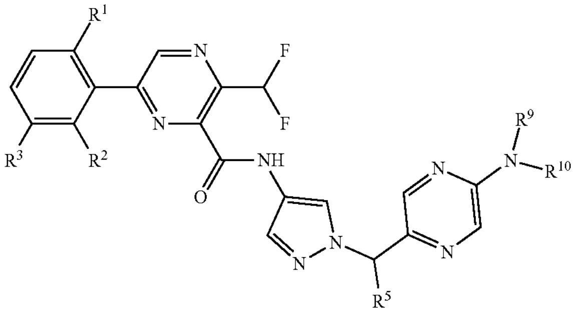

AAG-4

Scheme AAG illustrates an alternate synthetic sequence for modifying olefin intermediate AAF-1 to afford compounds of this invention. Amide protection can yield a SEM-protected intermediate (AAG-1) that can be reacted under oxidizing conditions to an aldehyde intermediate (AAG-2). Difluorination to AAG-3, followed by SEM-deprotection under acidic conditions can afford AAG-4.

Scheme AAH.

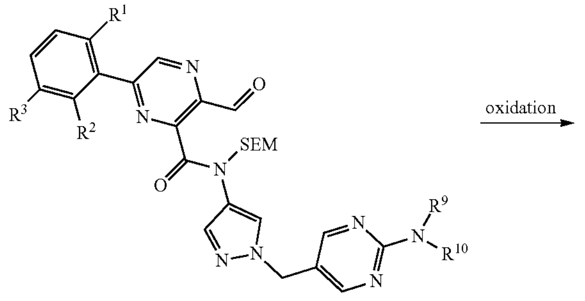

AAG-2

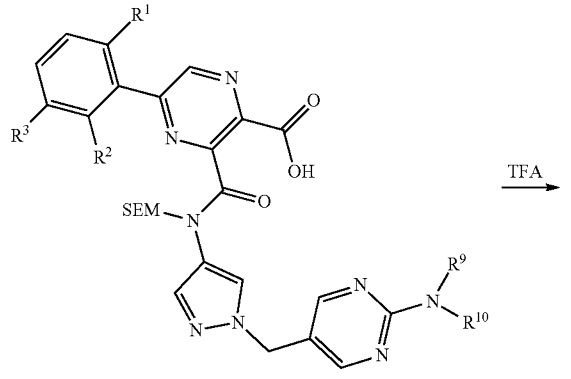

AAH-1

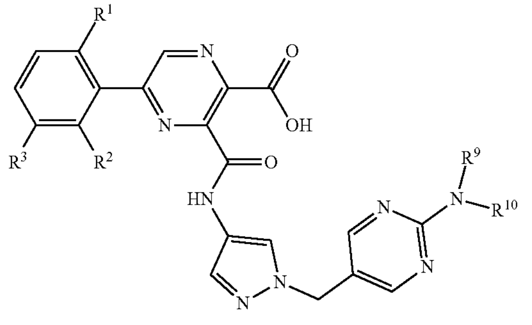

AAH-2

Scheme AAI.

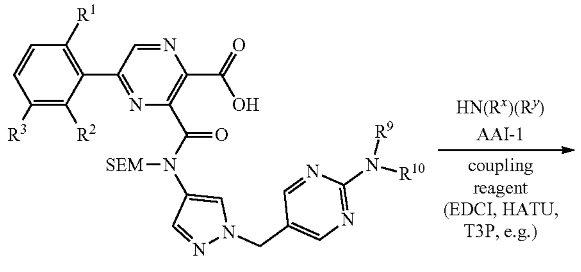

AAH-1

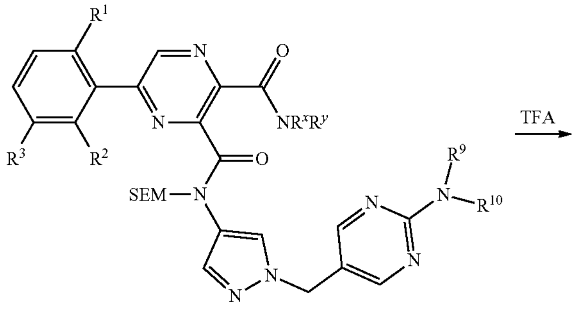

AAI-2

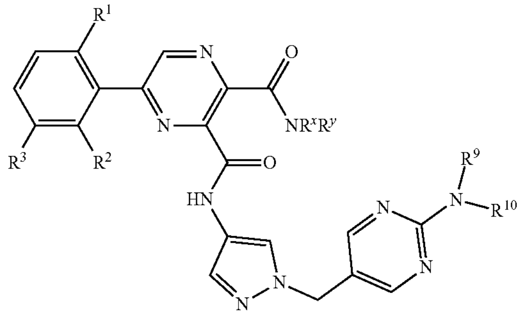

AAI-3

Scheme AAH illustrates an alternate synthetic sequence for modifying aldehyde intermediate AAG-2 to compounds of this invention. Oxidation of the aldehyde to the corresponding carboxylic acid moiety (AAH-1) can be performed using a variety of mild reaction conditions, an example of which is a Pinnick oxidation involving sodium chlorite as oxidant. SEM-deprotection as described above, can afford the desired carboxylic acid product AAH-2.

Scheme AAI illustrates the synthetic sequence for preparing amide derivatives (AAI-3) from carboxylic acid intermediate AAH-1. Reaction of carboxylic acid AAH-1 with an amine (AAI-1) under reaction conditions previously described can afford SEM-protected pyrazinyl carboxamides (AAI-2) that can undergo SEM-deprotection as described above to afford carboxamides (AAI-3) of this invention.

Scheme AAJ.

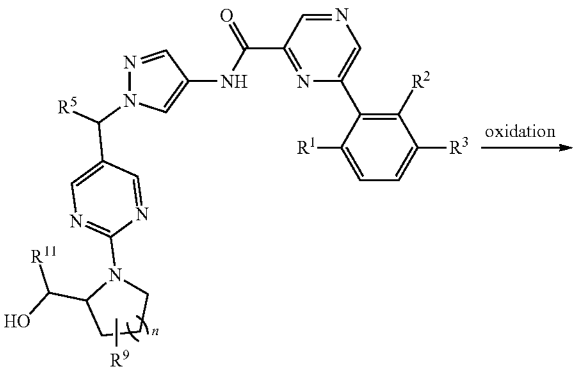

AAJ-1

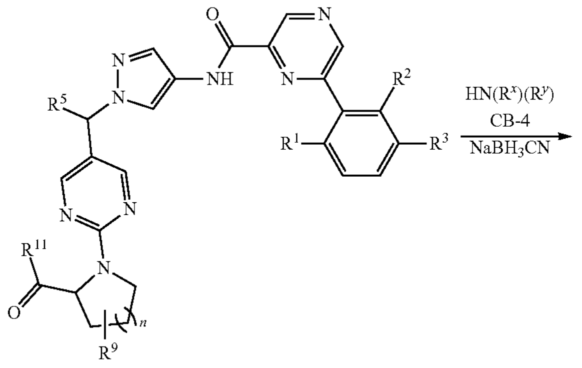

AAJ-2

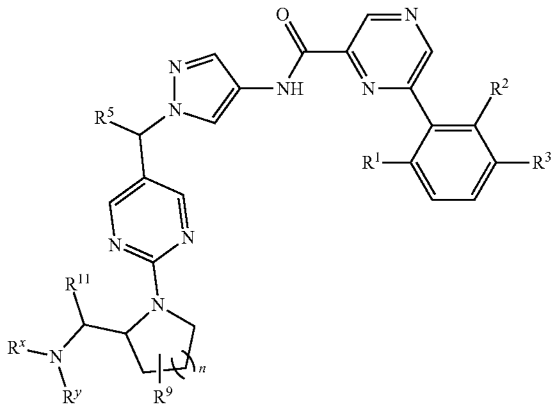

AAJ-3

Scheme AAJ illustrates a synthetic sequence for preparing of amine derivatives AAJ-3 as compounds of this invention. Oxidation of an alcohol such as AAJ-1 which can be performed using a variety of reagents, including DMP or chromium reagents, such as PDC, or under conditions of the Swern oxdation to afford a ketone or aldehyde intermediate (AAJ-2). Reductive amination in the presence of an amine (CB-4) and suitable reducing agent, such as $NaBH_3CN$, $NaHB(OAc)_3$ or the like, can afford compounds of this invention.

Scheme AAK.

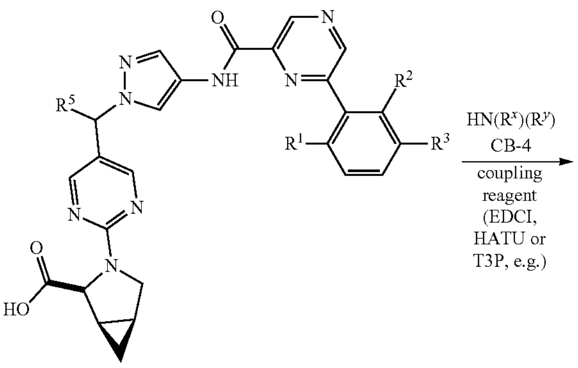

AAK-1

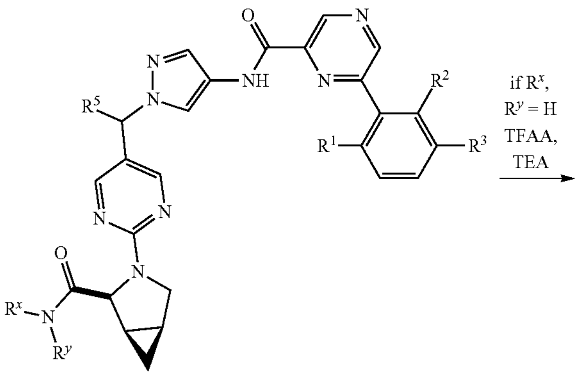

AAK-2

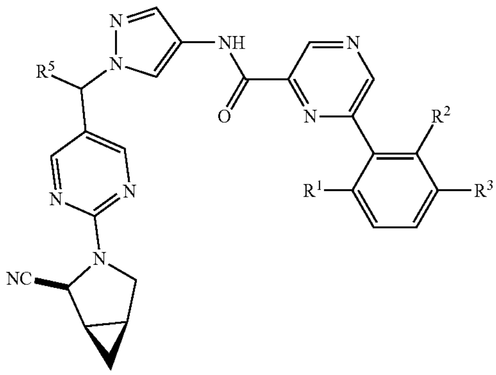

AAK-3

Scheme AAK illustrates a synthetic sequence that can be used to prepare amide compounds (AAK-2) or nitrile compounds (AAK-3) of this invention from a common carboxylic acid intermediate, AAK-1. Reaction of carboxylic acid AAK-1 with an amine (CB-4) in the presence of a suitable coupling agent, such as EDCI, HATU, T3P or the like, can afford amide compounds of this invention. In the case wherein $R^x$ and $R^y$=H, the primary amide represented by AAK-2 can be submitted to dehydration conditions to yield a nitrile compound (AAK-3) of this invention.

Scheme AAL.

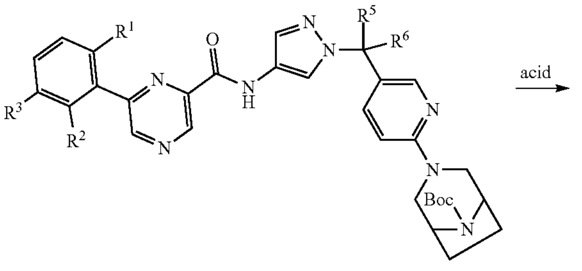

AAL-1

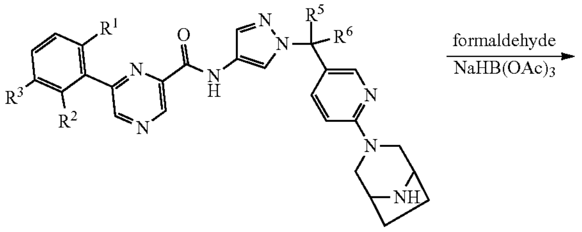

AAL-2

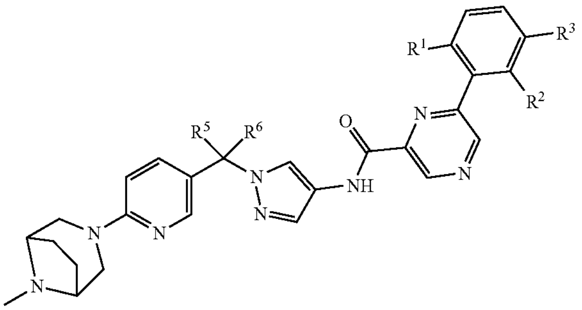

AAL-3

Scheme AAL illustrates a synthetic sequence for preparing tertiary amine compounds (AAL-3) of this invention. Deprotection of AAL-1 in the presence of strong acid, such as TFA, HCl or the like, can give a secondary amine (AAL-2) that can be further reacted with formaldehyde in the presence of a suitable reducing reagent as described above to give a tertiary amine compound (AAL-3) of this invention.

Intermediate AA

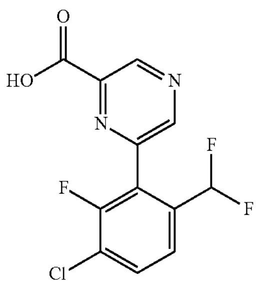 [SMILES: O=C(O)c1cncc(-c2c(C(F)F)ccc(Cl)c2F)n1]

6-(3-Chloro-6-(difluoromethyl)-2-fluorophenyl) pyrazine-2-carboxylic acid (Scheme AA)

Step 1. 1-Chloro-4-(difluoromethyl)-2-fluorobenzene: To a solution of 4-chloro-3-fluorobenzaldehyde (300 g, 1.89 mmol) in DCM (1.5 L) under a nitrogen atmosphere, cooled to 0° C. was added bis(2-methoxyethyl)aminosulfur trifluoride (456 mL, 2.08 mol) drop-wise into the mixture. The reaction mixture was stirred at rt for 12 h. The resulting mixture was poured slowly into an ice-water solution, then extracted with DCM. The organic layers were combined and washed with brine, dried over $Na_2SO_4$ and concentrated under reduced pressure to afford the title compound. $^1H$ NMR (400 MHz, $CDCl_3$) δ 7.53 (t, J=8.0 Hz, 1H), 7.34 (d, J=9.6 Hz, 1H), 7.27 (d, J=9.2 Hz, 1H), 6.64 (t, J=56 Hz, 1H).

Step 2. 2-(3-Chloro-6-(difluoromethyl)-2-fluorophenyl)-4,4,5,5-tetramethyl-1,3,2-dioxaborolane: To a solution of 1-chloro-4-(difluoromethyl)-2-fluorobenzene (300 g, 1.66 mol) in THF (1.8 L) under a nitrogen atmosphere, cooled to −78° C. was added LDA (997 mL, 1.99 mol, 2M in THF) drop-wise into the mixture. The reaction mixture was stirred at −78° C. for 30 min, then 2-isopropoxy-4,4,5,5-tetramethyl-1,3,2-dioxaborolane (508 mL, 2.49 mol) was added dropwise into the mixture. The reaction mixture was stirred at −78° C. for 30 min, then poured into a satd. aq. $NH_4Cl$ solution. The resulting mixture was filtered, then extracted with EtOAc. The organic layers were combined and washed with brine, dried over $Na_2SO_4$ and concentrated under reduced pressure to afford the title compound. $^1H$ NMR (400 MHz, $CDCl_3$) δ 7.53 (t, J=8.0 Hz, 1H), 7.37 (d, J=8.4 Hz, 1H), 7.02 (t, J=56 Hz, 1H), 1.39 (s, 12H).

Step 3. Methyl 6-(3-chloro-6-(difluoromethyl)-2-fluorophenyl)pyrazine-2-carboxylate: The reaction was conducted in two parallel vessels on the equivalent scale as specified. To a solution of 2-(3-chloro-6-(difluoromethyl)-2-fluorophenyl)-4,4,5,5-tetramethyl-1,3,2-dioxaborolane (127 g, 415 mmol), methyl 6-bromopyrazine-2-carboxylate (60.0 g, 276 mmol) and potassium fluoride (48.2 g, 829 mmol, 19.4 mL) in a mixture of dioxane (720 mL) and water (120 mL) under a nitrogen atmosphere was added 1,1'-bis(di-tert-butylphosphino)ferrocene palladium dichloride (11.3 g, 13.8 mmol). The reaction mixture was stirred at 120° C. for 12 h. The reaction mixtures from both reactions conducted in parallel were cooled to rt, combined, then concentrated under reduced pressure. The crude residue was suspended in EtOAc and the resulting mixture was filtered. The filtrate was washed with water, brine, dried over $Na_2SO_4$ and concentrated under reduced pressure to afford the title compound. $^1H$ NMR (400 MHz, $CDCl_3$) δ 9.36 (s, 1H), 8.96 (d, J=2.8 Hz, 1H), 7.65 (t, J=8.4 Hz, 1H), 8.56 (d, J=8.4 Hz, 1H), 6.99 (t, J=56 Hz, 1H), 4.06 (s, 3H).

Step 4. 6-(3-Chloro-6-(difluoromethyl)-2-fluorophenyl) pyrazine-2-carboxylic acid: To a solution of methyl 6-(3-chloro-6-(difluoromethyl)-2-fluorophenyl)pyrazine-2-carboxylate (350 g, 1.11 mol) in EtOH (1.75 L) at 10-20° C. was added 1M NaOH (2.10 L, 2.10 mol). The reaction mixture was stirred at rt for 30 min, then concentrated to afford a crude residue that was extracted with MTBE. The organic layers were discarded, and the pH of the aqueous layer was adjusted to 2-3 by addition of 2M HCl. The resulting mixture was filtered, and the filter cake was dried to afford the title compound. $^1H$ NMR (400 MHz, DMSO-d6) δ 13.9 (br s, 1H), 9.28 (s, 1H), 9.14 (s, 1H), 7.98 (t, J=8.0 Hz, 1H), 7.70 (d, J=8.4 Hz, 1H), 7.02 (t, J=56 Hz, 1H). MS=302.9 $[M+1]^+$.

TABLE AA

| The following compounds were prepared using procedures similar to those described above using the appropriate starting materials. | | | |
|---|---|---|---|
| Intermediate No. | Structure | Name | [M + H]+ or [M + Na]+ |
| AA-1 | 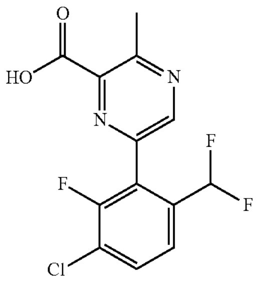 [SMILES: Cc1ncc(-c2c(C(F)F)ccc(Cl)c2F)nc1C(=O)O] | 6-(3-Chloro-6-(difluoro-methyl)-2-fluorophenyl)-3-methylpyrazine-2-carboxylic acid | Calcd.: 317.0 Found: 316.9 |
| AA-2 | 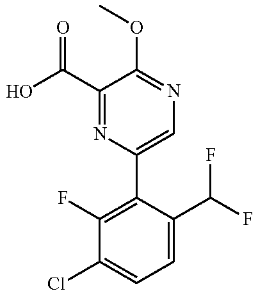 [SMILES: COc1ncc(-c2c(C(F)F)ccc(Cl)c2F)nc1C(=O)O] | 6-(3-Chloro-6-(difluoro-methyl)-2-fluorophenyl)-3-methoxypyrazine-2-carboxylic acid | Calcd.: 333.0 Found: 333.1 |
| AA-3 | 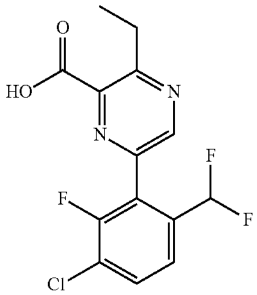 [SMILES: CCc1ncc(-c2c(C(F)F)ccc(Cl)c2F)nc1C(=O)O] | 6-(3-Chloro-6-(difluoro-methyl)-2-fluorophenyl)-3-ethylpyrazine-2-carboxylic acid | Calcd.: 331.0 Found: 331.0 |
| AA-4 | 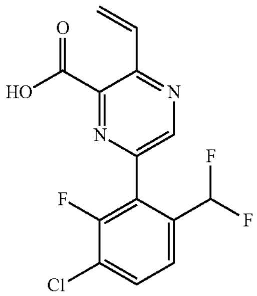 [SMILES: C=Cc1ncc(-c2c(C(F)F)ccc(Cl)c2F)nc1C(=O)O] | 6-(3-Chloro-6-(difluoro-methyl)-2-fluorophenyl)-3-vinylpyrazine-2-carboxylic acid | Calcd.: 329.0 Found: 328.9 |
| AA-5 | 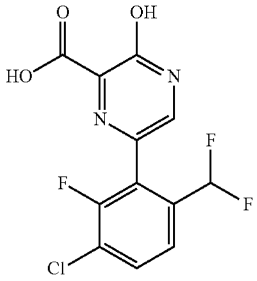 [SMILES: O=C(O)c1nc(-c2c(C(F)F)ccc(Cl)c2F)cnc1O] | 6-(3-Chloro-6-(difluoro-methyl)-2-fluorophenyl)-3-hydroxypyrazine-2-carboxylic acid | Calcd.: 319.0 Found: 319.1 |

TABLE AA-continued

The following compounds were prepared using procedures similar to those described above using the appropriate starting materials.

| Intermediate No. | Structure | Name | $[M + H]^+$ or $[M + Na]^+$ |
|---|---|---|---|
| AA-6 | 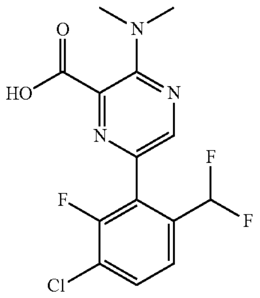 [SMILES: CN(C)c1ncc(-c2c(C(F)F)ccc(Cl)c2F)nc1C(=O)O] | 6-(3-Chloro-6-(difluoromethyl)-2-fluorophenyl)-3-(dimethylamino)pyrazine-2-carboxylic acid | Calcd.: 346.0 Found: 346.2 |
| AA-7 | 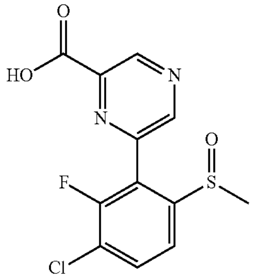 [SMILES: CS(=O)c1ccc(Cl)c(F)c1-c1cncc(C(=O)O)n1] | 6-(3-Chloro-2-fluoro-6-(methylsulfinyl)phenyl)-pyrazine-2-carboxylic acid | Calcd.: 315.0 Found: 315.2 |
| AA-8 | 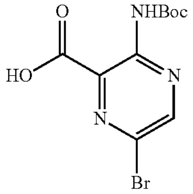 | 6-Bromo-3-((tert-butoxycarbonyl)amino)pyrazine-2-carboxylic acid | Calcd.: 318.0 Found: 318.2 |
| AA-9 | 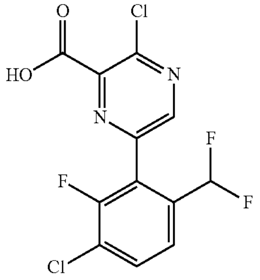 [SMILES: O=C(O)c1nc(-c2c(C(F)F)ccc(Cl)c2F)cnc1Cl] | 3-Chloro-6-(3-chloro-6-(difluoromethyl)-2-fluorophenyl)pyrazine-2-carboxylic acid | Calcd. $[M - 18]^+$: 319.0 Found: 319.0 |

Intermediate AA-10

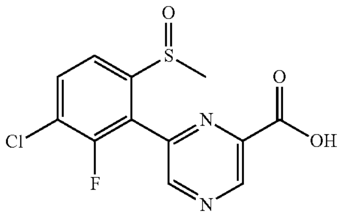 [SMILES: CS(=O)c1ccc(Cl)c(F)c1-c1cncc(C(=O)O)n1]

Methyl 6-(3-chloro-2-fluoro-6-(methylsulfinyl)phenyl)pyrazine-2-carboxylate (Scheme AD)

Step 1: 2-Bromo-4-chloro-3-fluoro-1-iodobenzene: To a mixture of 1-chloro-2-fluoro-4-iodobenzene (5.00 g, 19.5 mmol) in THF (50 mL) was added LDA (10.7 mL, 21.4 mmol, 2M in THF) dropwise at −70° C. under $N_2$, and the mixture was stirred at −70° C. for 0.5 h. Then 1,2-dibromo-1,1,2,2-tetrachloroethane (7.62 g, 23.4 mmol) in THF (10 mL) was added dropwise, and the mixture was stirred at −70° C. for 20 min, then warmed to 10° C. for another 1 h. The reaction was quenched by the addition of satd. aq. $NH_4Cl$ and extracted with EtOAc. The combined organic layers were dried over $Na_2SO_4$, filtered and concentrated to give crude product, which was purified by silica gel chromatography (petroleum ether) to give the title compound. $^1$H NMR (400 MHz, $CDCl_3$) δ 7.52-7.65 (m, 1H), 7.00-7.13 (m, 1H).

Step 2: S-(2-Bromo-4-chloro-3-fluorophenyl) ethanethioate: To a solution of 2-bromo-4-chloro-3-fluoro-1-iodobenzene (3.00 g, 8.95 mmol) in toluene (30 mL) was added potassium thioacetate (1.53 g, 13.4 mmol), copper(I) iodide (0.170 g, 0.895 mmol) and 1,10-phenanthroline (161 mg, 0.895 mmol), and the resulting mixture was heated to 90° C. for 16 h. The reaction was cooled to rt, filtered, diluted with water and extracted with EtOAc. The combined organic layers were washed with brine, dried over $Na_2SO_4$, filtered and concentrated to give a crude residue that was purified by silica gel chromatography (EtOAc/petroleum ether) to give the title compound. $^1$H NMR (400 MHz, $CDCl_3$) δ 7.38-7.45 (m, 1H), 7.27-7.33 (m, 1H), 2.48 (d, J 1.2 Hz, 3H).

Step 3: 2-Bromo-4-chloro-3-fluoro-1-(methylsulfinyl) benzene: To a solution of S-(2-bromo-4-chloro-3-fluorophenyl) ethanethioate (1.30 g, 4.58 mmol) in EtOH (10 mL) was added NaOH (0.550 g, 13.8 mmol) (dissolved into 2.5 mL of water) and iodomethane (0.781 g, 5.50 mmol), and the resulting mixture was stirred at 15° C. for 10 min. The reaction was concentrated, diluted with water, and extracted with EtOAc. The combined organic layers were washed with brine, dried over $Na_2SO_4$ and concentrated to give a crude product that was immediately dissolved in DCM (10 mL). mCPBA (1.58 g, 9.17 mmol) was added, and the resulting mixture was stirred at 15° C. for 1 h. The reaction mixture was quenched by the addition of satd. aq. $Na_2SO_3$ and allowed to stir for 30 min. The mixture was filtered and extracted with DCM. The organic layer was separated, dried over $Na_2SO_4$, filtered and concentrated to give a crude residue that was purified by silica gel chromatography (EtOAc/petroleum ether) to give the title compound. $^1$H NMR (400 MHz, $CDCl_3$) δ 7.70 (s, 1H), 7.24 (s, 1H), 2.81 (d, J 1.5 Hz, 3H).

Step 4: Methyl 6-(3-chloro-2-fluoro-6-(methylsulfinyl) phenyl)pyrazine-2-carboxylate: To a solution of 2-bromo-4-chloro-3-fluoro-1-(methylsulfinyl)benzene (200 mg, 0.737 mmol) in 1,4-dioxane (3 mL) were added methyl 6-(trimethylstannyl)pyrazine-2-carboxylate (288 mg, 0.958 mmol), tris(dibenzylideneacetone)dipalladium(0) (67 mg, 0.074 mmol) and 1,1'-bis(di-tert-butylphosphino)ferrocene (35 mg, 0.074 mmol), and the resulting mixture was heated to 100° C. for 15 h. The reaction was cooled to rt, filtered, and concentrated to give crude product that purified by prep-TLC (1:1 EtOAc/petroleum ether) to give the title compound. MS=329.2 (M+H).

Step 5: 6-(3-Chloro-2-fluoro-6-(methylsulfinyl)phenyl) pyrazine-2-carboxylic acid: To a solution of methyl 6-(3-chloro-2-fluoro-6-(methylsulfinyl)phenyl)pyrazine-2-carboxylate (180 mg, 0.548 mmol) in THF (0.5 mL) and water (0.5 mL) was added lithium hydroxide (39 mg, 1.64 mmol), and the mixture was stirred at 20° C. for 1 h. The reaction was diluted with water and extracted with DCM. The aq. layer was adjusted to pH=3 with 2M HCl then concentrated to give the crude title compound that was carried on without further purification. MS=315.2 (M+H).

Intermediate BA

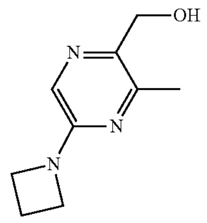

(5-(azetidin-1-yl)-3-methylpyrazin-2-yl)methanol (Scheme BA)

Step 1. (Methyl 5-(azetidin-1-yl)-3-methylpyrazine-2-carboxylate: Methyl 5-bromo-3-methylpyrazine-2-carboxylate (1.0 g, 4.33 mmol) was added to a vial with NMP (10.82 ml) at room temperature. Azetidine (1.0 g, 17.3 mmol) was added and the reaction mixture was stirred at 100° C. for 4 h. The solution was cooled to room temperature before aq $NaHCO_3$ was added. The resulting mixture was extracted with DCM, and the combined organic fractions were dried ($MgSO_4$) and concentrated in vacuo to provide the title compound. MS=208.1 $[M+1]^+$.

Step 2. (5-(azetidin-1-yl)-3-methylpyrazin-2-yl)methanol: The solution of methyl 5-(azetidin-1-yl)-3-methyl-pyrazine-2-carboxylate (767 mg, 3.7 mmol) in DCM (15 ml) was cooled to −78°. DIBAL-H (11.1 ml, 11.1 mmol, 1M in THF) was added dropwise and the reaction was stirred at −78 C for 1 h before it was warmed to 0° C. and stirred for 1 h at 0° C. The reaction was quenched with aq NaOH and $MgSO_4$ was added. The resulting suspension was filtered, and the filtrate was concentrated. The residue was purified by silica gel column chromatography eluting with DCM/MeOH to provide the title product. MS=180.0 $[M+1]^+$.

TABLE BA

The following compounds were prepared using procedures similar to those described above using the appropriate starting materials.

| Intermediate No. | Structure | Name | $[M + H]^+$ or $[M + Na]^+$ |
|---|---|---|---|
| BA-1 | 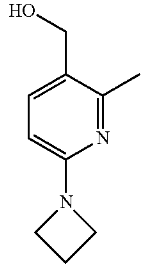 | (6-(azetidin-1-yl)-2-methylpyridin-3-yl)-methanol | Calcd.: 179.1<br>Found: 179.1 |

TABLE BA-continued

| The following compounds were prepared using procedures similar to those described above using the appropriate starting materials. | | | |
|---|---|---|---|
| Intermediate No. | Structure | Name | $[M + H]^+$ or $[M + Na]^+$ |
| BA-2 (GSN) | 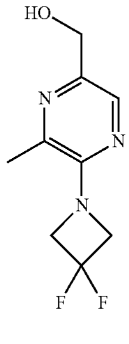 | (5-(3,3-difluoro-azetidin-1-yl)-6-methylpyrazin-2-yl)methanol | Calcd.: 216.1 Found: 216.0 |
| BA-3 | 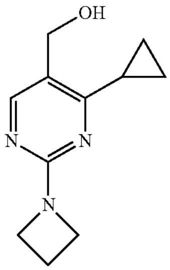 [SMILES: OCc1cnc(N2CCC2)nc1C1CC1] | (2-(azetidin-1-yl)-4-cyclopropylpyrimidin-5-yl)methanol | Calcd.: 206.1 Found: 206.1 |
| BA-4 | 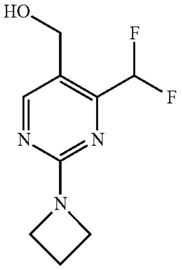 | (2-(azetidin-1-yl)-4-(difluoromethyl)-pyrimidin-5-yl)-methanol | Calcd.: 216.1 Found: 216.0 |

Intermediate BB

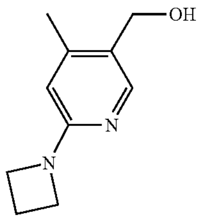

(6-(azetidin-1-yl)-4-methylpyridin-3-yl)methanol (Scheme BB)

Step 1. (6-(azetidin-1-yl)-4-methylpyridin-3-yl)methanol: (6-Fluoro-4-methylpyridin-3-yl)-methanol (460 mg, 3.26 mmol) was added to a vial with NMP (5 mL). Azetidine (744 mg, 13.0 mmol) was added, and the reaction mixture was heated to 80° C. for 2 h. The reaction was cooled to rt, and purified by silica gel column chromatography (MeOH/DCM) to provide the title compound. MS=179.1 $[M+1]^+$.

TABLE BB

The following compounds were prepared using procedures similar to those described above using the appropriate starting materials.

| Intermediate No. | Structure | Name | $[M + H]^+$ or $[M + Na]^+$ |
|---|---|---|---|
| BB-1 | 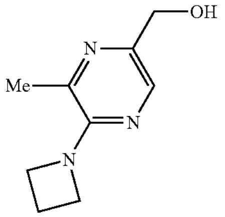 [SMILES: Cc1nc(CO)cnc1N1CCC1] | (5-(azetidin-1-yl)-6-methylpyrazin-2-yl)methanol | Calcd.: 180.1 Found: 180.0 |
| BB-2 | 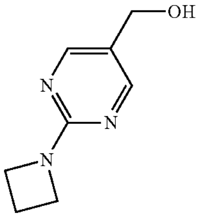 [SMILES: OCc1cnc(N2CCC2)nc1] | (2-(azetidin-1-yl)-pyrimidin-5-yl)-methanol | Calcd.: 166.1 Found: 166.1 |

Intermediate BC-1

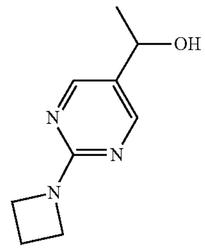

1-(2-(Azetidin-1-yl)pyrimidin-5-yl)ethanol (Scheme BC)

Step 1. 1-(2-(azetidin-1-yl)pyrimidin-5-yl)ethanone: A solution of 1-(2-chloropyrimidin-5-yl)ethanone (400 mg, 2.55 mmol), azetidine hydrochloride (239 mg, 2.55 mmol) and TEA (0.89 mL, 6.4 mmol) in EtOH (5 mL) was heated to 80° C. for 1 h. The reaction was cooled to rt, quenched with water, and extracted with EtOAc. The combined organic extracts were washed with brine, dried over $Na_2SO_4$, filtered and concentrated to give the title compound. MS=178.1 $[M+H]^+$.

Step 2. 1-(2-(azetidin-1-yl)pyrimidin-5-yl)ethanol: To a solution of 1-(2-(azetidin-1-yl)pyrimidin-5-yl)ethanone (200 mg, 1.13 mmol) in THF (3 mL) at 0° C. was added sodium borohydride (55.5 mg, 1.47 mmol), followed by dropwise addition of MeOH (0.5 mL), and the resulting mixture was stirred at rt for 0.5 h. The reaction was quenched with satd. aq. $NH_4Cl$ and extracted with EtOAc. The combined organic extracts were washed with brine, dried over $Na_2SO_4$, filtered and concentrated to give the title compound. MS=180.0 $[M+H]^+$.

Intermediate BC-2

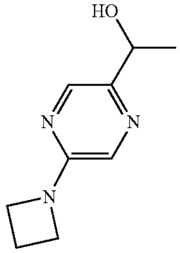

1-(5-(azetidin-1-yl)pyrazin-2-yl)ethan-1-ol (Scheme BC)

Step 1. 1-(5-(Azetidin-1-yl)pyrazin-2-yl)ethan-1-one: A mixture of 1-(5-chloropyrazin-2-yl)ethanone (130 mg, 0.830 mmol), azetidine hydrochloride (93 mg, 1.0 mmol) and TEA (0.29 mL, 2.1 mmol) in 1,4-dioxane (1.5 mL) was heated to 40° C. for 12 h. The reaction was cooled to rt, diluted with water and extracted with DCM. The combined organic layers were washed with water and brine, dried over $Na_2SO_4$, filtered and concentrated. The crude product was purified by silica gel chromatography (EtOAc/petroleum ether) to give the title compound. MS=178.1 $[M+1]^+$.

Step 2. 1-(5-(Azetidin-1-yl)pyrazin-2-yl)ethan-1-ol: To a solution of 1-(5-(azetidin-1-yl)pyrazin-2-yl)ethanone (120 mg, 0.677 mmol) in THF (1.5 mL) was added $NaBH_4$ (33 mg, 0.88 mmol) at 0° C., followed by MeOH (0.5 mL). The reaction mixture was stirred at 0° C. for 1 h, warmed to rt and continued stirring at rt for 1 h. The reaction was quenched with satd. aq. $NH_4Cl$ and extracted with EtOAc. The combined organic layers were washed with water and brine, dried over $Na_2SO_4$, filtered and concentrated to the title compound. MS=179.9 $[M+1]^+$.

TABLE BC

The following compounds were prepared using procedures similar to those described above using the appropriate starting materials.

| Intermediate No. | Structure | Name | [M + H]$^+$ |
|---|---|---|---|
| BC-3 | 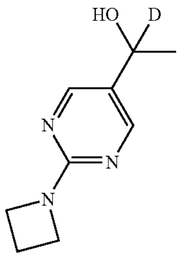 | 1-(2-(azetidin-1-yl)-pyrimidin-5-yl)ethan-1-d-1-ol | Calcd.: 181.1 Found: 181.1 |
| BC-4 | 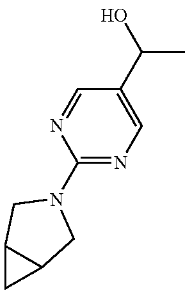 | 1-(2-(3-azabicyclo-[3.1.0]hexan-3-yl)-pyrimidin-5-yl)ethan-1-ol | Calcd.: 206.1 Found: 206.1 |
| BC-5 | 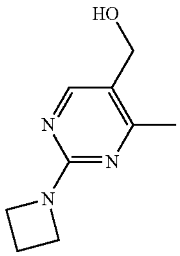 | (2-(azetidin-1-yl)-4-methylpyrimidin-5-yl)methanol | Calcd.: 180.1 Found: 180.1 |
| BC-6 | 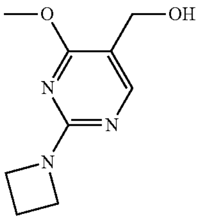 | (2-(azetidin-1-yl)-4-methoxypyrimidin-5-yl)methanol | Calcd.: 196.1 Found: 196.1 |

TABLE BC-continued

| The following compounds were prepared using procedures similar to those described above using the appropriate starting materials. | | | |
|---|---|---|---|
| Intermediate No. | Structure | Name | $[M + H]^+$ |
| BC-7 | 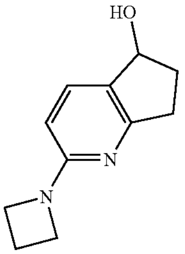 [SMILES: OC1CCc2nc(N3CCC3)ccc21] | 2-(azetidin-1-yl)-6,7-dihydro-5H-cyclopenta[b]pyridin-5-ol | Calcd.: 191.1<br>Found: 191.0 |

Intermediate BC-8

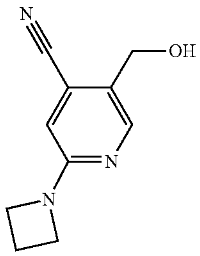 [SMILES: N#Cc1cc(N2CCC2)ncc1CO]

2-(azetidin-1-yl)-5-(hydroxymethyl)isonicotinonitrile (Scheme BC)

Step 1. 2-(Azetidin-1-yl)-5-chloroisonicotinonitrile: To a solution of 5-chloro-2-fluoroisonicotinonitrile (1.30 g, 8.30 mmol) in DMF (20 mL) was added $K_2CO_3$ (3.44 g, 24.9 mmol) and azetidine hydrochloride (855 mg, 9.13 mmol), and the resulting mixture was heated to 60° C. for 1 h. The reaction was cooled to rt, diluted with water and extracted with EtOAc. The combined organic layers were washed with, dried over anhydrous $Na_2SO_4$, filtered and concentrated to afford a crude residue that was purified by silica gel chromatography (EtOAc/petroleum ether) to give the title compound. MS=194.0 $[M+H]^+$.

Step 2. 2-(Azetidin-1-yl)-5-vinylisonicotinonitrile: A stirred solution of 2-(azetidin-1-yl)-5-chloroisonicotinonitrile (1.40 g, 7.23 mmol), methanesulfonato(2-dicyclohexylphosphino-2',6'-di-isopropoxy-1,1'-biphenyl)(2'-amino-1,1'-biphenyl-2-yl)palladium(II) (605 mg, 0.723 mmol), potassium vinyltrifluoroborate (1.94 g, 14.5 mmol) and $Cs_2CO_3$ (7.07 g, 21.7 mmol) in CPME (15 mL) and water (5 mL) was heated at 100° C. for 12 h. The reaction was cooled to rt, diluted with water and extracted with EtOAc. The combined organic layers were washed with brine, dried over anhydrous $Na_2SO_4$, filtered and concentrated to afford a crude residue that was purified by silica gel chromatography (EtOAc/petroleum ether) to give the title compound. MS=186.0 $[M+H]^+$.

Step 3. 2-(Azetidin-1-yl)-5-formylisonicotinonitrile: To a solution of 2-(azetidin-1-yl)-5-vinylisonicotinonitrile (1.00 g, 5.40 mmol) in THF (20 mL) and water (10 mL) was added osmium tetroxide (27.5 mL, 1.080 mmol, 10 mg/mL in water) and sodium periodate (4.62 g, 21.6 mmol), and the resulting mixture was stirred at 15° C. for 12 h. The reaction was quenched with satd. aq. $Na_2S_2O_3$ and stirred for 0.5 h, at which time, the mixture was extracted with EtOAc. The combined organic layers were washed with brine, dried over anhydrous $Na_2SO_4$, filtered and concentrated to give the title compound, which was used in next step directly. MS=187.9 $[M+H]^+$.

Step 4. 2-(Azetidin-1-yl)-5-(hydroxymethyl)isonicotinonitrile: To a solution of 2-(azetidin-1-yl)-5-formylisonicotinonitrile (1.00 g, 5.34 mmol) in MeOH (15 mL) was added $NaBH_4$ (404 mg, 10.7 mmol), and the resulting mixture was stirred at 15° C. for 1.5 h. The reaction was quenched with acetone, partially concentrated and diluted with water. The mixture was extracted with EtOAc, and the combined organic layers were washed with brine, dried over anhydrous $Na_2SO_4$, filtered and concentrated to give the title compound, which was used in next step directly. MS=190.0 $[M+H]^+$.

Intermediate BD

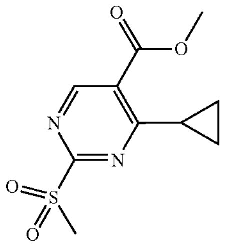 [SMILES: COC(=O)c1cnc(S(C)(=O)=O)nc1C1CC1]

Methyl 4-cyclopropyl-2-(methylsulfonyl)pyrimidine-5-carboxylate (Scheme BD)

Step 1. Methyl 2-(cyclopropanecarbonyl)-3-(dimethylamino)acrylate: To a 250 mL round-bottom flask under $N_2$ was added methyl 3-cyclopropyl-3-oxopropanoate (5.00 g, 35.2 mmol) and dioxane (50 ml). N,N-dimethylformamide dimethyl acetal (4.7 mL, 35 mmol) was added at rt, and the resulting mixture was heated to 100° C. for 3 h. The mixture was cooled to rt, concentrated, and used in the next step without purification. MS: 198.1 $[M+H]^+$.

Step 2. Methyl 4-cyclopropyl-2-(methylthio)pyrimidine-5-carboxylate: Methyl 2-(cyclopropanecarbonyl)-3-(dimethylamino)acrylate (4.50 g, 22.8 mmol) was added to a 250 mL round-bottom flask with potassium acetate (11.2 g, 114 mmol), 2-methyl-2-thiopseudourea hemisulfate hemihydrate (3.90 g, 13.2 mmol) and DMF (50 mL). The resulting mixture was heated to 80° C. for 3 h, then cooled to rt and quenched with water. The aq. layer was extracted with EtOAc, and the combined organic layers were washed with satd. aq. $NaHCO_3$, dried with $MgSO_4$, and concentrated. The crude material was purified on a silica gel column chromatography (EtOAc/hexanes) to provide the title compound. MS: 225.0 $[M+H]^+$.

Step 3. Methyl 4-cyclopropyl-2-(methylsulfonyl)pyrimidine-5-carboxylate: Methyl 4-cyclopropyl-2-(methylthio) pyrimidine-5-carboxylate (3.00 g, 13.4 mmol) was added to a flask with DCM (34 mL). mCPBA (6.95 g, 40.3 mmol) was added in multiple portions at rt, and the reaction mixture was stirred at rt for 2 h. The mixture was poured into satd. aq. $NaHCO_3$ and extracted with DCM. The combined organic layers were dried with $MgSO_4$ and concentrated to provide the title compound. MS: 257.0 $[M+H]^+$.

TABLE BD

The following compounds were prepared using procedures similar to those described for above using the appropriate starting materials.

| Intermediate No. | Structure | Name | $[M + H]^+$ |
|---|---|---|---|
| BD-1 | 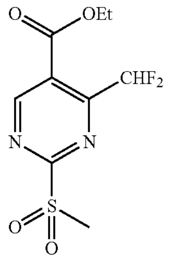 [SMILES: CCOC(=O)c1cnc(S(C)(=O)=O)nc1C(F)F] | Ethyl 4-(difluoromethyl)-2-(methylsulfonyl)-pyrimidine-5-carboxylate | Calcd.: 281.0 Found: 280.9 |

Intermediate BE

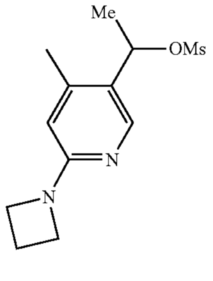 [SMILES: Cc1cc(N2CCC2)ncc1C(C)OS(C)(=O)=O]

1-(6-(Azetidin-1-yl)-4-methylpyridin-3-yl)ethyl methanesulfonate (Scheme BE)

Step 1. Methyl 6-(azetidin-1-yl)-4-methylnicotinate: Azetidine (1.7 mL, 25.3 mmol) was added to a solution of methyl 6-fluoro-4-methylnicotinate (1.1 g, 6.3 mmol) in ACN (16 mL), and the resulting mixture was heated to 50° C. for 2 h. The reaction was cooled to rt, and concentrated to afford a crude residue that was purified by silica gel chromatography (MeOH/DCM) to give the title compound.

Step 2. (6-(Azetidin-1-yl)-4-methylpyridin-3-yl)methanol: Methyl 6-(azetidin-1-yl)-4-methylnicotinate (1.0 g, 4.6 mmol) was added to THF (2 mL), and the solution was cooled to −78° C. $LiAlH_4$ (100 mg, 2.70 mmol) was added in several portions, and the resulting mixture was stirred at −78° C. for 1 h before warming to rt and stirring at rt for 5 h. The reaction was quenched with water, dried ($MgSO_4$), filtered, and concentrated to give the title compound that was carried on without purification. MS: 179 $[M+H]^+$ Step 3. 6-(Azetidin-1-yl)-4-methylnicotinaldehyde: A solution of DMP (2.97 g, 7.00 mmol) in DCM (15 mL) was added to a stirred solution of (6-(azetidin-1-yl)-4-methylpyridin-3-yl)methanol (830 mg, 4.60 mmol) in DCM (2 mL), and the resulting mixture was stirred at rt for 1 h. The reaction was quenched with satd. aq. $NaHCO_3$ and satd. aq. $Na_2S_2O_3$, and the mixture was extracted with DCM. The combined organic layers were washed with brine, dried ($MgSO_4$), filtered, and concentrated to give the title compound that was carried on without purification. MS: 177 $[M+H]^+$ Step 4. 1-(6-(Azetidin-1-yl)-4-methylpyridin-3-yl)ethan-1-ol: Methylmagnesium iodide (2.3 mL, 7.0 mmol, 3M in diethyl ether) was added dropwise to a stirred solution of 6-(azetidin-1-yl)-4-methylnicotinaldehyde (0.82 g, 4.6 mmol) in THF (15 mL) at −78° C., and the resulting mixture was stirred at −78° C. for 30 min. The reaction was warmed to rt and allowed to stir at rt for 3 h. The reaction was quenched with satd. aq. $NH_4Cl$, and after continuing to stir at rt for 2 h, was extracted with EtOAc. The combined organics were dried ($MgSO_4$), filtered and concentrated to provide the give the title compound that was carried on without purification. MS: 193 $[M+H]^+$ Step 5. 1-(6-(Azetidin-1-yl)-4-methylpyridin-3-yl)ethyl methanesulfonate: Methanesulfonyl chloride (0.26 mL, 3.2 mmol) was added to a stirred solution of 1-(6-(azetidin-1-yl)-4-methylpyridin-3-yl)ethan-1-ol (414 mg, 2.20 mmol) and TEA (0.90 mL, 6.5 mmol) in DCM (22 mL) at 0° C. The resulting mixture was stirred at 0° C. for 2 h, at which time, the reaction was diluted with water and extracted with DCM. The combined organic layers were dried ($Na_2SO_4$), filtered, and concentrated to give the title compound that was carried on without purification. MS: 271 $[M+H]^+$

TABLE BE

The following compounds were prepared using procedures similar to those described above using the appropriate starting materials.

| Intermediate No. | Structure | Name | $[M + H]^+$ or $[M + Na]^+$ |
|---|---|---|---|
| BE-1 | 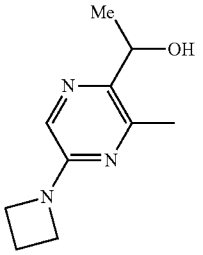 | 1-(5-(Azetidin-1-yl)-3-methylpyrazin-2-yl)ethan-1-ol | Calcd.: 194.1 Found: 194.0 |
| BE-2 | 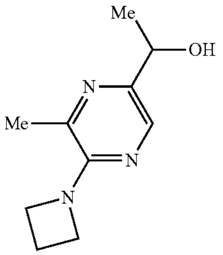 [SMILES: Cc1nc(C(C)O)cnc1N1CCC1] | 1-(5-(Azetidin-1-yl)-6-methylpyrazin-2-yl)ethan-1-ol | Calcd.: 194.1 Found: 194.0 |

Intermediate BF

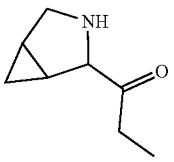

1-(3-Azabicyclo[3.1.0]hexan-2-yl)propan-1-one (Scheme BF) Step 1: 3-tert-Butyl 2-methyl 3-azabicyclo[3.1.0]hexane-2,3-dicarboxylate: To a solution of 3-(tert-butoxycarbonyl)-3-azabicyclo[3.1.0]hexane-2-carboxylic acid (200 mg, 0.880 mmol) in DCM (10 mL) and MeOH (1 mL) was added TMS-diazomethane (0.66 mL, 1.32 mmol) at 0° C. The reaction mixture was stirred at 0° C. for 2 h, at which time, the reaction was warmed to rt, diluted with water, and extracted with DCM. The combined organic layers were dried over $Na_2SO_4$, filtered and concentrated to give the title compound. MS=142.1 $[M-Boc+1]^+$.

Step 2: tert-Butyl 2-(1-hydroxycyclopropyl)-3-azabicyclo[3.1.0]hexane-3-carboxylate: To a solution of 3-tert-butyl 2-methyl 3-azabicyclo[3.1.0]hexane-2,3-dicarboxylate (150 mg, 0.622 mmol) in THF (1 mL) was added titanium(IV) isopropoxide (0.55 mL, 1.9 mmol), and the resulting mixture was stirred at rt for 30 min. Ethylmagnesium bromide (2.07 mL, 6.22 mmol, 3M in THF) was added, and the reaction was stirred at rt for 12 h. The reaction was cooled to 0° C., quenched with water and extracted with DCM. The combined organic layers were dried over $Na_2SO_4$, filtered and concentrated to give the title compound. MS=140.1 $[M-Boc+1]^+$.

Step 3: 1-(3-Azabicyclo[3.1.0]hexan-2-yl)propan-1-one: To a solution of tert-butyl 2-(1-hydroxycyclopropyl)-3-azabicyclo[3.1.0]hexane-3-carboxylate (70 mg, 0.29 mmol) in DCM (1.5 mL) was added TFA (0.70 mL, 9.1 mmol), and the resulting mixture was stirred at rt for 2 h. The reaction was concentrated to afford a crude residue that was purified by reversed-phase preparatory-HPLC (C18 stationary phase, water (0.1% TFA)-ACN) to afford the title compound. MS=140.0 $[M+H]^+$ Intermediate CA

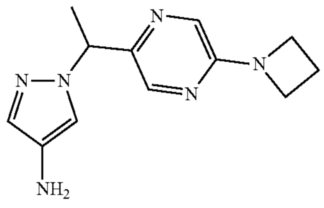 [SMILES: CC(c1cnc(N2CCC2)cn1)n1cc(N)cn1]

1-(1-(5-(Azetidin-1-yl)pyrazin-2-yl)ethyl)-1H-pyrazol-4-amine (Scheme CA)

Step 1. 2-(Azetidin-1-yl)-5-(1-(4-nitro-1H-pyrazol-1-yl)ethyl)pyrazine: To a solution of 1-(5-(azetidin-1-yl)pyrazin-2-yl)ethanol (100 mg, 0.558 mmol), triphenylphosphine (220 mg, 0.837 mmol) and 4-nitro-1H-pyrazole (69 mg, 0.61 mmol) in toluene (5 mL) was added DIAD (0.13 mL, 0.67 mmol) at 0° C., and the resulting mixture was warmed to rt and allowed to stir for 2 h. The reaction was diluted with water and extracted with EtOAc. The combined organic layers were washed with water and brine, dried over $Na_2SO_4$, filtered and concentrated to afford a crude residue that was purified by preparatory-TLC (1:1 petroleum ether/EtOAc) to afford the title compound. MS=275.0 $[M+1]^+$.

Step 2. 1-(1-(5-(Azetidin-1-yl)pyrazin-2-yl)ethyl)-1H-pyrazol-4-amine: To a mixture of 2-(azetidin-1-yl)-5-(1-(4-nitro-1H-pyrazol-1-yl)ethyl)pyrazine (78 mg, 0.28 mmol) and ammonium chloride (76 mg, 1.4 mmol) in EtOH (5 mL) and water (5 mL) was added iron (79 mg, 1.4 mmol), and the resulting mixture was heated to 60° C. for 2 h. The reaction was cooled to rt and diluted with DCM and water. The resulting suspension was filtered through a pad of Celite®, the filtrate layers were separated, and the aq. layer was extracted with DCM. The combined organic layers were washed with water and brine, dried over $Na_2SO_4$, filtered and concentrated to give the title compound which was carried to next step without further purification. MS=245.1 $[M+1]^+$.

TABLE CA

The following compounds were prepared using procedures similar to those described above using the appropriate starting materials.

| Intermediate No. | Structure | Name | $[M + H]^+$ or $[M + Na]^+$ |
|---|---|---|---|
| CA-1 | 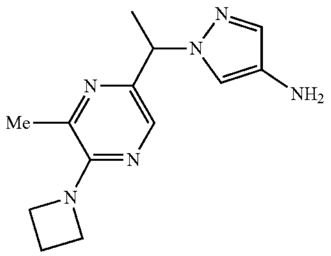 [SMILES: Cc1nc(C(C)n2cc(N)cn2)cnc1N1CCC1] | 1-(1-(5-(Azetidin-1-yl)-6-methylpyrazin-2-yl)ethyl)-1H-pyrazol-4-amine | Calcd.: 259.2<br>Found: 259 |
| CA-2 | 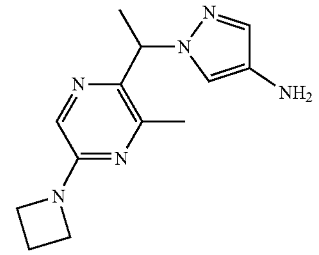 [SMILES: Cc1nc(N2CCC2)cnc1C(C)n1cc(N)cn1] | 1-(1-(5-(Azetidin-1-yl)-3-methylpyrazin-2-yl)ethyl)-1H-pyrazol-4-amine | Calcd.: 259.2<br>Found: 259 |
| CA-3 | 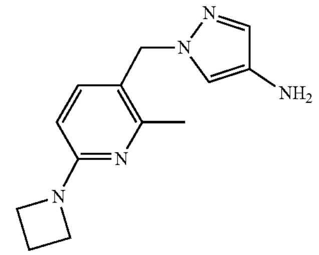 [SMILES: Cc1nc(N2CCC2)ccc1Cn1cc(N)cn1] | 1-((6-(Azetidin-1-yl)-2-methylpyridin-3-yl)methyl)-1H-pyrazol-4-amine | Calcd.: 244.2<br>Found: 244.1 |
| CA-4 | 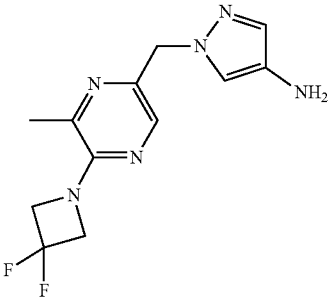 [SMILES: Cc1nc(Cn2cc(N)cn2)cnc1N1CC(F)(F)C1] | 1-((5-(3,3-Difluoroazetidin-1-yl)-6-methylpyrazin-2-yl)methyl)-1H-pyrazol-4-amine | Calcd.: 281.1<br>Found: 281 |

TABLE CA-continued

The following compounds were prepared using procedures similar to those described above using the appropriate starting materials.

| Intermediate No. | Structure | Name | $[M + H]^+$ or $[M + Na]^+$ |
|---|---|---|---|
| CA-5 | 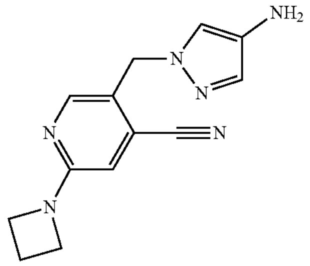 [SMILES: N#Cc1cc(N2CCC2)ncc1Cn1cc(N)cn1] | 5-((4-Amino-1H-pyrazol-1-yl)methyl)-2-(azetidin-1-yl)isonicotinonitrile | Calcd.: 255.1<br>Found: 255.0 |
| CA-6 | 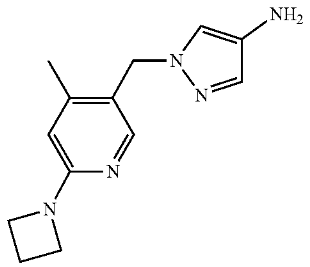 [SMILES: Cc1cc(N2CCC2)ncc1Cn1cc(N)cn1] | 1-((6-(Azetidin-1-yl)-4-methylpyridin-3-yl)methyl)-1H-pyrazol-4-amine | Calcd.: 244.2<br>Found: 244.1 |
| CA-7 | 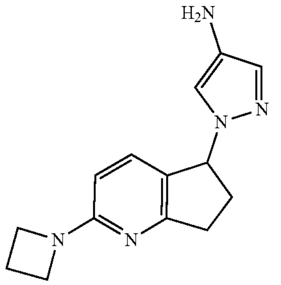 [SMILES: Nc1cnn(C2CCc3nc(N4CCC4)ccc32)c1] | 1-(2-(Azetidin-1-yl)-6,7-dihydro-5H-cyclopenta[b]pyridin-5-yl)-1H-pyrazol-4-amine | Calcd.: 256.1<br>Found: 256.1 |
| CA-8 | 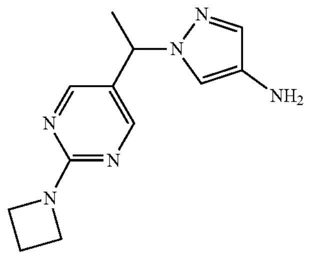 [SMILES: CC(c1cnc(N2CCC2)nc1)n1cc(N)cn1] | 1-(1-(2-(Azetidin-1-yl)pyrimidin-5-yl)ethyl)-1H-pyrazol-4-amine | Calcd.: 245.2<br>Found: 245.0 |
| CA-9 | 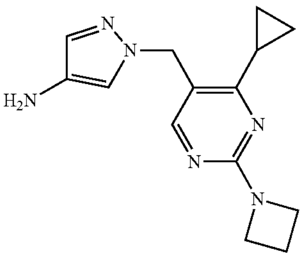 | 1-((2-(Azetidin-1-yl)-4-cyclopropylpyrimidin-5-yl)methyl)-1H-pyrazol-4-amine | Calcd.: 271.2<br>Found: 271.1 |

TABLE CA-continued

The following compounds were prepared using procedures similar to those described above using the appropriate starting materials.

| Intermediate No. | Structure | Name | $[M + H]^+$ or $[M + Na]^+$ |
|---|---|---|---|
| CA-10 | 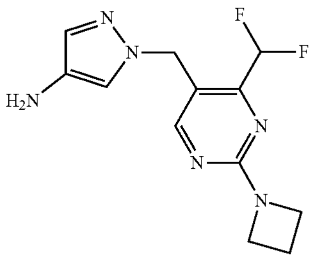 [SMILES: Nc1cnn(Cc2cnc(N3CCC3)nc2C(F)F)c1] | 1-((2-(Azetidin-1-yl)-4-(difluoromethyl)pyrimidin-5-yl)methyl)-1H-pyrazol-4-amine | Calcd.: 281.1 Found: 281.0 |
| CA-11 | 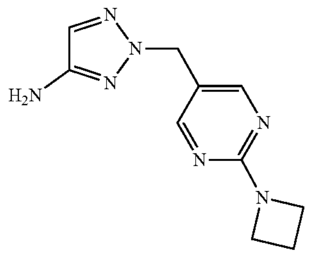 [SMILES: Nc1cnn(Cc2cnc(N3CCC3)nc2)n1] | 2-((2-(Azetidin-1-yl)pyrimidin-5-yl)methyl)-2H-1,2,3-triazol-4-amine | Calcd.: 232.1 Found: 232.0 |
| CA-12 | 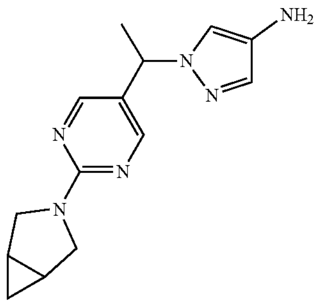 [SMILES: CC(c1cnc(N2CC3CC3C2)nc1)n1cc(N)cn1] | 1-(1-(2-(3-Azabicyclo[3.1.0]hexan-3-yl)pyrimidin-5-yl)ethyl)-1H-pyrazol-4-amine | Calcd.: 271.6 Found: 271.1 |
| CA-13 | 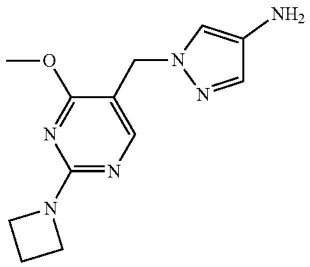 [SMILES: COc1nc(N2CCC2)ncc1Cn1cc(N)cn1] | 1-((2-(Azetidin-1-yl)-4-methoxypyrimidin-5-yl)methyl)-1H-pyrazol-4-amine | Calcd.: 261.1 Found: 261.0 |

TABLE CA-continued

The following compounds were prepared using procedures similar to those described above using the appropriate starting materials.

| Intermediate No. | Structure | Name | $[M + H]^+$ or $[M + Na]^+$ |
|---|---|---|---|
| CA-14 | 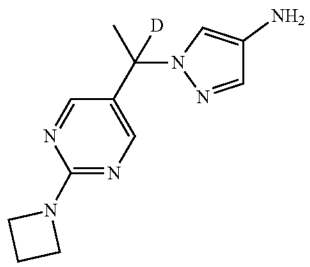 [SMILES: [2H]C(C)(c1cnc(N2CCC2)nc1)n1cc(N)cn1] | 1-(1-(2-(Azetidin-1-yl)pyrimidin-5-yl)ethyl-1-d)-1H-pyrazol-4-amine | Calcd.: 246.3 Found: 246.1 |
| CA-15 | 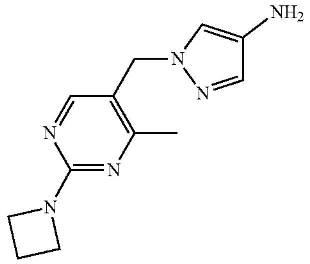 [SMILES: Cc1nc(N2CCC2)ncc1Cn1cc(N)cn1] | 1-((2-(Azetidin-1-yl)-4-methylpyrimidin-5-yl)methyl)-1H-pyrazol-4-amine | Calcd.: 245.3 Found: 245.1 |
| CA-16 | 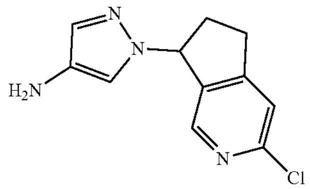 [SMILES: Nc1cnn(C2CCc3cc(Cl)ncc32)c1] | 1-(3-Chloro-6,7-dihydro-5H-cyclopenta[c]pyridin-7-yl)-1H-pyrazol-4-amine | Calcd.: 235.1 Found: 235.1 |

Intermediate CC

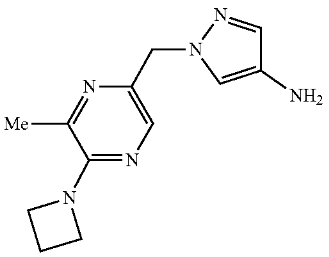 [SMILES: Cc1nc(Cn2cc(N)cn2)cnc1N1CCC1]

1-((5-(Azetidin-1-yl)-6-methylpyrazin-2-yl)methyl)-1H-pyrazol-4-amine (Scheme CC)

Step 1. (5-Chloro-6-methylpyrazin-2-yl)methanol: A solution of 5-chloro-6-methylpyrazine-2-carbaldehyde (950 mg, 6.07 mmol) in MeOH (8.3 mL) was cooled to 0° C., at which time $NaBH_4$ (241 mg, 6.37 mmol) was added. The resulting mixture was warmed to rt and allowed to stir for 3 h. The reaction was quenched with satd. aq. $NH_4Cl$ and concentrated. The resulting crude residue was diluted in EtOAc and washed with satd. aq. $NaHCO_3$ and brine. The combined organic extracts were dried ($Na_2SO_4$), filtered and concentrated to provide the title compound. MS=159.1 $[M+1]^+$ Step 2. 2-Chloro-3-methyl-5-((4-nitro-1H-pyrazol-1-yl)methyl)pyrazine: To a vial containing (5-chloro-6-methylpyrazin-2-yl)methanol (552 mg, 3.48 mmol), 4-nitro-1H-pyrazole (590 mg, 5.22 mmol) and triphenyl phosphine (1.37 g, 5.22 mmol) in THF (17 mL) was added DIAD (1.02 ml, 5.22 mmol), and the resulting mixture was heated to 50° C. overnight. The reaction was cooled to rt and concentrated to afford a crude residue that was purified by silica gel chromatography (MeOH/DCM) to give the title compound. MS=254 $[M+1]^+$ Step 3. 2-(Azetidin-1-yl)-3-methyl-5-((4-nitro-1H-pyrazol-1-yl)methyl)pyrazine: To a solution of 2-chloro-3-methyl-5-((4-nitro-1H-pyrazol-1-yl)methyl)pyrazine (310 mg, 0.550 mmol) in ACN (1.4 ml) was added azetidine (0.15 mL, 2.2 mmol), and the resulting mixture was heated to 50° C. for 2 h. The reaction was cooled to rt and concentrated to afford a crude residue that was purified by silica gel chromatography (MeOH/DCM) to give the title compound. MS=275 $[M+1]^+$ Step 4. 1-((5-(Azetidin-1-yl)-6-methylpyrazin-2-yl)methyl)-1H-pyrazol-4-amine: 2-(Azetidin-1-yl)-3-methyl-5-((4-nitro-1H-pyrazol-1-yl)methyl)pyrazine (325 mg, 1.18 mmol) was added to a vial with iron powder (0.53 g, 9.5 mmol) and ammonium chloride (634 mg, 11.8 mmol). EtOH (4.7 ml) and water (1.2 ml) were added, and the reaction mixture was heated to 80° C. for 4 h. The reaction was cooled to rt, filtered through a pad of Celite®, and diluted with satd. aq. $NaHCO_3$. The mixture was extracted with DCM, and the combined organic fractions were dried ($MgSO_4$) and concentrated to provide the title compound that was used without further purification. MS=245 $[M+1]^+$ Intermediate CC-1

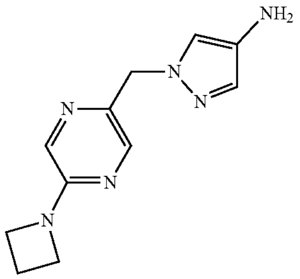

1-((5-(azetidin-1-yl)pyrazin-2-yl)methyl)-1H-pyrazol-4-amine (Scheme CC)

Step 1. tert-Butyl (1-((5-chloropyrazin-2-yl)methyl)-1H-pyrazol-4-yl)carbamate: A mixture of tert-butyl (1H-pyrazol-4-yl)carbamate (247 mg, 1.35 mmol), 2-chloro-5-(chloromethyl)pyrazine (200 mg, 1.23 mmol) and cesium carbonate (800 mg, 2.45 mmol) in DMF (6.1 mL) was stirred at 50° C. for 3 h. The reaction was cooled to rt, diluted with EtOAc and washed with brine. The organic layer was dried over $Na_2SO_4$, filtered and concentrated to afford a crude residue that was purified by silica gel chromatography (EtOAc/hexanes) to give the title compound. MS=310.1 $[M+1]^+$ Step 2. tert-Butyl (1-((5-(azetidin-1-yl)pyrazin-2-yl)methyl)-1H-pyrazol-4-yl)carbamate: A mixture of tert-butyl (1-((5-chloropyrazin-2-yl)methyl)-1H-pyrazol-4-yl)carbamate (80 mg, 0.26 mmol), azetidine (52 μL, 0.78 mmol), and potassium carbonate (107 mg, 0.78 mmol) in DMF (2.6 mL) was stirred at 90° C. for 3 h. The reaction was cooled to rt, diluted with EtOAc, and washed with brine. The organic layer was dried over $Na_2SO_4$, filtered and concentrated to afford a crude residue that was purified by silica gel chromatography (MeOH/DCM) to give the title compound. MS=331.1 $[M+1]^+$ Step 3. 1-((5-(Azetidin-1-yl)pyrazin-2-yl)methyl)-1H-pyrazol-4-amine: The title compound was prepared from tert-butyl (1-((5-(azetidin-1-yl)pyrazin-2-yl)methyl)-1H-pyrazol-4-yl)carbamate following procedures similar to those described above for Intermediate BF and was carried on without purification. MS=231.1 $[M+1]^+$ Intermediate CC-2

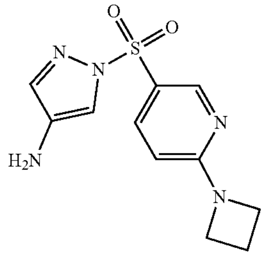 [SMILES: Nc1cnn(S(=O)(=O)c2ccc(N3CCC3)nc2)c1]

1-((6-(Azetidin-1-yl)pyridin-3-yl)sulfonyl)-1H-pyrazol-4-amine (Scheme CC)

Step 1. tert-Butyl (1-((6-chloropyridin-3-yl)sulfonyl)-1H-pyrazol-4-yl)carbamate: Sodium hydride (72 mg, 1.80 mmol, 60% w/w dispersion in mineral spirits) was added to a stirred solution of tert-butyl (1H-pyrazol-4-yl)carbamate (300 mg, 1.64 mmol) in THF (8 mL) at 0° C. The resulting mixture was warmed to rt for 15 min and recooled to 0° C. 6-Chloropyridine-3-sulfonyl chloride (417 mg, 1.96 mmol) was added, and the reaction mixture was stirred at rt for 1 h. The reaction was concentrated, and the crude residue was purified by silica gel chromatography (EtOAc/hexanes) to give the title compound. $^1H$ NMR (400 MHz, $CDCl_3$; mixture of rotational isomers) δ 8.87, 8.58 (br s, 1H), 8.27 (br s, 1H), 8.20, 7.96 (br d, 1H), 7.77, 7.69 (br s, 1H), 6.89, 6.81 (br s, 1H), 1.50, 1.46 (br s, 9H). Steps 2-3 1-((6-(Azetidin-1-yl)pyridin-3-yl)sulfonyl)-1H-pyrazol-4-amine: Steps 2-3 were performed using the procedures similar to steps 2-3 described for Intermediate CC-1. MS=280.0 $[M+1]^+$

TABLE CC

The following compounds were prepared using procedures similar to those described above using the appropriate starting materials.

| Intermediate No. | Structure | Name | $[M + H]^+$ or $[M + Na]^+$ |
|---|---|---|---|
| CC-3 | 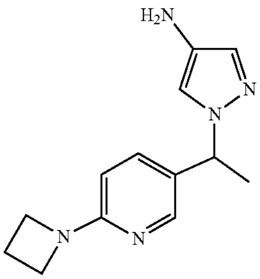 [SMILES: CC(c1ccc(N2CCC2)nc1)n1cc(N)cn1] | 1-(1-(6-(Azetidin-1-yl)pyridin-3-yl)ethyl)-1H-pyrazol-4-amine | Calcd.: 244.2 Found: 244.2 |

TABLE CC-continued

The following compounds were prepared using procedures similar to those described above using the appropriate starting materials.

| Intermediate No. | Structure | Name | $[M+H]^+$ or $[M+Na]^+$ |
|---|---|---|---|
| CC-4 | 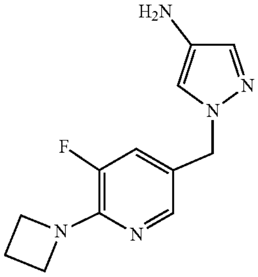 [SMILES: Nc1cnn(Cc2cnc(N3CCC3)c(F)c2)c1] | 1-((6-(Azetidin-1-yl)-5-fluoropyridin-3-yl)methyl)-1H-pyrazol-4-amine | Calcd.: 248.1 Found: 248.1 |
| CC-5 | 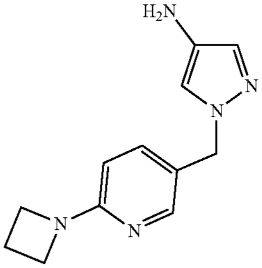 [SMILES: Nc1cnn(Cc2ccc(N3CCC3)nc2)c1] | 1-((6-(Azetidin-1-yl)pyridin-3-yl)methyl)-1H-pyrazol-4-amine | Calcd.: 230.1 Found: 230.1 |

Intermediate CD (AO)

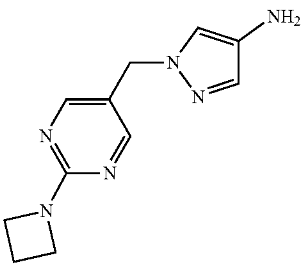 [SMILES: Nc1cnn(Cc2cnc(N3CCC3)nc2)c1]

1-((2-(Azetidin-1-yl)pyrimidin-5-yl)methyl)-1H-pyrazol-4-amine (Scheme CD)

Steps 1 and 2. tert-Butyl (1-((2-(azetidin-1-yl)pyrimidin-5-yl)methyl)-1H-pyrazol-4-yl)carbamate: Into a 3-L 3-necked round-bottom flask purged and maintained with an inert atmosphere of nitrogen, was placed BB-2 (80.0 g, 484 mmol). This was followed by the addition of DCM (1.60 L). The resulting mixture was cooled to 0° C., and tribromophosphane (144.2 g, 532.7 mmol) was added dropwise. The resulting solution was stirred at rt for 2 h. The solids were collected by filtration to afford a crude product that was charged into a 2-L 3-necked round-bottom flask purged and maintained with an inert atmosphere of nitrogen and dissolved in DMF (800 mL). $K_2CO_3$ (96.95 g, 701.4 mmol), and tert-butyl N-(1H-pyrazol-4-yl)carbamate (77.11 g, 420.9 mmol) were added, and the resulting solution was stirred overnight at 50° C. The reaction was then quenched by the addition of water, and the resulting solution was extracted with EtOAc. The combined organic layers were washed with brine and concentrated to afford a crude residue that was purified by silica gel chromatography (EtOAc/petroleum ether) to give the title compound. MS=331.1 $[M+H]^+$.

Step 3. 1-((2-(Azetidin-1-yl)pyrimidin-5-yl)methyl)-1H-pyrazol-4-amine: Into a 2-L 3-necked round-bottom flask purged and maintained with an inert atmosphere of nitrogen, was placed tert-butyl N-(1-[[2-(azetidin-1-yl)pyrimidin-5-yl]methyl]-1H-pyrazol-4-yl)carbamate (60.00 g, 181.6 mmol). This was followed by the addition of DCM (1.20 L). To this mixture was added TMSOTf (44.40 g, 199.8 mmol) dropwise with stirring at 0° C. The resulting solution was warmed to rt and allowed to stir for 1.5 h. The reaction was adjusted to pH=9-10 with 2M aq. $K_2CO_3$. The resulting mixture was extracted with DCM, and the organic layers were combined and concentrated to afford a crude residue that was subsequently washed with DCM/petroleum ether to yield a solid filter cake as the title compound. MS=231.0 $[M+H]^+$.

Intermediate CE

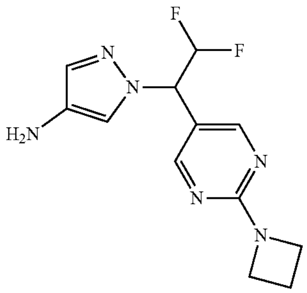 [SMILES: Nc1cnn(C(c2cnc(N3CCC3)nc2)C(F)F)c1]

1-(1-(2-(Azetidin-1-yl)pyrimidin-5-yl)-2,2-difluoroethyl)-1H-pyrazol-4-amine (Scheme CE)

Step 1. 2-(Azetidin-1-yl)pyrimidine-5-carbaldehyde: 2-Chloropyrimidine-5-carbaldehyde (2.00 g, 14.0 mmol) and TEA (2.35 mL, 16.8 mmol) were dissolved in dioxane (30 mL), and azetidine hydrochloride (1.44 g, 15.4 mmol) was added. The reaction mixture was stirred at rt for 2 h, at which time, the mixture was concentrated and resuspended in water. The mixture was extracted with EtOAc, and the combined organic layers were dried over $Na_2SO_4$, filtered and concentrated to afford a crude residue that was purified by silica gel chromatography (EtOAc/petroleum ether) to give the title compound. MS=164.0 $[M+H]^+$.

Step 2. 1-(2-(Azetidin-1-yl)pyrimidin-5-yl)-2,2-difluoroethanol: To a solution of 2-(azetidin-1-yl)pyrimidine-5-carbaldehyde (600 mg, 3.68 mmol) in DMF (10 mL) was added (difluoromethyl)trimethylsilane (2.28 g, 18.4 mmol) and cesium fluoride (1.12 g, 7.35 mmol), and the resulting mixture was stirred at rt for 12 h. TBAF (7.35 mL, 7.35 mmol, 1M in THF) was added, and the mixture continued stirring at rt for 1 h. The reaction was partitioned between water and EtOAc, the layers were separated, and the aq. layer was extracted with EtOAc. The combined organic layers were washed with brine, dried over anhydrous $Na_2SO_4$, filtered and concentrated to afford a crude residue that was purified by silica gel chromatography (EtOAc/petroleum ether) to give the title compound. MS=216.0 $[M+H]^+$.

Step 3. 2-(Azetidin-1-yl)-5-(2,2-difluoro-1-(4-nitro-1H-pyrazol-1-yl)ethyl)pyrimidine: A solution of 4-nitro-1H-pyrazole (420 mg, 3.72 mmol), 1-(2-(azetidin-1-yl)pyrimidin-5-yl)-2,2-difluoroethanol (400 mg, 1.86 mmol), (E)-diisopropyl diazene-1,2-dicarboxylate (752 mg, 3.72 mmol) and $Ph_3P$ (975 mg, 3.72 mmol) in THF (20 mL) was stirred at rt for 1 h. The mixture was concentrated to afford a crude residue that was purified by silica gel chromatography (EtOAc/petroleum ether) to give the title compound. MS=311.0 $[M+H]^+$.

Step 4. 1-(1-(2-(Azetidin-1-yl)pyrimidin-5-yl)-2,2-difluoroethyl)-1H-pyrazol-4-amine: To a solution of 2-(azetidin-1-yl)-5-(2,2-difluoro-1-(4-nitro-1H-pyrazol-1-yl)ethyl)pyrimidine (600 mg, 1.93 mmol) in EtOAc (9 mL) and MeOH (3 mL) was added platinum(IV) oxide (43.9 mg, 0.193 mmol) under $N_2$ atmosphere. The mixture was degassed and backfilled with $H_2$ (three times), and the resulting mixture was stirred under $H_2$ (15 psi) at rt for 1.5 h. The reaction was filtered through a pad of Celite®, and filtrate was concentrated to afford a crude residue that was purified by silica gel chromatography (MeOH/DCM) to give the title compound. MS=281.1 $[M+H]^+$.

Intermediate CF

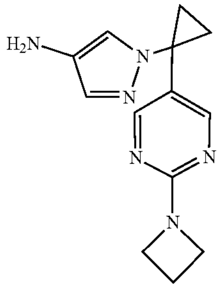 [SMILES: Nc1cnn(C2(c3cnc(N4CCC4)nc3)CC2)c1]

1-(1-(2-(Azetidin-1-yl)pyrimidin-5-yl)cyclopropyl)-1H-pyrazol-4-amine (Scheme CF)

Step 1. Ethyl 2-(azetidin-1-yl)pyrimidine-5-carboxylate: To a solution of ethyl 2-chloropyrimidine-5-carboxylate (5.00 g, 26.8 mmol) and TEA (11.2 mL, 80.0 mmol) in dioxane (50 mL) was added azetidine hydrochloride (3.01 g, 32.2 mmol). The reaction mixture was stirred at rt for 16 h, at which time, the reaction was poured into water and extracted with EtOAc. The combined organic layers were dried over $Na_2SO_4$ and concentrated to afford a crude residue that was purified by silica gel chromatography (MeOH/DCM) to give the title compound. MS=280.0 $[M+H]^+$.

Step 2. 1-(2-(Azetidin-1-yl)pyrimidin-5-yl)cyclo propanol: To a solution of titanium(IV) isopropoxide (686 mg, 2.41 mmol) and ethyl 2-(azetidin-1-yl)pyrimidine-5-carboxylate (1.00 g, 4.83 mmol) in THF (4 mL) was added ethylmagnesium bromide (4.83 mL, 14.5 mmol, 3M in diethyl ether) at rt over 30 min, and the resulting mixture was stirred at rt for 3 h. The reaction was quenched with satd. aq. $NH_4Cl$ and extracted with EtOAc. The combined organic layers were washed with water and brine, dried over $Na_2SO_4$, filtered and concentrated to afford a crude residue that was purified by reversed-phase preparatory-HPLC (C18 stationary phase, water (0.1% TFA)-ACN to give the title compound. MS=192.1 $[M+H]^+$.

Step 3. 2-(Azetidin-1-yl)-5-(1-(4-nitro-1H-pyrazol-1-yl)cyclopropyl)pyrimidine: To a solution of 1-(2-(azetidin-1-yl)pyrimidin-5-yl)cyclopropanol (120 mg, 0.628 mmol), triphenylphosphine (329 mg, 1.26 mmol) and 4-nitro-1H-pyrazole (71 mg, 0.63 mmol) in toluene (3 mL) was added (E)-di-tert-butyl diazene-1,2-dicarboxylate (217 mg, 0.941 mmol), and the resulting mixture was heated to 110° C. for 12 h. The reaction was cooled to rt and concentrated to afford a crude residue that was purified by reversed-phase preparatory-HPLC (C18 stationary phase, water (0.1% TFA)-ACN to give the title compound. MS=287.0 $[M+H]^+$.

Step 4. 1-(1-(2-(Azetidin-1-yl)pyrimidin-5-yl)cyclopropyl)-1H-pyrazol-4-amine: To a mixture of 2-(azetidin-1-yl)-5-(1-(4-nitro-1H-pyrazol-1-yl)cyclopropyl)pyrimidine (67 mg, 0.23 mmol) and ammonium chloride (62.6 mg, 1.17 mmol) in EtOH (5 mL) and water (5 mL) was added iron (65.3 mg, 1.17 mmol), and the resulting mixture was heated to 60° C. for 2 h. The reaction was cooled to rt, diluted with DCM and water, and filtered through a pad of Celite®. The layers were separated, and the aq. layer was extracted with DCM. The combined organic layers were washed with water and brine, dried over $Na_2SO_4$, filtered and concentrated to give the title compound which was carried to next step without further purification. MS=257.0 $[M+H]^+$.

Intermediate CG

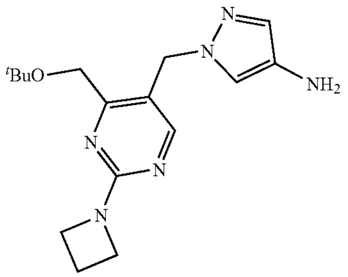 [SMILES: CC(C)(C)OCc1nc(N2CCC2)ncc1Cn1cc(N)cn1]

1-((2-(Azetidin-1-yl)-4-(tert-butoxymethyl)pyrimidin-5-yl)methyl)-1H-pyrazol-4-amine Step 1. Ethyl 4-(tert-butoxymethyl)-2-chloropyrimidine-5-carboxylate: To a solution of ethyl 2-chloropyrimidine-5-carboxylate (10.0 g, 53.6 mmol) in ACN (30 mL) and water (30 mL) was added 2-(tert-butoxy)acetic acid (21.3 g, 161 mmol), silver nitrate (36.4 g, 214 mmol) and ammonium persulfate (61.1 g, 268 mmol), and the resulting mixture was heated to 60° C. for 2 h. The reaction was poured into water and extracted with EtOAc. The combined organic layers were dried over $Na_2SO_4$, filtered, and concentrated to give a crude residue that was purified by silica gel chromatography (EtOAc/petroleum ether) to give the title compound. MS=273.0 $[M+H]^+$.

Step 2. Ethyl 2-(azetidin-1-yl)-4-(tert-butoxymethyl)pyrimidine-5-carboxylate: TEA (5.1 mL, 37 mmol) was added to a stirred solution of ethyl 4-(tert-butoxymethyl)-2-chloropyrimidine-5-carboxylate (4.00 g, 14.7 mmol) and azetidine hydrochloride (2.74 g, 29.3 mmol) in EtOH (40 mL), and the resulting mixture was heated to 70° C. for 2 h. The reaction was diluted with EtOAc and washed by water followed by brine. The organics were dried over $Na_2SO_4$, filtered and concentrated to give the crude title compound which was used in next step directly. MS=294.2 $[M+H]^+$.

Step 3. (2-(Azetidin-1-yl)-4-(tert-butoxymethyl)pyrimidin-5-yl)methanol: To solution of ethyl 2-(azetidin-1-yl)-4-(tert-butoxymethyl)pyrimidine-5-carboxylate (1.40 g, 4.77 mmol) in THF (30 mL) at 0° C. was added DIBAL-H (9.5 mL, 9.5 mmol, 1M in toluene) dropwise, and the resulting mixture was stirred at 0° C. for 2 h. The reaction was quenched by slow addition of 15% aq. NaOH at 0° C. The mixture was filtered, and the filtrate was concentrated to give a crude residue that was purified by silica gel chromatography (EtOAc/petroleum ether) to give the title compound. MS=252.1 $[M+H]^+$.

Step 4. 2-(Azetidin-1-yl)-4-(tert-butoxymethyl)-5-((4-nitro-1H-pyrazol-1-yl)methyl)pyrimidine: To a mixture of (2-(azetidin-1-yl)-4-(tert-butoxymethyl)pyrimidin-5-yl)methanol (600 mg, 2.39 mmol), 4-nitro-1H-pyrazole (324 mg, 2.86 mmol) and triphenylphosphine (939 mg, 3.58 mmol) in THF (15 mL) at 0° C. was added (E)-di-tert-butyl diazene-1,2-dicarboxylate (825 mg, 3.58 mmol), and the resulting mixture was warmed to rt and allowed to stir for 3 h. The reaction was concentrated to give a crude residue that was purified by silica gel chromatography (EtOAc/petroleum ether) to give the title compound. MS=347.1 $[M+H]^+$.

Step 5. 1-((2-(Azetidin-1-yl)-4-(tert-butoxymethyl)pyrimidin-5-yl)methyl)-1H-pyrazol-4-amine: To a solution of 2-(azetidin-1-yl)-4-(tert-butoxymethyl)-5-((4-nitro-1H-pyrazol-1-yl)methyl)pyrimidine (800 mg, 2.31 mmol) in EtOAc (9 mL) and MeOH (3 mL) was added platinum(IV) oxide (52 mg, 0.23 mmol), and the resulting mixture was degassed and backfilled with $H_2$. The mixture was stirred under $H_2$ (15 psi) at rt for 1 h, at which time, the reaction was filtered, and the filtrate was concentrated to give crude residue that was purified by preparatory-TLC (EtOAc) to give the title compound. MS=317.2 $[M+H]^+$.

Intermediate CH

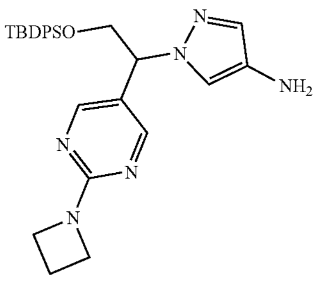

1-(1-(2-(Azetidin-1-yl)pyrimidin-5-yl)-2-((tert-butyldiphenylsilyl)oxy)ethyl)-1H-pyrazol-4-amine Step 1. 2-(Azetidin-1-yl)-5-vinyl pyrimidine: Azetidine hydrochloride (1.10 g, 11.7 mmol) was added to a stirred solution of 2-chloro-5-vinyl pyrimidine (1.50 g, 10.7 mmol) and TEA (2.97 mL, 21.3 mmol) in 1,4-dioxane (15 mL), and the resulting mixture was heated to 35° C. for 3 h. The reaction was poured into water and extracted with EtOAc. The combined organic layers were dried over $Na_2SO_4$, filtered and concentrated to give a crude residue that was purified by silica gel chromatography (EtOAc/petroleum ether) to give the title compound. MS=162.1 $[M+H]^+$.

Step 2. 1-(2-(Azetidin-1-yl)pyrimidin-5-yl)ethane-1,2-diol: An aq. solution of osmium(VIII) oxide (23 mL, 0.90 mmol, 10 mg/mL) and 4-methylmorpholine 4-oxide (1.05 g, 8.99 mmol) was added to a stirred solution of the 2-(azetidin-1-yl)-5-vinylpyrimidine (1.45 g, 8.99 mmol) in ACN (15 mL) and water (5 mL), and the resulting mixture was heated to 35° C. for 1 h. The reaction was cooled to 0° C., and quenched with satd. aq. $NaS_2O_3$ and continued stirring at 0° C. for 0.5 h. The mixture was filtered through a pad of Celite® and concentrated to afford a crude residue that was purified by reversed-phase preparatory-HPLC (C18 stationary phase, water (0.1% TFA)-ACN) to give the title compound. MS=196.0 $[M+H]^+$.

Step 3. 1-(2-(Azetidin-1-yl)pyrimidin-5-yl)-2-((tert-butyldiphenylsilyl)oxy)ethanol: To a stirred solution of 1-(2-(azetidin-1-yl)pyrimidin-5-yl)ethane-1,2-diol (2.61 g, 13.4 mmol) in DMF (20 mL) was added 1H-imidazole (2.00 g, 29.5 mmol) and tert-butylchlorodiphenylsilane (4.42 g, 16.1 mmol), and the resulting mixture was heated to 50° C. for 6 h. The reaction was diluted with water and extracted with EtOAc. The combined organic layers were washed with brine, dried over $Na_2SO_4$, filtered and concentrated to give a crude residue that was purified by silica gel chromatography (EtOAc/petroleum ether) to give the title compound. MS=434.1 $[M+H]^+$.

Step 4. 2-(Azetidin-1-yl)-5-(2-((tert-butyldiphenylsilyl)oxy)-1-(4-nitro-1H-pyrazol-1-yl)ethyl)pyrimidine: The stirred solution of 4-nitro-1H-pyrazole (344 mg, 3.04 mmol), 1-(2-(azetidin-1-yl)pyrimidin-5-yl)-2-((tert-butyldiphenylsilyl)oxy)ethanol (659 mg, 1.52 mmol), DIAD (615 mg, 3.04 mmol) and triphenylphosphine (797 mg, 3.04 mmol) in THF (10 mL) was heated to 50° C. for 2 h. The reaction was concentrated, resuspended in water and extracted with EtOAc. The combined organic layers were washed with brine, dried over $Na_2SO_4$, filtered and concentrated to give a crude residue that was purified by silica gel chromatography (EtOAc/petroleum ether) to give the title compound. MS=529.2 $[M+H]^+$.

Step 5. 1-(1-(2-(Azetidin-1-yl)pyrimidin-5-yl)-2-((tert-butyldiphenylsilyl)oxy)ethyl)-1H-pyrazol-4-amine: Iron (1.47 g, 26.3 mmol) and ammonium chloride (1.69 g, 31.6 mmol) were added to a stirred solution of 2-(azetidin-1-yl)-5-(2-((tert-butyldiphenylsilyl)oxy)-1-(4-nitro-1H-pyrazol-1-yl)ethyl)pyrimidine (2.78 g, 5.26 mmol) in EtOH (18 mL) and water (6 mL), and the resulting mixture was heated to 80° C. for 1 h. The reaction was diluted with water, filtered through a pad of Celite®, and the resulting filtrate was diluted further with EtOH and concentrated to afford a crude residue that was purified by reversed-phase preparatory-HPLC (C18 stationary phase, water (0.1% TFA)-ACN to give the title compound. MS=499.5 $[M+H]^+$.

Intermediate CI

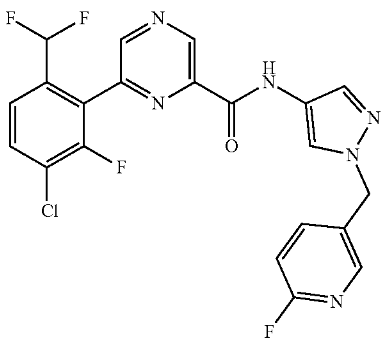 [SMILES: O=C(Nc1cnn(Cc2ccc(F)nc2)c1)c1cncc(-c2c(C(F)F)ccc(Cl)c2F)n1]

6-(3-Chloro-6-(difluoromethyl)-2-fluorophenyl)-N-(1-((6-fluoropyridin-3-yl)methyl)-1H-pyrazol-4-yl)pyrazine-2-carboxamide (Scheme CI)

To a solution of 6-(3-chloro-6-(difluoromethyl)-2-fluorophenyl)-N-(1H-pyrazol-4-yl)pyrazine-2-carboxamide (200 mg, 0.544 mmol) in DMF (2 mL) was added 5-(bromomethyl)-2-fluoropyridine (103 mg, 0.544 mmol) and $Cs_2CO_3$ (532 mg, 1.63 mmol), and the resulting mixture was stirred at for 6 h. The reaction was diluted with EtOAc and washed with brine. The organics were dried ($Na_2SO_4$), filtered and concentrated to afford a crude residue that was purified by silica gel chromatography (EtOAc/hexanes) to give the title compound. MS=477.1 $[M+1]^+$.

Intermediate CJ

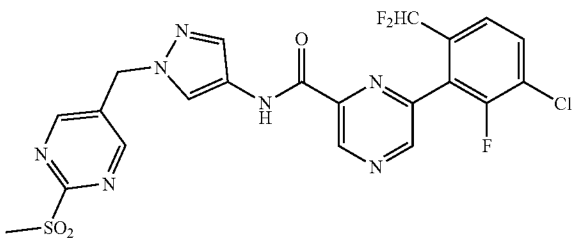 [SMILES: CS(=O)(=O)c1ncc(Cn2cc(NC(=O)c3cncc(-c4c(C(F)F)ccc(Cl)c4F)n3)cn2)cn1]

6-(3-Chloro-6-(difluoromethyl)-2-fluorophenyl)-N-(1-((2-(methylsulfonyl)pyrimidin-5-yl)methyl)-1H-pyrazol-4-yl)pyrazine-2-carboxamide (Scheme CJ)

Step 1. 5-(Bromomethyl)-2-(methylthio)pyrimidine: To a solution of (2-(methylthio)pyrimidin-5-yl)methanol (1.50 g, 9.60 mmol) in DCM (30 mL) at 0° C. was added carbon tetrabromide (4.14 g, 12.5 mmol) and triphenylphosphine (3.27 mg, 12.5 mmol). The resulting mixture was stirred at 0° C. for 2 h. The reaction mixture was purified directly by silica gel chromatography (EtOAc/hexanes) to give the title compound. MS=221.0 $[M+1]^+$.

Step 2. 6-(3-Chloro-6-(difluoromethyl)-2-fluorophenyl)-N-(1-((2-(methylthio)pyrimidin-5-yl)methyl)-1H-pyrazol-4-yl)pyrazine-2-carboxamide: To a solution of 6-(3-chloro-6-(difluoromethyl)-2-fluorophenyl)-N-(1H-pyrazol-4-yl)pyrazine-2-carboxamide and ammonium chloride (545 mg, 1.48 mmol) in DMF (10 mL) was added 5-(bromomethyl)-2-(methylthio)pyrimidine (325 mg, 1.48 mmol) and cesium carbonate (1.45 g, 4.45 mmol). The resulting mixture was stirred at rt for 16 h, at which time it was diluted with EtOAc and washed with water, followed by brine. The organic layer was dried ($Na_2SO_4$), filtered and concentrated to afford a crude residue that was purified by silica gel chromatography (EtOAc/hexanes) to give the title compound. MS=506.2 $[M+1]^+$.

Step 3. 6-(3-Chloro-6-(difluoromethyl)-2-fluorophenyl)-N-(1-((2-(methylsulfonyl)pyrimidin-5-yl)methyl)-1H-pyrazol-4-yl)pyrazine-2-carboxamide: To a suspension of 6-(3-chloro-6-(difluoromethyl)-2-fluorophenyl)-N-(1-((2-(methylthio)pyrimidin-5-yl)methyl)-1H-pyrazol-4-yl)pyrazine-2-carboxamide (1.26 g, 2.49 mmol) in DCM (20 mL) was added mCPBA (1.17 g, 5.23 mmol), and the resulting mixture was stirred at rt for 2 h. The reaction was diluted with DCM and washed with 1M aq. $Na_2CO_3$. The organic layer was dried ($Na_2SO_4$), filtered and concentrated to afford a crude residue that was purified by silica gel chromatography eluting with (EtOAc:EtOH/hexanes) to give the title compound. MS=538.2 $[M+1]^+$.

TABLE CJ

The following compounds were prepared using procedures similar to those described above using the appropriate starting materials.

| Intermediate No. | Structure | Name | $[M + H]^+$ or $[M + Na]^+$ | Chiral column |
|---|---|---|---|---|
| CJ-1 | 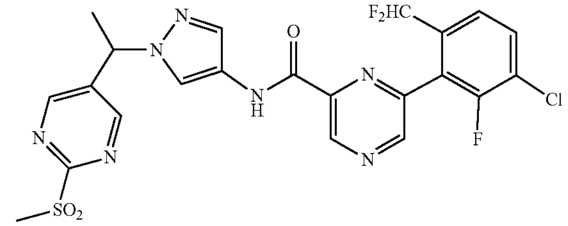 [SMILES: CC(c1cnc(S(C)(=O)=O)nc1)n1cc(NC(=O)c2cncc(-c3c(C(F)F)ccc(Cl)c3F)n2)cn1] | rac-6-(3-Chloro-6-(difluoromethyl)-2-fluorophenyl)-N-(1-(1-(2-(methylsulfonyl)pyrimidin-5-yl)ethyl)-1H-pyrazol-4-yl)pyrazine-2-carboxamide | Calcd.: 551.9 Found: 552.0 | |
| CJ-2 | 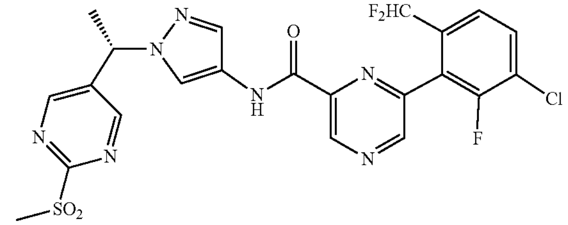 | (S)-6-(3-Chloro-6-(difluoromethyl)-2-fluorophenyl)-N-(1-(1-(2-(methylsulfonyl)pyrimidin-5-yl)ethyl)-1H-pyrazol-4-yl)pyrazine-2-carboxamide | Calcd.: 551.9 Found: 552.0 | CHIRALPAK AD-3 |
| CJ-3 | 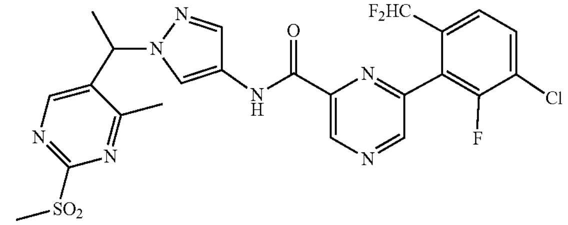 [SMILES: Cc1nc(S(C)(=O)=O)ncc1C(C)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(4-methyl-2-(methylsulfonyl)pyrimidin-5-yl)ethyl)-1H-pyrazol-4-yl)pyrazine-2-carboxamide | Calcd.: 565.1 Found: 565.9 | |

EXAMPLES

Example 1

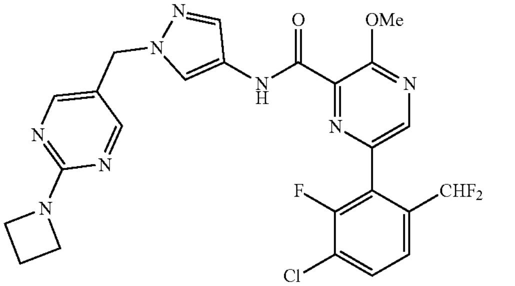

N-(1-((2-(Azetidin-1-yl)pyrimidin-5-yl)methyl)-1H-pyrazol-4-yl)-6-(3-chloro-6-(difluoromethyl)-2-fluorophenyl)-3-methoxypyrazine-2-carboxamide (Scheme AAA)

Step 1: N-(1-((2-(Azetidin-1-yl)pyrimidin-5-yl)methyl)-1H-pyrazol-4-yl)-6-(3-chloro-6-(difluoromethyl)-2-fluorophenyl)-3-methoxypyrazine-2-carboxamide: 1-((2-(Azetidin-1-yl)pyrimidin-5-yl)methyl)-1H-pyrazol-4-amine (18 mg, 0.078 mmol) was added to a stirred solution of 6-(3-chloro-6-(difluoromethyl)-2-fluorophenyl)-3-methoxypyrazine-2-carboxylic acid (26 mg, 0.078 mmol), EDC (30 mg, 0.16 mmol) in pyridine (0.5 mL), and the resulting mixture was stirred at rt for 2 h. The reaction was purified by prep-HPLC (Method Column Agela Durashell C18 150*30 5u Condition water (0.04% $NH_3H_2O$+10 mM $NH_4HCO_3$)-ACN Begin B 37 End B 67 Gradient Time (min) 10 100% B Hold Time (min) 2 FlowRate (ml/min) 25), eluting with Acetonitrile/Water+0.05% $NH_3 \cdot H_2O$, to give the title compound. $^1H$ NMR (500 MHz, $CD_3OD$) δ 8.59 (d, J=2.7 Hz, 1H), 8.34 (s, 2H), 8.22 (s, 1H), 7.78-7.84 (m, 1H), 7.71 (s, 1H), 7.66 (d, J=8.2 Hz, 1H), 6.80-7.12 (m, 1H), 5.21 (s, 2H), 4.18 (s, 3H), 4.15 (d, J=7.6 Hz, 4H), 2.36-2.48 (m, 2H). MS=545.2 (M+H). MS: 545.2 $[M+H]^+$

Example 2

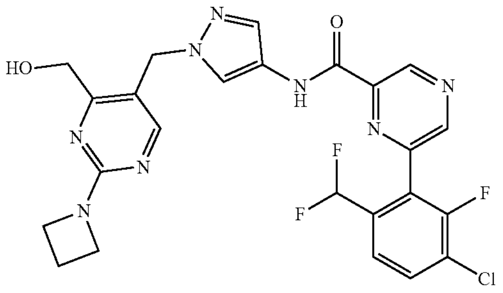 [SMILES: O=C(Nc1cnn(Cc2cnc(N3CCC3)nc2CO)c1)c1cncc(-c2c(C(F)F)ccc(Cl)c2F)n1]

N-(1-((2-(Azetidin-1-yl)-4-(hydroxymethyl)pyrimidin-5-yl)methyl)-1H-pyrazol-4-yl)-6-(3-chloro-6-(difluoromethyl)-2-fluorophenyl)pyrazine-2-carboxamide (Scheme AAA and deprotection)

Step 1. N-(1-((2-(Azetidin-1-yl)-4-(tert-butoxymethyl)pyrimidin-5-yl)methyl)-1H-pyrazol-4-yl)-6-(3-chloro-6-(difluoromethyl)-2-fluorophenyl)pyrazine-2-carboxamide: The title compound was prepared following procedures similar to those described above for Example 1. MS=601.4 $[M+H]^+$.

Step 2. N-(1-((2-(Azetidin-1-yl)-4-(hydroxymethyl)pyrimidin-5-yl)methyl)-1H-pyrazol-4-yl)-6-(3-chloro-6-(difluoromethyl)-2-fluorophenyl)pyrazine-2-carboxamide: The title compound was prepared following procedures similar to those described above for Intermediate BF, Step 3, in which the final compound was purified by reversed-phase preparatory-HPLC (C18 stationary phase, water (0.1% TFA)-ACN). $^1H$ NMR (400 MHz, $CDCl_3$) δ 9.44-9.52 (m, 2H), 9.04 (d, J 2.9 Hz, 1H), 8.38 (s, 1H), 8.12 (s, 1H), 7.67-7.76 (m, 1H), 7.58-7.66 (m, 2H), 6.40-6.77 (m, 1H), 5.19 (s, 2H), 4.63 (s, 2H), 4.36 (br t, J 7.6 Hz, 4H), 2.49 (quint, J 7.6 Hz, 2H). MS=545.1 $[M+H]^+$.

Example 3

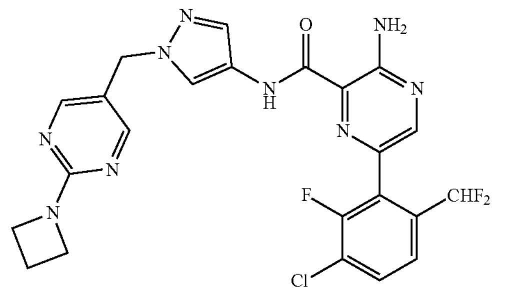 [SMILES: Nc1ncc(-c2c(C(F)F)ccc(Cl)c2F)nc1C(=O)Nc1cnn(Cc2cnc(N3CCC3)nc2)c1]

3-Amino-N-(1-((2-(azetidin-1-yl)pyrimidin-5-yl)methyl)-1H-pyrazol-4-yl)-6-(3-chloro-6-(difluoromethyl)-2-fluorophenyl)pyrazine-2-carboxamide The title compound was prepared following procedures similar to those described above for Intermediate BF, Step 3, in which the final compound was purified by reversed-phase preparatory-HPLC (C18 stationary phase, water (0.1% TFA)-ACN). MS=530.2 $[M+H]^+$. $^1H$ NMR (400 MHz, DMSO-d6) δ 10.48 (s, 1H), 8.43 (d, J=2.4 Hz, 1H), 8.34 (s, 2H), 8.14 (s, 1H), 7.90-7.77 (m, 1H), 7.71-7.54 (m, 2H), 7.18 (t, J=54.6 Hz, 1H), 5.13 (s, 2H), 3.99 (t, J=7.6, 4H), 2.27 (p, J=7.6 Hz, 2H).

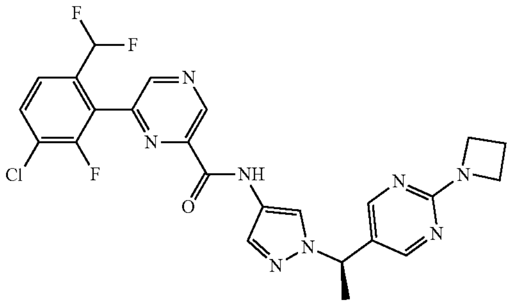

and

-continued

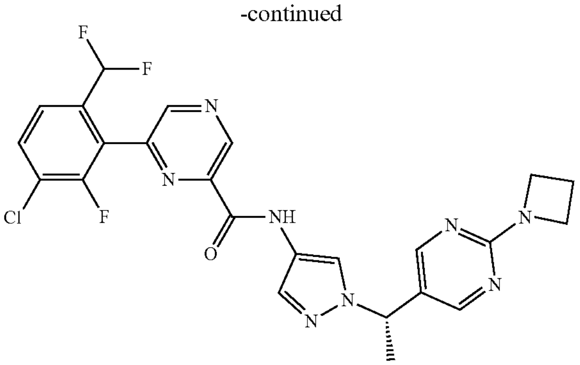

Examples 4 and 5

(R)—N-(1-(1-(2-(Azetidin-1-yl)pyrimidin-5-yl)ethyl)-1H-pyrazol-4-yl)-6-(3-chloro-6-(difluoromethyl)-2-fluorophenyl)pyrazine-2-carboxamide and (S)—N-(1-(1-(2-(Azetidin-1-yl)pyrimidin-5-yl)ethyl)-1H-pyrazol-4-yl)-6-(3-chloro-6-(difluoromethyl)-2-fluorophenyl)pyrazine-2-carboxamide (Scheme AAA)

Step 1: N-(1-(1-(2-(Azetidin-1-yl)pyrimidin-5-yl)ethyl)-1H-pyrazol-4-yl)-6-(3-chloro-6-(difluoromethyl)-2-fluorophenyl)pyrazine-2-carboxamide: To a solution of 1-(1-(2-(azetidin-1-yl)pyrimidin-5-yl)ethyl)-1H-pyrazol-4-amine (160 mg, 0.655 mmol) and 6-(3-chloro-6-(difluoromethyl)-2-fluorophenyl)pyrazine-2-carboxylic acid (198 mg, 0.655 mmol) in pyridine (1.5 mL) was added EDC (251 mg, 1.310 mmol) at 0° C., and the resulting mixture was warmed to rt for 2 h. The reaction was diluted with water and extracted with EtOAc. The combined organic layers were dried over $Na_2SO_4$, filtered, and concentrated. The residue was purified by reverse prep-HPLC (Instrument EB Method Column Phenomenex Synergi C18 150*30 mm*4 um Condition water (0.1% TFA)-ACN Begin B 33 End B 53 Gradient Time (min) 10 100% B Hold Time (min) 2 FlowRate (ml/min) 25 Injections 5 HPLC 3) to the title compound as a mixture of enantiomers, which were separated by SFC (Instrument SFC-80 Method Column YMC CHIRAL Amylose-C (250 mm*30 mm, 10 um) Condition 0.1% $NH_3H_2O$ MeOH Begin B 55% End B 55% Gradient Time (min) 100% B), the first eluted isomer Example 4: $^1H$ NMR (400 MHz, $CD_3OD$) δ 9.38 (s, 1H), 9.01 (d, J=1.8 Hz, 1H), 8.36 (s, 2H), 8.28 (s, 1H), 7.84 (t, J=7.9 Hz, 1H), 7.77 (s, 1H), 7.67 (d, J=7.9 Hz, 1H), 6.87 (t, J=54.6 Hz, 1H), 5.54 (q, J=6.9 Hz, 1H), 4.20 (t, J=7.5 Hz, 4H), 2.40-2.49 (m, 2H), 1.87 (d, J=7.0 Hz, 3H), MS=529.1 (M+H); the second eluted isomer Example 5: $^1H$ NMR (400 MHz, $CD_3OD$) δ 9.38 (s, 1H), 9.02 (d, J=1.8 Hz, 1H), 8.36 (s, 2H), 8.28 (s, 1H), 7.84 (t, J=7.9 Hz, 1H), 7.77 (s, 1H), 7.67 (d, J=7.9 Hz, 1H), 6.87 (t, J=54.6 Hz, 1H), 5.54 (q, J=6.9 Hz, 1H), 4.20 (t, J=7.5 Hz, 4H), 2.40-2.49 (m, 2H), 1.87 (d, J=7.0 Hz, 3H). MS=529.1 (M+H).

Examples 6 and 7

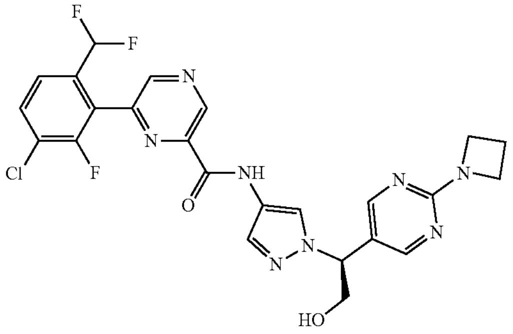

and

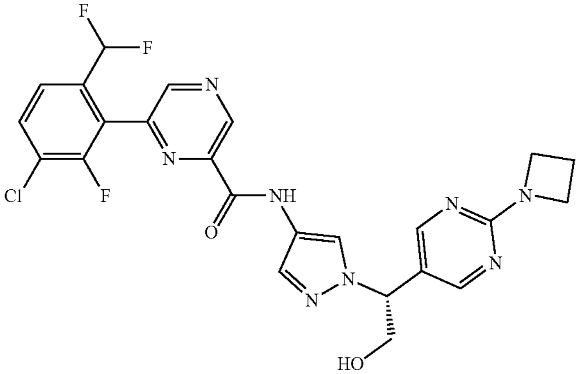

(R)—N-(1-(1-(2-(Azetidin-1-yl)pyrimidin-5-yl)-2-hydroxyethyl)-1H-pyrazol-4-yl)-6-(3-chloro-6-(difluoromethyl)-2-fluorophenyl)pyrazine-2-carboxamide and (S)—N-(1-(1-(2-(Azetidin-1-yl)pyrimidin-5-yl)-2-hydroxyethyl)-1H-pyrazol-4-yl)-6-(3-chloro-6-(difluoromethyl)-2-fluorophenyl)pyrazine-2-carboxamide (Scheme AAA and deprotection)

Step 1. N-(1-(1-(2-(Azetidin-1-yl)pyrimidin-5-yl)-2-((tert-butyldiphenylsilyl)oxy)ethyl)-1H-pyrazol-4-yl)-6-(3-chloro-6-(difluoromethyl)-2-fluorophenyl)pyrazine-2-carboxamide: Pyridine (0.39 mL, 4.8 mmol) was added to a stirred solution of 1-(1-(2-(azetidin-1-yl)pyrimidin-5-yl)-2-((tert-butyldiphenylsilyl)oxy)ethyl)-1H-pyrazol-4-amine (600 mg, 1.20 mmol), 6-(3-chloro-6-(difluoromethyl)-2-fluorophenyl)pyrazine-2-carboxylic acid (546 mg, 1.80 mmol) and EDC (692 mg, 3.61 mmol) in DCM (10 mL), and the mixture was stirred at 30° C. for 1 h. The reaction was concentrated to afford a crude residue that was purified by reversed-phase preparatory-HPLC (C18 stationary phase, water (0.1% TFA)-ACN) to give the title compound. MS=783.3 $[M+H]^+$.

Step 2. N-(1-(1-(2-(Azetidin-1-yl)pyrimidin-5-yl)-2-hydroxyethyl)-1H-pyrazol-4-yl)-6-(3-chloro-6-(difluoromethyl)-2-fluorophenyl)pyrazine-2-carboxamide: TBAF (0.13 mL, 0.13 mmol, 1M in THF) was added to a stirred solution of N-(1-(1-(2-(azetidin-1-yl)pyrimidin-5-yl)-2-((tert-butyldiphenylsilyl)oxy)ethyl)-1H-pyrazol-4-yl)-6-(3-chloro-6-(difluoromethyl)-2-fluorophenyl)pyrazine-2-carboxamide (50 mg, 0.064 mmol) in THF (2 mL), and the resulting mixture was heated to 35° C. for 1 h. The reaction was purified by reversed-phase preparatory-HPLC (C18 stationary phase, water (0.1% TFA)-ACN) to give the title compound as a racemic mixture that was separated by chiral SFC chromatography (SFC, DAICEL CHIRALCEL OD; 40% Base-EtOH (contained 0.1% $NH_3H_2O$) in $CO_2$) to give the title compounds. The first eluted isomer Example 6: $^1H$ NMR (400 MHz, $CDCl_3$) δ 9.36-9.50 (m, 2H), 8.98 (br s, 1H), 8.43 (br s, 2H), 8.09 (br s, 1H), 7.54-7.69 (m, 3H), 6.52 (br t, J=54.2 Hz, 1H), 5.22 (br s, 1H), 4.23-4.32 (m, 4H), 4.20 (br s, 2H), 2.42 (br s, 2H), MS=545.2 (M+H); the second eluted isomer Example 7: $^1H$ NMR (400 MHz, $CDCl_3$) δ 9.43 (s, 2H), 8.99 (d, J=2.7 Hz, 1H), 8.44 (s, 2H), 8.09 (s, 1H), 7.57-7.69 (m, 3H), 6.38-6.68 (m, 1H), 5.22 (br t, J=4.6 Hz, 1H), 4.28 (t, J=7.7 Hz, 4H), 4.15-4.23 (m, 2H), 2.43 (q, J=7.7 Hz, 2H), MS=545.1 $[M+H]^+$.

TABLE AAA

The following compounds were prepared using procedures similar to those described above using the appropriate starting materials.

| Example | Structure | Name | $[M + H]^+$ or $[M + Na]^+$ | Chiral Column |
|---|---|---|---|---|
| 8 | 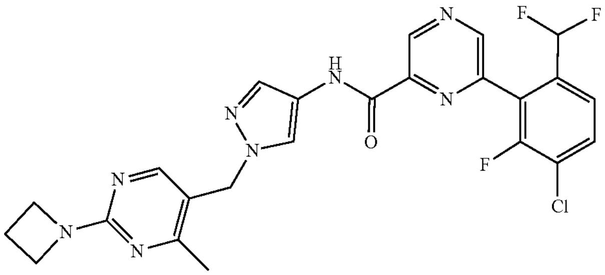 [SMILES: Cc1nc(N2CCC2)ncc1Cn1cc(NC(=O)c2cncc(-c3c(C(F)F)ccc(Cl)c3F)n2)cn1] | N-(1-((2-(Azetidin-1-yl)-4-methylpyrimidin-5-yl)methyl)-1H-pyrazol-4-yl)-6-(3-chloro-6-(difluoromethyl)-2-fluorophenyl)pyrazine-2-carboxamide | Calcd.: 529.1 Found: 529.2 | |

TABLE AAA-continued

The following compounds were prepared using procedures similar to those described above using the appropriate starting materials.

| Example | Structure | Name | [M + H]+ or [M + Na]+ | Chiral Column |
|---|---|---|---|---|
| 9 | 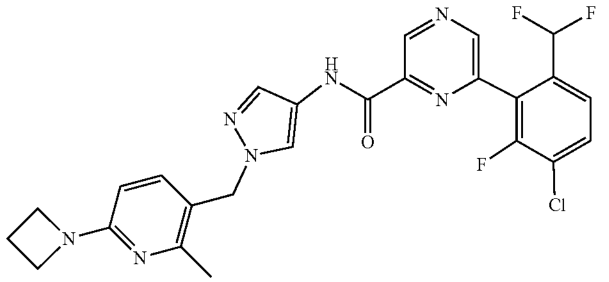 [SMILES: Cc1nc(N2CCC2)ccc1Cn1cc(NC(=O)c2cncc(-c3c(C(F)F)ccc(Cl)c3F)n2)cn1] | N-(1-((6-(Azetidin-1-yl)-2-methylpyridin-3-yl)methyl)-1H-pyrazol-4-yl)-6-(3-chloro-6-(difluoromethyl)-2-fluorophenyl)pyrazine-2-carboxamide | Calcd.: 528.1 Found: 528.4 | |
| 10 | 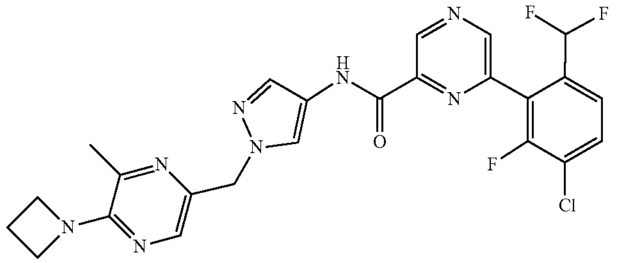 [SMILES: Cc1nc(Cn2cc(NC(=O)c3cncc(-c4c(C(F)F)ccc(Cl)c4F)n3)cn2)cnc1N1CCC1] | N-(1-((5-(Azetidin-1-yl)-6-methylpyrazin-2-yl)methyl)-1H-pyrazol-4-yl)-6-(3-chloro-6-(difluoromethyl)-2-fluorophenyl)pyrazine-2-carboxamide | Calcd.: 529.1 Found: 529.5 | |
| 11 | 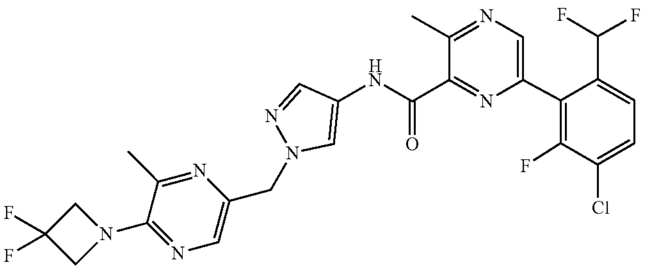 [SMILES: Cc1ncc(-c2c(C(F)F)ccc(Cl)c2F)nc1C(=O)Nc1cnn(Cc2cnc(N3CC(F)(F)C3)c(C)n2)c1] | 6-(3-Chloro-6-(difluoromethyl)-2-fluorophenyl)-N-(1-((5-(3,3-difluoroazetidin-1-yl)-6-methylpyrazin-2-yl)methyl)-1H-pyrazol-4-yl)-3-methylpyrazine-2-carboxamide | Calcd.: 579.1 Found: 579.3 | |
| 12 | 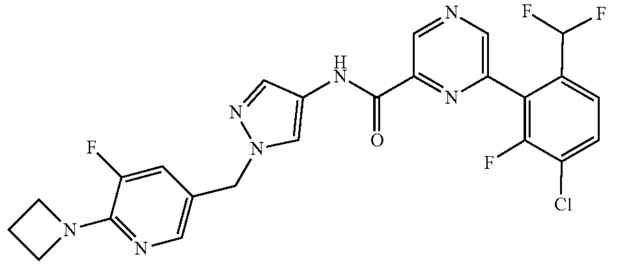 [SMILES: O=C(Nc1cnn(Cc2cnc(N3CCC3)c(F)c2)c1)c1cncc(-c2c(C(F)F)ccc(Cl)c2F)n1] | N-(1-((6-(Azetidin-1-yl)-5-fluoropyridin-3-yl)methyl)-1H-pyrazol-4-yl)-6-(3-chloro-6-(difluoromethyl)-2-fluorophenyl)pyrazine-2-carboxamide | Calcd.: 532.1 Found: 532.3 | |
| 13 | 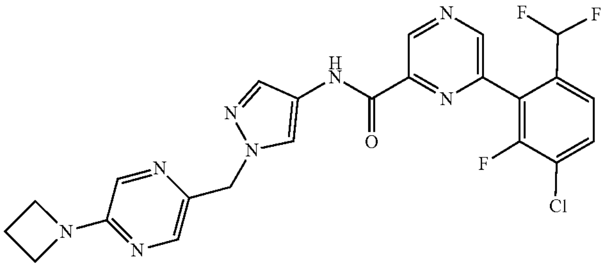 [SMILES: O=C(Nc1cnn(Cc2cnc(N3CCC3)cn2)c1)c1cncc(-c2c(C(F)F)ccc(Cl)c2F)n1] | N-(1-((5-(Azetidin-1-yl)pyrazin-2-yl)methyl)-1H-pyrazol-4-yl)-6-(3-chloro-6-(difluoromethyl)-2-fluorophenyl)pyrazine-2-carboxamide | Calcd.: 515.1 Found: 515.3 | |

TABLE AAA-continued

The following compounds were prepared using procedures similar to those described above using the appropriate starting materials.

| Example | Structure | Name | [M + H]+ or [M + Na]+ | Chiral Column |
|---|---|---|---|---|
| 14 | 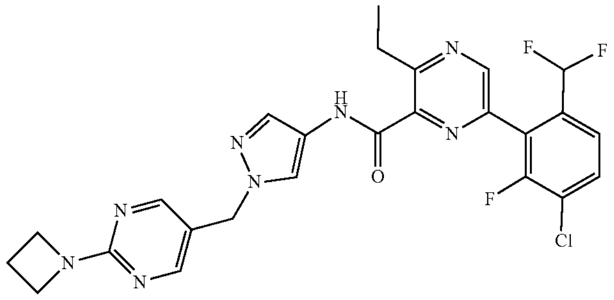 [SMILES: CCc1ncc(-c2c(C(F)F)ccc(Cl)c2F)nc1C(=O)Nc1cnn(Cc2cnc(N3CCC3)nc2)c1] | N-(1-((2-(Azetidin-1-yl)pyrimidin-5-yl)methyl)-1H-pyrazol-4-yl)-6-(3-chloro-6-(difluoromethyl)-2-fluorophenyl)-3-ethylpyrazine-2-carboxamide | Calcd.: 543.2 Found: 543.2 | |
| 15 | 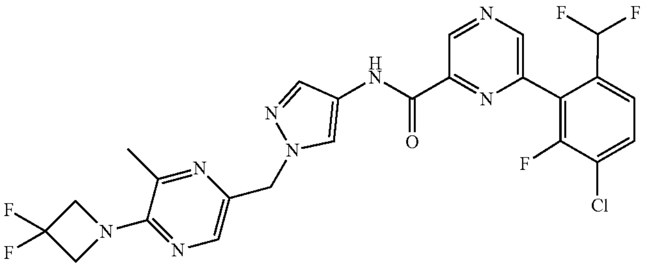 [SMILES: Cc1nc(Cn2cc(NC(=O)c3cncc(-c4c(C(F)F)ccc(Cl)c4F)n3)cn2)cnc1N1CC(F)(F)C1] | 6-(3-Chloro-6-(difluoromethyl)-2-fluorophenyl)-N-(1-((5-(3,3-difluoroazetidin-1-yl)-6-methylpyrazin-2-yl)methyl)-1H-pyrazol-4-yl)pyrazine-2-carboxamide | Calcd.: 565.1 Found: 565 | |
| 16 | 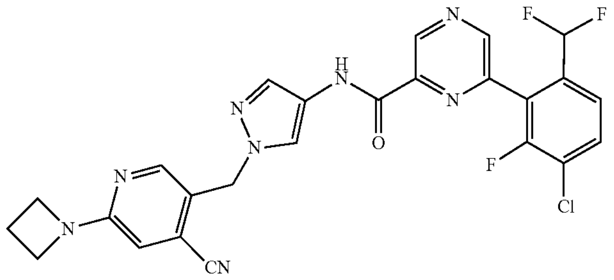 [SMILES: N#Cc1cc(N2CCC2)ncc1Cn1cc(NC(=O)c2cncc(-c3c(C(F)F)ccc(Cl)c3F)n2)cn1] | N-(1-((6-(Azetidin-1-yl)-4-cyanopyridin-3-yl)methyl)-1H-pyrazol-4-yl)-6-(3-chloro-6-(difluoromethyl)-2-fluorophenyl)pyrazine-2-carboxamide | Calcd.: 539.1 Found: 539.1 | |
| 17 | 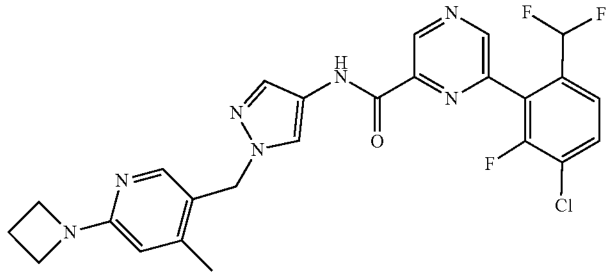 [SMILES: Cc1cc(N2CCC2)ncc1Cn1cc(NC(=O)c2cncc(-c3c(C(F)F)ccc(Cl)c3F)n2)cn1] | N-(1-((6-(Azetidin-1-yl)-4-methylpyridin-3-yl)methyl)-1H-pyrazol-4-yl)-6-(3-chloro-6-(difluoromethyl)-2-fluorophenyl)pyrazine-2-carboxamide | Calcd.: 528.1 Found: 528.4 | |
| 18 | 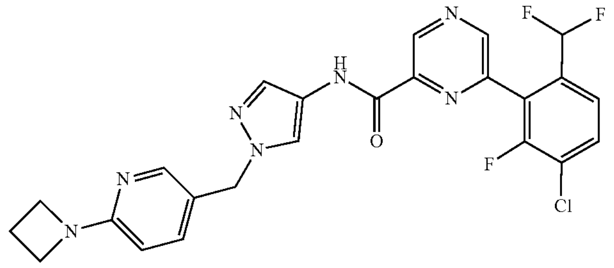 [SMILES: O=C(Nc1cnn(Cc2ccc(N3CCC3)nc2)c1)c1cncc(-c2c(C(F)F)ccc(Cl)c2F)n1] | N-(1-((6-(Azetidin-1-yl)pyridin-3-yl)methyl)-1H-pyrazol-4-yl)-6-(3-chloro-6-(difluoromethyl)-2-fluorophenyl)pyrazine-2-carboxamide | Calcd.: 514.1 Found: 514.3 | |

TABLE AAA-continued

| The following compounds were prepared using procedures similar to those described above using the appropriate starting materials. | | | | |
|---|---|---|---|---|
| Example | Structure | Name | $[M + H]^+$ or $[M + Na]^+$ | Chiral Column |
| 19 | 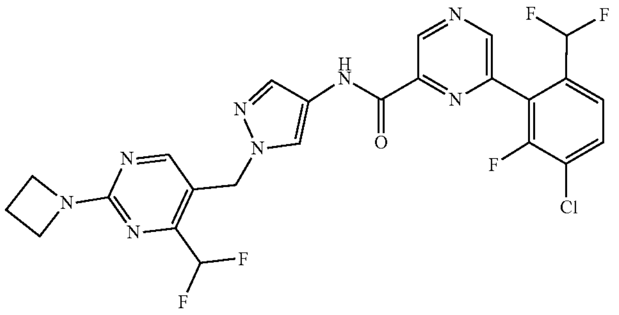 [SMILES: O=C(Nc1cnn(Cc2cnc(N3CCC3)nc2C(F)F)c1)c1cncc(-c2c(C(F)F)ccc(Cl)c2F)n1] | N-(1-((2-(Azetidin-1-yl)-4-(difluoromethyl) pyrimidin-5-yl)methyl)-1H-pyrazol-4-yl)-6-(3-chloro-6-(difluoromethyl)-2-fluorophenyl)pyrazine-2-carboxamide | Calcd.: 565.1 Found: 565.3 | |
| 20 | 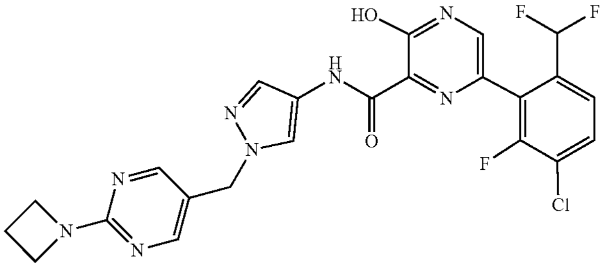 [SMILES: O=C(Nc1cnn(Cc2cnc(N3CCC3)nc2)c1)c1nc(-c2c(C(F)F)ccc(Cl)c2F)cnc1O] | N-(1-((2-(Azetidin-1-yl)pyrimidin-5-yl)methyl)-1H-pyrazol-4-yl)-6-(3-chloro-6-(difluoromethyl)-2-fluorophenyl)-3-hydroxypyrazine-2-carboxamide | Calcd.: 531.1 Found: 531.2 | |
| 21 | 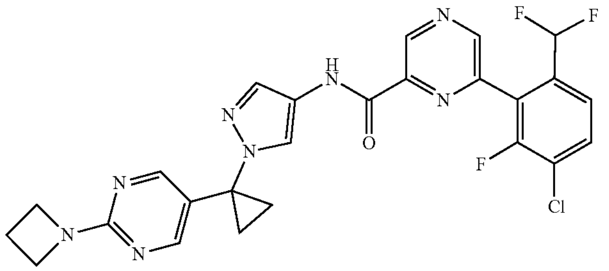 [SMILES: O=C(Nc1cnn(C2(c3cnc(N4CCC4)nc3)CC2)c1)c1cncc(-c2c(C(F)F)ccc(Cl)c2F)n1] | N-(1-(1-(2-(Azetidin-1-yl)pyrimidin-5-yl)cyclopropyl)-1H-pyrazol-4-yl)-6-(3-chloro-6-(difluoromethyl)-2-fluorophenyl)pyrazine-2-carboxamide | Calcd.: 541.1 Found: 541.3 | |
| 22 | 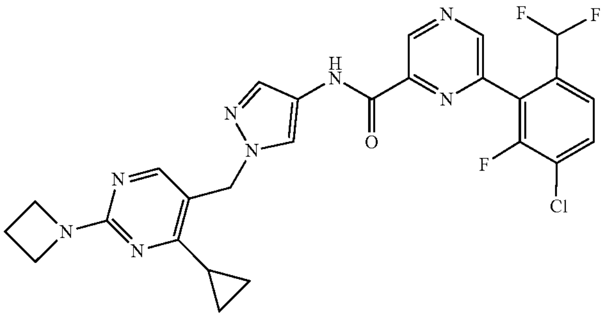 [SMILES: O=C(Nc1cnn(Cc2cnc(N3CCC3)nc2C2CC2)c1)c1cncc(-c2c(C(F)F)ccc(Cl)c2F)n1] | N-(1-((2-(Azetidin-1-yl)-4-cyclopropylpyrimidin-5-yl)methyl)-1H-pyrazol-4-yl)-6-(3-chloro-6-(difluoromethyl)-2-fluorophenyl)pyrazine-2-carboxamide | Calcd.: 555.2 Found: 555.3 | |
| 23 | 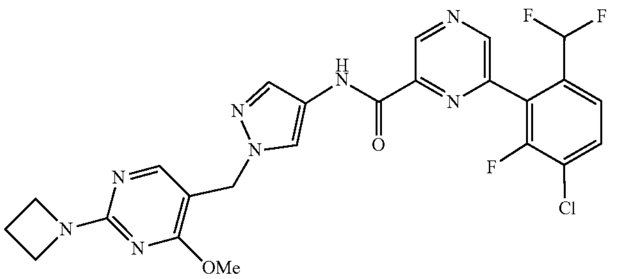 [SMILES: COc1nc(N2CCC2)ncc1Cn1cc(NC(=O)c2cncc(-c3c(C(F)F)ccc(Cl)c3F)n2)cn1] | N-(1-((2-(Azetidin-1-yl)-4-methoxypyrimidin-5-yl)methyl)-1H-pyrazol-4-yl)-6-(3-chloro-6-(difluoromethyl)-2-fluorophenyl)pyrazine-2-carboxamide | Calcd.: 545.1 Found: 545.1 | |

TABLE AAA-continued

The following compounds were prepared using procedures similar to those described above using the appropriate starting materials.

| Example | Structure | Name | $[M + H]^+$ or $[M + Na]^+$ | Chiral Column |
|---|---|---|---|---|
| 24 | 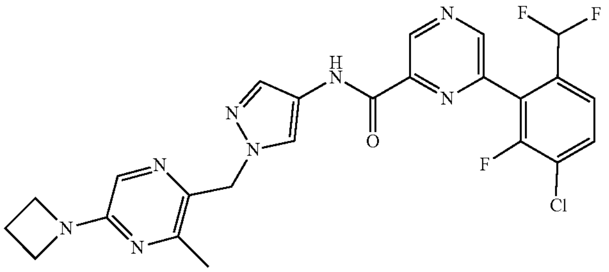 [SMILES: Cc1nc(N2CCC2)cnc1Cn1cc(NC(=O)c2cncc(-c3c(C(F)F)ccc(Cl)c3F)n2)cn1] | N-(1-((5-(Azetidin-1-yl)-3-methylpyrazin-2-yl)methyl)-1H-pyrazol-4-yl)-6-(3-chloro-6-(difluoromethyl)-2-fluorophenyl)pyrazine-2-carboxamide | Calcd.: 529.1 Found: 529.4 | |
| 25 | 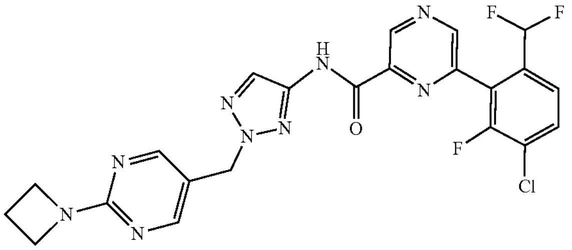 [SMILES: O=C(Nc1cnn(Cc2cnc(N3CCC3)nc2)n1)c1cncc(-c2c(C(F)F)ccc(Cl)c2F)n1] | N-(2-((2-(Azetidin-1-yl)pyrimidin-5-yl)methyl)-2H-1,2,3-triazol-4-yl)-6-(3-chloro-6-(difluoromethyl)-2-fluorophenyl)pyrazine-2-carboxamide | Calcd.: 516.1 Found: 516.2 | |
| 26 | 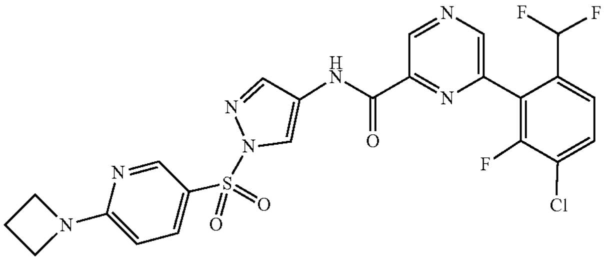 [SMILES: O=C(Nc1cnn(S(=O)(=O)c2ccc(N3CCC3)nc2)c1)c1cncc(-c2c(C(F)F)ccc(Cl)c2F)n1] | N-(1-((6-(Azetidin-1-yl)pyridin-3-yl)sulfonyl)-1H-pyrazol-4-yl)-6-(3-chloro-6-(difluoromethyl)-2-fluorophenyl)pyrazine-2-carboxamide | Calcd.: 564.1 Found: 564.2 | |
| 27 | 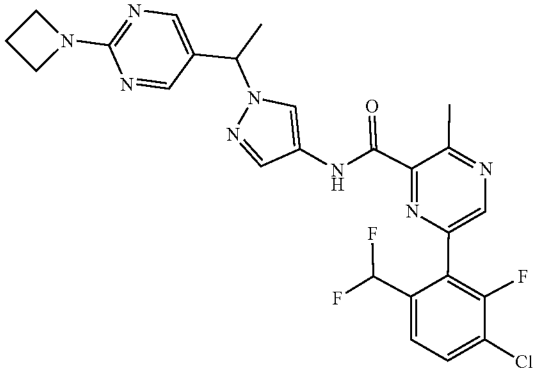 [SMILES: Cc1ncc(-c2c(C(F)F)ccc(Cl)c2F)nc1C(=O)Nc1cnn(C(C)c2cnc(N3CCC3)nc2)c1] | (S or R)-N-(1-(1-(2-(azetidin-1-yl)pyrimidin-5-yl)ethyl)-1H-pyrazol-4-yl)-6-(3-chloro-6-(difluoromethyl)-2-fluorophenyl)-3-methylpyrazine-2-carboxamide | Calcd.: 543.2 Found: 542.9 | DAICEL CHIRALCEL OD-H |

TABLE AAA-continued

The following compounds were prepared using procedures similar to those described above using the appropriate starting materials.

| Example | Structure | Name | [M + H]+ or [M + Na]+ | Chiral Column |
|---|---|---|---|---|
| 28 | 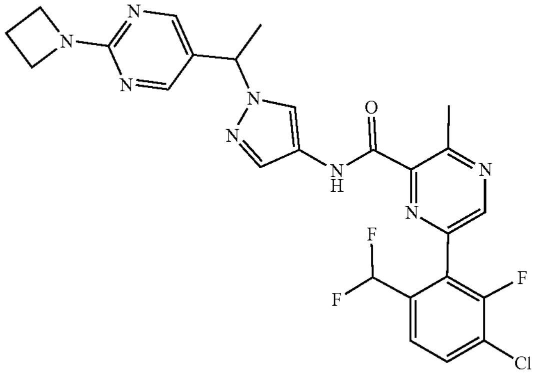 [SMILES: Cc1ncc(-c2c(C(F)F)ccc(Cl)c2F)nc1C(=O)Nc1cnn(C(C)c2cnc(N3CCC3)nc2)c1] | (R or S)-N-(1-(1-(2-(azetidin-1-yl)pyrimidin-5-yl)ethyl)-1H-pyrazol-4-yl)-6-(3-chloro-6-(difluoromethyl)-2-fluorophenyl)-3-methylpyrazine-2-carboxamide | Calcd.: 543.2 Found: 542.9 | DAICEL CHIRALCEL OD-H |
| 29 | 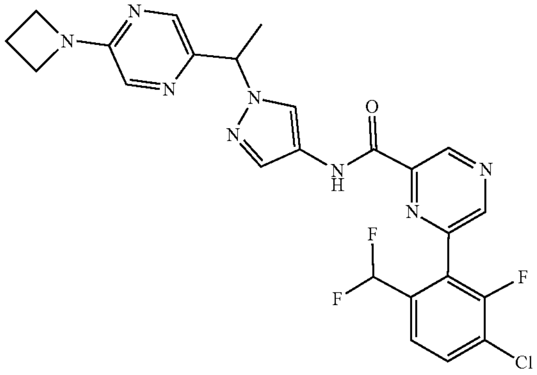 [SMILES: CC(c1cnc(N2CCC2)cn1)n1cc(NC(=O)c2cncc(-c3c(C(F)F)ccc(Cl)c3F)n2)cn1] | (S or R)-N-(1-(1-(5-(azetidin-1-yl)pyrazin-2-yl)ethyl)-1H-pyrazol-4-yl)-6-(3-chloro-6-(difluoromethyl)-2-fluorophenyl)pyrazine-2-carboxamide | Calcd.: 529.1 Found: 529.4 | DAICEL CHIRALCEL OD-H |
| 30 | 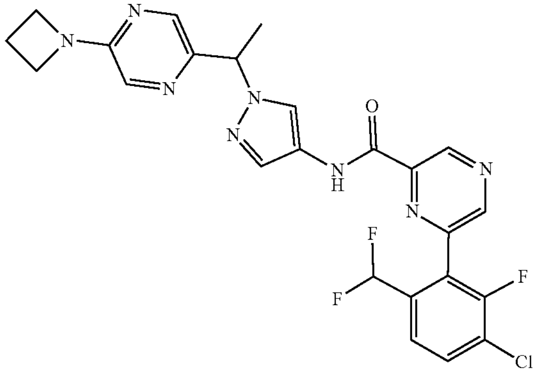 [SMILES: CC(c1cnc(N2CCC2)cn1)n1cc(NC(=O)c2cncc(-c3c(C(F)F)ccc(Cl)c3F)n2)cn1] | (R or S)-N-(1-(1-(5-(azetidin-1-yl)pyrazin-2-yl)ethyl)-1H-pyrazol-4-yl)-6-(3-chloro-6-(difluoromethyl)-2-fluorophenyl)pyrazine-2-carboxamide | Calcd.: 529.1 Found: 529.4 | DAICEL CHIRALCEL OD-H |
| 31 | 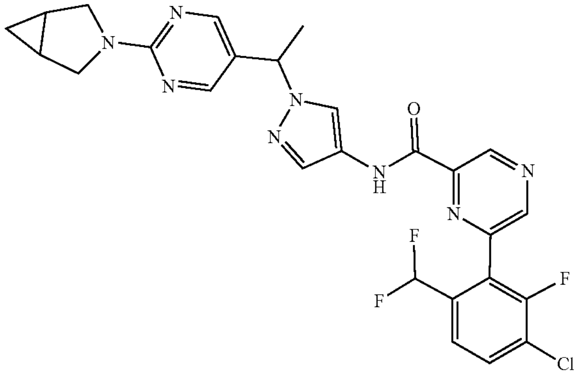 [SMILES: CC(c1cnc(N2CC3CC3C2)nc1)n1cc(NC(=O)c2cncc(-c3c(C(F)F)ccc(Cl)c3F)n2)cn1] | N-(1-((1S or 1R)-1-(2-(3-azabicyclo[3.1.0]hexan-3-yl)pyrimidin-5-yl)ethyl)-1H-pyrazol-4-yl)-6-(3-chloro-6-(difluoromethyl)-2-fluorophenyl)pyrazine-2-carboxamide | Calcd.: 555.2 Found: 555.0 | DAICEL YMC CHIRAL Amylose-C |

TABLE AAA-continued

| The following compounds were prepared using procedures similar to those described above using the appropriate starting materials. | | | | |
|---|---|---|---|---|
| Example | Structure | Name | $[M + H]^+$ or $[M + Na]^+$ | Chiral Column |
| 32 | 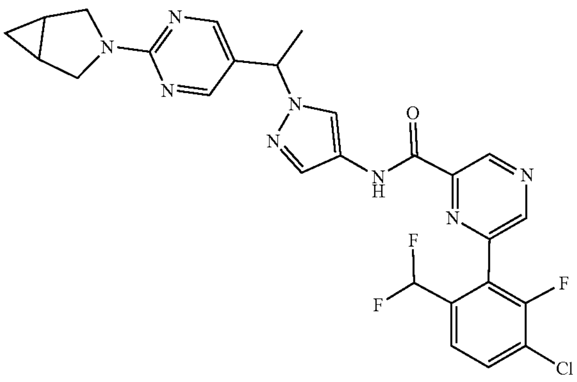 [SMILES: CC(c1cnc(N2CC3CC3C2)nc1)n1cc(NC(=O)c2cncc(-c3c(C(F)F)ccc(Cl)c3F)n2)cn1] | N-(1-((1R or 1S)-1-(2-(3-azabicyclo[3.1.0]hexan-3-yl)pyrimidin-5-yl)ethyl)-1H-pyrazol-4-yl)-6-(3-chloro-6-(difluoromethyl)-2-fluorophenyl)pyrazine-2-carboxamide | Calcd.: 555.2 Found: 555.0 | DAICEL YMC CHIRAL Amylose-C |
| 33 | 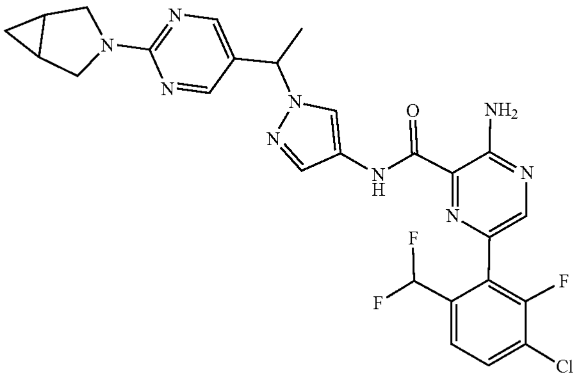 [SMILES: CC(c1cnc(N2CC3CC3C2)nc1)n1cc(NC(=O)c2nc(-c3c(C(F)F)ccc(Cl)c3F)cnc2N)cn1] | N-(1-((1S or 1R)-1-(2-(3-azabicyclo[3.1.0]hexan-3-yl)pyrimidin-5-yl)ethyl)-1H-pyrazol-4-yl)-3-amino-6-(3-chloro-6-(difluoromethyl)-2-fluorophenyl)pyrazine-2-carboxamide | Calcd.: 570.2 Found: 570.4 | REGIS (s,s) WHELK-O1 |
| 34 | 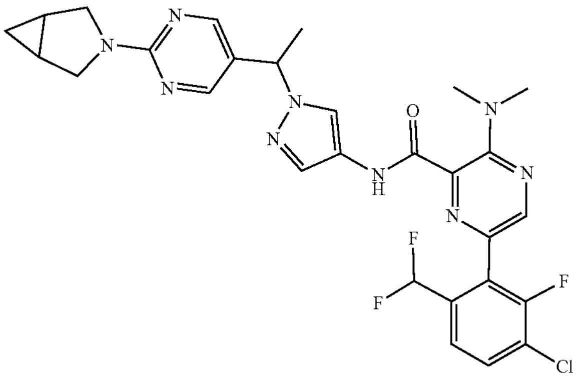 [SMILES: CC(c1cnc(N2CC3CC3C2)nc1)n1cc(NC(=O)c2nc(-c3c(C(F)F)ccc(Cl)c3F)cnc2N(C)C)cn1] | N-(1-((1R or 1S)-1-(2-(3-azabicyclo[3.1.0]hexan-3-yl)pyrimidin-5-yl)ethyl)-1H-pyrazol-4-yl)-6-(3-chloro-6-(difluoromethyl)-2-fluorophenyl)-3-(dimethylamino)pyrazine-2-carboxamide | Calcd.: 598.2 Found: 598.4 | DAICEL CHIRALCEL OD-H |

TABLE AAA-continued

| The following compounds were prepared using procedures similar to those described above using the appropriate starting materials. | | | | |
|---|---|---|---|---|
| Example | Structure | Name | [M + H]+ or [M + Na]+ | Chiral Column |
| 35 | 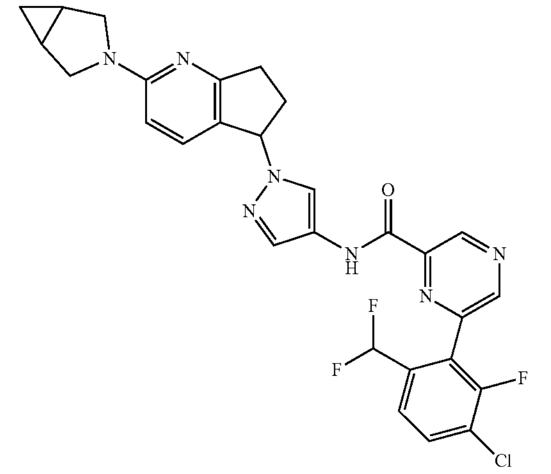 [SMILES: O=C(Nc1cnn(C2CCc3nc(N4CC5CC5C4)ccc32)c1)c1cncc(-c2c(C(F)F)ccc(Cl)c2F)n1] | (S or R)-N-(1-(2-(azetidin-1-yl)-6,7-dihydro-5H-cyclopenta[b]pyridin-5-yl)-1H-pyrazol-4-yl)-6-(3-chloro-6-(difluoromethyl)-2-fluorophenyl)pyrazine-2-carboxamide | Calcd.: 540.1 Found: 540.1 | AS-H |
| 36 | 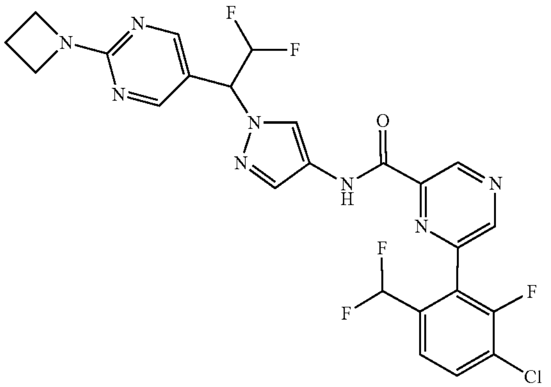 [SMILES: O=C(Nc1cnn(C(c2cnc(N3CCC3)nc2)C(F)F)c1)c1cncc(-c2c(C(F)F)ccc(Cl)c2F)n1] | (S or R)-N-(1-(1-(2-(azetidin-1-yl)pyrimidin-5-yl)-2,2-difluoroethyl)-1H-pyrazol-4-yl)-6-(3-chloro-6-(difluoromethyl)-2-fluorophenyl)pyrazine-2-carboxamide | Calcd.: 565.1 Found: 565.1 | DAICEL CHIRALPAK AD-H |
| 37 | 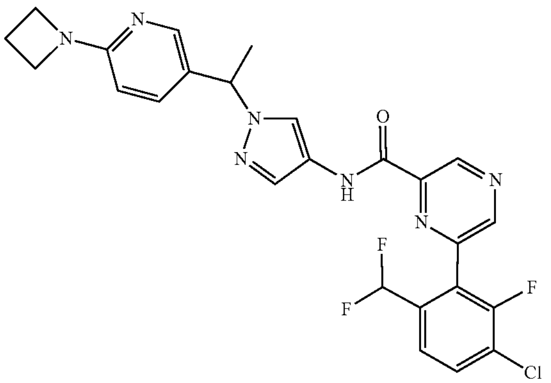 [SMILES: CC(c1ccc(N2CCC2)nc1)n1cc(NC(=O)c2cncc(-c3c(C(F)F)ccc(Cl)c3F)n2)cn1] | (S or R)-N-(1-(1-(6-(azetidin-1-yl)pyridin-3-yl)ethyl)-1H-pyrazol-4-yl)-6-(3-chloro-6-(difluoromethyl)-2-fluorophenyl)pyrazine-2-carboxamide | Calcd.: 528.1 Found: 528.3 | DAICEL CHIRALPAK AD-H |

TABLE AAA-continued

The following compounds were prepared using procedures similar to those described above using the appropriate starting materials.

| Example | Structure | Name | [M + H]+ or [M + Na]+ | Chiral Column |
|---|---|---|---|---|
| 38 | 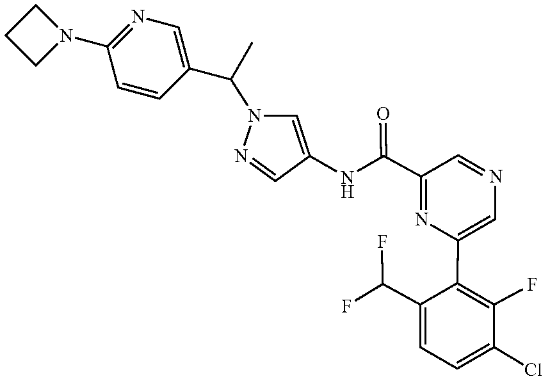 [SMILES: CC(c1ccc(N2CCC2)nc1)n1cc(NC(=O)c2cncc(-c3c(C(F)F)ccc(Cl)c3F)n2)cn1] | (R or S)-N-(1-(1-(6-(azetidin-1-yl)pyridin-3-yl)ethyl)-1H-pyrazol-4-yl)-6-(3-chloro-6-(difluoromethyl)-2-fluorophenyl)pyrazine-2-carboxamide | Calcd.: 528.1 Found: 528.3 | DAICEL CHIRALPAK AD-H |
| 39 | 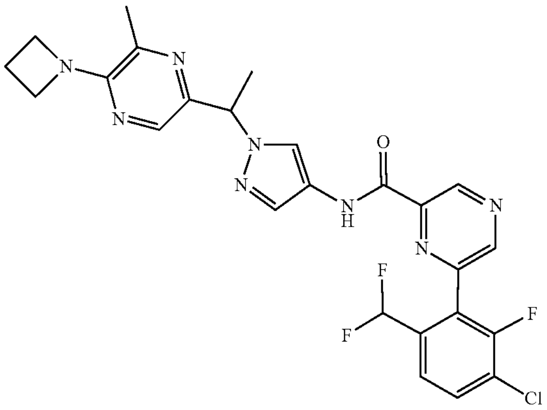 [SMILES: Cc1nc(C(C)n2cc(NC(=O)c3cncc(-c4c(C(F)F)ccc(Cl)c4F)n3)cn2)cnc1N1CCC1] | (S or R)-N-(1-(1-(5-(azetidin-1-yl)-6-methylpyrazin-2-yl)ethyl)-1H-pyrazol-4-yl)-6-(3-chloro-6-(difluoromethyl)-2-fluorophenyl)pyrazine-2-carboxamide | Calcd.: 543.2 Found: 543.0 | WHELK-01 (R,R) |
| 40 | 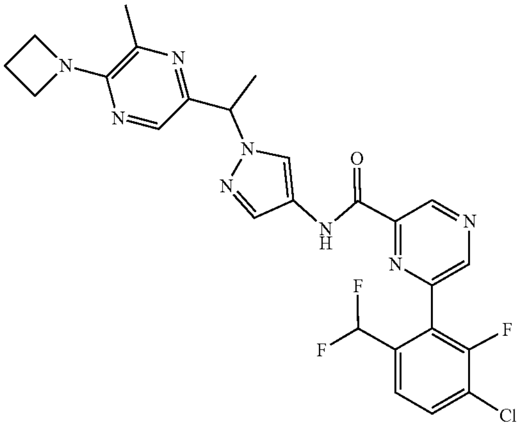 [SMILES: Cc1nc(C(C)n2cc(NC(=O)c3cncc(-c4c(C(F)F)ccc(Cl)c4F)n3)cn2)cnc1N1CCC1] | (R or S)-N-(1-(1-(5-(azetidin-1-yl)-6-methylpyrazin-2-yl)ethyl)-1H-pyrazol-4-yl)-6-(3-chloro-6-(difluoromethyl)-2-fluorophenyl)pyrazine-2-carboxamide | Calcd.: 543.2 Found: 543.0 | WHELK-01 (R,R) |

TABLE AAA-continued

The following compounds were prepared using procedures similar to those described above using the appropriate starting materials.

| Example | Structure | Name | [M + H]+ or [M + Na]+ | Chiral Column |
|---|---|---|---|---|
| 41 | 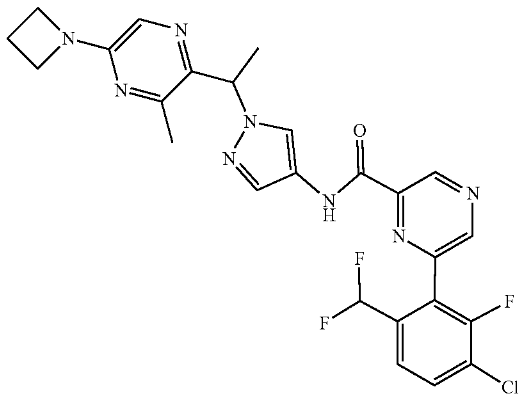 [SMILES: Cc1nc(N2CCC2)cnc1C(C)n1cc(NC(=O)c2cncc(-c3c(C(F)F)ccc(Cl)c3F)n2)cn1] | (S or R)-N-(1-(1-(5-(azetidin-1-yl)-3-methylpyrazin-2-yl)ethyl)-1H-pyrazol-4-yl)-6-(3-chloro-6-(difluoromethyl)-2-fluorophenyl)pyrazine-2-carboxamide | Calcd.: 543.2 Found: 543 | OD-H |
| 42 | 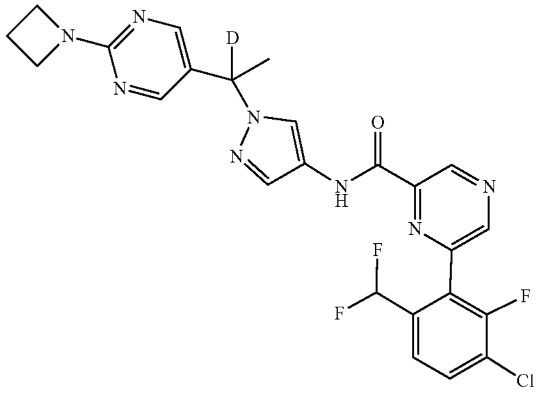 [SMILES: [2H]C(C)(c1cnc(N2CCC2)nc1)n1cc(NC(=O)c2cncc(-c3c(C(F)F)ccc(Cl)c3F)n2)cn1] | (S or R)-N-(1-(1-(2-(azetidin-1-yl)pyrimidin-5-yl)ethyl-1-d)-1H-pyrazol-4-yl)-6-(3-chloro-6-(difluoromethyl)-2-fluorophenyl)pyrazine-2-carboxamide | Calcd.: 530.2 Found: 530.0 | WHELK 01 (R,R) |
| 43 | 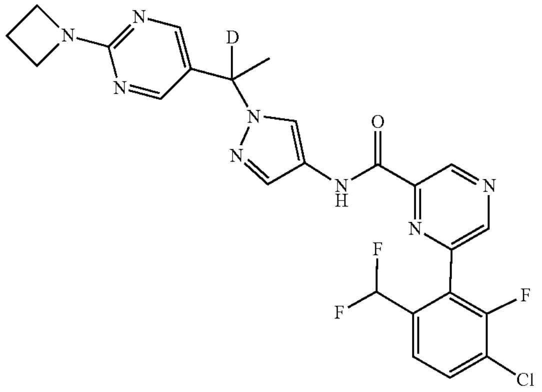 [SMILES: [2H]C(C)(c1cnc(N2CCC2)nc1)n1cc(NC(=O)c2cncc(-c3c(C(F)F)ccc(Cl)c3F)n2)cn1] | (R or S)-N-(1-(1-(2-(azetidin-1-yl)pyrimidin-5-yl)ethyl-1-d)-1H-pyrazol-4-yl)-6-(3-chloro-6-(difluoromethyl)-2-fluorophenyl)pyrazine-2-carboxamide | Calcd.: 530.2 Found: 530.0 | WHELK 01 (R,R) |

TABLE AAA-continued

The following compounds were prepared using procedures similar to those described above using the appropriate starting materials.

| Example | Structure | Name | [M + H]+ or [M + Na]+ | Chiral Column |
|---|---|---|---|---|
| 44 | 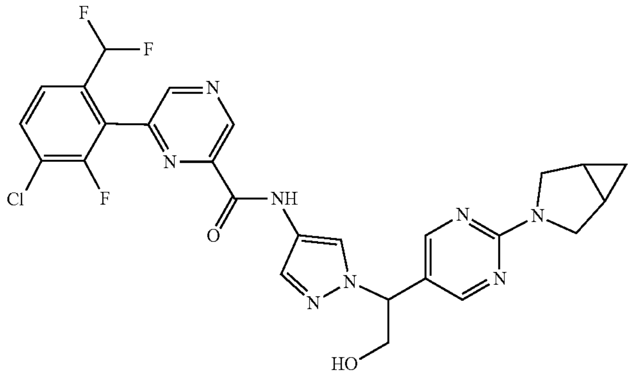 [SMILES: O=C(Nc1cnn(C(CO)c2cnc(N3CC4CC4C3)nc2)c1)c1cncc(-c2c(C(F)F)ccc(Cl)c2F)n1] | N-(1-((S or R)-1-(2-(3-Azabicyclo[3.1.0]hexan-3-yl)pyrimidin-5-yl)-2-hydroxyethyl)-1H-pyrazol-4-yl)-6-(3-chloro-6-(difluoromethyl)-2-fluorophenyl)pyrazine-2-carboxamide | Calcd.: 571.2 Found: 571.2 | DAICEL CHIRALPAK IC |
| 45 | 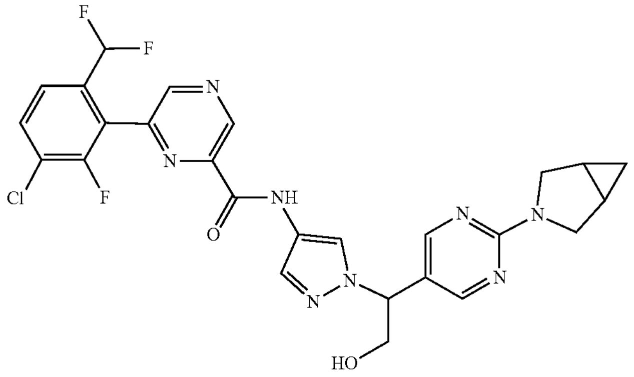 [SMILES: O=C(Nc1cnn(C(CO)c2cnc(N3CC4CC4C3)nc2)c1)c1cncc(-c2c(C(F)F)ccc(Cl)c2F)n1] | N-(1-((R or S)-1-(2-(3-Azabicyclo[3.1.0]hexan-3-yl)pyrimidin-5-yl)-2-hydroxyethyl)-1H-pyrazol-4-yl)-6-(3-chloro-6-(difluoromethyl)-2-fluorophenyl)pyrazine-2-carboxamide | Calcd.: 571.2 Found: 571.2 | DAICEL CHIRALPAK IC |
| 46 | 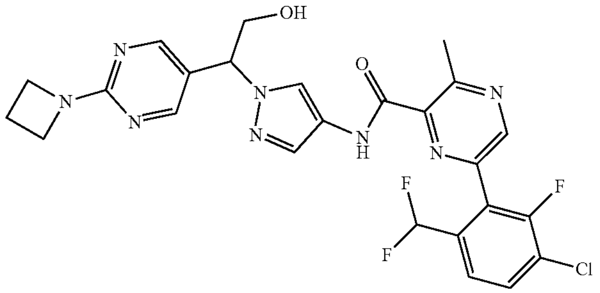 [SMILES: Cc1ncc(-c2c(C(F)F)ccc(Cl)c2F)nc1C(=O)Nc1cnn(C(CO)c2cnc(N3CCC3)nc2)c1] | (S or R)-N-(1-(1-(2-(Azetidin-1-yl)pyrimidin-5-yl)-2-hydroxyethyl)-1H-pyrazol-4-yl)-6-(3-chloro-6-(difluoromethyl)-2-fluorophenyl)-3-methylpyrazine-2-carboxamide | Calcd.: 559.2 Found: 559.2 | DAICEL CHIRALCEL OD-H |
| 47 | 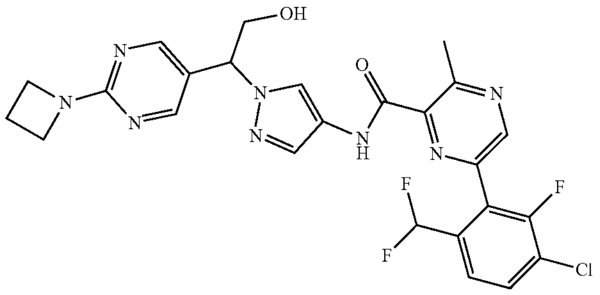 [SMILES: Cc1ncc(-c2c(C(F)F)ccc(Cl)c2F)nc1C(=O)Nc1cnn(C(CO)c2cnc(N3CCC3)nc2)c1] | (R or S)-N-(1-(1-(2-(Azetidin-1-yl)pyrimidin-5-yl)-2-hydroxyethyl)-1H-pyrazol-4-yl)-6-(3-chloro-6-(difluoromethyl)-2-fluorophenyl)-3-methylpyrazine-2-carboxamide | Calcd.: 559.2 Found: 559.2 | DAICEL CHIRALCEL OD-H |

TABLE AAA-continued

The following compounds were prepared using procedures similar to those described above using the appropriate starting materials.

| Example | Structure | Name | [M + H]+ or [M + Na]+ | Chiral Column |
| --- | --- | --- | --- | --- |
| 48 | 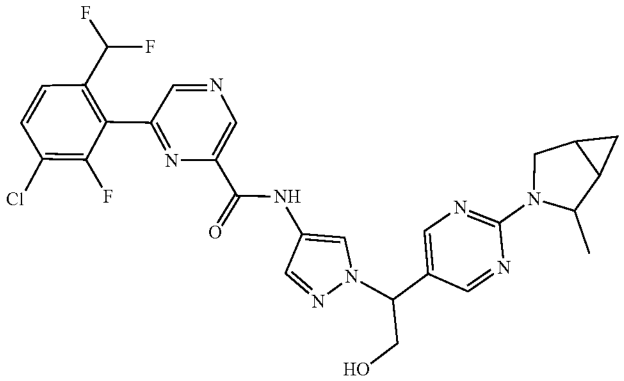 [SMILES: CC1C2CC2CN1c1ncc(C(CO)n2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((S or R)-2-hydroxy-1-(2-((1S,2R,5R or 1R, 2S, 5S)-2-methyl-3-azabicyclo[3.1.0]hexan-3-yl)pyrimidin-5-yl)ethyl)-1H-pyrazol-4-yl)pyrazine-2-carboxamide | Calcd.: 585.2 Found: 585.0 | DAICEL CHIRALPAK AD |
| 49 | 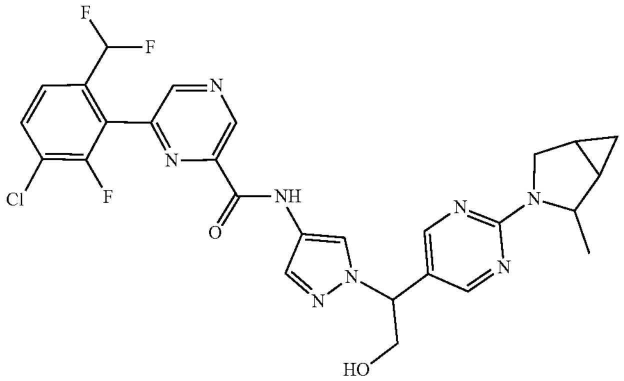 [SMILES: CC1C2CC2CN1c1ncc(C(CO)n2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((R or S)-2-hydroxy-1-(2-((1S,2R,5R or 1R,2S, 5S)-2-methyl-3-azabicyclo[3.1.0]hexan-3-yl)pyrimidin-5-yl)ethyl)-1H-pyrazol-4-yl)pyrazine-2-carboxamide | Calcd.: 585.2 Found: 585.0 | DAICEL CHIRALPAK AD |
| 50 | 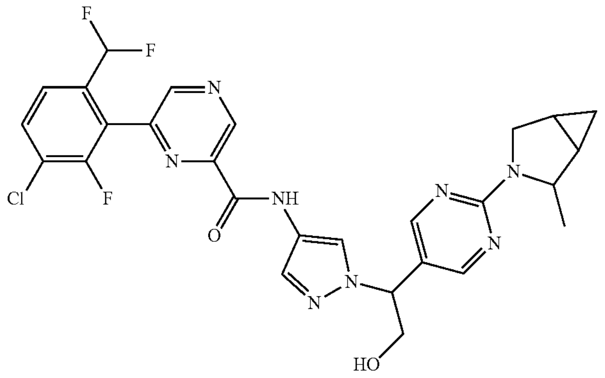 [SMILES: CC1C2CC2CN1c1ncc(C(CO)n2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((S or R)-2-hydroxy-1-(2-((1R,2S,5S or 1S,2R, 5R)-2-methyl-3-azabicyclo[3.1.0]hexan-3-yl)pyrimidin-5-yl)ethyl)-1H-pyrazol-4-yl)pyrazine-2-carboxamide | Calcd.: 585.2 Found: 585.2 | DAICEL CHIRALPAK AD |
| 51 | 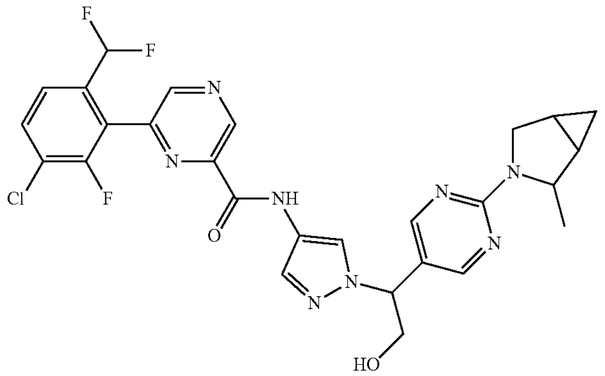 [SMILES: CC1C2CC2CN1c1ncc(C(CO)n2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((R or S)-2-hydroxy-1-(2-((1R,2S,5S or 1S,2R, 5R)-2-methyl-3-azabicyclo[3.1.0]hexan-3-yl)pyrimidin-5-yl)ethyl)-1H-pyrazol-4-yl)pyrazine-2-carboxamide | Calcd.: 585.2 Found: 585.1 | Phenomenex-Cellulose-2 |

Example 52

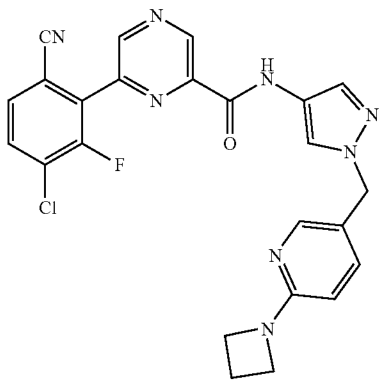 [SMILES: N#Cc1ccc(Cl)c(F)c1-c1cncc(C(=O)Nc2cnn(Cc3ccc(N4CCC4)nc3)c2)n1]

N-(1-((6-(Azetidin-1-yl)pyridin-3-yl)methyl)-1H-pyrazol-4-yl)-6-(3-chloro-6-cyano-2-fluorophenyl)pyrazine-2-carboxamide (Scheme AAB)

Step 1. Methyl 6-(3-chloro-6-cyano-2-fluorophenyl)pyrazine-2-carboxylate: To a solution of 4-chloro-3-fluoro-2-iodobenzonitrile (500 mg, 1.78 mmol) in 1,4-dioxane (10 mL) were added methyl 6-(trimethylstannyl)pyrazine-2-carboxylate (1.07 g, 3.55 mmol), tris(dibenzylideneacetone) dipalladium(0) (163 mg, 0.178 mmol) and 1,1'-bis(di-tert-butylphosphino)ferrocene (84 mg, 0.18 mmol) in a glove box. The resulting mixture was heated at 120° C. for 12 h under $N_2$. The reaction was cooled to rt, concentrated and purified by silica gel chromatography (EtOAc/hexanes) to give the title compound. MS=291.9 $[M+H]^+$.

Step 2. N-(1-((6-(Azetidin-1-yl)pyridin-3-yl)methyl)-1H-pyrazol-4-yl)-6-(3-chloro-6-cyano-2-fluorophenyl)pyrazine-2-carboxamide: To a solution of 1-((6-(azetidin-1-yl) pyridin-3-yl)methyl)-1H-pyrazol-4-amine (79 mg, 0.34 mmol) in toluene (5 mL) was added trimethylaluminum (0.21 mL, 0.43 mmol, 2M in toluene) at rt. After 10 min, a solution of 1-((6-(azetidin-1-yl)pyridin-3-yl)methyl)-1H-pyrazol-4-amine (79 mg, 0.34 mmol) in DCM (2 mL) was added dropwise, and the resulting mixture was heated to 80° C. for 12 h. The reaction was concentrated and the resulting crude residue was purified by reversed-phase preparatory-HPLC (C18 stationary phase, water-ACN (0.05% TFA) to give the title compound. $^1$H NMR (500 MHz, $CD_3OD$) δ 9.45 (s, 1H), 9.28 (d, J=2.9 Hz, 1H), 8.34 (s, 1H), 7.92-7.96 (m, 1H), 7.85-7.90 (m, 3H), 7.80 (s, 1H), 6.82 (d, J=9.3 Hz, 1H), 5.30 (s, 2H), 4.34 (t, J=7.7 Hz, 4H), 2.59 (q, J=7.7 Hz, 2H). MS=489.1 $[M+H]^+$.

TABLE AAB

The following compound was prepared using procedures similar to those described above using the appropriate starting materials.

| Example | Structure | Name | $[M + H]^+$ |
|---|---|---|---|
| 53 | 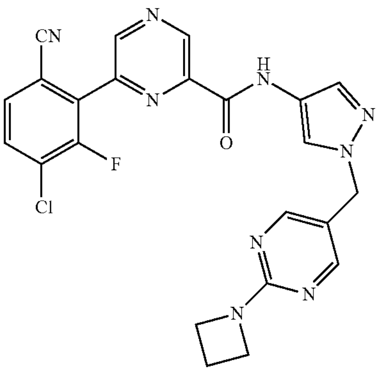 [SMILES: N#Cc1ccc(Cl)c(F)c1-c1cncc(C(=O)Nc2cnn(Cc3cnc(N4CCC4)nc3)c2)n1] | N-(1-((2-(Azetidin-1-yl)pyrimidin-5-yl)methyl)-1H-pyrazol-4-yl)-6-(3-chloro-6-cyano-2-fluorophenyl)pyrazine-2-carboxamide | Calcd.: 490.1 Found: 490.1 |

Examples 54 and 55

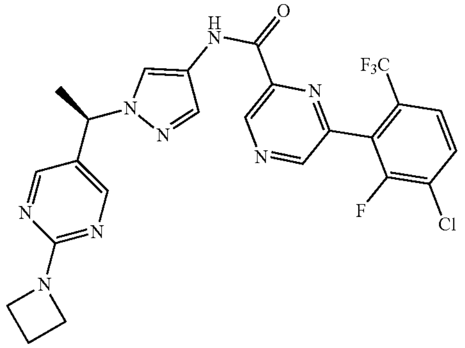

and

-continued

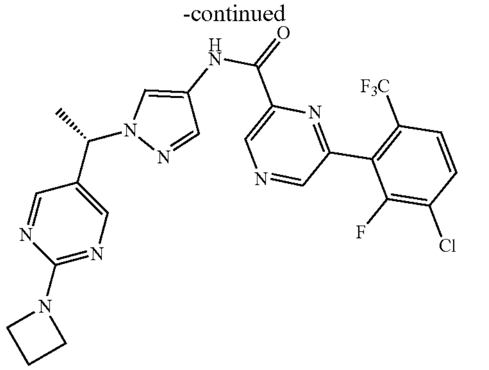

(R)—N-(1-(1-(2-(Azetidin-1-yl)pyrimidin-5-yl)ethyl)-1H-pyrazol-4-yl)-6-(3-chloro-2-fluoro-6-(trifluoromethyl)phenyl)pyrazine-2-carboxamide and (S)—N-(1-(1-(2-(Azetidin-1-yl)pyrimidin-5-yl)ethyl)-1H-pyrazol-4-yl)-6-(3-chloro-2-fluoro-6-(trifluoromethyl)phenyl)pyrazine-2-carboxamide (Scheme AAC)

Step 1. N-(1-(1-(2-(Azetidin-1-yl)pyrimidin-5-yl)ethyl)-1H-pyrazol-4-yl)-6-(trimethylstannyl)-pyrazine-2-carboxamide: A solution of N-(1-(1-(2-(azetidin-1-yl)pyrimidin-5-yl)ethyl)-1H-pyrazol-4-yl)-6-bromopyrazine-2-carboxamide (1.00 g, 2.33 mmol), 1,1,1,2,2,2-hexamethyldistannane (1.09 g, 3.33 mmol) and tetrakis(triphenylphosphine)palladium(0) (135 mg, 0.116 mmol) in toluene (20 mL) was heated at 80° C. for 16 h under an $N_2$ atmosphere. The reaction was cooled to rt and concentrated to afford a crude residue that was purified by silica gel chromatography (petroleum ether) to give the title compound. MS=515.1 $[M+H]^+$.

Step 2. (R)—N-(1-(1-(2-(Azetidin-1-yl)pyrimidin-5-yl)ethyl)-1H-pyrazol-4-yl)-6-(3-chloro-2-fluoro-6-(trifluoromethyl)phenyl)pyrazine-2-carboxamide and (S)—N-(1-(1-(2-(Azetidin-1-yl)pyrimidin-5-yl)ethyl)-1H-pyrazol-4-yl)-6-(3-chloro-2-fluoro-6-(trifluoromethyl)phenyl)pyrazine-2-carboxamide: To a solution of 1-chloro-2-fluoro-3-iodo-4-(trifluoromethyl)benzene (60 mg, 0.19 mmol) in 1,4-dioxane (2 mL) was added N-(1-(1-(2-(azetidin-1-yl)pyrimidin-5-yl)ethyl)-1H-pyrazol-4-yl)-6-(trimethyl-stannyl)pyrazine-2-carboxamide (100 mg, 0.175 mmol), tris(dibenzylideneacetone)dipalladium(0) (16 mg, 0.018 mmol) and 1,1'-bis(di-tert-butylphosphino)ferrocene (8.3 mg, 0.018 mmol), and the resulting mixture was heated to 110° C. for 15 h under an $N_2$ atmosphere. The reaction was cooled to rt, filtered, concentrated to afford a crude residue that was purified by reversed-phase preparatory-HPLC (C18 stationary phase, water-ACN (0.05% $NH_3$) to yield a racemic mixture that was separated by chiral chromatography (SFC, DAICEL CHIRALCEL OD-H; 0.1% $NH_3H_2O$-EtOH, Begin B 30%, End B 30%) to give the title compounds. The faster-eluting isomer Example 54: $^1$H NMR (400 MHz, $CDCl_3$) δ 9.51 (s, 1H), 9.43 (s, 1H), 8.89 (s, 1H), 8.26 (s, 2H), 8.14 (s, 1H), 7.70-7.77 (m, 1H), 7.62-7.68 (m, 1H), 7.58 (s, 1H), 5.36 (q, J 7.1 Hz, 1H), 4.15 (t, J 7.6 Hz, 4H), 2.38 (quint, J 7.5 Hz, 2H), 1.89 (d, J 7.1 Hz, 3H), MS=547.2 $[M+H]^+$; the slower-eluting isomer Example 55: $^1$H NMR (400 MHz, $CDCl_3$) δ 9.52 (br s, 1H), 9.41 (br s, 1H), 8.91 (br s, 1H), 8.35 (br s, 2H), 8.12-8.23 (m, 1H), 7.75 (br t, J 7.2 Hz, 1H), 7.57-7.70 (m, 2H), 5.40 (br d, J 6.1 Hz, 1H), 4.16-4.31 (m, 4H), 2.44 (br d, J 6.8 Hz, 2H), 1.91 (br d, J 5.4 Hz, 3H), MS=547.2 $[M+H]^+$.

TABLE AAC

The following compounds were prepared using procedures similar to those described above using the appropriate starting materials.

| Example | Structure | Name | $[M + H]^+$ or $[M + Na]^+$ | Chiral Column |
|---|---|---|---|---|
| 56 | 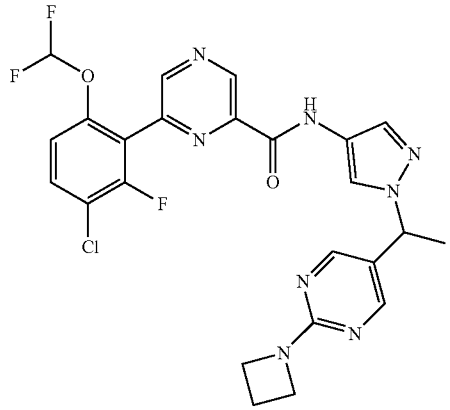 [SMILES: CC(c1cnc(N2CCC2)nc1)n1cc(NC(=O)c2cncc(-c3c(OC(F)F)ccc(Cl)c3F)n2)cn1] | (R or S)-N-(1-(1-(2-(Azetidin-1-yl)pyrimidin-5-yl)ethyl)-1H-pyrazol-4-yl)-6-(3-chloro-6-(difluoromethoxy)-2-fluorophenyl)pyrazine-2-carboxamide | Calcd.: 545.1 Found: 545.2 | DAICEL CHIRALCEL OD-H |

TABLE AAC-continued

The following compounds were prepared using procedures similar to those described above using the appropriate starting materials.

| Example | Structure | Name | [M + H]+ or [M + Na]+ | Chiral Column |
|---|---|---|---|---|
| 57 | 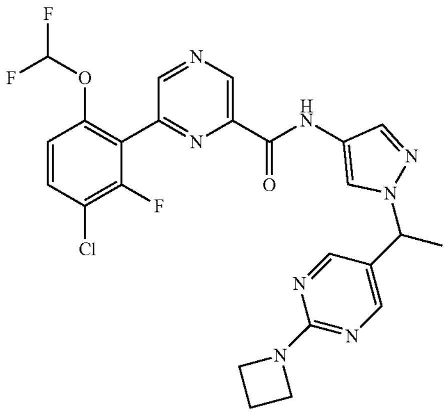 [SMILES: CC(c1cnc(N2CCC2)nc1)n1cc(NC(=O)c2cncc(-c3c(OC(F)F)ccc(Cl)c3F)n2)cn1] | (S or R)-N-(1-(1-(2-(Azetidin-1-yl)pyrimidin-5-yl)ethyl)-1H-pyrazol-4-yl)-6-(3-chloro-6-(difluoromethoxy)-2-fluorophenyl)pyrazine-2-carboxamide | Calcd.: 545.1 Found: 545.2 | DAICEL CHIRALCEL OD-H |
| 58 | 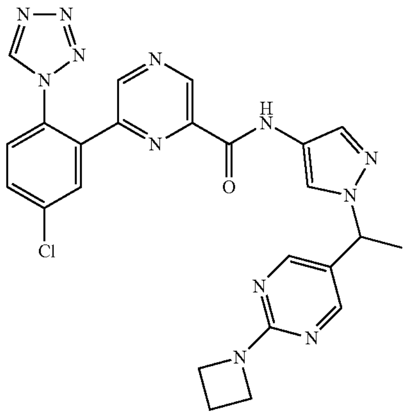 [SMILES: CC(c1cnc(N2CCC2)nc1)n1cc(NC(=O)c2cncc(-c3cc(Cl)ccc3-n3cnnn3)n2)cn1] | (S or R)-N-(1-(1-(2-(Azetidin-1-yl)pyrimidin-5-yl)ethyl)-1H-pyrazol-4-yl)-6-(5-chloro-2-(1H-tetrazol-1-yl)phenyl)pyrazine-2-carboxamide | Calcd.: 529.2 Found: 529.1 | DAICEL CHIRALCEL OJ-H |
| 59 | 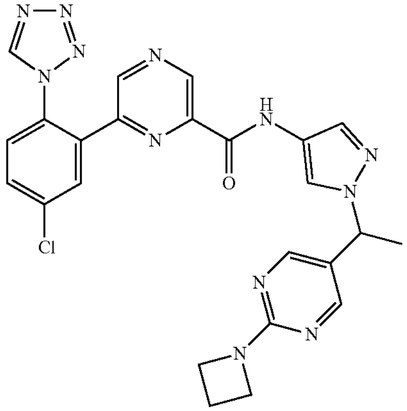 [SMILES: CC(c1cnc(N2CCC2)nc1)n1cc(NC(=O)c2cncc(-c3cc(Cl)ccc3-n3cnnn3)n2)cn1] | (R or S)-N-(1-(1-(2-(Azetidin-1-yl)pyrimidin-5-yl)ethyl)-1H-pyrazol-4-yl)-6-(5-chloro-2-(1H-tetrazol-1-yl)phenyl)pyrazine-2-carboxamide | Calcd.: 529.2 Found: 529.1 | DAICEL CHIRALCEL OJ-H |

TABLE AAC-continued

The following compounds were prepared using procedures similar to those described above using the appropriate starting materials.

| Example | Structure | Name | $[M + H]^+$ or $[M + Na]^+$ | Chiral Column |
|---|---|---|---|---|
| 60 | 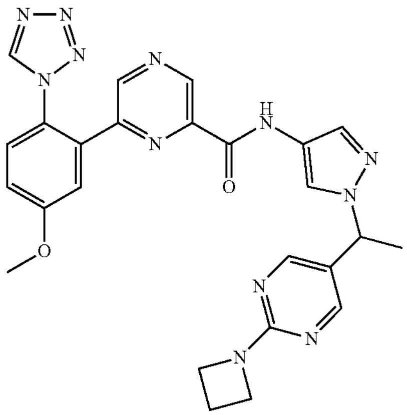 [SMILES: COc1ccc(-n2cnnn2)c(-c2cncc(C(=O)Nc3cnn(C(C)c4cnc(N5CCC5)nc4)c3)n2)c1] | (S or R)-N-(1-(1-(2-(Azetidin-1-yl)pyrimidin-5-yl)ethyl)-1H-pyrazol-4-yl)-6-(5-methoxy-2-(1H-tetrazol-1-yl)phenyl)pyrazine-2-carboxamide | Calcd.: 525.2 Found: 525.2 | DAICEL CHIRALCEL OJ |
| 61 | 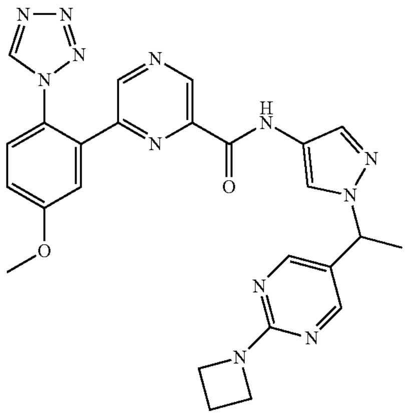 [SMILES: COc1ccc(-n2cnnn2)c(-c2cncc(C(=O)Nc3cnn(C(C)c4cnc(N5CCC5)nc4)c3)n2)c1] | (R or S)-N-(1-(1-(2-(Azetidin-1-yl)pyrimidin-5-yl)ethyl)-1H-pyrazol-4-yl)-6-(5-methoxy-2-(1H-tetrazol-1-yl)phenyl)pyrazine-2-carboxamide | Calcd.: 525.2 Found: 525.2 | DAICEL CHIRALCEL OJ |
| 62 | 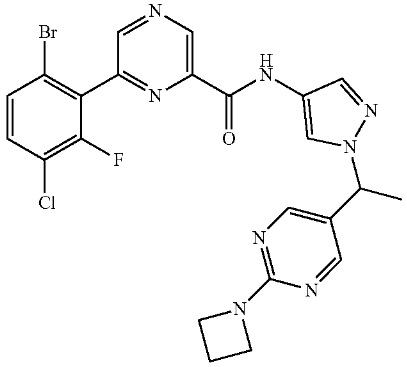 [SMILES: CC(c1cnc(N2CCC2)nc1)n1cc(NC(=O)c2cncc(-c3c(Br)ccc(Cl)c3F)n2)cn1] | N-(1-(1-(2-(Azetidin-1-yl)pyrimidin-5-yl)ethyl)-1H-pyrazol-4-yl)-6-(6-bromo-3-chloro-2-fluorophenyl)pyrazine-2-carboxamide | Calcd.: 557.1 Found: 557.1 | |

TABLE AAC-continued

The following compounds were prepared using procedures similar to those described above using the appropriate starting materials.

| Example | Structure | Name | [M + H]+ or [M + Na]+ | Chiral Column |
|---|---|---|---|---|
| 63 | 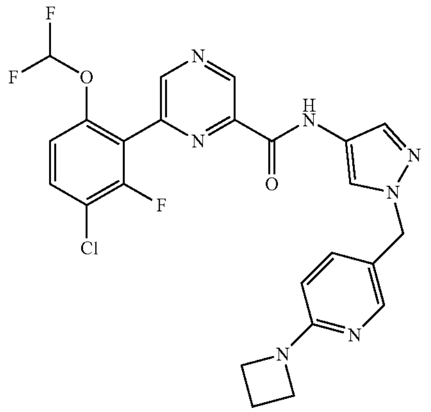 [SMILES: O=C(Nc1cnn(Cc2ccc(N3CCC3)nc2)c1)c1cncc(-c2c(OC(F)F)ccc(Cl)c2F)n1] | N-(1-((6-(Azetidin-1-yl)pyridin-3-yl)methyl)-1H-pyrazol-4-yl)-6-(3-chloro-6-(difluoromethoxy)-2-fluorophenyl)pyrazine-2-carboxamide | Calcd.: 530.1 Found: 530.2 | |
| 64 | 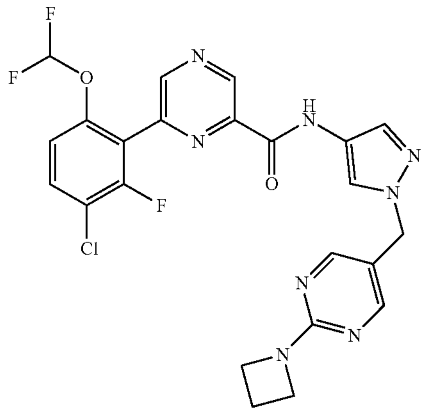 [SMILES: O=C(Nc1cnn(Cc2cnc(N3CCC3)nc2)c1)c1cncc(-c2c(OC(F)F)ccc(Cl)c2F)n1] | N-(1-((2-(Azetidin-1-yl)pyrimidin-5-yl)methyl)-1H-pyrazol-4-yl)-6-(3-chloro-6-(difluoromethoxy)-2-fluorophenyl)pyrazine-2-carboxamide | Calcd.: 531.1 Found: 531.4 | |
| 65 | 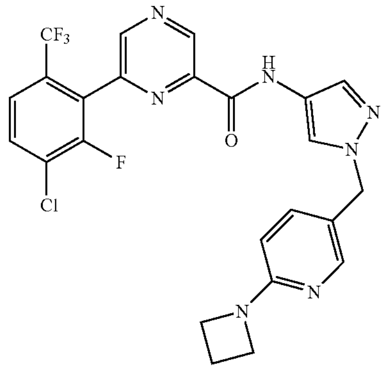 [SMILES: O=C(Nc1cnn(Cc2ccc(N3CCC3)nc2)c1)c1cncc(-c2c(C(F)(F)F)ccc(Cl)c2F)n1] | N-(1-((2-(Azetidin-1-yl)pyrimidin-5-yl)methyl)-1H-pyrazol-4-yl)-6-(3-chloro-2-fluoro-6-(trifluoromethyl)phenyl)pyrazine-2-carboxamide | Calcd.: 533.8 Found: 533.3 | |

Examples 66 and 67

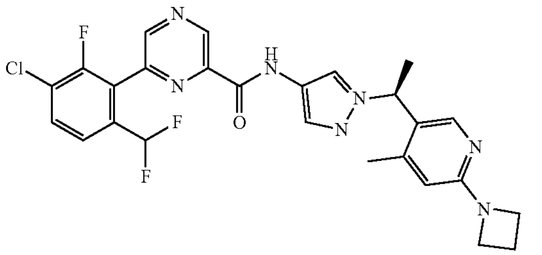

and

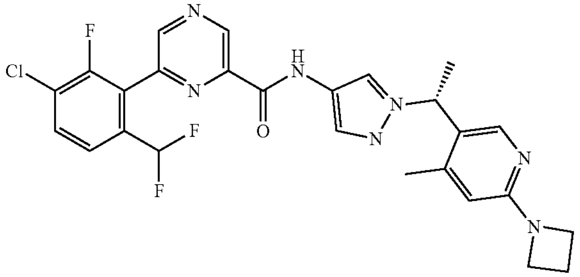

(S)—N-(1-(1-(6-(Azetidin-1-yl)-4-methylpyridin-3-yl)ethyl)-1H-pyrazol-4-yl)-6-(3-chloro-6-(difluoromethyl)-2-fluorophenyl)pyrazine-2-carboxamide and (R)—N-(1-(1-(6-(Azetidin-1-yl)-4-methylpyridin-3-yl)ethyl)-1H-pyrazol-4-yl)-6-(3-chloro-6-(difluoromethyl)-2-fluorophenyl)pyrazine-2-carboxamide (Scheme AAD)

1-(6-(Azetidin-1-yl)-4-methylpyridin-3-yl)ethyl methanesulfonate (0.15 g, 0.56 mmol) was added to a stirred solution of 6-(3-chloro-6-(difluoromethyl)-2-fluorophenyl)-N-(1H-pyrazol-4-yl)pyrazine-2-carboxamide (0.20 g, 0.56 mmol) and cesium carbonate (0.36 g, 1.1 mmol) in DMF (5.5 mL), and the resulting mixture was heated to 60° C. for 2 h. The reaction was cooled to rt, diluted with brine, and extracted with EtOAc. The combined organic fractions were dried ($MgSO_4$), filtered, and concentrated to afford a crude residue that was purified with silica gel chromatography (MeOH/DCM) to give the racemic title compound which was separated by chiral SFC (DAICEL CHIRALCEL OD-H 30% methanol (0.1% DEA)/$CO_2$) to give the first eluted isomer: $^1H$ NMR (500 MHz, DMSO-d6) δ 10.82 (s, 1H), 9.32 (s, 1H), 9.13 (s, 1H), 8.00-7.97 (m, 5H), 7.72 (t, J=3 Hz, 3H), 7.28-7.12 (m, 1H), 6.18 (s, 1H), 5.65 (q, J=7.0 Hz, 1H), 3.91-3.88 (m, 5H), 2.55 (s, 1H), 2.31-2.25 (m, 3H), 2.10 (s, 3H), 1.77-1.74 (m, 3H). MS=542.3 $[M+H]^+$, and the second eluted isomer: $^1H$ NMR (500 MHz, DMSO-d6) δ 10.81 (s, 1H), 9.32 (s, 1H), 9.15 (s, 1H), 8.02-7.98 (m, 5H), 7.75-7.71 (m, 3H), 7.21 (t, J=11 Hz, 1H), 6.18 (s, 1H), 5.67-5.65 (m, 1H), 3.93-3.89 (m, 5H), 2.55 (s, 1H), 2.32-2.26 (m, 3H), 2.10 (s, 3H), 1.77-1.74 (m, 3H). MS=542.3 $[M+H]^+$.

Example 68

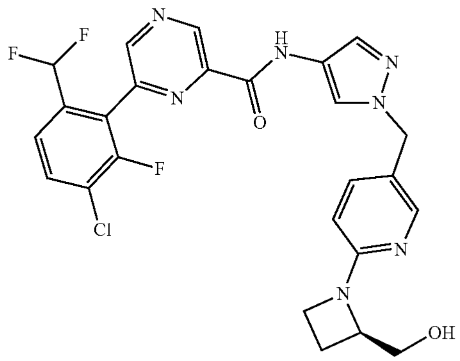 [SMILES: O=C(Nc1cnn(Cc2ccc(N3CC[C@@H]3CO)nc2)c1)c1cncc(-c2c(C(F)F)ccc(Cl)c2F)n1]

(R)-6-(3-Chloro-6-(difluoromethyl)-2-fluorophenyl)-N-(1-((6-(2-(hydroxymethyl)azetidin-1-yl)pyridin-3-yl)methyl)-1H-pyrazol-4-yl)pyrazine-2-carboxamide (Scheme AAE)

(R)-2-Azetidinemethanol (37 mg, 0.42 mmol) was added to a stirred solution of 6-(3-chloro-6-(difluoromethyl)-2-fluorophenyl)-N-(1-((6-fluoropyridin-3-yl)methyl)-1H-pyrazol-4-yl)pyrazine-2-carboxamide (50 mg, 0.11 mmol) and DIEA (92 μl, 0.52 mmol) in NMP (1.1 mL), and the resulting mixture was heated to 130° C. for 24 h. The reaction was cooled to rt and purified by reversed-phase preparatory-HPLC (C18 stationary phase, water-ACN (0.05% $NH_3$) to give the title compound. $^1H$ NMR (600 MHz, $CD_3OD$) δ 9.38 (s, 1H), 9.01 (d, J=1.9 Hz, 1H), 8.17 (s, 1H), 8.01 (d, J=1.7 Hz, 1H), 7.83 (t, J=7.8 Hz, 1H), 7.74 (s, 1H), 7.66 (d, J=8.5 Hz, 1H), 7.51 (dd, J=8.7, 2.2 Hz, 1H), 7.00 (t, J=54.7 Hz, 1H), 6.49 (d, J=8.6 Hz, 1H), 5.19 (s, 2H), 4.42-4.31 (m, 1H), 3.97-3.88 (m, 1H), 3.83 (q, J=7.8 Hz, 1H), 3.78-3.67 (m, 2H), 2.35-2.28 (m, 1H), 2.27-2.19 (m, 1H). MS=544.3 $[M+H]^+$.

Examples 69 and 70

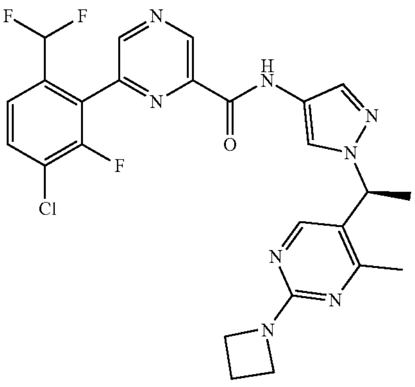

and

-continued

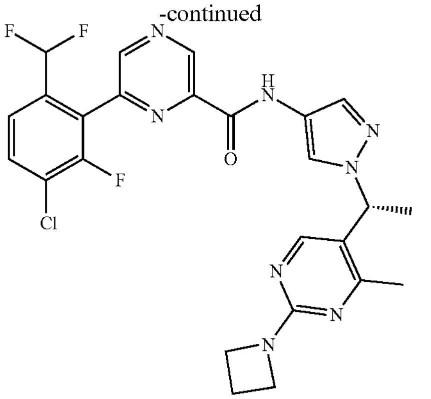

(S)—N-(1-(1-(2-(Azetidin-1-yl)-4-methylpyrimidin-5-yl)ethyl)-1H-pyrazol-4-yl)-6-(3-chloro-6-(difluoromethyl)-2-fluorophenyl)pyrazine-2-carboxamide and (R)—N-(1-(1-(2-(Azetidin-1-yl)-4-methylpyrimidin-5-yl)ethyl)-1H-pyrazol-4-yl)-6-(3-chloro-6-(difluoromethyl)-2-fluorophenyl)pyrazine-2-carboxamide (Scheme AAE)

Azetidine (24 μL, 0.35 mmol) was added to a stirred solution of 6-(3-chloro-6-(difluoromethyl)-2-fluorophenyl)-

N-(1-(1-(4-methyl-2-(methylsulfonyl)pyrimidin-5-yl)ethyl)-1H-pyrazol-4-yl)pyrazine-2-carboxamide (40 mg, 0.071 mmol) and DIEA (62 μL, 0.35 mmol) in NMP (0.7 mL), and the resulting mixture was heated to 90° C. for 2 h. The mixture was cooled to rt, diluted with brine and extracted with EtOAc. The combined organic fractions were dried ($Na_2SO_4$), filtered and concentrated to afford a crude residue that was purified by preparative reverse phase HPLC, eluting with acetonitrile/water+0.1% TFA, to give the title compound as a racemic mixture, which were separated by chiral SFC (DAICEL CHIRALCEL OJ-H 20% ethanol/$CO_2$) to give the first eluted isomer Example 69: $^1$H NMR (600 MHz, $CD_3OD$) δ 9.39 (s, 1H), 9.01 (d, J=2.1 Hz, 1H), 8.15 (s, 1H), 8.14-8.13 (m, 1H), 7.88-7.79 (m, 1H), 7.76 (d, J=0.6 Hz, 1H), 7.67 (d, J=8.5 Hz, 1H), 7.00 (t, J=54.7 Hz, 1H), 5.68 (q, J=7.0 Hz, 1H), 4.19-4.04 (m, 4H), 2.37 (p, J=7.5 Hz, 2H), 2.29 (s, 3H), 1.84 (d, J=7.0 Hz, 3H). MS=543.0 $[M+H]^+$. The second eluted isomer Example 70: $^1$H NMR (600 MHz, $CD_3OD$) δ 9.39 (s, 1H), 9.01 (d, J=2.1 Hz, 1H), 8.15 (s, 1H), 8.14 (s, 1H), 7.86-7.81 (m, 1H), 7.76 (d, J=0.5 Hz, 1H), 7.67 (d, J=8.4 Hz, 1H), 7.00 (t, J=54.7 Hz, 1H), 5.68 (q, J=7.1 Hz, 1H), 4.21-4.03 (m, 4H), 2.37 (p, J=7.5 Hz, 2H), 2.29 (s, 3H), 1.84 (d, J=7.0 Hz, 3H). MS=543.0 $[M+H]^+$.

TABLE AAE

The following compounds were prepared using procedures similar to those described above using the appropriate starting materials. In some examples, racemic products or diatereomeric mixtures were separated using chiral columns (SFC or HPLC) specified in the table.

| Example | Structure | Name | $[M + H]^+$ or $[M + Na]^+$ | Chiral column |
|---|---|---|---|---|
| 71 | 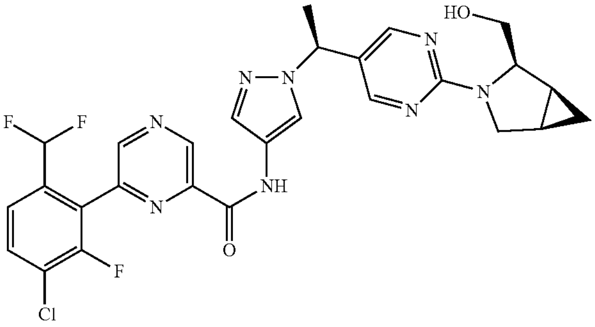 [SMILES: C[C@@H](c1cnc(N2C[C@@H]3C[C@@H]3[C@@H]2CO)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-((S or R)-1-(2-((1S,2R,5R or 1R,2S,5S)-2-(hydroxymethyl)-3-azabicyclo[3.1.0]hexan-3-yl)pyrimidin-5-yl)ethyl)-1H-pyrazol-4-yl)pyrazine-2-carboxamide | Calcd.: 585.2 Found: 585.2 | DAICEL YMC CHIRAL Amylose-C |
| 72 | 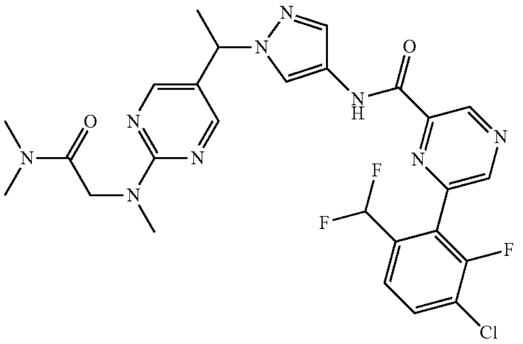 [SMILES: CC(c1cnc(N(C)CC(=O)N(C)C)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((2-(dimethylamino)-2-oxoethyl)(methyl)amino)pyrimidin-5-yl)ethyl)-1H-pyrazol-4-yl)pyrazine-2-carboxamide | Calcd.: 588.0 Found: 588.2 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | $[M + H]^+$ or $[M + Na]^+$ | Chiral column |
|---|---|---|---|---|
| 73 | 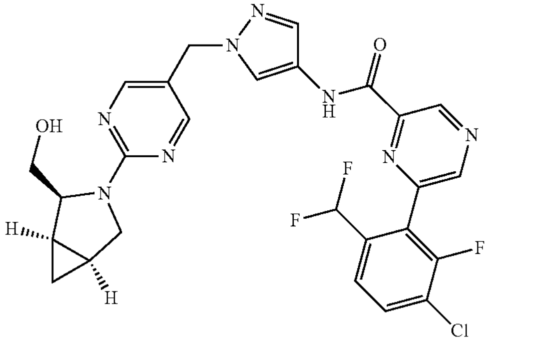 [SMILES: O=C(Nc1cnn(Cc2cnc(N3C[C@H]4C[C@H]4[C@H]3CO)nc2)c1)c1cncc(-c2c(C(F)F)ccc(Cl)c2F)n1] | 6-(3-Chloro-6-(difluoromethyl)-2-fluorophenyl)-N-(1-((2-((1R,2S,5S)-2-(hydroxymethyl)-3-azabicyclo[3.1.0]hexan-3-yl)pyrimidin-5-yl) methyl)-1H-pyrazol-4-yl)pyrazine-2-carboxamide | Calcd.: 571.2 Found: 571.4 | |
| 74 | 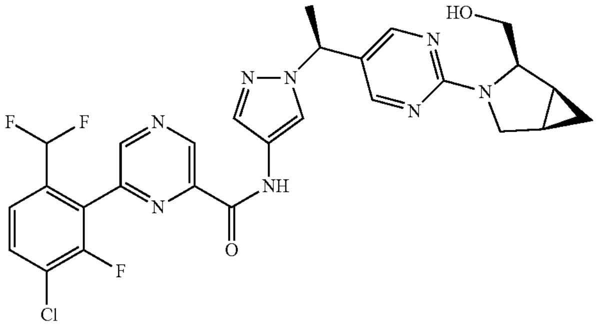 [SMILES: C[C@@H](c1cnc(N2C[C@@H]3C[C@@H]3[C@@H]2CO)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-((S or R)-1-(2-((1S,2R,5R or 1R,2S,5S)-2-(hydroxymethyl)-3-azabicyclo[3.1.0]hexan-3-yl)pyrimidin-5-yl)ethyl)-1H-pyrazol-4-yl)pyrazine-2-carboxamide | Calcd.: 585.2 Found: 585.2 | DAICEL YMC CHIRAL Amylose-C |
| 75 | 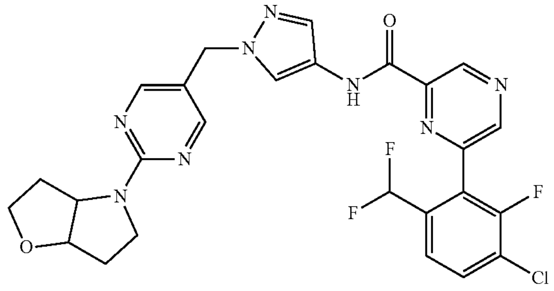 | 6-(3-Chloro-6-(difluoromethyl)-2-fluorophenyl)-N-(1-((2-(hexahydro-4H-furo[3,2-b]pyrrol-4-yl)pyrimidin-5-yl)methyl)-1H-pyrazol-4-yl)pyrazine-2-carboxamide | Calcd.: 571.0 Found: 571.3 | |
| 76 | 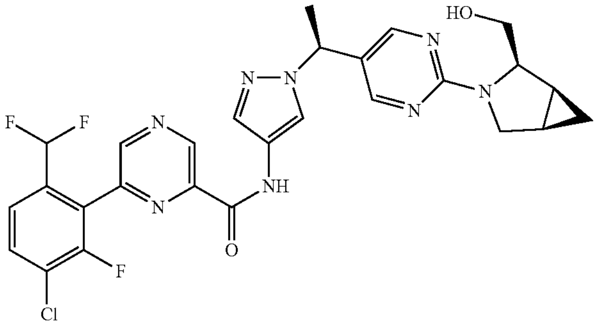 [SMILES: C[C@@H](c1cnc(N2C[C@@H]3C[C@@H]3[C@@H]2CO)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-((S or R)-1-(2-((1S,2R,5R or 1R,2S,5S)-2-(hydroxymethyl)-3-azabicyclo[3.1.0]hexan-3-yl)pyrimidin-5-yl)ethyl)-1H-pyrazol-4-yl)pyrazine-2-carboxamide | Calcd.: 585.2 Found: 585.2 | DAICEL YMC CHIRAL Amylose-C |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | $[M + H]^+$ or $[M + Na]^+$ | Chiral column |
| --- | --- | --- | --- | --- |
| 77 | 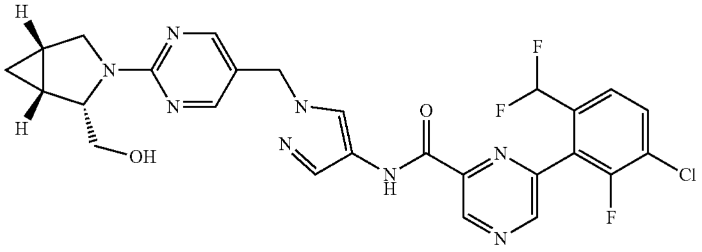 [SMILES: N=C/C(=C\NCc1cnc(N2C[C@H]3C[C@H]3[C@H]2CO)nc1)NC(=O)c1cncc(-c2c(C(F)F)ccc(Cl)c2F)n1] | 6-(3-Chloro-6-(difluoromethyl)-2-fluorophenyl)-N-(1-((2-((1R,2S,5S or 1S,2R,5R)-2-(hydroxymethyl)-3-azabicyclo[3.1.0]hexan-3-yl)pyrimidin-5-yl)methyl)-1H-pyrazol-4-yl)pyrazine-2-carboxamide | Calcd.: 571.2 Found: 571.4 | AS-H |
| 78 | 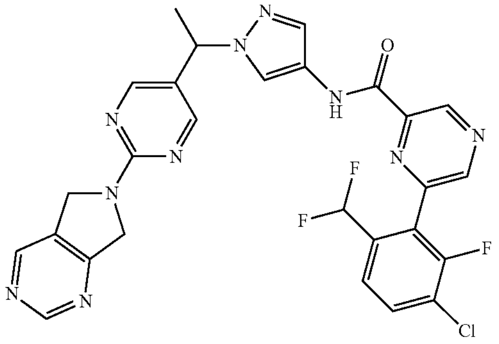 [SMILES: CC(c1cnc(N2Cc3cncnc3C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-(5,7-dihydro-6H-pyrrolo[3,4-d]pyrimidin-6-yl) pyrimidin-5-yl)ethyl)-1H-pyrazol-4-yl)pyrazine-2-carboxamide | Calcd.: 593.0 Found: 593.1 | |
| 79 | 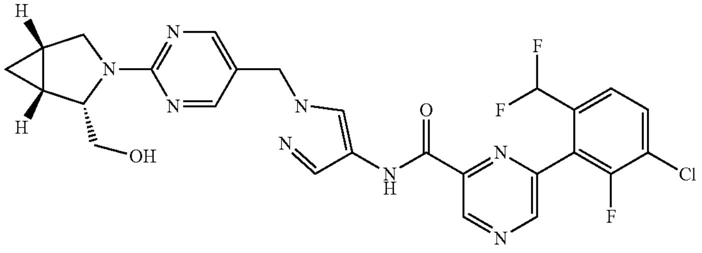 [SMILES: N=C/C(=C\NCc1cnc(N2C[C@H]3C[C@H]3[C@H]2CO)nc1)NC(=O)c1cncc(-c2c(C(F)F)ccc(Cl)c2F)n1] | 6-(3-Chloro-6-(difluoromethyl)-2-fluorophenyl)-N-(1-((2-((1R,2S,5S or 1S,2R,5R)-2-(hydroxymethyl)-3-azabicyclo[3.1.0]hexan-3-yl)pyrimidin-5-yl)methyl)-1H-pyrazol-4-yl)pyrazine-2-carboxamide | Calcd.: 571.2 Found: 571.4 | AS-H |
| 80 | 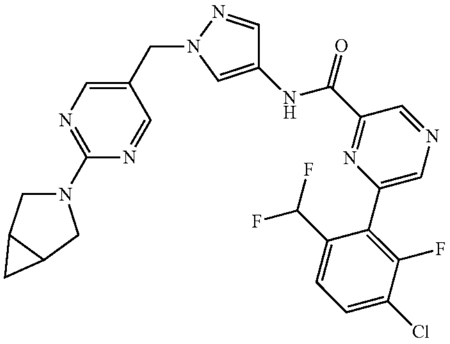 [SMILES: O=C(Nc1cnn(Cc2cnc(N3CC4CC4C3)nc2)c1)c1cncc(-c2c(C(F)F)ccc(Cl)c2F)n1] | N-(1-((2-(3-Azabicyclo[3.1.0]hexan-3-yl)pyrimidin-5-yl)methyl)-1H-pyrazol-4-yl)-6-(3-chloro-6-(difluoromethyl)-2-fluorophenyl)pyrazine-2-carboxamide | Calcd.: 541.1 Found: 541.2 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | [M + H]+ or [M + Na]+ | Chiral column |
|---|---|---|---|---|
| 81 | 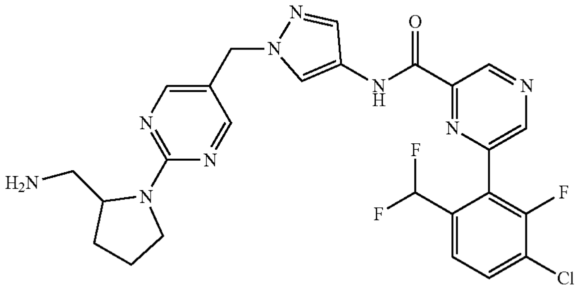 [SMILES: NCC1CCCN1c1ncc(Cn2cc(NC(=O)c3cncc(-c4c(C(F)F)ccc(Cl)c4F)n3)cn2)cn1] | N-(1-((2-(2-(Aminomethyl) pyrrolidin-1-yl)pyrimidin-5-yl)methyl)-1H-pyrazol-4-yl)-6-(3-chloro-6-(difluoromethyl)-2-fluorophenyl)pyrazine-2-carboxamide | Calcd.: 558.0 Found: 557.9 | |
| 82 | 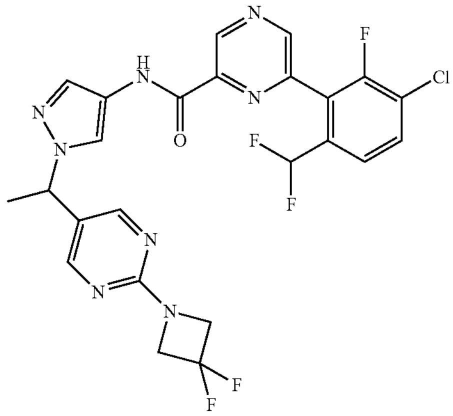 [SMILES: CC(c1cnc(N2CC(F)(F)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-(3,3-difluoroazetidin-1-yl)pyrimidin-5-yl)ethyl)-1H-pyrazol-4-yl)pyrazine-2-carboxamide | Calcd.: 565.9 Found: 566.0 | |
| 83 | 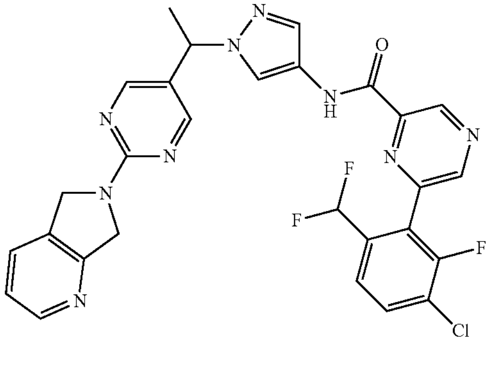 [SMILES: CC(c1cnc(N2Cc3cccnc3C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-(5,7-dihydro-6H-pyrrolo[3,4-b]pyridin-6-yl)pyrimidin-5-yl)ethyl)-1H-pyrazol-4-yl)pyrazine-2-carboxamide | Calcd.: 592.2 Found: 592.2 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | [M + H]+ or [M + Na]+ | Chiral column |
|---|---|---|---|---|
| 84 | 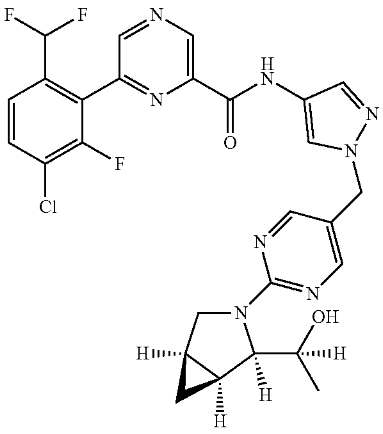 [SMILES: C[C@H](O)[C@H]1[C@H]2C[C@H]2CN1c1ncc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((2-((1S,2R,5R)-2-((S)-1-hydroxyethyl)-3-azabicyclo[3.1.0]hexan-3-yl)pyrimidin-5-yl)methyl)-1H-pyrazol-4-yl)pyrazine-2-carboxamide | Calcd.: 585.2 Found: 585.3 | |
| 85 | 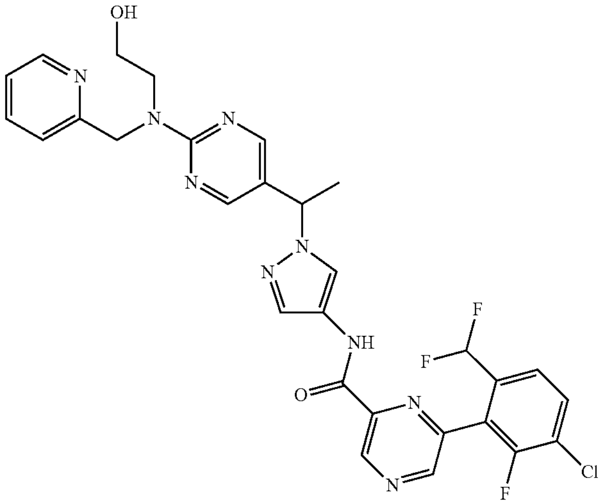 [SMILES: CC(c1cnc(N(CCO)Cc2ccccn2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((2-hydroxyethyl)(pyridin-2-ylmethyl)amino) pyrimidin-5-yl)ethyl)-1H-pyrazol-4-yl)pyrazine-2-carboxamide | Calcd.: 623.2 Found: 624.2 | |
| 86 | 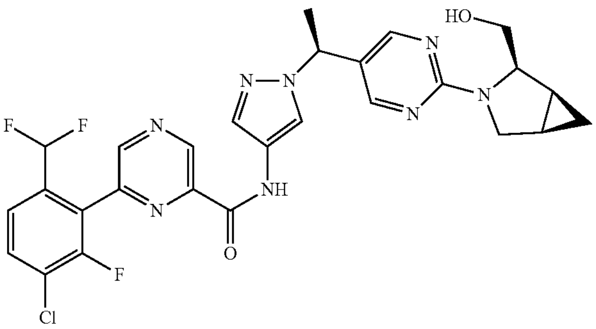 [SMILES: C[C@@H](c1cnc(N2C[C@@H]3C[C@@H]3[C@@H]2CO)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-((S or R)-1-(2-((1S,2R,5R or 1R,2S,5S)-2-(hydroxymethyl)-3-azabicyclo[3.1.0]hexan-3-yl)pyrimidin-5-yl)ethyl)-1H-pyrazol-4-yl)pyrazine-2-carboxamide | Calcd.: 585.2 Found: 585.2 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | $[M + H]^+$ or $[M + Na]^+$ | Chiral column |
|---|---|---|---|---|
| 87 | 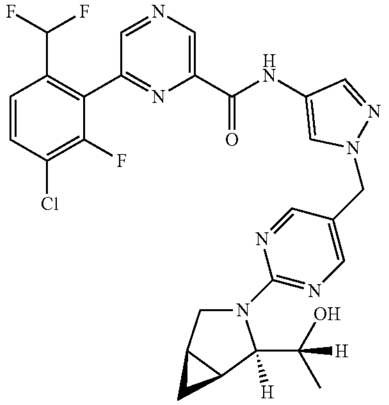 [SMILES: C[C@@H](O)[C@H]1[C@H]2C[C@H]2CN1c1ncc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((2-((1S,2R,5R)-2-((R)-1-hydroxyethyl)-3-azabicyclo[3.1.0]hexan-3-yl)pyrimidin-5-yl)methyl)-1H-pyrazol-4-yl)pyrazine-2-carboxamide | Calcd.: 585.2 Found: 585.3 | |
| 88 | 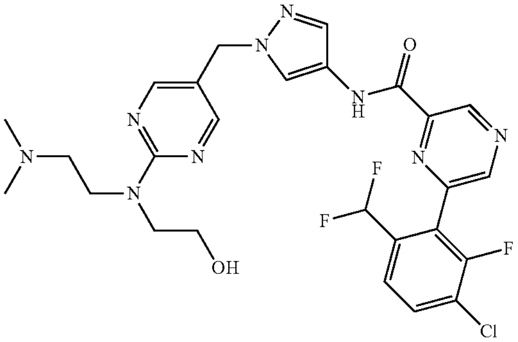 [SMILES: CN(C)CCN(CCO)c1ncc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((2-((2-(dimethylamino)ethyl)(2-hydroxyethyl) amino)pyrimidin-5-yl)methyl)-1H-pyrazol-4-yl)pyrazine-2-carboxamide | Calcd.: 590.2 Found: 590.3 | |
| 89 | 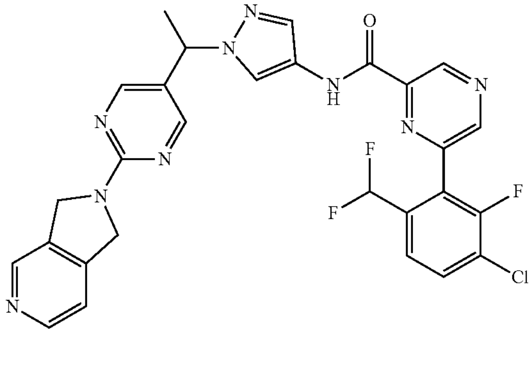 [SMILES: CC(c1cnc(N2Cc3ccncc3C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-(1,3-dihydro-2H-pyrrolo[3,4-c]pyridin-2-yl)pyrimidin-5-yl)ethyl)-1H-pyrazol-4-yl)pyrazine-2-carboxamide | Calcd.: 592.2 Found: 592.1 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | [M + H]+ or [M + Na]+ | Chiral column |
|---|---|---|---|---|
| 90 | 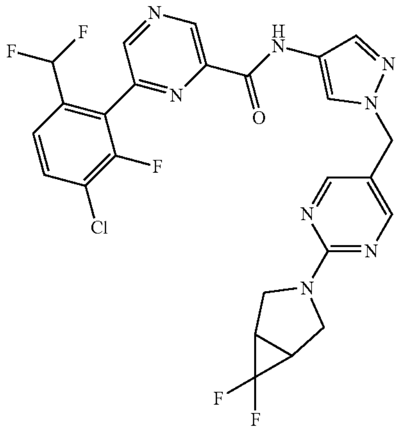 [SMILES: O=C(Nc1cnn(Cc2cnc(N3CC4C(C3)C4(F)F)nc2)c1)c1cncc(-c2c(C(F)F)ccc(Cl)c2F)n1] | 6-(3-Chloro-6-(difluoromethyl)-2-fluorophenyl)-N-(1-((2-(6,6-difluoro-3-azabicyclo[3.1.0]hexan-3-yl)pyrimidin-5-yl)methyl)-1H-pyrazol-4-yl)pyrazine-2-carboxamide | Calcd.: 577.1 Found: 577.4 | |
| 91 | 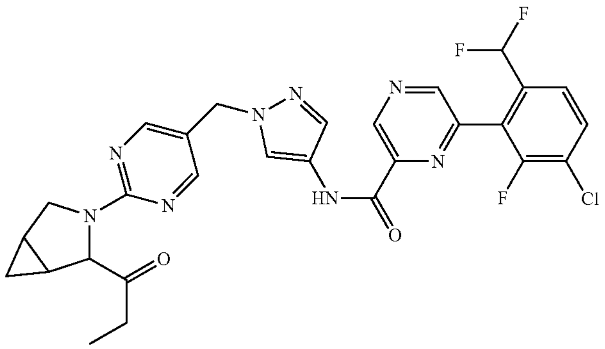 [SMILES: CCC(=O)C1C2CC2CN1c1ncc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((2-(2-propionyl-3-azabicyclo[3.1.0]hexan-3-yl)pyrimidin-5-yl)methyl)-1H-pyrazol-4-yl)pyrazine-2-carboxamide | Calcd.: 597.2 Found: 597.2 | |
| 92 | 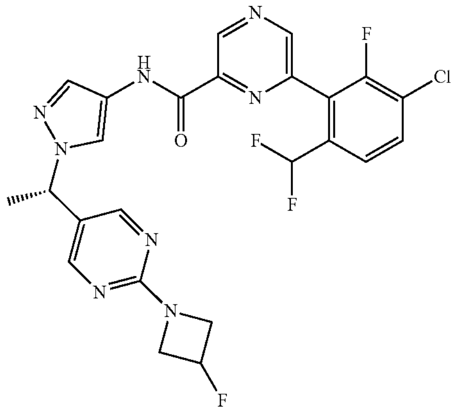 [SMILES: C[C@@H](c1cnc(N2CC(F)C2)nc1)n1cc(NC(=O)c2cncc(-c3c(C(F)F)ccc(Cl)c3F)n2)cn1] | (S)-6-(3-Chloro-6-(difluoromethyl)-2-fluorophenyl)-N-(1-(1-(2-(3-fluoroazetidin-1-yl)pyrimidin-5-yl)ethyl)-1H-pyrazol-4-yl)pyrazine-2-carboxamide | Calcd.: 547.1 Found: 547.3 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | [M + H]+ or [M + Na]+ | Chiral column |
|---|---|---|---|---|
| 93 | 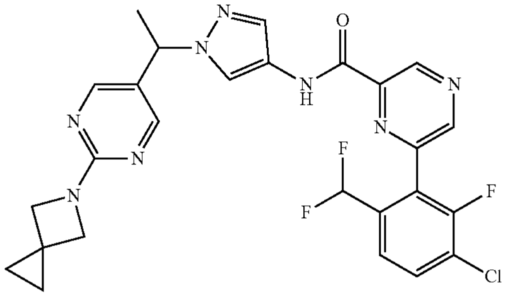 [SMILES: CC(c1cnc(N2CC3(CC3)C2)nc1)n1cc(NC(=O)c2cncc(-c3c(C(F)F)ccc(Cl)c3F)n2)cn1] | (R or S)-N-(1-(1-(2-(5-Azaspiro[2.3]hexan-5-yl)pyrimidin-5-yl)ethyl)-1H-pyrazol-4-yl)-6-(3-chloro-6-(difluoromethyl)-2-fluorophenyl)pyrazine-2-carboxamide | Calcd.: 555.2 Found: 555.3 | AD-H |
| 94 | 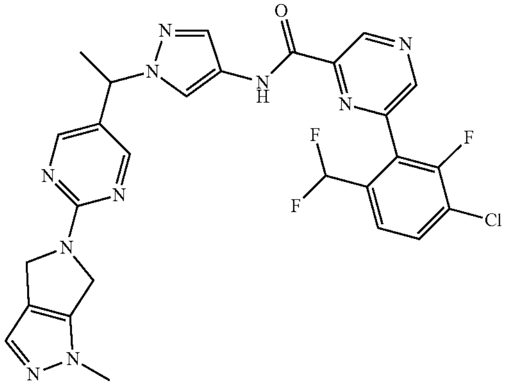 [SMILES: CC(c1cnc(N2Cc3cnn(C)c3C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-(1-methyl-4,6-dihydropyrrolo[3,4-c]pyrazol-5(1H)-yl)pyrimidin-5-yl)ethyl)-1H-pyrazol-4-yl)pyrazine-2-carboxamide | Calcd.: 595.2 Found: 595.1 | |
| 95 | 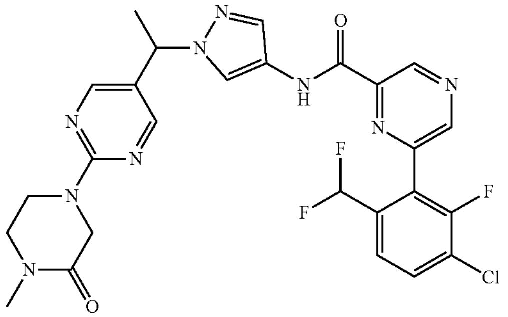 [SMILES: CC(c1cnc(N2CCN(C)C(=O)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-(4-methyl-3-oxopiperazin-1-yl)pyrimidin-5-yl)ethyl)-1H-pyrazol-4-yl)pyrazine-2-carboxamide | Calcd.: 586.2 Found: 586.1 | |
| 96 | 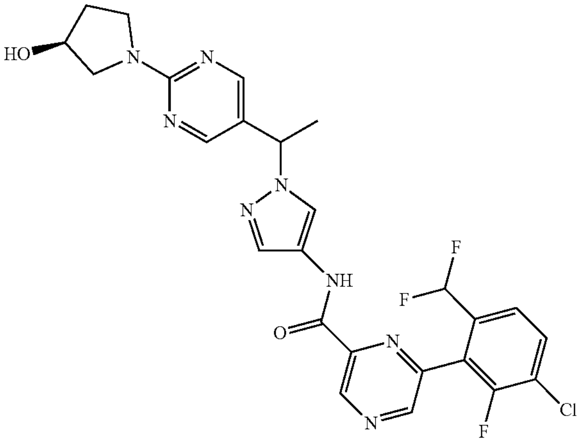 [SMILES: CC(c1cnc(N2CC[C@H](O)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-((R and S)-1-(2-((S)-3-hydroxypyrrolidin-1-yl)pyrimidin-5-yl)ethyl)-1H-pyrazol-4-yl)pyrazine-2-carboxamide | Calcd. 558.2 Found: 559.1 | |

TABLE AAE-continued

| The following compounds were prepared using procedures similar to those described above using the appropriate starting materials. In some examples, racemic products or diatereomeric mixtures were separated using chiral columns (SFC or HPLC) specified in the table. | | | | |
|---|---|---|---|---|
| Example | Structure | Name | $[M + H]^+$ or $[M + Na]^+$ | Chiral column |
| 97 | 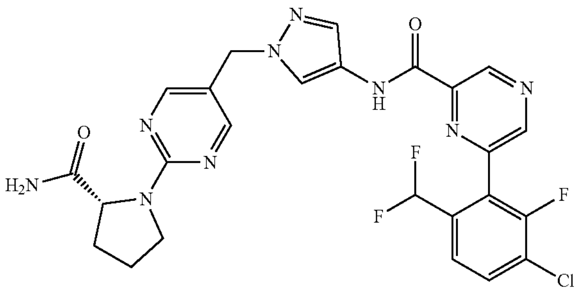 [SMILES: NC(=O)[C@H]1CCCN1c1ncc(Cn2cc(NC(=O)c3cncc(-c4c(C(F)F)ccc(Cl)c4F)n3)cn2)cn1] | (R)-N-(1-((2-(2-Carbamoylpyrrolidin-1-yl)pyrimidin-5-yl)methyl)-1H-pyrazol-4-yl)-6-(3-chloro-6-(difluoromethyl)-2-fluorophenyl)pyrazine-2-carboxamide | Calcd. 572.2 Found: 572.3 | |
| 98 | 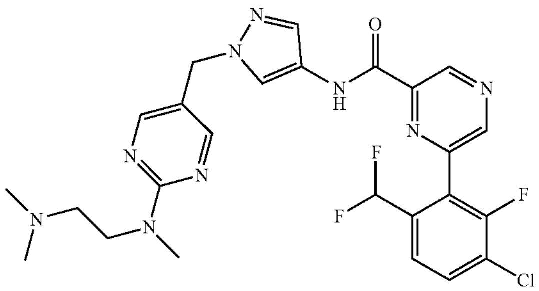 [SMILES: CN(C)CCN(C)c1ncc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((2-((2-(dimethyl-amino)ethyl)(methyl)amino)pyrimidin-5-yl)methyl)-1H-pyrazol-4-yl)pyrazine-2-carboxamide | Calcd. 560.2 Found: 560.4 | |
| 99 | 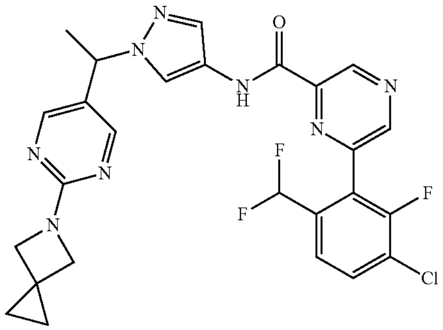 [SMILES: CC(c1cnc(N2CC3(CC3)C2)nc1)n1cc(NC(=O)c2cncc(-c3c(C(F)F)ccc(Cl)c3F)n2)cn1] | N-(1-(1-(2-(5-Azaspiro[2.3]hexan-5-yl)pyrimidin-5-yl)ethyl)-1H-pyrazol-4-yl)-6-(3-chloro-6-(difluoromethyl)-2-fluorophenyl)pyrazine-2-carboxamide | Calcd.: 555.2 Found: 555.3 | |
| 100 | 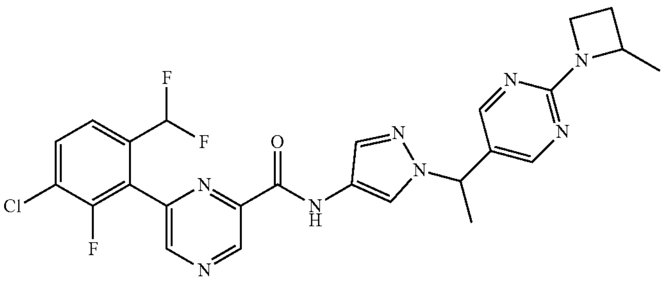 [SMILES: CC1CCN1c1ncc(C(C)n2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((R and S)-1-(2-((R and S)-2-methylazetidin-1-yl)pyrimidin-5-yl)ethyl)-1H-pyrazol-4-yl)pyrazine-2-carboxamide | Calcd.: 543.2 Found: 543.3 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | $[M + H]^+$ or $[M + Na]^+$ | Chiral column |
|---|---|---|---|---|
| 101 | 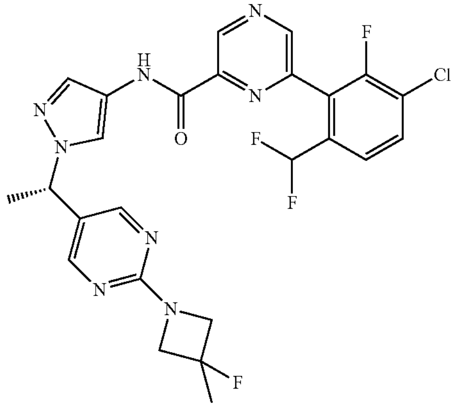 [SMILES: C[C@@H](c1cnc(N2CC(C)(F)C2)nc1)n1cc(NC(=O)c2cncc(-c3c(C(F)F)ccc(Cl)c3F)n2)cn1] | (S)-6-(3-Chloro-6-(difluoromethyl)-2-fluorophenyl)-N-(1-(1-(2-(3-fluoro-3-methylazetidin-1-yl)pyrimidin-5-yl)ethyl)-1H-pyrazol-4-yl)pyrazine-2-carboxamide | Calcd.: 561.2 Found: 561.0 | |
| 102 | 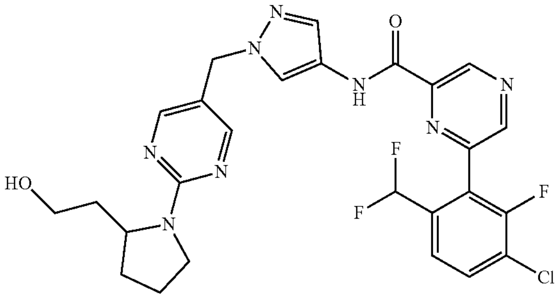 [SMILES: O=C(Nc1cnn(Cc2cnc(N3CCCC3CCO)nc2)c1)c1cncc(-c2c(C(F)F)ccc(Cl)c2F)n1] | (S or R)-6-(3-Chloro-6-(difluoromethyl)-2-fluorophenyl)-N-(1-((2-(2-(2-hydroxyethyl)pyrrolidin-1-yl)pyrimidin-5-yl)methyl)-1H-pyrazol-4-yl)pyrazine-2-carboxamide | Calcd.: 573.2 Found: 573.3 | DAICEL CHIRAL-PAK AD |
| 103 | 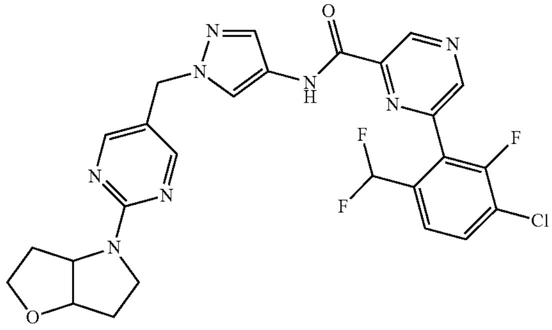 [SMILES: O=C(Nc1cnn(Cc2cnc(N3CCC4OCCC43)nc2)c1)c1cncc(-c2c(C(F)F)ccc(Cl)c2F)n1] | 6-(3-Chloro-6-(difluoromethyl)-2-fluorophenyl)-N-(1-((2-((3aS,6aS or 3aR,6aR)-hexahydro-4H-furo[3,2-b]pyrrol-4-yl)pyrimidin-5-yl)methyl)-1H-pyrazol-4-yl)pyrazine-2-carboxamide | Calcd.: 571.2 Found: 571.2 | AD-H |
| 104 | 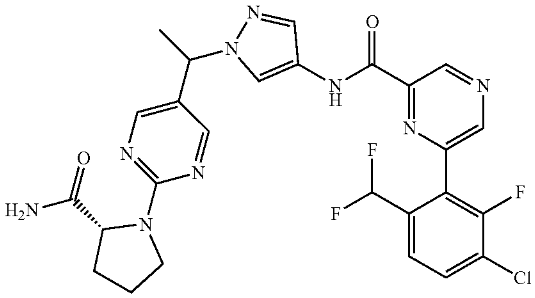 [SMILES: CC(c1cnc(N2CCC[C@@H]2C(N)=O)nc1)n1cc(NC(=O)c2cncc(-c3c(C(F)F)ccc(Cl)c3F)n2)cn1] | N-(1-((R and S)-1-(2-((R)-2-Carbamoylpyrrolidin-1-yl)pyrimidin-5-yl)ethyl)-1H-pyrazol-4-yl)-6-(3-chloro-6-(difluoromethyl)-2-fluorophenyl)pyrazine-2-carboxamide | Calcd.: 586.2 Found: 586.0 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | $[M + H]^+$ or $[M + Na]^+$ | Chiral column |
|---|---|---|---|---|
| 105 | 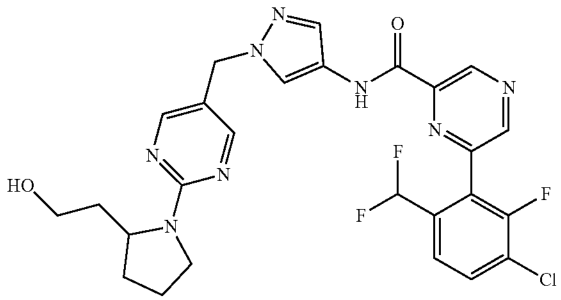 [SMILES: O=C(Nc1cnn(Cc2cnc(N3CCCC3CCO)nc2)c1)c1cncc(-c2c(C(F)F)ccc(Cl)c2F)n1] | (S or R)-6-(3-Chloro-6-(difluoromethyl)-2-fluorophenyl)-N-(1-((2-(2-(2-hydroxyethyl)pyrrolidin-1-yl)pyrimidin-5-yl)methyl)-1H-pyrazol-4-yl)pyrazine-2-carboxamide | Calcd.: 573.2 Found: 573.3 | DAICEL CHIRALPAK AD |
| 106 | 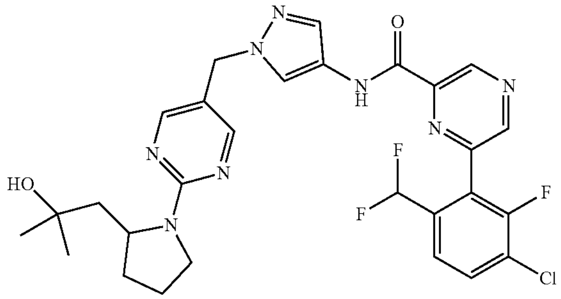 [SMILES: CC(C)(O)CC1CCCN1c1ncc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((2-(2-(2-hydroxy-2-methylpropyl)pyrrolidin-1-yl)pyrimidin-5-yl)methyl)-1H-pyrazol-4-yl)pyrazine-2-carboxamide | Calcd.: 601.2 Found: 601.2 | |
| 107 | 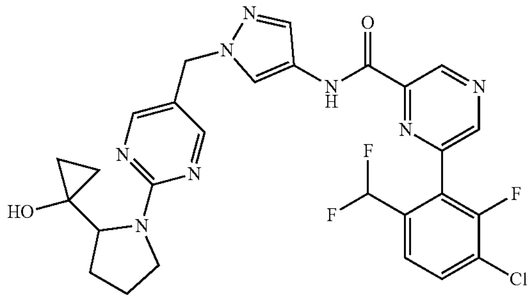 [SMILES: O=C(Nc1cnn(Cc2cnc(N3CCCC3C3(O)CC3)nc2)c1)c1cncc(-c2c(C(F)F)ccc(Cl)c2F)n1] | 6-(3-Chloro-6-(difluoromethyl)-2-fluorophenyl)-N-(1-((2-(2-(1-hydroxycyclopropyl)pyrrolidin-1-yl)pyrimidin-5-yl)methyl)-1H-pyrazol-4-yl)pyrazine-2-carboxamide | Calcd.: 585.2 Found: 585.4 | |
| 108 | 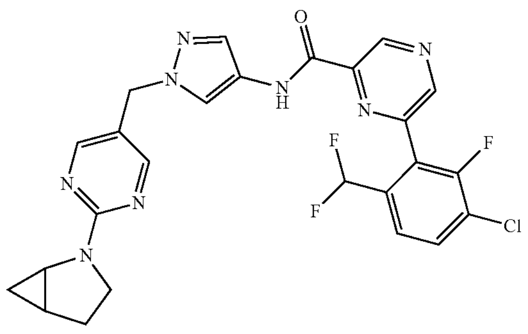 [SMILES: O=C(Nc1cnn(Cc2cnc(N3CCC4CC43)nc2)c1)c1cncc(-c2c(C(F)F)ccc(Cl)c2F)n1] | N-(1-((2-(2-Azabicyclo[3.1.0]hexan-2-yl)pyrimidin-5-yl)methyl)-1H-pyrazol-4-yl)-6-(3-chloro-6-(difluoromethyl)-2-fluorophenyl)pyrazine-2-carboxamide | Calcd.: 585.2 Found: 585.4 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | [M + H]+ or [M + Na]+ | Chiral column |
|---|---|---|---|---|
| 109 | 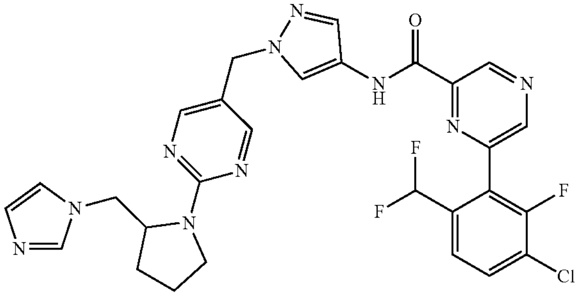 [SMILES: O=C(Nc1cnn(Cc2cnc(N3CCCC3Cn3ccnc3)nc2)c1)c1cncc(-c2c(C(F)F)ccc(Cl)c2F)n1] | N-(1-((2-(2-((1H-Imidazol-1-yl)methyl)pyrrolidin-1-yl)pyrimidin-5-yl)methyl)-1H-pyrazol-4-yl)-6-(3-chloro-6-(difluoromethyl)-2-fluorophenyl)pyrazine-2-carboxamide | Calcd.: 609.2 Found: 609.4 | |
| 110 | 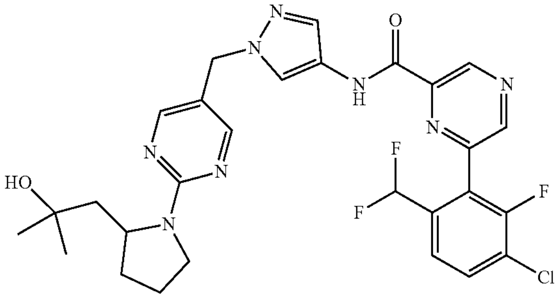 [SMILES: CC(C)(O)CC1CCCN1c1ncc(Cn2cc(NC(=O)c3cncc(-c4c(C(F)F)ccc(Cl)c4F)n3)cn2)cn1] | (S or R)-6-(3-Chloro-6-(difluoromethyl)-2-fluorophenyl)-N-(1-((2-(2-(2-hydroxy-2-methylpropyl)pyrrolidin-1-yl)pyrimidin-5-yl)methyl)-1H-pyrazol-4-yl)pyrazine-2-carboxamide | Calcd.: 601.2 Found: 601.2 | |
| 111 | 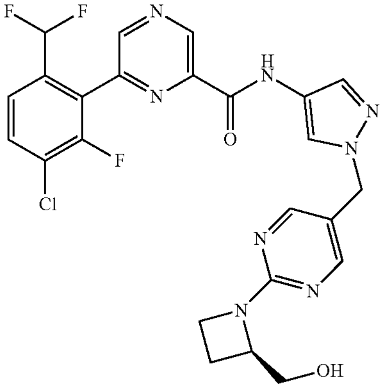 [SMILES: O=C(Nc1cnn(Cc2cnc(N3CC[C@@H]3CO)nc2)c1)c1cncc(-c2c(C(F)F)ccc(Cl)c2F)n1] | (R)-6-(3-Chloro-6-(difluoromethyl)-2-fluorophenyl)-N-(1-((2-(2-(hydroxymethyl)azetidin-1-yl)pyrimidin-5-yl)methyl)-1H-pyrazol-4-yl)pyrazine-2-carboxamide | Calcd.: 545.1 Found: 545.0 | |
| 112 | 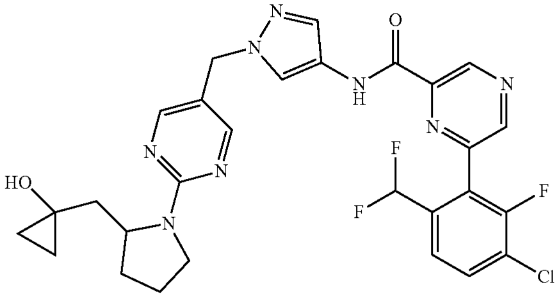 [SMILES: O=C(Nc1cnn(Cc2cnc(N3CCCC3CC3(O)CC3)nc2)c1)c1cncc(-c2c(C(F)F)ccc(Cl)c2F)n1] | (S or R)-6-(3-Chloro-6-(difluoromethyl)-2-fluorophenyl)-N-(1-((2-(2-((1-hydroxycyclopropyl)methyl)pyrrolidin-1-yl)pyrimidin-5-yl)methyl)-1H-pyrazol-4-yl)pyrazine-2-carboxamide | Calcd.: 599.2 Found: 599.2 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | $[M + H]^+$ or $[M + Na]^+$ | Chiral column |
|---|---|---|---|---|
| 113 | 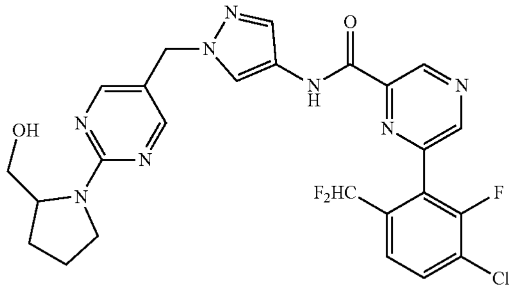 [SMILES: O=C(Nc1cnn(Cc2cnc(N3CCCC3CO)nc2)c1)c1cncc(-c2c(C(F)F)ccc(Cl)c2F)n1] | 6-(3-Chloro-6-(difluoromethyl)-2-fluorophenyl)-N-(1-((2-(2-(hydroxymethyl)pyrrolidin-1-yl)pyrimidin-5-yl)methyl)-1H-pyrazol-4-yl)pyrazine-2-carboxamide | Calcd.: 559.2 Found: 559.3 | |
| 114 | 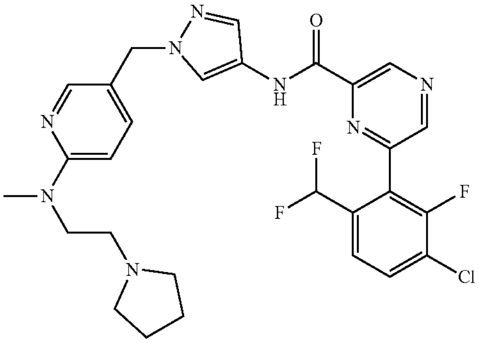 [SMILES: CN(CCN1CCCC1)c1ccc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((6-(methyl(2-(pyrrolidin-1-yl)ethyl)amino)pyridin-3-yl)methyl)-1H-pyrazol-4-yl)pyrazine-2-carboxamide | Calcd.: 585.2 Found: 585.2 | |
| 115 | 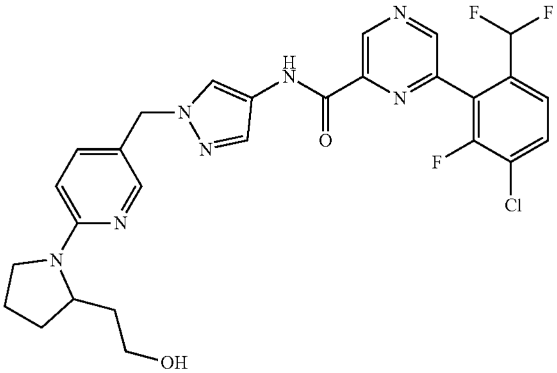 [SMILES: O=C(Nc1cnn(Cc2ccc(N3CCCC3CCO)nc2)c1)c1cncc(-c2c(C(F)F)ccc(Cl)c2F)n1] | 6-(3-Chloro-6-(difluoromethyl)-2-fluorophenyl)-N-(1-((6-(2-(2-hydroxyethyl)pyrrolidin-1-yl)pyridin-3-yl)methyl)-1H-pyrazol-4-yl)pyrazine-2-carboxamide | Calcd.: 572.2 Found: 572.1 | |
| 116 | 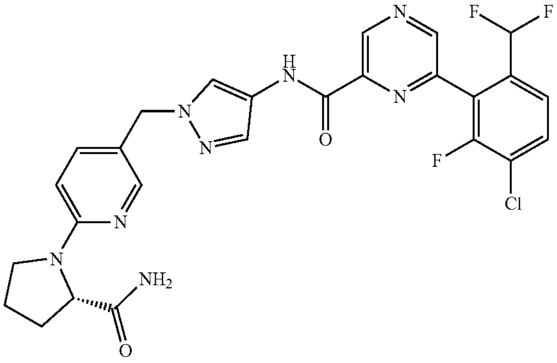 [SMILES: NC(=O)[C@@H]1CCCN1c1ccc(Cn2cc(NC(=O)c3cncc(-c4c(C(F)F)ccc(Cl)c4F)n3)cn2)cn1] | (S)-N-(1-((6-(2-Carbamoylpyrrolidin-1-yl)pyridin-3-yl)methyl)-1H-pyrazol-4-yl)-6-(3-chloro-6-(difluoromethyl)-2-fluorophenyl)pyrazine-2-carboxamide | Calcd.: 571.2 Found: 571.1 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | $[M + H]^+$ or $[M + Na]^+$ | Chiral column |
|---|---|---|---|---|
| 117 | 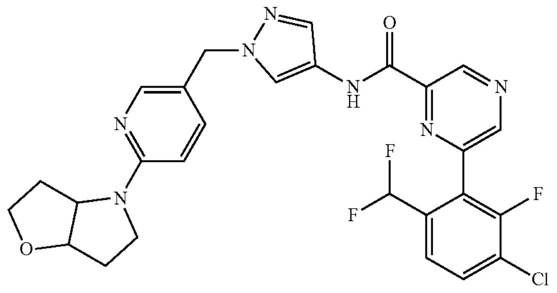 [SMILES: O=C(Nc1cnn(Cc2ccc(N3CCC4OCCC43)nc2)c1)c1cncc(-c2c(C(F)F)ccc(Cl)c2F)n1] | 6-(3-Chloro-6-(difluoromethyl)-2-fluorophenyl)-N-(1-((6-(hexahydro-4H-furo[3,2-b]pyrrol-4-yl)pyridin-3-yl)methyl)-1H-pyrazol-4-yl)pyrazine-2-carboxamide | Calcd.: 570.2 Found: 570.3 | |
| 118 | 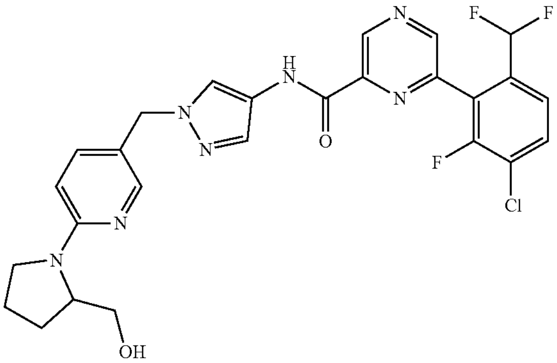 [SMILES: O=C(Nc1cnn(Cc2ccc(N3CCCC3CO)nc2)c1)c1cncc(-c2c(C(F)F)ccc(Cl)c2F)n1] | 6-(3-Chloro-6-(difluoromethyl)-2-fluorophenyl)-N-(1-((6-(2-(hydroxymethyl) pyrrolidin-1-yl)pyridin-3-yl)methyl)-1H-pyrazol-4-yl)pyrazine-2-carboxamide | Calcd.: 558.2 Found: 558.0 | |
| 119 | 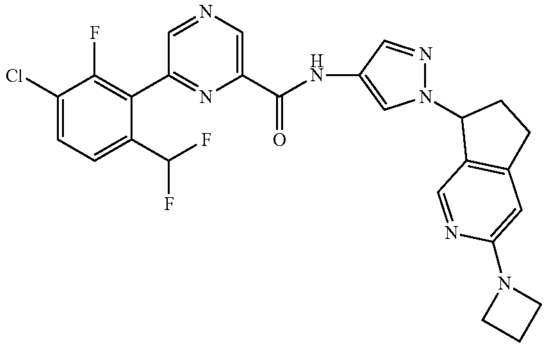 [SMILES: O=C(Nc1cnn(C2CCc3cc(N4CCC4)ncc32)c1)c1cncc(-c2c(C(F)F)ccc(Cl)c2F)n1] | (R or S)-N-(1-(3-(Azetidin-1-yl)-6,7-dihydro-5H-cyclopenta[c]pyridin-7-yl)-1H-pyrazol-4-yl)-6-(3-chloro-6-(difluoromethyl)-2-fluorophenyl)pyrazine-2-carboxamide | Calcd.: 540.2 Found: 540.1 | |
| 120 | 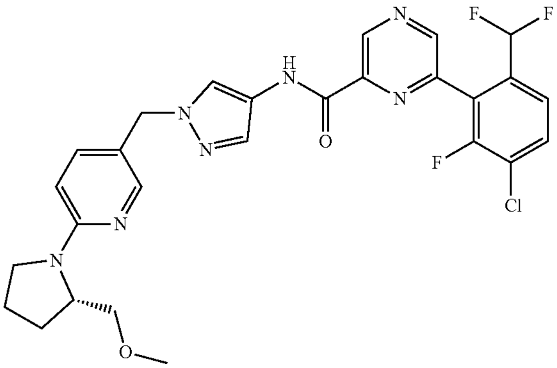 [SMILES: COC[C@@H]1CCCN1c1ccc(Cn2cc(NC(=O)c3cncc(-c4c(C(F)F)ccc(Cl)c4F)n3)cn2)cn1] | (S)-6-(3-Chloro-6-(difluoromethyl)-2-fluorophenyl)-N-(1-((6-(2-(methoxymethyl) pyrrolidin-1-yl)pyridin-3-yl) methyl)-1H-pyrazol-4-yl)pyrazine-2-carboxamide | Calcd.: 572.2 Found: 572.1 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | $[M+H]^+$ or $[M+Na]^+$ | Chiral column |
|---|---|---|---|---|
| 121 | 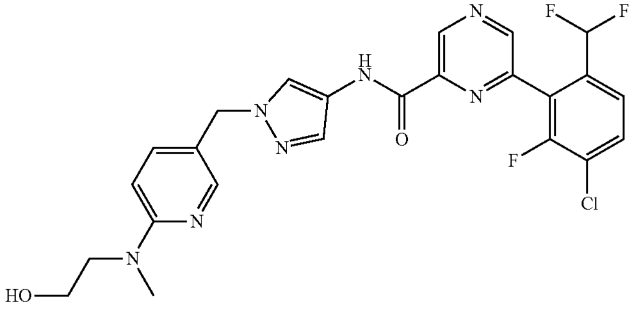 [SMILES: CN(CCO)c1ccc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((6-((2-hydroxyethyl)(methyl)amino)pyridin-3-yl)methyl)-1H-pyrazol-4-yl)pyrazine-2-carboxamide | Calcd.: 532.1 Found: 532.1 | |
| 122 | 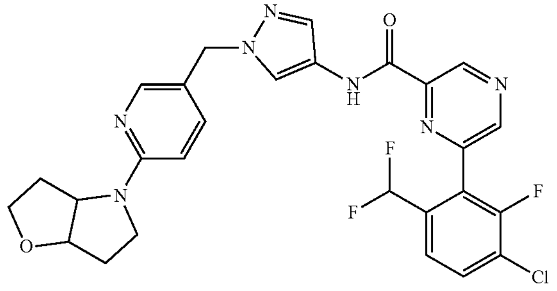 | 6-(3-Chloro-6-(difluoromethyl)-2-fluorophenyl)-N-(1-((6-((3aR,6aR or 3aS,6aS)-hexahydro-4H-furo[3,2-b]pyrrol-4-yl)pyridin-3-yl)methyl)-1H-pyrazol-4-yl)pyrazine-2-carboxamide | Calcd.: 570.2 Found: 570.3 | OJ-H |
| 123 | 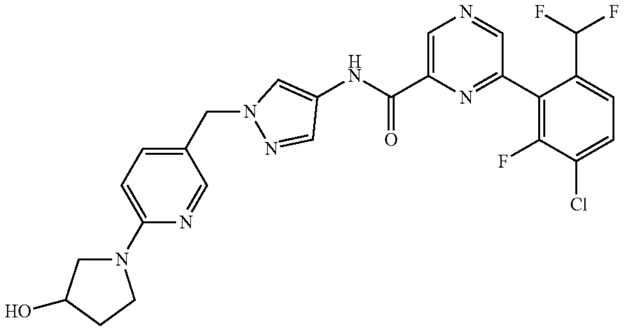 [SMILES: O=C(Nc1cnn(Cc2ccc(N3CCC(O)C3)nc2)c1)c1cncc(-c2c(C(F)F)ccc(Cl)c2F)n1] | 6-(3-Chloro-6-(difluoromethyl)-2-fluorophenyl)-N-(1-((6-(3-hydroxypyrrolidin-1-yl)pyridin-3-yl)methyl)-1H-pyrazol-4-yl)pyrazine-2-carboxamide | Calcd.: 544.1 Found: 544.1 | |
| 125 | 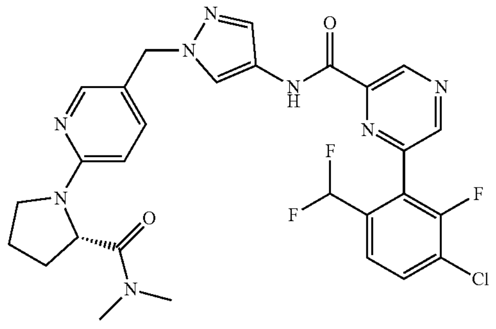 [SMILES: CN(C)C(=O)[C@@H]1CCCN1c1ccc(Cn2cc(NC(=O)c3cncc(-c4c(C(F)F)ccc(Cl)c4F)n3)cn2)cn1] | (S)-6-(3-Chloro-6-(difluoromethyl)-2-fluorophenyl)-N-(1-((6-(2-(dimethylcarbamoyl)pyrrolidin-1-yl)pyridin-3-yl)methyl)-1H-pyrazol-4-yl)pyrazine-2-carboxamide | Calcd.: 599.1 Found: 598.1 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | $[M + H]^+$ or $[M + Na]^+$ | Chiral column |
|---|---|---|---|---|
| 126 | 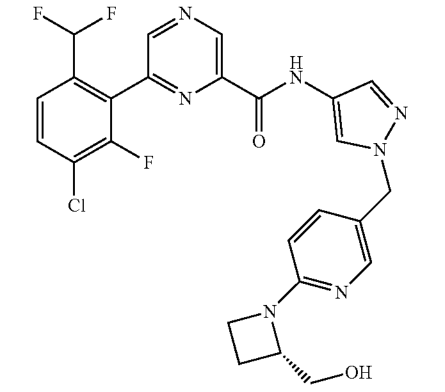 [SMILES: O=C(Nc1cnn(Cc2ccc(N3CC[C@H]3CO)nc2)c1)c1cncc(-c2c(C(F)F)ccc(Cl)c2F)n1] | (S)-6-(3-Chloro-6-(difluoromethyl)-2-fluorophenyl)-N-(1-((6-(2-(hydroxymethyl)azetidin-1-yl)pyridin-3-yl)methyl)-1H-pyrazol-4-yl)pyrazine-2-carboxamide | Calcd.: 544.1 Found: 544.0 | |
| 127 | 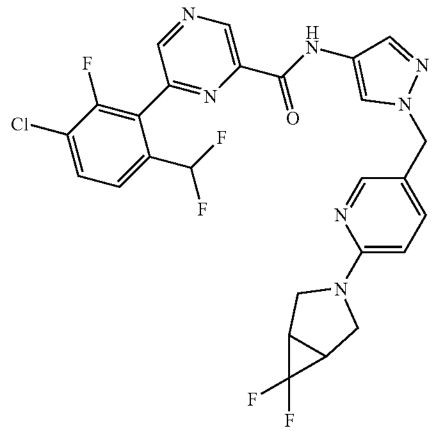 [SMILES: O=C(Nc1cnn(Cc2ccc(N3CC4C(C3)C4(F)F)nc2)c1)c1cncc(-c2c(C(F)F)ccc(Cl)c2F)n1] | 6-(3-Chloro-6-(difluoromethyl)-2-fluorophenyl)-N-(1-((6-(6,6-difluoro-3-azabicyclo[3.1.0]hexan-3-yl)pyridin-3-yl)methyl)-1H-pyrazol-4-yl)pyrazine-2-carboxamide | Calcd.: 576.1 Found: 576.1 | |
| 128 | 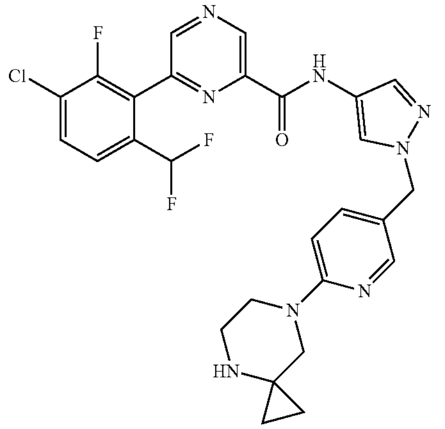 [SMILES: O=C(Nc1cnn(Cc2ccc(N3CCNC4(CC4)C3)nc2)c1)c1cncc(-c2c(C(F)F)ccc(Cl)c2F)n1] | N-(1-((6-(4,7-Diazaspiro[2.5]octan-7-yl)pyridin-3-yl)methyl)-1H-pyrazol-4-yl)-6-(3-chloro-6-(difluoromethyl)-2-fluorophenyl)pyrazine-2-carboxamide | Calcd.: 569.2 Found: 569.4 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | $[M + H]^+$ or $[M + Na]^+$ | Chiral column |
|---|---|---|---|---|
| 129 | 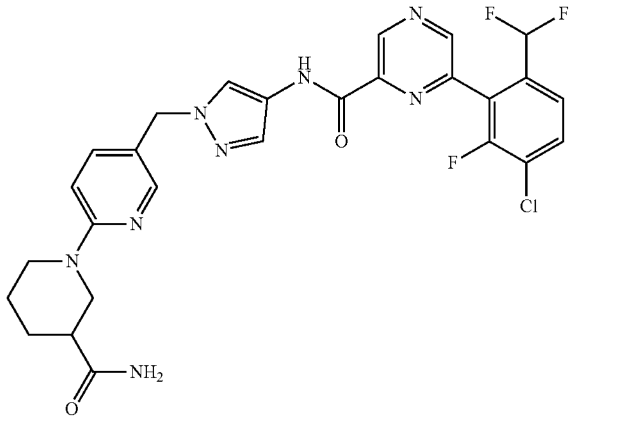 [SMILES: NC(=O)C1CCCN(c2ccc(Cn3cc(NC(=O)c4cncc(-c5c(C(F)F)ccc(Cl)c5F)n4)cn3)cn2)C1] | N-(1-((6-(3-Carbamoylpiperidin-1-yl)pyridin-3-yl) methyl)-1H-pyrazol-4-yl)-6-(3-chloro-6-(difluoromethyl)-2-fluorophenyl)pyrazine-2-carboxamide | Calcd.: 585.2 Found: 585.1 | |
| 130 | 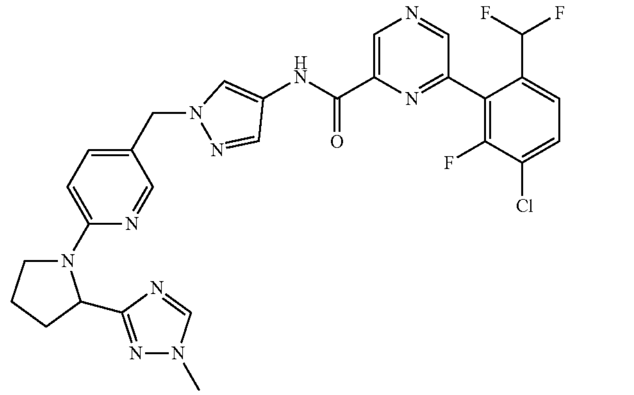 [SMILES: Cn1cnc(C2CCCN2c2ccc(Cn3cc(NC(=O)c4cncc(-c5c(C(F)F)ccc(Cl)c5F)n4)cn3)cn2)n1] | 6-(3-Chloro-6-(difluoromethyl)-2-fluorophenyl)-N-(1-((6-(2-(1-methyl-1H-1,2,4-triazol-3-yl)pyrrolidin-1-yl)pyridin-3-yl)methyl)-1H-pyrazol-4-yl)pyrazine-2-carboxamide | Calcd.: 609.2 Found: 609.1 | |
| 131 | 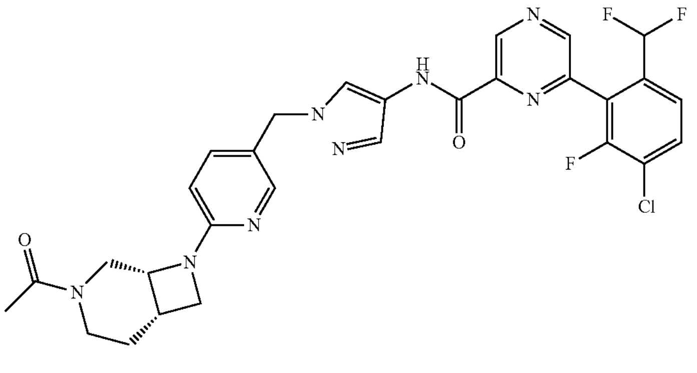 [SMILES: CC(=O)N1CC[C@H]2CN(c3ccc(CN/C=C(\C=N)NC(=O)c4cncc(-c5c(C(F)F)ccc(Cl)c5F)n4)cn3)[C@H]2C1] | N-(1-((6-((1R,6S)-3-Acetyl-3,8-diazabicyclo [4.2.0]octan-8-yl)pyridin-3-yl)methyl)-1H-pyrazol-4-yl)-6-(3-chloro-6-(difluoromethyl)-2-fluorophenyl)pyrazine-2-carboxamide | Calcd.: 611.2 Found: 611.1 | |

TABLE AAE-continued

The following compounds were prepared using procedures similar to those described above using the appropriate starting materials. In some examples, racemic products or diatereomeric mixtures were separated using chiral columns (SFC or HPLC) specified in the table.

| Example | Structure | Name | $[M + H]^+$ or $[M + Na]^+$ | Chiral column |
|---|---|---|---|---|
| 132 | 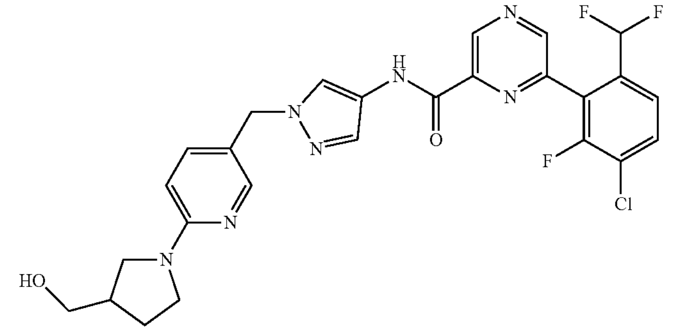 [SMILES: O=C(Nc1cnn(Cc2ccc(N3CCC(CO)C3)nc2)c1)c1cncc(-c2c(C(F)F)ccc(Cl)c2F)n1] | 6-(3-Chloro-6-(difluoromethyl)-2-fluorophenyl)-N-(1-((6-(3-(hydroxymethyl)pyrrolidin-1-yl)pyridin-3-yl)methyl)-1H-pyrazol-4-yl)pyrazine-2-carboxamide | Calcd.: 558.2 Found: 558.0 | |
| 133 | 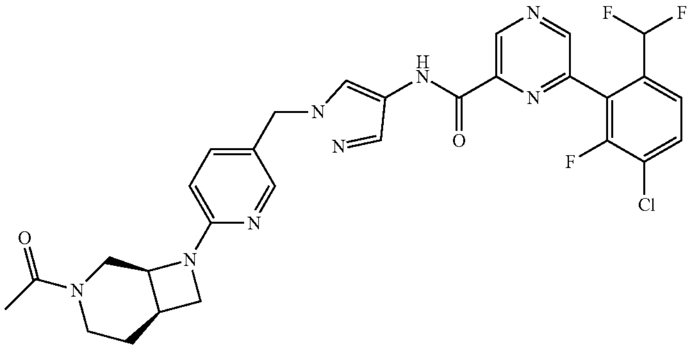 [SMILES: CC(=O)N1CC[C@@H]2CN(c3ccc(CN/C=C(\C=N)NC(=O)c4cncc(-c5c(C(F)F)ccc(Cl)c5F)n4)cn3)[C@@H]2C1] | N-(1-((6-((1S,6R)-3-Acetyl-3,8-diazabicyclo[4.2.0]octan-8-yl)pyridin-3-yl)methyl)-1H-pyrazol-4-yl)-6-(3-chloro-6-(difluoromethyl)-2-fluorophenyl)pyrazine-2-carboxamide | Calcd.: 611.2 Found: 611.2 | |

Examples 134 and 135

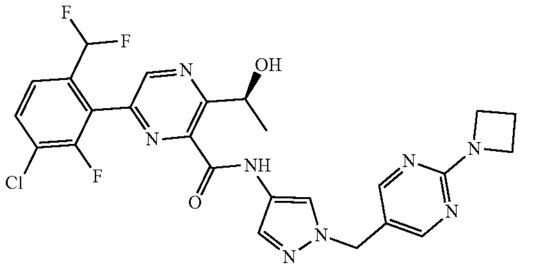

and

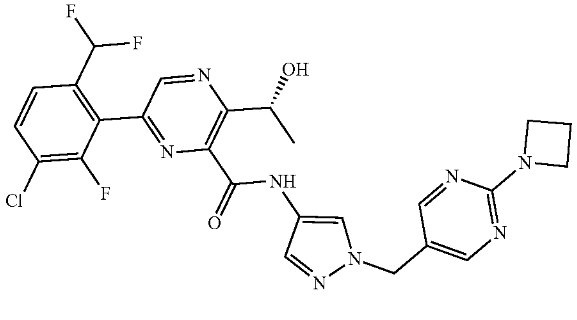

(S)—N-(1-((2-(Azetidin-1-yl)pyrimidin-5-yl)methyl)-1H-pyrazol-4-yl)-6-(3-chloro-6-(difluoromethyl)-2-fluorophenyl)-3-(1-hydroxyethyl)pyrazine-2-carboxamide and (R)—N-(1-((2-(Azetidin-1-yl)pyrimidin-5-yl)methyl)-1H-pyrazol-4-yl)-6-(3-chloro-6-(difluoromethyl)-2-fluorophenyl)-3-(1-hydroxyethyl)pyrazine-2-carboxamide (Scheme AAF)

To a solution of N-(1-((2-(azetidin-1-yl)pyrimidin-5-yl)methyl)-1H-pyrazol-4-yl)-6-(3-chloro-6-(difluoromethyl)-2-fluorophenyl)-3-vinylpyrazine-2-carboxamide (41 mg, 0.076 mmol) in IPA (5 mL) was added phenylsilane (21 mg, 0.19 mmol) and tris(2,2,6,6-tetramethyl-3,5-heptanedionato)manganese(III) (9.2 mg, 0.015 mmol). The reaction atmosphere was replaced with 02 via a balloon, and the resulting mixture was vigorously stirred at rt for 12 h. The reaction was concentrated and partitioned between water and EtOAc. The layers were separated, and the aq. layer was extracted with EtOAc. The combined organic layers were washed with brine, dried over anhydrous $Na_2SO_4$, filtered and concentrated to afford a crude residue that was purified by reversed-phase preparatory-HPLC (C18 stationary phase, water (0.1% TFA)-ACN Begin B 33%, End B 63%) to give a racemic mixture that was separated by SFC (Phenomenex-Cellulose, 0.1% $NH_3H_2O$-MeOH Begin B 55% End B 55%) to give the title compounds. The first eluted isomer Example 134: $^1H$ NMR (400 MHz, $CD_3OD$) δ 8.97 (d, J=2.2 Hz, 1H), 8.29 (s, 2H), 8.21 (s, 1H), 7.80 (t, J=7.8 Hz, 1H), 7.61-7.70

(m, 2H), 6.76-7.09 (m, 1H), 5.80 (br d, J=6.6 Hz, 1H), 5.15 (s, 2H), 4.10 (t, J=7.6 Hz, 4H), 2.35 (br t, J=7.5 Hz, 2H), 1.60 (d, J=6.4 Hz, 3H); MS=559.2 $[M+1]^+$. The second eluted isomer Example 135: $^1H$ NMR (400 MHz, $CD_3OD$) δ 8.97 (d, J=2.2 Hz, 1H), 8.29 (s, 2H), 8.21 (s, 1H), 7.80 (t, J=7.8 Hz, 1H), 7.60-7.72 (m, 2H), 6.74-7.09 (m, 1H), 5.80 (q, J=6.4 Hz, 1H), 5.15 (s, 2H), 4.10 (t, J=7.5 Hz, 4H), 2.36 (t, J=7.6 Hz, 2H), 1.60 (d, J=6.6 Hz, 3H). MS=559.2 $[M+H]^+$.

Example 136

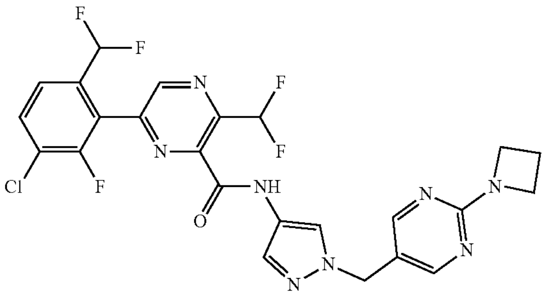 [SMILES: O=C(Nc1cnn(Cc2cnc(N3CCC3)nc2)c1)c1nc(-c2c(C(F)F)ccc(Cl)c2F)cnc1C(F)F]

N-(1-((2-(Azetidin-1-yl)pyrimidin-5-yl)methyl)-1H-pyrazol-4-yl)-6-(3-chloro-6-(difluoromethyl)-2-fluorophenyl)-3-(difluoromethyl)pyrazine-2-carboxamide (Scheme AAG)

Step 1. N-(1-((2-(Azetidin-1-yl)pyrimidin-5-yl)methyl)-1H-pyrazol-4-yl)-6-(3-chloro-6-(difluoromethyl)-2-fluorophenyl)-N-((2-(trimethylsilyl)ethoxy)methyl)-3-vinylpyrazine-2-carboxamide: To a solution of N-(1-((2-(azetidin-1-yl)pyrimidin-5-yl)methyl)-1H-pyrazol-4-yl)-6-(3-chloro-6-(difluoromethyl)-2-fluorophenyl)-3-vinylpyrazine-2-carboxamide (300 mg, 0.555 mmol) in DMF (4 mL) was added NaH (44.4 mg, 1.11 mmol, 60 wt % in mineral spirits), and the resulting mixture was stirred at rt for 5 min. SEM-Cl (0.20 mL, 1.1 mmol) was added, and the mixture continued stirring at rt for 2 h. The reaction was diluted with water and extracted with EtOAc. The combined organic layers were washed with brine, dried over anhydrous $Na_2SO_4$, filtered and concentrated to give a crude residue that was purified by silica gel chromatography (EtOAc/petroleum ether) to give the title compound. MS=671.2 $[M+H]^+$.

Step 2. N-(1-((2-(Azetidin-1-yl)pyrimidin-5-yl)methyl)-1H-pyrazol-4-yl)-6-(3-chloro-6-(difluoromethyl)-2-fluorophenyl)-3-formyl-N-((2-(trimethylsilyl)ethoxy)methyl) pyrazine-2-carboxamide: To a solution of N-(1-((2-(azetidin-1-yl)pyrimidin-5-yl)methyl)-1H-pyrazol-4-yl)-6-(3-chloro-6-(difluoromethyl)-2-fluorophenyl)-N-((2-(trimethylsilyl)ethoxy)methyl)-3-vinylpyrazine-2-carboxamide (100 mg, 0.149 mmol) in THF (5 mL) and water (2 mL) were added osmium tetroxide (0.76 mL, 0.030 mmol, 10 mg/mL aq. solution) and sodium periodate (159 mg, 0.745 mmol), and the resulting mixture was stirred at rt for 12 h. The reaction was quenched with satd. aq. $Na_2S_2O_3$ and allowed to stir at rt for 30 min, at which time, the mixture was extracted with EtOAc. The combined organic layers were washed with brine, dried over anhydrous $Na_2SO_4$, filtered and concentrated to give the title compound which was used in next step directly. MS=673.2 $[M+H]^+$.

Step 3. N-(1-((2-(Azetidin-1-yl)pyrimidin-5-yl)methyl)-1H-pyrazol-4-yl)-6-(3-chloro-6-(difluoromethyl)-2-fluorophenyl)-3-(difluoromethyl)-N-((2-(trimethylsilyl)ethoxy) methyl)pyrazine-2-carboxamide: To a solution of N-(1-((2-(azetidin-1-yl)pyrimidin-5-yl)methyl)-1H-pyrazol-4-yl)-6-(3-chloro-6-(difluoromethyl)-2-fluorophenyl)-3-formyl-N-((2-(trimethylsilyl)ethoxy)methyl)pyrazine-2-carboxamide (60 mg, 0.089 mmol) in THF (2 mL) was added DAST (0.12 mL, 0.89 mmol) at 0° C., and the resulting mixture was warmed to 35° C. and allowed to stir at 35° C. for 12 h. The reaction was quenched with satd. aq. $NaHCO_3$ and water, and the resulting mixture was extracted with EtOAc. The combined organic layers were washed with brine, dried over anhydrous $Na_2SO_4$, filtered and concentrated to give a crude residue that was purified by preparatory-TLC ((1:1) EtOAc/petroleum ether) to give the title compound. MS=695.1 $[M+H]^+$.

Step 4. N-(1-((2-(Azetidin-1-yl)pyrimidin-5-yl)methyl)-1H-pyrazol-4-yl)-6-(3-chloro-6-(difluoromethyl)-2-fluorophenyl)-3-(difluoromethyl)pyrazine-2-carboxamide: A solution of N-(1-((2-(azetidin-1-yl)pyrimidin-5-yl)methyl)-1H-pyrazol-4-yl)-6-(3-chloro-6-(difluoromethyl)-2-fluorophenyl)-3-(difluoromethyl)-N-((2-(trimethylsilyl) ethoxy)methyl)pyrazine-2-carboxamide (40 mg, 0.058 mmol) in TFA (1 mL) was stirred at 50° C. for 12 h. The mixture was concentrated purified by reversed-phase preparatory-HPLC (C18 stationary phase, water (0.1% TFA)-ACN) to afford the title compound. $^1H$ NMR (400 MHz, $CD_3OD$) δ 9.13 (d, J=2.4 Hz, 1H), 8.43 (s, 2H), 8.28 (s, 1H), 7.75-8.04 (m, 2H), 7.73 (d, J=0.8 Hz, 1H), 7.69 (d, J=8.6 Hz, 1H), 6.82-7.15 (m, 1H), 5.23 (s, 2H), 4.23 (t, J=7.8 Hz, 4H), 2.39-2.52 (m, 2H). MS=565.1 $[M+H]^+$.

Example 137

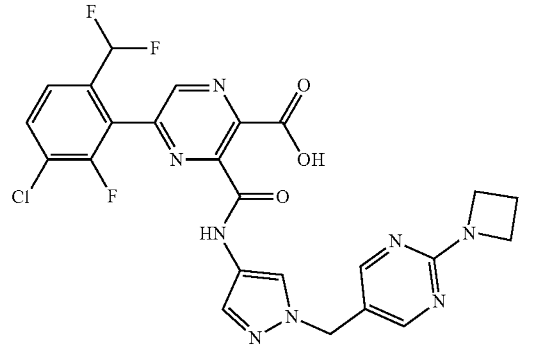 [SMILES: O=C(O)c1ncc(-c2c(C(F)F)ccc(Cl)c2F)nc1C(=O)Nc1cnn(Cc2cnc(N3CCC3)nc2)c1]

3-((1-((2-(Azetidin-1-yl)pyrimidin-5-yl)methyl)-1H-pyrazol-4-yl)carbamoyl)-5-(3-chloro-6-(difluoromethyl)-2-fluorophenyl)pyrazine-2-carboxylic acid (Scheme AAH)

Step 1. 3-((1-((2-(Azetidin-1-yl)pyrimidin-5-yl)methyl)-1H-pyrazol-4-yl)((2-(trimethylsilyl)ethoxy)-methyl)carbamoyl)-5-(3-chloro-6-(difluoromethyl)-2-fluorophenyl) pyrazine-2-carboxylic acid: To a solution of N-(1-((2-(azetidin-1-yl)pyrimidin-5-yl)methyl)-1H-pyrazol-4-yl)-6-(3-chloro-6-(difluoro-methyl)-2-fluorophenyl)-3-formyl-N-((2-(trimethylsilyl)ethoxy)methyl)pyrazine-2-carboxamide (50 mg, 0.074 mmol) in water (1 mL) and ACN (1 mL) were added sodium dihydrogenphosphate dihydrate (58 mg, 0.37 mmol), sulfamic acid (36 mg, 0.37 mmol) and sodium chlorite (20 mg, 0.22 mmol), and the resulting mixture was stirred at 15° C. for 30 min. The reaction was diluted with water and extracted with EtOAc, and the combined organic layers were washed with brine, dried over anhydrous $Na_2SO_4$, filtered and concentrated to afford a crude residue that was purified by reversed-phase preparatory-HPLC (C18 stationary phase, water (0.1% TFA)-ACN) to afford the title compound. MS=689.1 $[M+H]^+$.

Step 2. 3-((1-((2-(Azetidin-1-yl)pyrimidin-5-yl)methyl)-1H-pyrazol-4-yl)carbamoyl)-5-(3-chloro-6-(difluoromethyl)-2-fluorophenyl)pyrazine-2-carboxylic acid: The title compound was prepared following procedures similar to those described above for Intermediate BF, Step 3, in which the final compound was purified by reversed-phase preparatory-HPLC (C18 stationary phase, water (0.1% TFA)-ACN). $^1H$ NMR (400 MHz, $CD_3OD$) δ 9.00 (br s, 1H), 8.32 (s, 2H), 8.18 (s, 1H), 7.84 (br t, J=7.6 Hz, 1H), 7.62-7.70 (m, 2H), 6.81-7.18 (m, 1H), 5.17 (s, 2H), 4.05-4.19 (m, 4H), 2.38 (t, J=7.6 Hz, 2H). MS=559.1 $[M+H]^+$.

Example 138

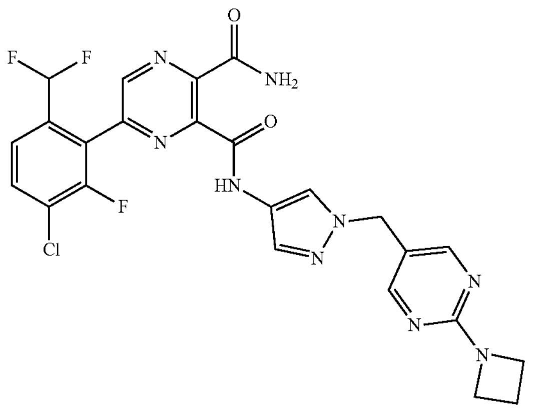 [SMILES: NC(=O)c1ncc(-c2c(C(F)F)ccc(Cl)c2F)nc1C(=O)Nc1cnn(Cc2cnc(N3CCC3)nc2)c1]

$N^2$-(1-((2-(Azetidin-1-yl)pyrimidin-5-yl)methyl)-1H-pyrazol-4-yl)-6-(3-chloro-6-(difluoromethyl)-2-fluorophenyl)pyrazine-2,3-dicarboxamide (Scheme AAI)

Step 1. $N^2$-(1-((2-(Azetidin-1-yl)pyrimidin-5-yl)methyl)-1H-pyrazol-4-yl)-6-(3-chloro-6-(difluoromethyl)-2-fluorophenyl)-$N^2$-((2-(trimethylsilyl)ethoxy)methyl)pyrazine-2,3-dicarboxamide: To a solution of 3-((1-((2-(azetidin-1-yl)pyrimidin-5-yl)methyl)-1-pyrazol-4-yl)((2-(trimethylsilyl)ethoxy)-methyl)carbamoyl)-5-(3-chloro-6-(difluoromethyl)-2H-fluorophenyl)pyrazine-2-carboxylic acid (13 mg, 0.019 mmol), HATU (8.6 mg, 0.023 mmol) and DIEA (10 μL, 0.057 mmol) in DCM (2 mL) was added $NH_4Cl$ (1.2 mg, 0.023 mmol), and the resulting mixture was allowed to stir at rt for 1 h. The reaction was diluted with water and extracted with DCM. The combined organic layers were washed with brine, dried over $Na_2SO_4$, filtered and concentrated to give the title compound which was used in next step directly. MS=688.2 (M+H).

Step 2. $N^2$-(1-((2-(Azetidin-1-yl)pyrimidin-5-yl)methyl)-1H-pyrazol-4-yl)-6-(3-chloro-6-(difluoromethyl)-2-fluorophenyl)pyrazine-2,3-dicarboxamide: The title compound was prepared following procedures similar to those described above for Intermediate BF, Step 3, in which the final compound was purified by reversed-phase preparatory-HPLC (C18 stationary phase, water (0.1% TFA)-ACN). $^1H$ NMR (400 MHz, $CD_3OD$) δ 8.98 (d, J=2.7 Hz, 1H), 8.37 (s, 2H), 8.18 (s, 1H), 7.78-7.86 (m, 1H), 7.61-7.68 (m, 2H), 6.82-7.11 (m, 1H), 5.19 (s, 2H), 4.12-4.22 (m, 4H), 2.41 (t, J=7.7 Hz, 2H). MS=558.1 $[M+H]^+$.

Example 139

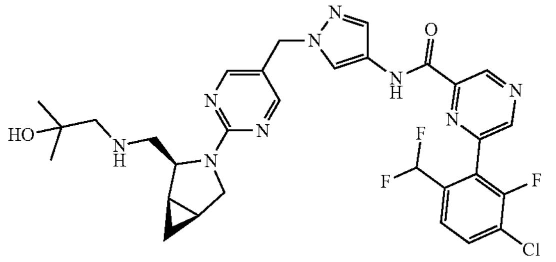 [SMILES: CC(C)(O)CNC[C@@H]1[C@@H]2C[C@@H]2CN1c1ncc(Cn2cc(NC(=O)c3cncc(-c4c(C(F)F)ccc(Cl)c4F)n3)cn2)cn1]

6-(3-Chloro-6-(difluoromethyl)-2-fluorophenyl)-N-(1-((2-((1R,2S,5S)-2-(((2-hydroxy-2-methylpropyl)amino)methyl)-3-azabicyclo[3.1.0]hexan-3-yl)pyrimidin-5-yl)methyl)-1H-pyrazol-4-yl)pyrazine-2-carboxamide (Scheme AAJ)

Step 1. 6-(3-Chloro-6-(difluoromethyl)-2-fluorophenyl)-N-(1-((2-((1R,2S,5S)-2-formyl-3-azabicyclo[3.1.0]hexan-3-yl)pyrimidin-5-yl)methyl)-1H-pyrazol-4-yl)pyrazine-2-carboxamide: Dess-Martin Periodinane (66 mg, 0.16 mmol) and sodium bicarbonate (16 mg, 0.19 mmol) were added to a stirred solution of 6-(3-chloro-6-(difluoromethyl)-2-fluorophenyl)-N-(1-((2-((1R,2S,5S)-2-(hydroxymethyl)-3-azabicyclo[3.1.0]hexan-3-yl)pyrimidin-5-yl)methyl)-1H-pyrazol-4-yl)pyrazine-2-carboxamide (74 mg, 0.13 mmol) in DCM (4 mL) at rt, and the resulting mixture was stirred at rt for 3 h. The reaction was quenched with 2M aq. $NaS_2O_3$ and extracted with DCM. The combined organic layers were dried ($Na_2SO_4$), filtered and concentrated to afford a crude residue that was purified by silica gel chromatography ((3:1) EtOAc:EtOH/hexanes) to give the title compound. MS=569.2 $[M+1]^+$.

Step 2. 6-(3-Chloro-6-(difluoromethyl)-2-fluorophenyl)-N-(1-((2-((1R,2S,5S)-2-(((2-hydroxy-2-methylpropyl)amino)methyl)-3-azabicyclo[3.1.0]hexan-3-yl)pyrimidin-5-yl)methyl)-1H-pyrazol-4-yl)pyrazine-2-carboxamide: 1-Amino-2-methylpropan-2-ol (10 mg, 0.11 mmol) was added to a stirred solution of 6-(3-chloro-6-(difluoromethyl)-2-fluorophenyl)-N-(1-((2-((1R,2R,5R)-2-formylbicyclo[3.1.0]hexan-3-yl)pyrimidin-5-yl)methyl)-1H-pyrazol-4-yl)pyrazine-2-carboxamide (16 mg, 0.028 mmol) in DCE (1 mL, 5% AcOH), and the resulting mixture was stirred at rt for 0.5 h. Sodium triacetoxyboronhydride (12 mg, 0.056 mmol) was added to this mixture, which was stirred at rt for 3 h. The reaction was quenched with 1M $Na_2CO_3$ and extracted with DCM. The combined organic layers were dried ($Na_2SO_4$), filtered and concentrated to afford a crude residue that was purified by reversed-phase preparatory-HPLC (C18 stationary phase, water (0.1% TFA)-ACN) to afford the title compound. $^1H$ NMR (400 MHz, DMSO-d6) δ 10.83 (s, 1H), 9.84 (br, 1H), 9.32 (s, 1H), 9.14 (s, 1H), 8.79 (br, 1H), 8.44 (s, 2H), 825 (s, 1H), 7.98 (t, J=7.8 Hz, 1H), 7.70 (m, 2H), 7.17 (t, J=54.3 Hz, 1H), 5.20 (s, 2H), 4.22-

4.19 (m, 1H), 3.79-3.75 (m, 1H), 3.66-3.61 (m, 1H), 3.50-3.41 (m, 1H), 3.16-2.99 (m, 2H), 2.85-2.74 (m, 1H), 1.97-1.86 (m, 1H), 1.71-1.63 (m, 1H), 1.23 (s, 3H), 1.21 (s, 3H), 0.70-0.63 (m, 1H), 0.43-0.38 (m, 1H). MS=642.2 $[M+H]^+$.

TABLE AAJ

The following compounds were prepared using procedures similar to those described above using the appropriate starting materials. In some examples, racemic products or diatereomeric mixtures were separated using chiral columns (SFC or HPLC) specified in the table.

| Example | Structure | IUPAC Name | $[M + H]^+$ or $[M + Na]^+$ | Chiral Column |
|---|---|---|---|---|
| 140 | 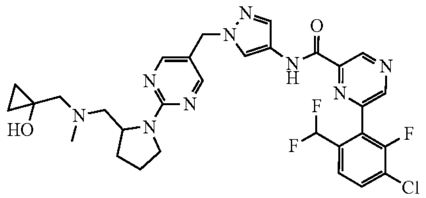 [SMILES: CN(CC1CCCN1c1ncc(Cn2cc(NC(=O)c3cncc(-c4c(C(F)F)ccc(Cl)c4F)n3)cn2)cn1)CC1(O)CC1] | (S or R)-6-(3-Chloro-6-(difluoromethyl)-2-fluorophenyl)-N-(1-((2-(2-((((1-hydroxycyclopropyl)methyl)(methyl)amino)methyl)pyrrolidin-1-yl)pyrimidin-5-yl)methyl)-1H-pyrazol-4-yl)pyrazine-2-carboxamide | Calcd.: 642.1 Found: 642.2 | Chiral IG column second peak |
| 141 | 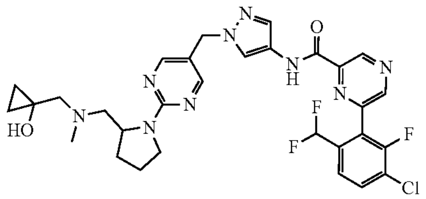 [SMILES: CN(CC1CCCN1c1ncc(Cn2cc(NC(=O)c3cncc(-c4c(C(F)F)ccc(Cl)c4F)n3)cn2)cn1)CC1(O)CC1] | (R or S)-6-(3-Chloro-6-(difluoromethyl)-2-fluorophenyl)-N-(1-((2-(2-((((1-hydroxycyclopropyl)methyl)(methyl)amino)methyl)pyrrolidin-1-yl)pyrimidin-5-yl)methyl)-1H-pyrazol-4-yl)pyrazine-2-carboxamide | Calcd.: 642.1 Found: 642.2 | Chiral IG column First peak |
| 142 | 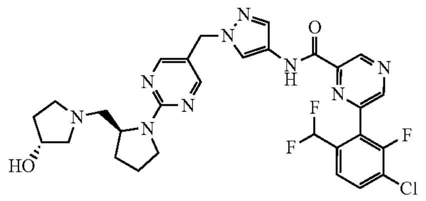 [SMILES: O=C(Nc1cnn(Cc2cnc(N3CCC[C@H]3CN3CC[C@@H](O)C3)nc2)c1)c1cncc(-c2c(C(F)F)ccc(Cl)c2F)n1] | 6-(3-Chloro-6-(difluoromethyl)-2-fluorophenyl)-N-(1-((2-((S)-2-(((R)-3-hydroxypyrrolidin-1-yl)methyl)pyrrolidin-1-yl)pyrimidin-5-yl)methyl)-1H-pyrazol-4-yl)pyrazine-2-carboxamide | Calcd.: 628.1 Found: 628.3 | |
| 143 | 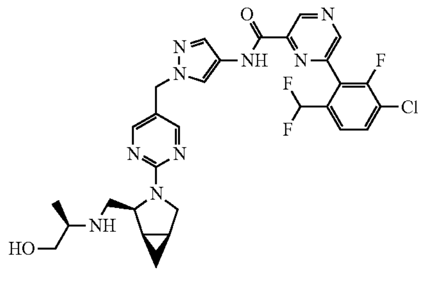 [SMILES: C[C@H](CO)NC[C@@H]1[C@@H]2C[C@@H]2CN1c1ncc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((2-((1R,2S,5S)-2-((((R)-1-hydroxypropan-2-yl)amino)methyl)-3-azabicyclo[3.1.0]hexan-3-yl)pyrimidin-5-yl)methyl)-1H-pyrazol-4-yl)pyrazine-2-carboxamide | Calcd.: 628.1 Found: 628.2 | |
| 144 | 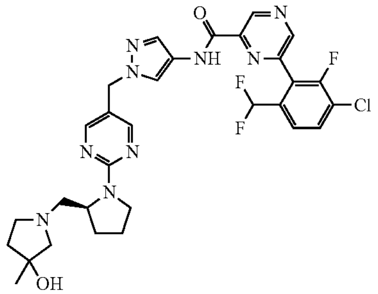 [SMILES: CC1(O)CCN(C[C@@H]2CCCN2c2ncc(Cn3cc(NC(=O)c4cncc(-c5c(C(F)F)ccc(Cl)c5F)n4)cn3)cn2)C1] | 6-(3-Chloro-6-(difluoromethyl)-2-fluorophenyl)-N-(1-((2-((2S)-2-((3-hydroxy-3-methylpyrrolidin-1-yl)methyl)pyrrolidin-1-yl)pyrimidin-5-yl)methyl)-1H-pyrazol-4-yl)pyrazine-2-carboxamide | Calcd.: 642.1 Found: 642.3 | |

TABLE AAJ-continued

The following compounds were prepared using procedures similar to those described above using the appropriate starting materials. In some examples, racemic products or diatereomeric mixtures were separated using chiral columns (SFC or HPLC) specified in the table.

| Example | Structure | IUPAC Name | $[M + H]^+$ or $[M + Na]^+$ | Chiral Column |
| --- | --- | --- | --- | --- |
| 145 | 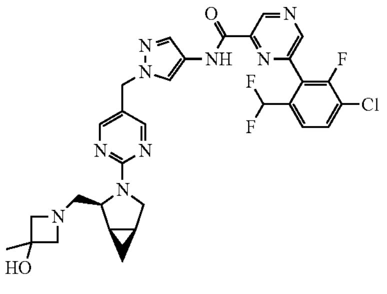 [SMILES: CC1(O)CN(C[C@@H]2[C@@H]3C[C@@H]3CN2c2ncc(Cn3cc(NC(=O)c4cncc(-c5c(C(F)F)ccc(Cl)c5F)n4)cn3)cn2)C1] | 6-(3-Chloro-6-(difluoromethyl)-2-fluorophenyl)-N-(1-((2-((1R,2S,5S)-2-((3-hydroxy-3-methylazetidin-1-yl)methyl)-3-azabicyclo[3.1.0]hexan-3-yl)pyrimidin-5-yl)methyl)-1H-pyrazol-4-yl)pyrazine-2-carboxamide | Calcd.: 640.0 Found: 640.2 | |
| 146 | 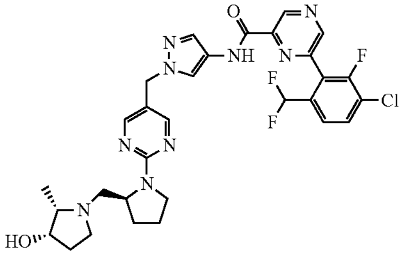 [SMILES: C[C@H]1[C@@H](O)CCN1C[C@@H]1CCCN1c1ncc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((2-((S)-2-(((2S,3S)-3-hydroxy-2-methylpyrrolidin-1-yl)methyl)pyrrolidin-1-yl)pyrimidin-5-yl)methyl)-1H-pyrazol-4-yl)pyrazine-2-carboxamide | Calcd.: 642.1 Found: 642.2 | |
| 147 | 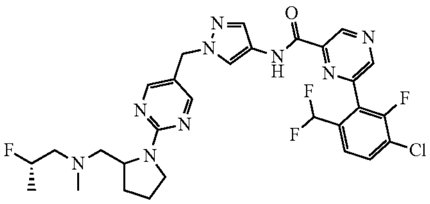 [SMILES: C[C@H](F)CN(C)CC1CCCN1c1ncc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((2-(2-((((S)-2-fluoropropyl)(methyl)amino)methyl) pyrrolidin-1-yl)pyrimidin-5-yl)methyl)-1H-pyrazol-4-yl)pyrazine-2-carboxamide | Calcd.: 632.1 Found: 632.4 | |
| 148 | 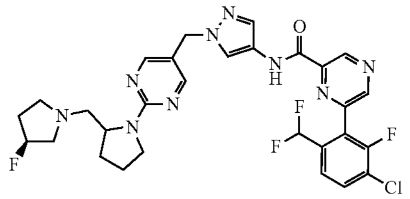 [SMILES: O=C(Nc1cnn(Cc2cnc(N3CCCC3CN3CC[C@H](F)C3)nc2)c1)c1cncc(-c2c(C(F)F)ccc(Cl)c2F)n1] | 6-(3-Chloro-6-(difluoromethyl)-2-fluorophenyl)-N-(1-((2-(2-(((S)-3-fluoropyrrolidin-1-yl)methyl)pyrrolidin-1-yl)pyrimidin-5-yl)methyl)-1H-pyrazol-4-yl)pyrazine-2-carboxamide | Calcd.: 630.0 Found: 630.4 | |
| 149 | 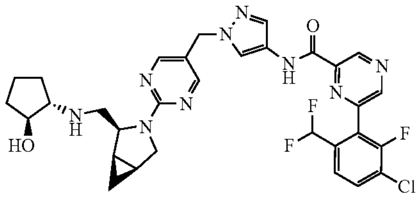 [SMILES: O=C(Nc1cnn(Cc2cnc(N3C[C@H]4C[C@H]4[C@H]3CN[C@H]3CCC[C@@H]3O)nc2)c1)c1cncc(-c2c(C(F)F)ccc(Cl)c2F)n1] | 6-(3-Chloro-6-(difluoromethyl)-2-fluorophenyl)-N-(1-((2-((1R,2S,5S)-2-((((1S,2S)-2-hydroxycyclopentyl)amino)methyl)-3-azabicyclo[3.1.0]hexan-3-yl)pyrimidin-5-yl)methyl)-1H-pyrazol-4-yl)pyrazine-2-carboxamide | Calcd.: 654.1 Found: 654.2 | |
| 150 | 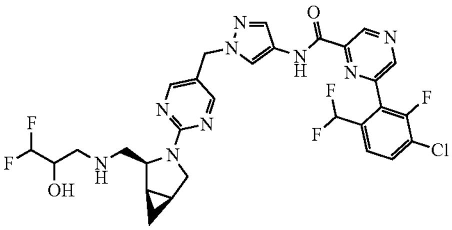 [SMILES: O=C(Nc1cnn(Cc2cnc(N3C[C@H]4C[C@H]4[C@H]3CNCC(O)C(F)F)nc2)c1)c1cncc(-c2c(C(F)F)ccc(Cl)c2F)n1] | 6-(3-Chloro-6-(difluoromethyl)-2-fluorophenyl)-N-(1-((2-((1R,2S,5S)-2-(((3,3-difluoro-2-hydroxypropyl)amino)methyl)-3-azabicyclo[3.1.0]hexan-3-yl)pyrimidin-5-yl)methyl)-1H-pyrazol-4-yl)pyrazine-2-carboxamide | Calcd.: 664.0 Found: 664.1 | |

TABLE AAJ-continued

The following compounds were prepared using procedures similar to those described above using the appropriate starting materials. In some examples, racemic products or diatereomeric mixtures were separated using chiral columns (SFC or HPLC) specified in the table.

| Example | Structure | IUPAC Name | $[M + H]^+$ or $[M + Na]^+$ | Chiral Column |
|---|---|---|---|---|
| 151 | 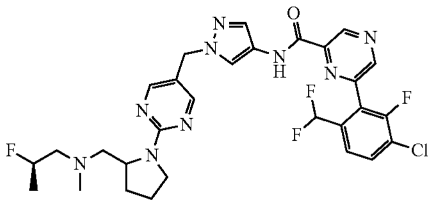 [SMILES: C[C@@H](F)CN(C)CC1CCCN1c1ncc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((2-(2-((((R)-2-fluoropropyl)(methyl)amino)methyl)pyrrolidin-1-yl)pyrimidin-5-yl)methyl)-1H-pyrazol-4-yl)pyrazine-2-carboxamide | Calcd.: 632.1 Found: 632.4 | |
| 152 | 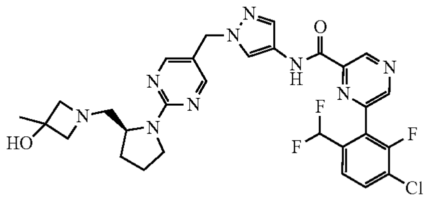 [SMILES: CC1(O)CN(C[C@@H]2CCCN2c2ncc(Cn3cc(NC(=O)c4cncc(-c5c(C(F)F)ccc(Cl)c5F)n4)cn3)cn2)C1] | (S)-6-(3-Chloro-6-(difluoromethyl)-2-fluorophenyl)-N-(1-((2-(2-((3-hydroxy-3-methylazetidin-1-yl)methyl)pyrrolidin-1-yl)pyrimidin-5-yl)methyl)-1H-pyrazol-4-yl)pyrazine-2-carboxamide | Calcd.: 628.1 Found: 628.2 | |
| 153 | 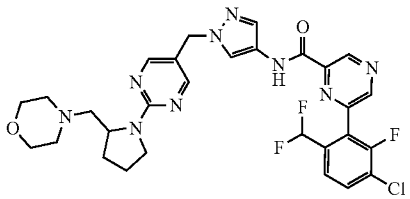 [SMILES: O=C(Nc1cnn(Cc2cnc(N3CCCC3CN3CCOCC3)nc2)c1)c1cncc(-c2c(C(F)F)ccc(Cl)c2F)n1] | 6-(3-Chloro-6-(difluoromethyl)-2-fluorophenyl)-N-(1-((2-(2-(morpholinomethyl)pyrrolidin-1-yl)pyrimidin-5-yl)methyl)-1H-pyrazol-4-yl)pyrazine-2-carboxamide | Calcd.: 628.1 Found: 628.4 | |
| 154 | 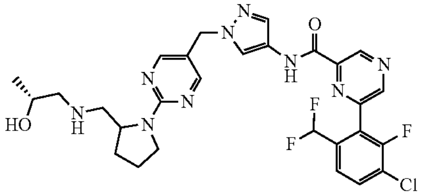 [SMILES: C[C@@H](O)CNCC1CCCN1c1ncc(Cn2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-((2-(2-((((R)-2-hydroxypropyl)amino)methyl)pyrrolidin-1-yl)pyrimidin-5-yl)methyl)-1H-pyrazol-4-yl)pyrazine-2-carboxamide | Calcd.: 616.0 Found: 616.4 | |
| 155 | 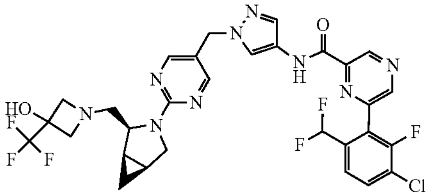 [SMILES: O=C(Nc1cnn(Cc2cnc(N3C[C@H]4C[C@H]4[C@H]3CN3CC(O)(C(F)(F)F)C3)nc2)c1)c1cncc(-c2c(C(F)F)ccc(Cl)c2F)n1] | 6-(3-Chloro-6-(difluoromethyl)-2-fluorophenyl)-N-(1-((2-((1R,2S,5S)-2-((3-hydroxy-3-(trifluoromethyl)azetidin-1-yl)methyl)-3-azabicyclo[3.1.0]hexan-3-yl)pyrimidin-5-yl)methyl)-1H-pyrazol-4-yl)pyrazine-2-carboxamide | Calcd.: 694.0 Found: 694.1 | |
| 156 | 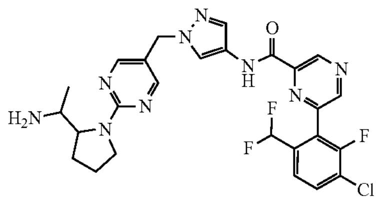 [SMILES: CC(N)C1CCCN1c1ncc(Cn2cc(NC(=O)c3cncc(-c4c(C(F)F)ccc(Cl)c4F)n3)cn2)cn1] | N-(1-((2-(2-(1-Aminoethyl)pyrrolidin-1-yl)pyrimidin-5-yl)methyl)-1H-pyrazol-4-yl)-6-(3-chloro-6-(difluoromethyl)-2-fluorophenyl)pyrazine-2-carboxamide | Calcd.: 572.0 Found: 572.2 | CHIRAL PAK IG Mixture of peak 1 and 2 |
| 157 | 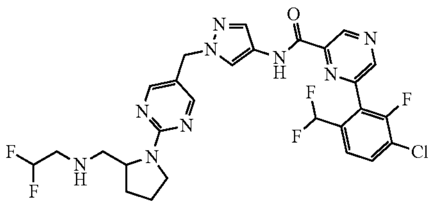 [SMILES: O=C(Nc1cnn(Cc2cnc(N3CCCC3CNCC(F)F)nc2)c1)c1cncc(-c2c(C(F)F)ccc(Cl)c2F)n1] | 6-(3-Chloro-6-(difluoromethyl)-2-fluorophenyl)-N-(1-((2-(2-(((2,2-difluoroethyl)amino)methyl)pyrrolidin-1-yl)pyrimidin-5-yl)methyl)-1H-pyrazol-4-yl)pyrazine-2-carboxamide | Calcd.: 622.0 Found: 622.3 | |

TABLE AAJ-continued

The following compounds were prepared using procedures similar to those described above using the appropriate starting materials. In some examples, racemic products or diatereomeric mixtures were separated using chiral columns (SFC or HPLC) specified in the table.

| Example | Structure | IUPAC Name | [M + H]$^+$ or [M + Na]$^+$ | Chiral Column |
|---|---|---|---|---|
| 158 | 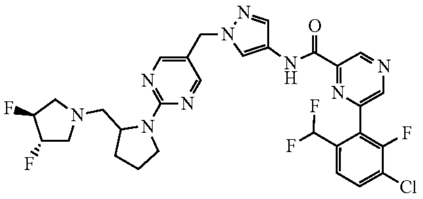 [SMILES: O=C(Nc1cnn(Cc2cnc(N3CCCC3CN3C[C@H](F)[C@@H](F)C3)nc2)c1)c1cncc(-c2c(C(F)F)ccc(Cl)c2F)n1] | 6-(3-Chloro-6-(difluoromethyl)-2-fluorophenyl)-N-(1-((2-(2-(((35,4S)-3,4-difluoropyrrolidin-1-yl)methyl)pyrrolidin-1-yl)pyrimidin-5-yl)methyl)-1H-pyrazol-4-yl)pyrazine-2-carboxamide | Calcd.: 648.0 Found: 648.4 | |
| 159 | 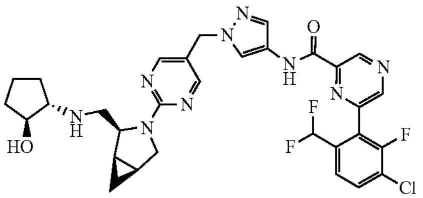 [SMILES: O=C(Nc1cnn(Cc2cnc(N3C[C@H]4C[C@H]4[C@H]3CN[C@H]3CCC[C@@H]3O)nc2)c1)c1cncc(-c2c(C(F)F)ccc(Cl)c2F)n1] | 6-(3-Chloro-6-(difluoromethyl)-2-fluorophenyl)-N-(1-((2-((1R,2S,5S)-2-((((1S,2S)-2-hydroxycyclopentyl)amino)methyl)-3-azabicyclo[3.1.0]hexan-3-yl)pyrimidin-5-yl)methyl)-1H-pyrazol-4-yl)pyrazine-2-carboxamide | Calcd.: 654.1 Found: 654.2 | |
| 160 | 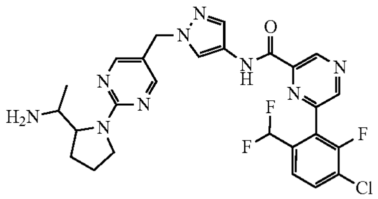 [SMILES: CC(N)C1CCCN1c1ncc(Cn2cc(NC(=O)c3cncc(-c4c(C(F)F)ccc(Cl)c4F)n3)cn2)cn1] | N-(1-((2-(2-(1-Aminoethyl)pyrrolidin-1-yl)pyrimidin-5-yl)methyl)-1H-pyrazol-4-yl)-6-(3-chloro-6-(difluoromethyl)-2-fluorophenyl)pyrazine-2-carboxamide | Calcd.: 572.0 Found: 572.1 | CHIRAL PAK IG Peak 3 |
| 161 | 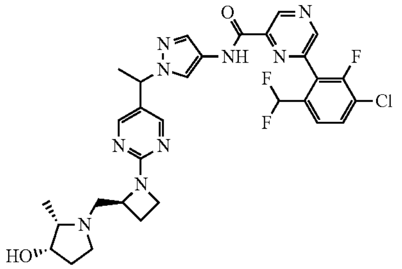 [SMILES: CC(c1cnc(N2CC[C@H]2CN2CC[C@H](O)[C@@H]2C)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-(((2S,3S)-3-hydroxy-2-methylpyrrolidin-1-yl)methyl)azetidin-1-yl)pyrimidin-5-yl)ethyl)-1H-pyrazol-4-yl)pyrazine-2-carboxamide | Calcd. 642.2 found 642.2 | |
| 162 | 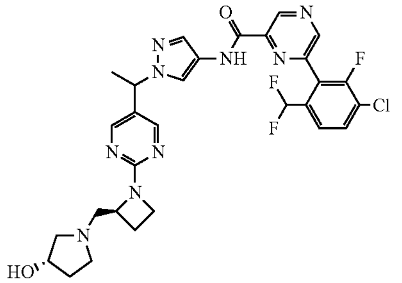 [SMILES: CC(c1cnc(N2CC[C@H]2CN2CC[C@H](O)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-(((S)-3-hydroxypyrrolidin-1-yl)methyl)azetidin-1-yl)pyrimidin-5-yl)ethyl)-1H-pyrazol-4-yl)pyrazine-2-carboxamide | Calcd. 628.2 found 628.2 | |
| 163 | 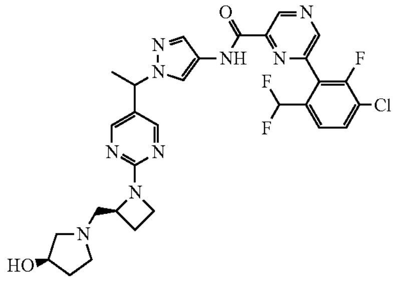 [SMILES: CC(c1cnc(N2CC[C@H]2CN2CC[C@@H](O)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-(((R)-3-hydroxypyrrolidin-1-yl)methyl)azetidin-1-yl)pyrimidin-5-yl)ethyl)-1H-pyrazol-4-yl)pyrazine-2-carboxamide | Calcd. 628.2 found 628.3 | |

TABLE AAJ-continued

The following compounds were prepared using procedures similar to those described above using the appropriate starting materials. In some examples, racemic products or diatereomeric mixtures were separated using chiral columns (SFC or HPLC) specified in the table.

| Example | Structure | IUPAC Name | $[M + H]^+$ or $[M + Na]^+$ | Chiral Column |
|---|---|---|---|---|
| 164 | 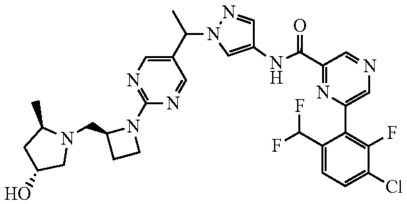 [SMILES: CC(c1cnc(N2CC[C@H]2CN2C[C@H](O)C[C@H]2C)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-(((2R,4R)-4-hydroxy-2-methylpyrrolidin-1-yl)methyl)azetidin-1-yl)pyrimidin-5-yl)ethyl)-1H-pyrazol-4-yl)pyrazine-2-carboxamide | Calcd. 641.2 found 642.2 | |
| 165 | 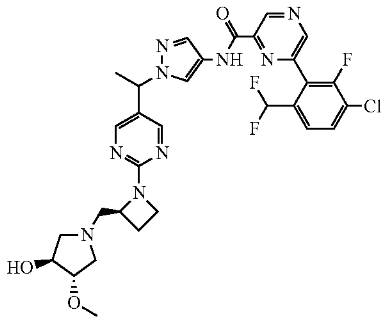 [SMILES: CO[C@H]1CN(C[C@@H]2CCN2c2ncc(C(C)n3cc(NC(=O)c4cncc(-c5c(C(F)F)ccc(Cl)c5F)n4)cn3)cn2)C[C@@H]1O] | 6-(3-Chloro-6-(difluoromethyl)-2-fluorophenyl)-N-(1-(1-(2-((S)-2-(((3S,4S)-3-hydroxy-4-methoxypyrrolidin-1-yl)methyl)azetidin-1-yl)pyrimidin-5-yl)ethyl)-1H-pyrazol-4-yl)pyrazine-2-carboxamide | Calcd. 658.2 found 658.3 | |
| 166 | 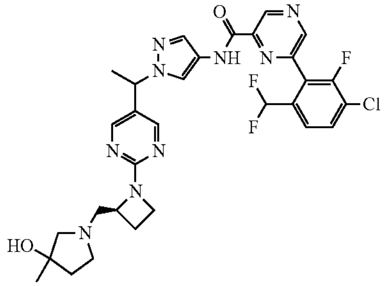 [SMILES: CC(c1cnc(N2CC[C@H]2CN2CCC(C)(O)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((2S)-2-((3-hydroxy-3-methylpyrrolidin-1-yl)methyl)azetidin-1-yl)pyrimidin-5-yl)ethyl)-1H-pyrazol-4-yl)pyrazine-2-carboxamide | Calcd. 642.2 found 642.3 | |
| 167 | 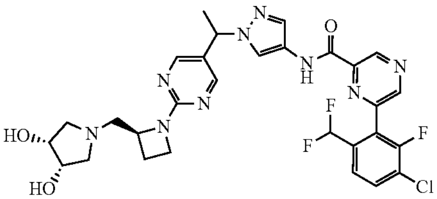 [SMILES: CC(c1cnc(N2CC[C@H]2CN2C[C@@H](O)[C@@H](O)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-(((3R,4S)-3,4-dihydroxypyrrolidin-1-yl)methyl)azetidin-1-yl)pyrimidin-5-yl)ethyl)-1H-pyrazol-4-yl)pyrazine-2-carboxamide | Calcd. 643.2 found 644.1 | |
| 168 | 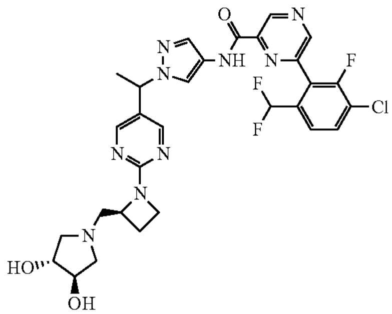 [SMILES: CC(c1cnc(N2CC[C@H]2CN2C[C@@H](O)[C@H](O)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-(((3R,4R)-3,4-dihydroxypyrrolidin-1-yl)methyl)azetidin-1-yl)pyrimidin-5-yl)ethyl)-1H-pyrazol-4-yl)pyrazine-2-carboxamide | Calcd. 644.2 found 644.1 | |

TABLE AAJ-continued

The following compounds were prepared using procedures similar to those described above using the appropriate starting materials. In some examples, racemic products or diatereomeric mixtures were separated using chiral columns (SFC or HPLC) specified in the table.

| Example | Structure | IUPAC Name | $[M + H]^+$ or $[M + Na]^+$ | Chiral Column |
|---|---|---|---|---|
| 169 | 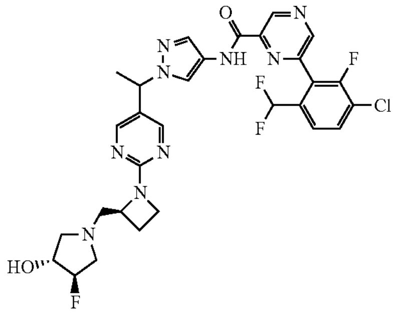 [SMILES: CC(c1cnc(N2CC[C@H]2CN2C[C@@H](O)[C@H](F)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-(((3R,4R)-3-fluoro-4-hydroxypyrrolidin-1-yl)methyl)azetidin-1-yl)pyrimidin-5-yl)ethyl)-1H-pyrazol-4-yl)pyrazine-2-carboxamide | Calcd. 646.2 found 646.2 | |
| 170 | 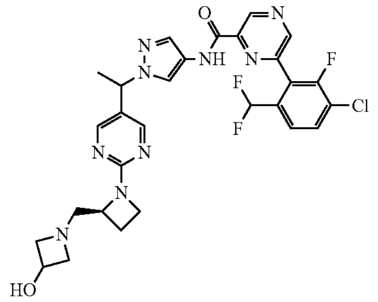 [SMILES: CC(c1cnc(N2CC[C@H]2CN2CC(O)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-((3-hydroxyazetidin-1-yl)methyl)azetidin-1-yl)pyrimidin-5-yl)ethyl)-1H-pyrazol-4-yl)pyrazine-2-carboxamide | Calcd. 614.2 found 614.3 | |
| 171 | 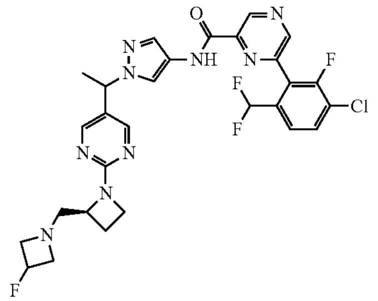 [SMILES: CC(c1cnc(N2CC[C@H]2CN2CC(F)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-((3-fluoroazetidin-1-yl)methyl)azetidin-1-yl)pyrimidin-5-yl)ethyl)-1H-pyrazol-4-yl)pyrazine-2-carboxamide | Calcd. 616.2 found 616.2 | |
| 172 | 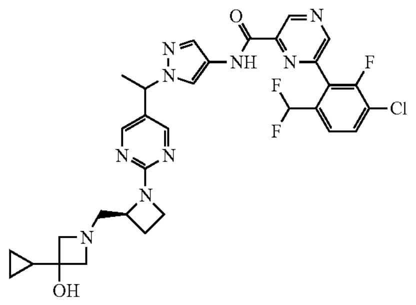 [SMILES: CC(c1cnc(N2CC[C@H]2CN2CC(O)(C3CC3)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-((3-cyclopropyl-3-hydroxyazetidin-1-yl)methyl)azetidin-1-yl)pyrimidin-5-yl)ethyl)-1H-pyrazol-4-yl)pyrazine-2-carboxamide | Calcd. 654.2 found 654.2 | |

TABLE AAJ-continued

| The following compounds were prepared using procedures similar to those described above using the appropriate starting materials. In some examples, racemic products or diatereomeric mixtures were separated using chiral columns (SFC or HPLC) specified in the table. | | | | |
|---|---|---|---|---|
| Example | Structure | IUPAC Name | [M + H]+ or [M + Na]+ | Chiral Column |
| 173 | 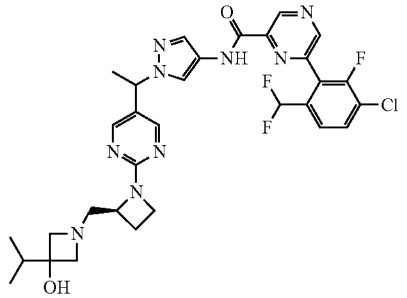 [SMILES: CC(c1cnc(N2CC[C@H]2CN2CC(O)(C(C)C)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-((3-hydroxy-3-isopropylazetidin-1-yl)methyl)azetidin-1-yl)pyrimidin-5-yl)ethyl)-1H-pyrazol-4-yl)pyrazine-2-carboxamide | Calcd. 656.2 found 656.3 | |
| 174 | 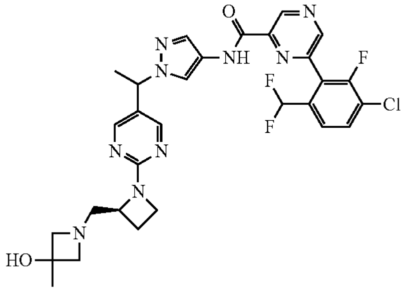 [SMILES: CC(c1cnc(N2CC[C@H]2CN2CC(C)(O)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-((3-hydroxy-3-methylazetidin-1-yl)methyl)azetidin-1-yl)pyrimidin-5-yl)ethyl)-1H-pyrazol-4-yl)pyrazine-2-carboxamide | Calcd. 628.2 found 628.2 | |
| 175 | 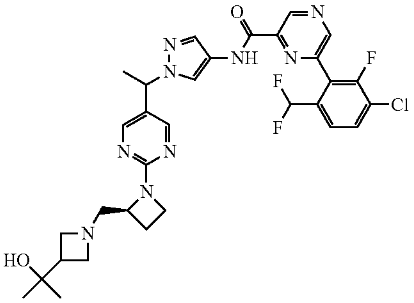 [SMILES: CC(c1cnc(N2CC[C@H]2CN2CC(C(C)(C)O)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-((3-(2-hydroxypropan-2-yl)azetidin-1-yl)methyl)azetidin-1-yl)pyrimidin-5-yl)ethyl)-1H-pyrazol-4-yl)pyrazine-2-carboxamide | Calcd. 656.2 found 656.2 | |
| 176 | 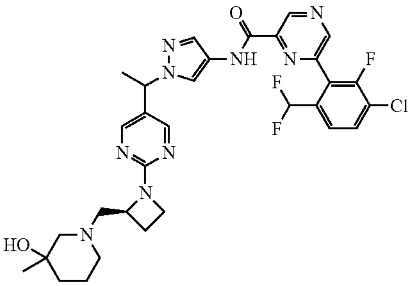 [SMILES: CC(c1cnc(N2CC[C@H]2CN2CCCC(C)(O)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((2S)-2-((3-hydroxy-3-methylpiperidin-1-yl)methyl)azetidin-1-yl)pyrimidin-5-yl)ethyl)-1H-pyrazol-4-yl)pyrazine-2-carboxamide | Calcd. 656.2 found 656.3 | |
| 177 | 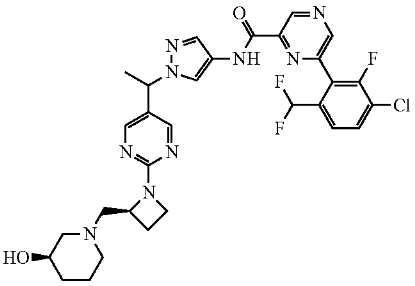 [SMILES: CC(c1cnc(N2CC[C@H]2CN2CCC[C@@H](O)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-(((R)-3-hydroxypiperidin-1-yl)methyl)azetidin-1-yl)pyrimidin-5-yl)ethyl)-1H-pyrazol-4-yl)pyrazine-2-carboxamide | Calcd. 642.2 found 642.3 | |

TABLE AAJ-continued

The following compounds were prepared using procedures similar to those described above using the appropriate starting materials. In some examples, racemic products or diatereomeric mixtures were separated using chiral columns (SFC or HPLC) specified in the table.

| Example | Structure | IUPAC Name | $[M + H]^+$ or $[M + Na]^+$ | Chiral Column |
|---|---|---|---|---|
| 178 | 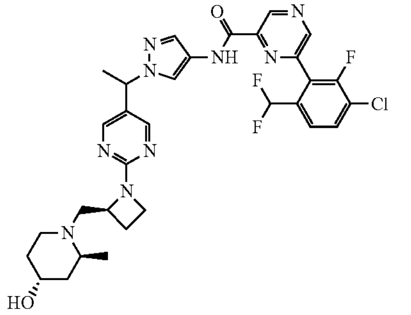 [SMILES: CC(c1cnc(N2CC[C@H]2CN2CC[C@@H](O)C[C@@H]2C)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-(((2S,4R)-4-hydroxy-2-methylpiperidin-1-yl)methyl)azetidin-1-yl)pyrimidin-5-yl)ethyl)-1H-pyrazol-4-yl)pyrazine-2-carboxamide | Calcd. 656.2 found 656.3 | |
| 179 | 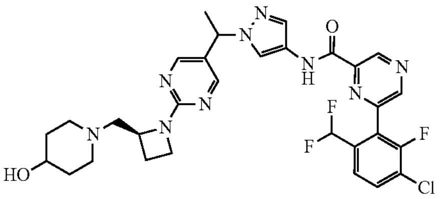 [SMILES: CC(c1cnc(N2CC[C@H]2CN2CCC(O)CC2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-((4-hydroxypiperidin-1-yl)methyl)azetidin-1-yl)pyrimidin-5-yl)ethyl)-1H-pyrazol-4-yl)pyrazine-2-carboxamide | Calcd. 641.2 found 642.3 | |
| 180 | 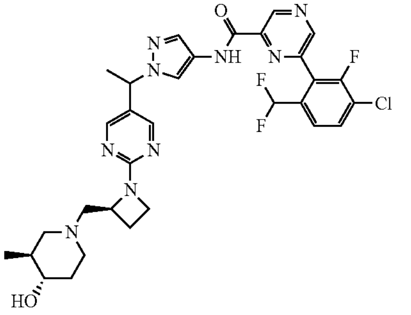 [SMILES: CC(c1cnc(N2CC[C@H]2CN2CC[C@H](O)[C@@H](C)C2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-(((3S,4S)-4-hydroxy-3-methylpiperidin-1-yl)methyl)azetidin-1-yl)pyrimidin-5-yl)ethyl)-1H-pyrazol-4-yl)pyrazine-2-carboxamide | Calcd. 656.2 found 656.3 | |
| 181 | 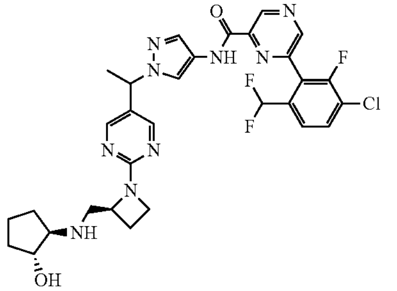 [SMILES: CC(c1cnc(N2CC[C@H]2CN[C@@H]2CCC[C@H]2O)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-((((1R,2R)-2-hydroxycyclopentyl)amino)methyl) azetidin-1-yl)pyrimidin-5-yl)ethyl)-1H-pyrazol-4-yl)pyrazine-2-carboxamide | Calcd. 642.2 found 642.3 | |
| 182 | 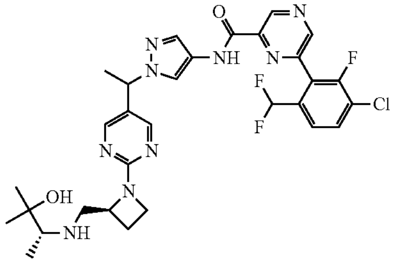 [SMILES: CC(c1cnc(N2CC[C@H]2CN[C@H](C)C(C)(C)O)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-((((R)-3-hydroxy-3-methylbutan-2-yl)amino)methyl)azetidin-1-yl)pyrimidin-5-yl)ethyl)-1H-pyrazol-4-yl)pyrazine-2-carboxamide | Calcd. 644.2 found 644.3 | |

TABLE AAJ-continued

The following compounds were prepared using procedures similar to those described above using the appropriate starting materials. In some examples, racemic products or diatereomeric mixtures were separated using chiral columns (SFC or HPLC) specified in the table.

| Example | Structure | IUPAC Name | $[M + H]^+$ or $[M + Na]^+$ | Chiral Column |
|---|---|---|---|---|
| 183 | 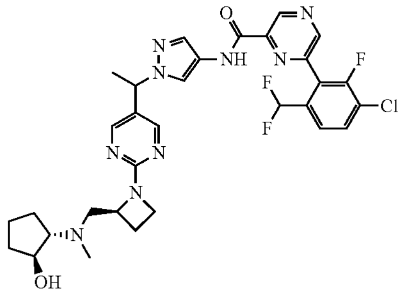 [SMILES: CC(c1cnc(N2CC[C@H]2CN(C)[C@H]2CCC[C@@H]2O)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-((((1S,2S)-2-hydroxycyclopentyl)(methyl)amino)methyl)azetidin-1-yl)pyrimidin-5-yl)ethyl)-1H-pyrazol-4-yl)pyrazine-2-carboxamide | Calcd. 656.2 found 656.2 | |
| 184 | 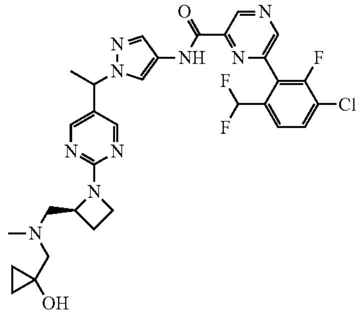 [SMILES: CC(c1cnc(N2CC[C@H]2CN(C)CC2(O)CC2)nc1)n1cc(NC(=O)c2cncc(-c3c(C(F)F)ccc(Cl)c3F)n2)cn1] | 6-(3-Chloro-6-(difluoromethyl)-2-fluorophenyl)-N-(1-(1-(2-((S)-2-((((1S,2S)-2-hydroxycyclopentyl)(methyl)amino)methyl)azetidin-1-yl)pyrimidin-5-yl)ethyl)-1H-pyrazol-4-yl)pyrazine-2-carboxamide | Calcd. 642.2 found 642.3 | |
| 185 | 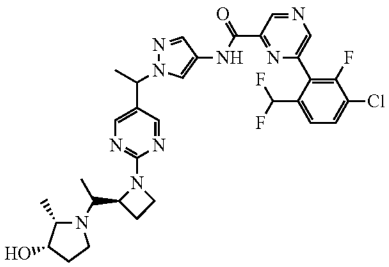 | 6-(3-Chloro-6-(difluoromethyl)-2-fluorophenyl)-N-(1-(1-(2-((S)-2-((R)-1-((2S,3S)-3-hydroxy-2-methylpyrrolidin-1-yl)ethyl)azetidin-1-yl)pyrimidin-5-yl)ethyl)-1H-pyrazol-4-yl)pyrazine-2-carboxamide | Calcd. 656.2 found 656.2 | |
| 186 | 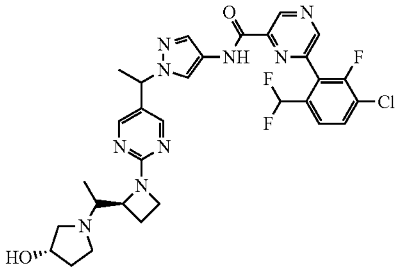 [SMILES: CC([C@@H]1CCN1c1ncc(C(C)n2cc(NC(=O)c3cncc(-c4c(C(F)F)ccc(Cl)c4F)n3)cn2)cn1)N1CC[C@H](O)C1] | 6-(3-Chloro-6-(difluoromethyl)-2-fluorophenyl)-N-(1-(1-(2-((S)-2-((R)-1-((S)-3-hydroxypyrrolidin-1-yl)ethyl)azetidin-1-yl)pyrimidin-5-yl)ethyl)-1H-pyrazol-4-yl)pyrazine-2-carboxamide | Calcd. 642.2 found 642.3 | |
| 187 | 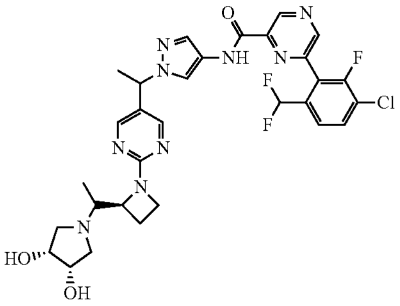 [SMILES: CC([C@@H]1CCN1c1ncc(C(C)n2cc(NC(=O)c3cncc(-c4c(C(F)F)ccc(Cl)c4F)n3)cn2)cn1)N1C[C@@H](O)[C@@H](O)C1] | 6-(3-Chloro-6-(difluoromethyl)-2-fluorophenyl)-N-(1-(1-(2-((S)-2-((R)-1-((3R,4S)-3,4-dihydroxypyrrolidin-1-yl)ethyl)azetidin-1-yl)pyrimidin-5-yl)ethyl)-1H-pyrazol-4-yl)pyrazine-2-carboxamide | Calcd. 658.2 found 658.2 | |

TABLE AAJ-continued

The following compounds were prepared using procedures similar to those described above using the appropriate starting materials. In some examples, racemic products or diatereomeric mixtures were separated using chiral columns (SFC or HPLC) specified in the table.

| Example | Structure | IUPAC Name | $[M + H]^+$ or $[M + Na]^+$ | Chiral Column |
|---|---|---|---|---|
| 188 | 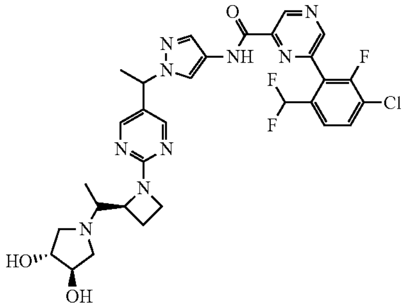 [SMILES: CC([C@@H]1CCN1c1ncc(C(C)n2cc(NC(=O)c3cncc(-c4c(C(F)F)ccc(Cl)c4F)n3)cn2)cn1)N1C[C@@H](O)[C@H](O)C1] | 6-(3-Chloro-6-(difluoromethyl)-2-fluorophenyl)-N-(1-(1-(2-((S)-2-((R)-1-((3R,4R)-3,4-dihydroxypyrrolidin-1-yl)ethyl)azetidin-1-yl)pyrimidin-5-yl)ethyl)-1H-pyrazol-4-yl)pyrazine-2-carboxamide | Calcd. 658.2 found 658.3 | |
| 189 | 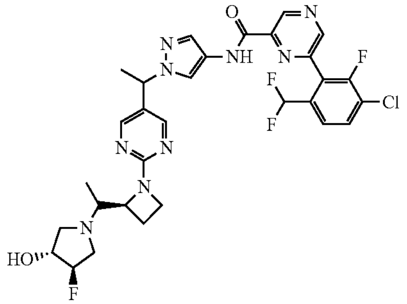 [SMILES: CC([C@@H]1CCN1c1ncc(C(C)n2cc(NC(=O)c3cncc(-c4c(C(F)F)ccc(Cl)c4F)n3)cn2)cn1)N1C[C@@H](O)[C@H](F)C1] | 6-(3-Chloro-6-(difluoromethyl)-2-fluorophenyl)-N-(1-(1-(2-((S)-2-((R)-1-((3R,4R)-3-fluoro-4-hydroxypyrrolidin-1-yl)ethyl)azetidin-1-yl)pyrimidin-5-yl)ethyl)-1H-pyrazol-4-yl)pyrazine-2-carboxamide | Calcd. 660.2 found 660.2 | |
| 190 | 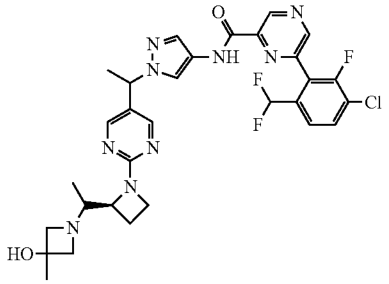 [SMILES: CC([C@@H]1CCN1c1ncc(C(C)n2cc(NC(=O)c3cncc(-c4c(C(F)F)ccc(Cl)c4F)n3)cn2)cn1)N1CC(C)(O)C1] | 6-(3-Chloro-6-(difluoromethyl)-2-fluorophenyl)-N-(1-(1-(2-((S)-2-((R)-1-(3-hydroxy-3-methylazetidin-1-yl)ethyl)azetidin-1-yl)pyrimidin-5-yl)ethyl)-1H-pyrazol-4-yl)pyrazine-2-carboxamide | Calcd. 642.2 found 642.3 | |
| 191 | 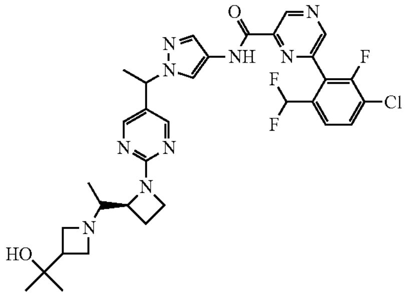 [SMILES: CC([C@@H]1CCN1c1ncc(C(C)n2cc(NC(=O)c3cncc(-c4c(C(F)F)ccc(Cl)c4F)n3)cn2)cn1)N1CC(C(C)(C)O)C1] | 6-(3-Chloro-6-(difluoromethyl)-2-fluorophenyl)-N-(1-(1-(2-((S)-2-((R)-1-(3-(2-hydroxypropan-2-yl)azetidin-1-yl)ethyl)azetidin-1-yl)pyrimidin-5-yl)ethyl)-1H-pyrazol-4-yl)pyrazine-2-carboxamide | Calcd. 670.3 found 670.3 | |
| 192 | 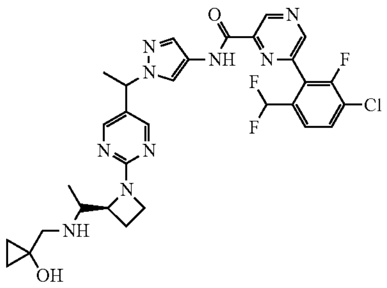 [SMILES: CC(NCC1(O)CC1)[C@@H]1CCN1c1ncc(C(C)n2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-(1-(2-((S)-2-((R)-1-(((1-hydroxycyclopropyl)methyl)amino) ethyl)azetidin-1-yl)pyrimidin-5-yl)ethyl)-1H-pyrazol-4-yl)pyrazine-2-carboxamide | Calcd. 642.2 found 642.3 | |

TABLE AAJ-continued

The following compounds were prepared using procedures similar to those described above using the appropriate starting materials. In some examples, racemic products or diatereomeric mixtures were separated using chiral columns (SFC or HPLC) specified in the table.

| Example | Structure | IUPAC Name | $[M + H]^+$ or $[M + Na]^+$ | Chiral Column |
|---|---|---|---|---|
| 193 | 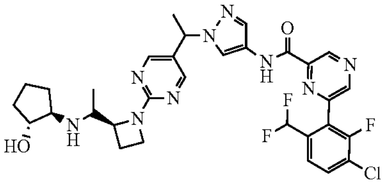 [SMILES: CC(N[C@@H]1CCC[C@H]1O)[C@@H]1CCN1c1ncc(C(C)n2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-(1-(2-((S)-2-((R)-1-(((1R,2R)-2-hydroxycyclopentyl)amino)ethyl)azetidin-1-yl)pyrimidin-5-yl)ethyl)-1H-pyrazol-4-yl)pyrazine-2-carboxamide | Calcd. 655.2 found 656.3 | |
| 194 | 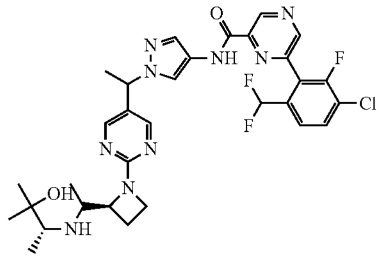 [SMILES: CC(N[C@H](C)C(C)(C)O)[C@@H]1CCN1c1ncc(C(C)n2cc(NC(=O)c3cncc(-c4c(C(F)F)ccc(Cl)c4F)n3)cn2)cn1] | 6-(3-Chloro-6-(difluoromethyl)-2-fluorophenyl)-N-(1-(1-(2-((S)-2-((R)-1-(((R)-3-hydroxy-3-methylbutan-2-yl)amino)ethyl)azetidin-1-yl)pyrimidin-5-yl)ethyl)-1H-pyrazol-4-yl)pyrazine-2-carboxamide | Calcd. 658.3 found 658.3 | |

Example 195

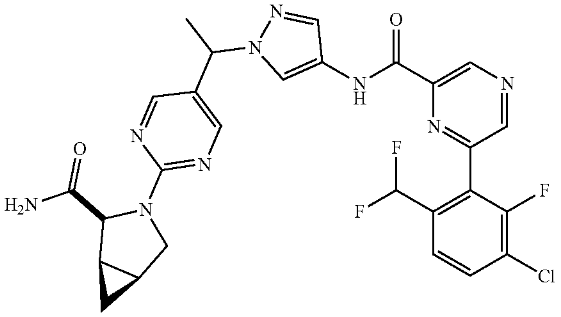 [SMILES: CC(c1cnc(N2C[C@H]3C[C@H]3[C@H]2C(N)=O)nc1)n1cc(NC(=O)c2cncc(-c3c(C(F)F)ccc(Cl)c3F)n2)cn1]

(cis)-3-(5-(1-(4-(6-(3-Chloro-6-(difluoromethyl)-2-fluorophenyl)pyrazine-2-carboxamido)-1H-pyrazol-1-yl)ethyl)pyrimidin-2-yl)-3-azabicyclo[3.1.0]hexane-2-carboxamide (Scheme AAK)

To a mixture of (cis)-3-(5-(1-(4-(6-(3-chloro-6-(difluoromethyl)-2-fluorophenyl)pyrazine-2-carboxamido)-1H-pyrazol-1-yl)ethyl)pyrimidin-2-yl)-3-azabicyclo[3.1.0]hexane-2-carboxylic acid (320 mg, 0.534 mmol) in DMF (3 mL) was added 1-hydroxy-1H-benzotriazole, ammonium salt (163 mg, 1.07 mmol) and EDC (205 mg, 1.07 mmol), and the resulting mixture was stirred at rt for 16 h. The reaction was filtered, and the filtrate was purified by reversed-phase preparatory-HPLC (C18 stationary phase, water (0.1% TFA)-ACN) to afford the title compound. $^1H$ NMR (400 MHz, $CDCl_3$) δ 9.47-9.50 (m, 2H), 9.05 (d, J=2.8 Hz, 1H), 8.31 (d, J=2.8 Hz, 2H), 8.17 (s, 1H), 7.72-7.74 (m, 1H), 7.63-7.68 (m, 1H), 7.59 (s, 1H), 6.59 (t, J=56.0 Hz, 1H), 5.90-6.01 (m, 2H), 5.38-5.42 (m, 1H), 4.48 (d, J=5.6 Hz, 1H), 3.88 (d, J=11.2 Hz, 1H), 3.71-3.76 (m, 1H), 2.09-2.12 (m, 1H), 1.90 (d, J=7.2 Hz, 3H), 1.78-1.81 (m, 1H), 0.81-0.86 (m, 1H), 0.70-0.72 (m, 1H). MS=598.1 $[M+H]^+$.

Examples 196-199

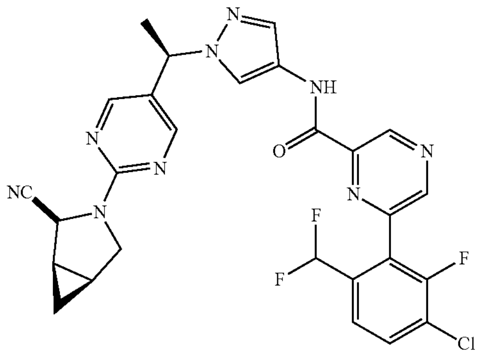

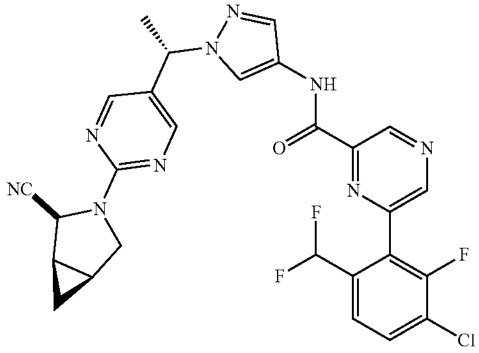

-continued

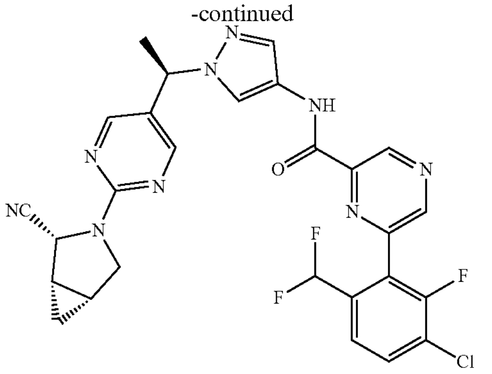

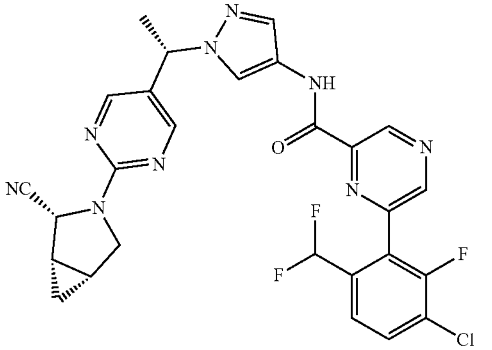

6-(3-Chloro-6-(difluoromethyl)-2-fluorophenyl)-N-(1-((R)-1-(2-((1R,2S,5S)-2-cyano-3-azabicyclo[3.1.0]hexan-3-yl)pyrimidin-5-yl)ethyl)-1H-pyrazol-4-yl)pyrazine-2-carboxamide: 6-(3-chloro-6-(difluoromethyl)-2-fluorophenyl)-N-(1-((R)-1-(2-((1S,2R,5R)-2-cyano-3-azabicyclo[3.1.0]hexan-3-yl)pyrimidin-5-yl)ethyl)-1H-pyrazol-4-yl)pyrazine-2-carboxamide: 6-(3-chloro-6-(difluoromethyl)-2-fluorophenyl)-N-(1-((S)-1-(2-((1R,2S,5S)-2-cyano-3-azabicyclo[3.1.0]hexan-3-yl)pyrimidin-5-yl)ethyl)-1H-pyrazol-4-yl)pyrazine-2-carboxamide: 6-(3-chloro-6-(difluoromethyl)-2-fluorophenyl)-N-(1-((S)-1-(2-((1S,2R,5R)-2-cyano-3-azabicyclo[3.1.0]hexan-3-yl)pyrimidin-5-yl)ethyl)-1H-pyrazol-4-yl)pyrazine-2-carboxamide (Scheme AAK)

To a mixture of (cis)-3-(5-(1-(4-(6-(3-chloro-6-(difluoromethyl)-2-fluorophenyl)pyrazine-2-carboxamido)-1H-pyrazol-1-yl)ethyl)pyrimidin-2-yl)-3-azabicyclo[3.1.0]hexane-2-carboxamide (220 mg, 0.368 mmol) in DCM (5 mL) was added TEA (77 μL, 0.55 mmol). TFAA (78 μL, 0.55 mmol) was added to the mixture at 0° C., and the resulting mixture was warmed to rt and allowed to stir for 16 h. The reaction was concentrated, and the crude residue was purified by preparatory-TLC ((1:1) EtOAc/petroleum ether) to give the mixture of four stereoisomers, which were separated by Chiral SFC (DAICEL CHIRALPAK AD 0.1% $NH_3H_2O$ EtOH, Begin B 55%, End B 55%) to the first eluting isomer Example 196: $^1$H NMR (400 MHz, $CDCl_3$) δ 9.51 (s, 1H), 9.46 (s, 1H), 9.04 (d, J=2.4 Hz, 1H), 8.35 (s, 2H), 8.16 (s, 1H), 7.74 (m, 1H), 7.66 (d, J=8.4 Hz, 1H), 7.59 (s, 1H), 6.59 (t, J=54.0 Hz, 1H), 5.41 (q, J=6.8 Hz, 1H), 4.72 (d, J=5.2 Hz, 1H), 3.86 (d, J=7.6 Hz, 1H), 3.63 (dd, J=10.8 Hz, 4.0 Hz, 1H), 2.10-2.12 (m, 1H), 1.91 (d, J=8.0 Hz, 4H), 1.06-1.08 (m, 1H), 0.79-0.80 (m, 1H). MS=580.1 $[M+H]^+$.

The mixture of other three isomers required an additional separation by chiral SFC (REGIS (s,s) WHELK-01, 0.1% $NH_3 \cdot H_2O$-EtOH Begin B 45%, End B 45%). The second overall eluting isomer Example 197: $^1$H NMR (400 MHz, $CDCl_3$) δ 9.51 (s, 1H), 9.46 (s, 1H), 9.04 (d, J=2.4 Hz, 1H), 8.33 (s, 2H), 8.17 (s, 1H), 7.74 (m, 1H), 7.66 (d, J=8.4 Hz, 1H), 7.60 (s, 1H), 6.59 (t, J=54.0 Hz, 1H), 5.42 (q, J=6.8 Hz, 1H), 4.71 (d, J=5.2 Hz, 1H), 3.86 (d, J=7.6 Hz, 1H), 3.63 (dd, J=10.8 Hz, 4.0 Hz, 1H), 2.09-2.12 (m, 1H), 1.91 (d, J=8.0 Hz, 4H), 1.04-1.07 (m, 1H), 0.77-0.81 (m, 1H). MS=580.1 $[M+H]^+$. The third overall eluting isomer Example 198: $^1$H NMR (400 MHz, $CDCl_3$) δ 9.50 (s, 1H), 9.46 (s, 1H), 9.04 (d, J=2.4 Hz, 1H), 8.35 (s, 2H), 8.17 (s, 1H), 7.74 (m, 1H), 7.66 (d, J=8.4 Hz, 1H), 7.60 (s, 1H), 6.59 (t, J=54.0 Hz, 1H), 5.42 (q, J=6.8 Hz, 1H), 4.71 (d, J=5.2 Hz, 1H), 3.86 (d, J=7.6 Hz, 1H), 3.63 (dd, J=10.8 Hz, 4.0 Hz, 1H), 2.09-2.12 (m, 1H), 1.91 (d, J=8.0 Hz, 4H), 1.04-1.10 (m, 1H), 0.77-0.81 (m, 1H). MS=580.1 $[M+H]^+$. The fourth overall eluting isomer Example 199: $^1$H NMR (400 MHz, $CDCl_3$) δ 9.51 (s, 1H), 9.46 (s, 1H), 9.04 (d, J=2.4 Hz, 1H), 8.33 (s, 2H), 8.17 (s, 1H), 7.74 (m, 1H), 7.66 (d, J=8.4 Hz, 1H), 7.60 (s, 1H), 6.59 (t, J=54.0 Hz, 1H), 5.42 (q, J=6.8 Hz, 1H), 4.71 (d, J=5.2 Hz, 1H), 3.86 (d, J=7.6 Hz, 1H), 3.63 (dd, J=10.8 Hz, 4.0 Hz, 1H), 2.09-2.12 (m, 1H), 1.91 (d, J=8.0 Hz, 4H), 1.04-1.09 (m, 1H), 0.77-0.81 (m, 1H). MS=580.1 $[M+H]^+$.

TABLE AAK

The following compounds were prepared using procedures similar to those described above using the appropriate starting materials. In some examples, racemic products or diatereomeric mixtures were separated using chiral columns (SFC or HPLC) specified in the table.

| Example | Structure | IUPAC Name | $[M + H]^+$ or $[M + Na]^+$ | Chiral Column |
|---|---|---|---|---|
| 200 | 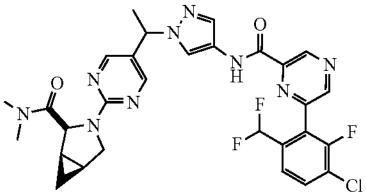 | (1R,2S,5S or 1S,2R,5R)-3-(5-((R or S)-1-(4-(6-(3-Chloro-6-(difluoromethyl)-2-fluorophenyl)pyrazine-2-carboxamido)-1H-pyrazol-1-yl)ethyl)pyrimidin-2-yl)-N,N-dimethyl-3-azabicyclo[3.1.0]hexane-2-carboxamide | $[M/2 + H]^+$ Calcd.: 313.6 Found: 313.7 | DAICEL CHIRALPAK AD and IG |

TABLE AAK-continued

The following compounds were prepared using procedures similar to those described above using the appropriate starting materials. In some examples, racemic products or diatereomeric mixtures were separated using chiral columns (SFC or HPLC) specified in the table.

| Example | Structure | IUPAC Name | $[M + H]^+$ or $[M + Na]^+$ | Chiral Column |
|---|---|---|---|---|
| 201 | 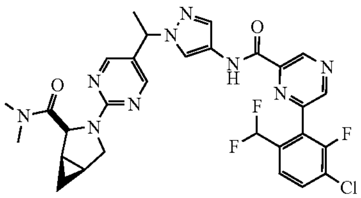 | (1R,2S,5S or 1S,2R,5R)-3-(5-((S or R)-1-(4-(6-(3-Chloro-6-(difluoromethyl)-2-fluorophenyl)pyrazine-2-carboxamido)-1H-pyrazol-1-yl)ethyl)pyrimidin-2-yl)-N,N-dimethyl-3-azabicyclo[3.1.0]hexane-2-carboxamide | $[M/2 + H]^+$ Calcd.: 313.6 Found: 313.6 | DAICEL CHIRALPAK AD and IG |
| 202 | 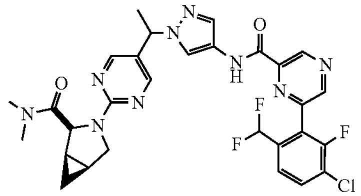 | (1R,2S,5S or 1S,2R,5R)-3-(5-((R or S)-1-(4-(6-(3-Chloro-6-(difluoromethyl)-2-fluorophenyl)pyrazine-2-carboxamido)-1H-pyrazol-1-yl)ethyl)pyrimidin-2-yl)-N,N-dimethyl-3-azabicyclo[3.1.0]hexane-2-carboxamide | Calcd.: 626.2 Found: 626.1 | DAICEL CHIRALPAK AD |
| 203 | 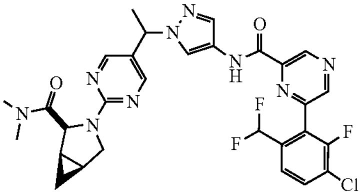 | (1R,2S,5S or 1S,2R,5R)-3-(5-((S or R)-1-(4-(6-(3-Chloro-6-(difluoromethyl)-2-fluorophenyl)pyrazine-2-carboxamido)-1H-pyrazol-1-yl)ethyl)pyrimidin-2-yl)-N,N-dimethyl-3-azabicyclo[3.1.0]hexane-2-carboxamide | [M/2 + H]+ Calcd.: 313.6 Found: 313.6 | DAICEL CHIRALPAK AD |

Example 204

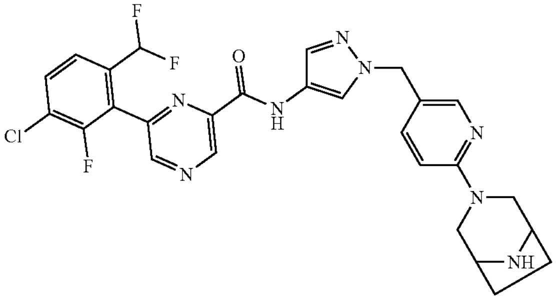 [SMILES: O=C(Nc1cnn(Cc2ccc(N3CC4CCC(C3)N4)nc2)c1)c1cncc(-c2c(C(F)F)ccc(Cl)c2F)n1]

N-(1-((6-(3,8-Diazabicyclo[3.2.1]octan-3-yl)pyridin-3-yl)methyl)-1H-pyrazol-4-yl)-6-(3-chloro-6-(difluoromethyl)-2-fluorophenyl)pyrazine-2-carboxamide (Scheme AAL)

TFA (274 µl) was added to a stirred mixture of tert-butyl 3-(5-((4-(6-(3-chloro-6-(difluoromethyl)-2-fluorophenyl)pyrazine-2-carboxamido)-1H-pyrazol-1-yl)methyl)pyridin-2-yl)-3,8-diazabicyclo[3.2.1]-octane-8-carboxylate (55 mg, 0.082 mmol) in DCM (548 µl) and the mixture was stirred at room temperature for 2 h. After evaporation of the volatile components, the residue was purified by reversed-phase preparatory-HPLC (C18 stationary phase, water (0.1% TFA)-ACN to give the title compound. $^1$H NMR (600 MHz, $CD_3OD$) δ 9.39 (s, 1H), 9.02 (d, J=1.9 Hz, 1H), 8.23 (s, 1H), 8.14 (d, J=2.0 Hz, 1H), 7.84 (dd, J=7.8 Hz, 1H), 7.74 (s, 1H), 7.69-7.62 (m, 2H), 7.11-6.89 (m, 2H), 5.26 (s, 2H), 4.22-4.17 (m, 4H), 3.26 (d, J=12.3 Hz, 2H), 2.18-1.94 (m, 4H). MS=569.4 $[M+H]^+$.

Example 205

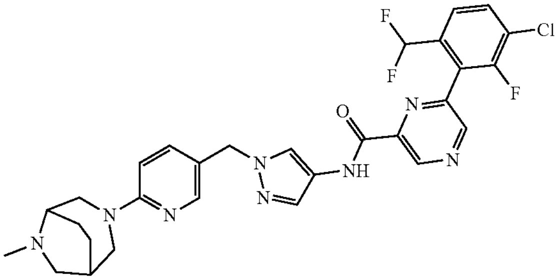 [SMILES: CN1CC2CCC1CN(c1ccc(Cn3cc(NC(=O)c4cncc(-c5c(C(F)F)ccc(Cl)c5F)n4)cn3)cn1)C2]

6-(3-Chloro-6-(difluoromethyl)-2-fluorophenyl)-N-(1-((6-(8-methyl-3,8-diazabicyclo[3.2.1]octan-3-yl)pyridin-3-yl)methyl)-1H-pyrazol-4-yl)pyrazine-2-carboxamide (Scheme AAL)

Sodium triacetoxyborohydride (47 mg, 0.22 mmol) was added to a stirred mixture of N-(1-((6-(3,8-diazabicyclo[3.2.1]octan-3-yl)pyridin-3-yl)methyl)-1H-pyrazol-4-yl)-6-(3-chloro-6-(difluoromethyl)-2-fluorophenyl)pyrazine-2-carboxamide (25 mg, 0.044 mmol), formaldehyde (16 µl, 0.22 mmol, 37% w/v aq. solution), acetic acid (2.5 µl, 0.044 mmol) in MeOH (440 µl) and the mixture was stirred at rt for 4 h. After evaporation of the solvent, the residue was purified by reversed-phase preparatory-HPLC (C18 stationary phase, water (0.1% TFA)-ACN to give the title compound. $^1$H NMR (600 MHz, $CD_3OD$) δ 9.39 (s, 1H), 9.02 (d, J=1.9 Hz, 1H), 8.22 (s, 1H), 8.16 (d, J=1.9 Hz, 1H), 7.84 (d, J=7.8 Hz, 1H), 7.74 (s, 1H), 7.68-7.60 (m, 2H), 7.11-6.86 (m, 2H), 5.25 (s, 2H), 4.27 (d, J=13.4 Hz, 2H), 4.08 (s, 2H), 2.89 (s, 3H), 2.30 (s, 2H), 2.07 (d, J=8.5 Hz, 2H). MS=583.4 $[M+H]^+$.

Example 206

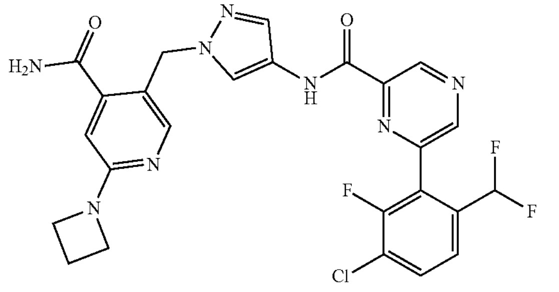 [SMILES: NC(=O)c1cc(N2CCC2)ncc1Cn1cc(NC(=O)c2cncc(-c3c(C(F)F)ccc(Cl)c3F)n2)cn1]

N-(1-((6-(Azetidin-1-yl)-4-carbamoylpyridin-3-yl)methyl)-1H-pyrazol-4-yl)-6-(3-chloro-6-(difluoromethyl)-2-fluorophenyl)pyrazine-2-carboxamide To a solution of N-(1-((6-(azetidin-1-yl)-4-cyanopyridin-3-yl)methyl)-1H-pyrazol-4-yl)-6-(3-chloro-6-(difluoromethyl)-2-fluorophenyl)pyrazine-2-carboxamide (60 mg, 0.11 mmol) in DMSO (3 mL) and EtOH (2 mL) at 0° C. were added $K_2CO_3$ (31 mg, 0.22 mmol) and $H_2O_2$ (0.029 mL, 0.33 mmol). After stirring at 0° C. for 1 h, the reaction was diluted with satd. aq. $Na_2S_2O_3$ and purified by reversed-phase preparatory-HPLC (C18 stationary phase, water (0.1% TFA)-ACN to give the title compound: $^1$H NMR (400 MHz, $CD_3OD$) δ 9.38 (s, 1H), 9.02 (d, J=2.2 Hz, 1H), 8.19 (s, 1H), 7.72-7.86 (m, 3H), 7.66 (d, J=8.6 Hz, 1H), 6.78-7.16 (m, 2H), 5.39 (s, 2H), 4.33 (t, J=7.7 Hz, 4H), 2.52-2.65 (m, 2H). MS=557.2 $[M+H]^+$.

Example 207

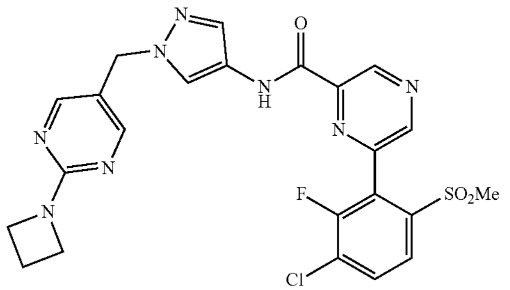 [SMILES: CS(=O)(=O)c1ccc(Cl)c(F)c1-c1cncc(C(=O)Nc2cnn(Cc3cnc(N4CCC4)nc3)c2)n1]

N-(1-((2-(Azetidin-1-yl)pyrimidin-5-yl)methyl)-1H-pyrazol-4-yl)-6-(3-chloro-2-fluoro-6-(methylsulfonyl)phenyl)pyrazine-2-carboxamide A mixture of N-(1-((2-(azetidin-1-yl)pyrimidin-5-yl)methyl)-1H-pyrazol-4-yl)-6-(3-chloro-2-fluoro-6-(methylsulfinyl)phenyl)pyrazine-2-carboxamide (30 mg, 0.057 mmol) and oxone (70 mg, 0.11 mmol) in THF (1 mL) and water (0.2 mL) was stirred at rt for 3 h. The reaction was quenched with satd. aq. $Na_2SO_3$ and extracted with DCM. The combined organic layers were dried over $Na_2SO_4$, filtered and concentrated to give a crude residue that was purified by reversed-phase preparatory-HPLC (C18 stationary phase, water (10 mM, $NH_4HCO_3$)-ACN to give the title compound. $^1$H NMR (400 MHz, $CDCl_3$) δ 9.51 (d, J 7.3 Hz, 1H), 9.27 (br s, 1H), 8.93 (br d, J 9.3 Hz, 1H), 8.25-8.34 (m, 2H), 8.08-8.14 (m, 1H), 7.99 (br d, J 8.6 Hz, 1H), 7.77-7.88 (m, 1H), 7.50-7.57 (m, 1H), 5.10 (br d, J 9.5 Hz, 2H), 4.11-4.19 (m, 4H), 2.95-3.02 (m, 3H), 2.29-2.46 (m, 2H). MS=543.1 $[M+H]^+$.

Example 208

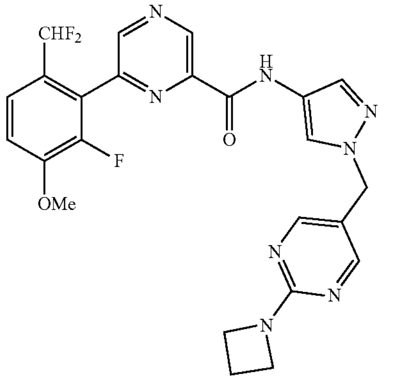 [SMILES: COc1ccc(C(F)F)c(-c2cncc(C(=O)Nc3cnn(Cc4cnc(N5CCC5)nc4)c3)n2)c1F]

N-(1-((2-(Azetidin-1-yl)pyrimidin-5-yl)methyl)-1H-pyrazol-4-yl)-6-(6-(difluoromethyl)-2-fluoro-3-methoxyphenyl)pyrazine-2-carboxamide $Me_4$-$^t$BuXPhos Pd G3 (1.0 mg, 1.2 μmol) was added to a stirred mixture of $Cs_2CO_3$ (38 mg, 0.12 mmol) and N-(1-((2-(azetidin-1-yl)pyrimidin-5-yl)methyl)-1H-pyrazol-4-yl)-6-(3-chloro-6-(difluoromethyl)-2-fluorophenyl)pyrazine-2-carboxamide (30 mg, 0.058 mmol) in dioxane (0.5 mL) and MeOH (0.5 mL) in a glove box. The resulting mixture was heated to 100° C. for 8 h, at which time, the reaction was directly purified by reversed-phase preparatory-HPLC (C18 stationary phase, water (0.1% TFA)-ACN to give the title compound. $^1$H NMR (400 MHz, $CD_3OD$) δ 9.37 (s, 1H), 8.98 (d, J=2.2 Hz, 1H), 8.43 (s, 2H), 8.28 (s, 1H), 7.77 (s, 1H), 7.61 (d, J=8.7 Hz, 1H), 7.41 (t, J=8.4 Hz, 1H), 6.74-7.09 (t, J=55.2 Hz, 1H), 5.24 (s, 2H), 4.24 (t, J=7.6 Hz, 4H), 4.01 (s, 3H), 2.46 (quint, J=7.7 Hz, 2H). MS=511.1 $[M+H]^+$.

Factor XIa Assay

The effectiveness of a compound of the present invention as an inhibitor of Coagulation factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at rt or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the half-maximal inhibitory concentrations ($IC_{50}$), or the inhibitory constant, $K_i$.

Compounds were pre-incubated for 30 min at 25° C. with human (0.04 nM) factor XIa in 50 mM HEPES buffer with 150 mM sodium chloride, 5 mM calcium chloride, 0.1% PEG 8000, pH 7.4. factor XIa enzymatic activity was determined by addition of the substrate glycine-proline-arginine-7-amido-4-trifluoromethylcoumarin (GPR-AFC) and measurement of the fluorescence at 400/505 nm after a 60 min incubation at 25° C. The % inhibition for each data point was calculated from the data and analyzed using the log (inhibitor) vs. response four parameters equation to determine the half-maximal inhibitory concentrations ($IC_{50}$). The $IC_{50}$ were converted to equilibrium inhibitory constants (Ki) using the Cheng-Prusoff equation.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

Plasma Kallikrein Assay

The effectiveness of a compound of the present invention as an inhibitor of plasma kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at rt or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the half-maximal inhibitory concentrations ($IC_{50}$), or the inhibitory constant, $K_i$.

Plasma kallikrein determinations were made in 50 mM HEPES buffer at pH 7.4 containing 150 mM NaCl, 5 mM $CaCl_2$), and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K—P—R-AFC (Sigma #C6608) at a concentration of 100 mM.

Activity assays were performed by diluting a stock solution of substrate at least tenfold to a final concentration ≤0.2 Km into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). $IC_{50}$ was determined by inflection point from a four parameter logistic curve fit. Ki was calculated using the Cheng Prusoff equation, $Ki=IC_{50}/(1+([S]/Km))$.

The activities shown by this assay indicate that the compounds of the invention may be therapeutically useful for treating or preventing various ophthalmic, cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, reocclusion or restenosis of recanalized vessels, hereditary angioedema, uveitis, posterior uveitis, wet age related macular edema, diabetic macular edema, diabetic retinopathy and retinal vein occlusion.

Plasma Kallikrein $IC_{50}$ (nM) and FXIa $IC_{50}$ (nM) for selected compounds are as follows:

| Example | Plasma Kallikrein $IC_{50}$ (nM) | FXIa $IC_{50}$ (nM) |
|---|---|---|
| 1 | 10.2 | 921 |
| 2 | 15.8 | 1112 |
| 3 | 40.5 | 10000 |
| 4 | 23.1 | 1316 |
| 5 | 6.6 | 1348 |
| 6 | 22.9 | 1693 |
| 7 | 52.1 | 1424 |
| 8 | 4.2 | 458 |
| 9 | 5.2 | 5104 |
| 10 | 5.2 | 647 |
| 11 | 6.2 | 1706 |
| 12 | 6.2 | 3513 |
| 13 | 7.2 | 1845 |
| 14 | 8.0 | 312 |
| 15 | 8.1 | 3689 |
| 16 | 8.4 | 1053 |
| 17 | 10.2 | 1368 |
| 18 | 13.1 | 1999 |
| 19 | 14.6 | 4631 |
| 20 | 15.4 | 10000 |
| 21 | 17.0 | 973 |
| 22 | 22.3 | 4368 |
| 23 | 26.0 | 1757 |
| 24 | 26.8 | 10000 |
| 25 | 41.3 | 6090 |
| 26 | 45.9 | 5354 |
| 27 | 3.8 | 869 |
| 28 | 11.9 | 927 |
| 29 | 20.7 | 1774 |
| 30 | 7.8 | 2167 |
| 31 | 27.0 | 2718 |
| 32 | 8.1 | 1524 |
| 33 | 26.5 | 10000 |
| 34 | 28.1 | 3333 |
| 35 | 33.2 | 10000 |
| 36 | 44.3 | 4425 |
| 37 | 25.6 | 2696 |
| 38 | 5.0 | 2575 |
| 39 | 1.3 | 478 |
| 40 | 3.7 | 794 |
| 41 | 2.1 | 4212 |
| 42 | 4.7 | 1111 |
| 43 | 19.5 | 1174 |
| 44 | 10.3 | 1460 |
| 45 | 23.2 | 992 |
| 46 | 3.7 | 595 |
| 47 | 10.6 | 326 |
| 48 | 730.1 | 10000 |
| 49 | 17.6 | 10000 |

-continued

| Example | Plasma Kallikrein $IC_{50}$ (nM) | FXIa $IC_{50}$ (nM) |
|---|---|---|
| 50 | 1122.0 | 10000 |
| 51 | 3772.0 | 10000 |
| 52 | 17.1 | 10000 |
| 53 | 30.7 | 10000 |
| 54 | 25.7 | 3032 |
| 55 | 24.4 | 3936 |
| 56 | 27.7 | 1488 |
| 57 | 6.8 | 1170 |
| 58 | 8.1 | 413 |
| 59 | 1.8 | 372 |
| 60 | 47.0 | 730 |
| 61 | 14.0 | 662 |
| 62 | 17.8 | 2149 |
| 63 | 17.3 | 5038 |
| 64 | 9.6 | 292 |
| 65 | 22.2 | 538 |
| 66 | 3.9 | 639 |
| 67 | 153.3 | 10000 |
| 68 | 26.3 | 10000 |
| 69 | 64.3 | 8066 |
| 70 | 1.4 | 485 |
| 71 | 2.5 | 2262 |
| 72 | 2.5 | 10000 |
| 73 | 3.7 | 1495 |
| 74 | 4.3 | 1015 |
| 75 | 5.0 | 10000 |
| 76 | 5.4 | 4635 |
| 77 | 5.6 | 2951 |
| 78 | 5.6 | 10000 |
| 79 | 5.9 | 2858 |
| 80 | 6.7 | 1993 |
| 81 | 7.4 | 3945 |
| 82 | 9.3 | 6013 |
| 83 | 9.4 | 8083 |
| 84 | 11.3 | 7241 |
| 85 | 11.8 | 10000 |
| 86 | 13.3 | 10000 |
| 87 | 13.6 | 8427 |
| 88 | 14.9 | 10000 |
| 89 | 17.3 | 10000 |
| 90 | 17.8 | 10000 |
| 91 | 17.9 | 10000 |
| 92 | 18.5 | 5017 |
| 93 | 19.9 | 4306 |
| 94 | 20.0 | 8234 |
| 95 | 21.7 | 10000 |
| 96 | 25.9 | 3714 |
| 97 | 26.9 | 8933 |
| 98 | 28.2 | 10000 |
| 99 | 29.8 | 3659 |
| 100 | 20.6 | 10000 |
| 101 | 31.2 | 7640 |
| 102 | 31.2 | 2252 |
| 103 | 31.3 | 10000 |
| 104 | 32.9 | 10000 |
| 105 | 36.8 | 3385 |
| 106 | 41.3 | 10000 |
| 107 | 43.5 | 10000 |
| 108 | 45.0 | 10000 |
| 109 | 45.9 | 10000 |
| 110 | 46.2 | 10000 |
| 111 | 46.5 | 2997 |
| 112 | 49.2 | 10000 |
| 113 | 65.1 | 10000 |
| 114 | 2.7 | 10000 |
| 115 | 3.5 | 10000 |
| 116 | 3.6 | 10000 |
| 117 | 5.4 | 10000 |
| 118 | 12.5 | 10000 |
| 119 | 14.5 | 3585 |
| 120 | 17.8 | 10000 |
| 121 | 18.4 | 10000 |
| 122 | 19.5 | 10000 |
| 123 | 27.3 | 3333 |
| 125 | 28.3 | 10000 |
| 126 | 30.5 | 10000 |

-continued

| Example | Plasma Kallikrein $IC_{50}$ (nM) | FXIa $IC_{50}$ (nM) |
|---|---|---|
| 127 | 31.3 | 10000 |
| 128 | 32.2 | 10000 |
| 129 | 32.8 | 10000 |
| 130 | 35.0 | 10000 |
| 131 | 37.6 | 10000 |
| 132 | 49.0 | 10000 |
| 133 | 49.5 | 10000 |
| 134 | 9.4 | 852 |
| 135 | 2.8 | 120 |
| 136 | 8.6 | 838 |
| 137 | 21.2 | 4103 |
| 138 | 14.6 | 2322 |
| 139 | 0.3 | 502 |
| 140 | 0.2 | 1286 |
| 141 | 0.3 | 4734 |
| 142 | 0.4 | 2172 |
| 143 | 0.4 | 528 |
| 144 | 0.4 | 2343 |
| 145 | 0.5 | 366 |
| 146 | 0.6 | 7222 |
| 147 | 0.6 | 5497 |
| 148 | 0.6 | 2932 |
| 149 | 0.6 | 1477 |
| 150 | 0.6 | 650 |
| 151 | 1.0 | 7722 |
| 152 | 1.0 | 6017 |
| 153 | 1.1 | 10000 |
| 154 | 1.2 | 4133 |
| 155 | 1.8 | 3677 |
| 156 | 7.3 | 10000 |
| 157 | 9.3 | 10000 |
| 158 | 9.5 | 10000 |
| 159 | 12.0 | 10000 |
| 160 | 42.9 | 10000 |
| 161 | 2.0 | 9632 |
| 162 | 1.0 | 5189 |
| 163 | 1.2 | 4845 |
| 164 | 3.4 | 10000 |
| 165 | 1.4 | 4272 |
| 166 | 0.7 | 5769 |
| 167 | 1.0 | 5825 |
| 168 | 2.0 | 6351 |
| 169 | 1.5 | 9177 |
| 170 | 1.6 | 10000 |
| 171 | 4.9 | 10000 |
| 172 | 1.8 | 10000 |
| 173 | 1.0 | 8919 |
| 174 | 2.3 | 10000 |
| 175 | 0.6 | 5077 |
| 176 | 1.4 | 10000 |
| 177 | 1.2 | 10000 |
| 178 | 3.3 | 10000 |
| 179 | 0.7 | 9430 |
| 180 | 1.1 | 10000 |
| 181 | 4.2 | 10000 |
| 182 | 6.1 | 10000 |
| 183 | 4.2 | 10000 |
| 184 | 2.2 | 10000 |
| 185 | 1.5 | 10000 |
| 186 | 1.4 | 10000 |
| 187 | 1.0 | 3333 |
| 188 | 3.2 | 3333 |
| 189 | 1.2 | 10000 |
| 190 | 3.5 | 10000 |
| 191 | 1.1 | 10000 |
| 192 | 4.1 | 10000 |
| 193 | 8.1 | 10000 |
| 194 | 21.6 | 10000 |
| 195 | 11.0 | 8800 |
| 196 | 4.7 | 10000 |
| 197 | 411.6 | 10000 |
| 198 | 188.5 | 10000 |
| 199 | 1.5 | 4790 |
| 200 | 2.4 | 1123 |
| 201 | 6.2 | 10000 |
| 202 | 1.0 | 2257 |

-continued

| Example | Plasma Kallikrein $IC_{50}$ (nM) | FXIa $IC_{50}$ (nM) |
|---|---|---|
| 203 | 77.8 | 10000 |
| 204 | 17.5 | 10000 |
| 205 | 14.1 | 10000 |
| 206 | 24.4 | 820 |
| 207 | 17.2 | 675 |
| 208 | 33.9 | 827 |

What is claimed is:

1. A compound of the formula:

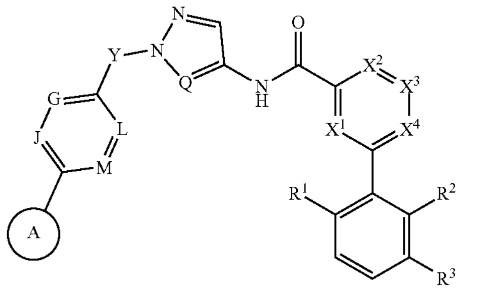

wherein

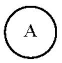

is selected from

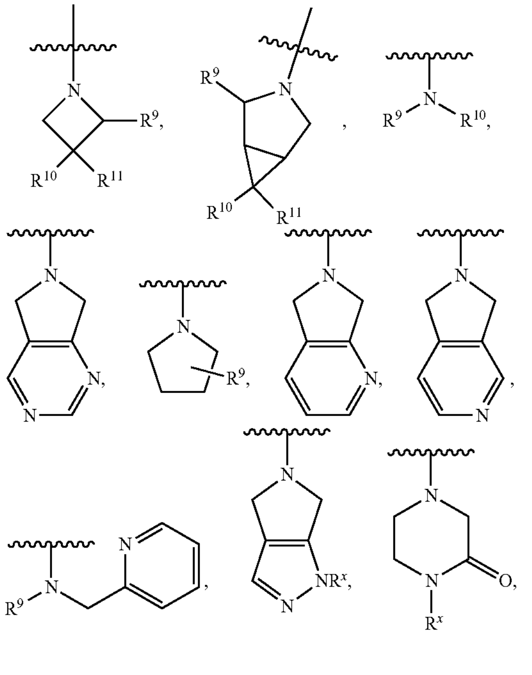

-continued

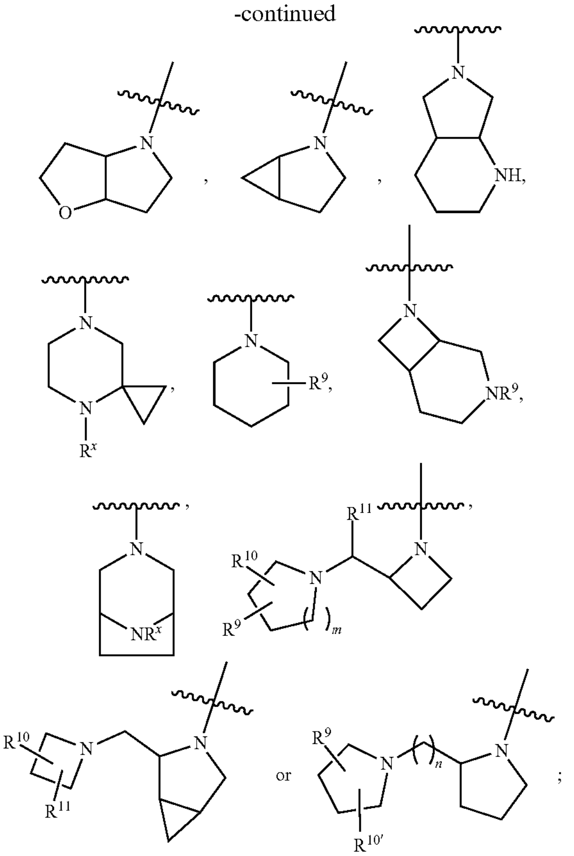

$X^1$ is CH or N;
$X^2$ is N or $CR^4$;
$X^3$ is N;
$X^4$ is CH or N;
Y is $CR^5R^6$ or $SO_2$;
Q is N or CH;
G is N or $CR^7$;
J is N or $CR^7$;
L is N or $CR^7$;
M is Nor $CR^7$;
$R^1$ is selected from the group consisting of hydrogen, halo, cyano, $R^x$, $OR^x$, heteroaryl and $SO_2R^X$;
$R^2$ is hydrogen or halo;
$R^3$ is hydrogen, halo or $OR^x$;
$R^4$ is hydrogen, $R^x$, $OR^x$, (C═O)$OR^x$, (C═O)$NR^xR^y$, $C_{1-3}$ alkyl-$OR^x$ or $NR^xR^Y$;
$R^5$ is hydrogen or $C_{1-3}$ alkyl, which is optionally substituted with one to three substituents selected from deuterium, halo and hydroxy;
$R^6$ is hydrogen, deuterium or $C_{1-3}$ alkyl;
or $R^5$ and $R^6$ can be taken together with the carbon atom between them to form a $C_{3-6}$ cycloalkyl group;
each $R^7$ is independently selected from the group consisting of halo, cyano, $R^x$, $OR^x$, cyclopropyl, (C═O)$NR^xR^y$ and $NR^xR^y$;
or $R^5$ and $R^7$ can be taken together with the atoms between them to form a $C_{3-6}$ cycloalkyl group;
each $R^9$ is independently selected from the group consisting of hydrogen, halo, hydroxy, cyano, triazolyl, cyclopropyl, (C═O)$NR^xR^y$, (C═O)$R^x$ and $C_{1-3}$ alkyl, wherein said triazolyl group is optionally substituted with $R^x$, said cyclopropyl group is optionally substituted with $R^x$ or $OR^x$, and said alkyl group is optionally substituted with one to four substituents selected from halo, hydroxy, heteroaryl, heterocyclyl, $C_{3-6}$ cycloalkyl, $C_{3-6}$ cycloalkyl($R^{10}$), $OR^x$, (C=O)$NR^xR^y$ and $NR^xR^y$;

$R^{10}$ is hydrogen, halo, hydroxy or $C_{1-3}$ alkyl, wherein said alkyl is optionally substituted with one to four substituents selected from halo and hydroxy;

$R^{11}$ is hydrogen, halo, hydroxy or $R^x$;

or $R^{10}$ and $R^{11}$ can be taken together with the atoms between them to form a $C_{3-6}$ cycloalkyl group;

each $R^x$ is independently hydrogen or $C_{1-6}$ alkyl, which is optionally substituted with one to four substituents selected from halo and hydroxy;

each $R^y$ is independently selected from the group consisting of hydrogen, $C_{1-6}$ alkyl, $C_{3-6}$ cycloalkyl, $CH_2$-$C_{3-6}$ cycloalkyl and heterocyclyl, wherein said alkyl is optionally substituted with one to four substituents selected from halo and hydroxy, said cycloalkyl is optionally substituted with one or two $R^x$ or $OR^x$ and said heterocyclyl is optionally substituted with one or two $R^{10}$;

m is an integer from zero to two;

n is an integer from zero to two;

or a pharmaceutically acceptable salt thereof.

2. The compound of claim 1 wherein Q is CH; or a pharmaceutically acceptable salt thereof.

3. The compound of claim 1 wherein wherein

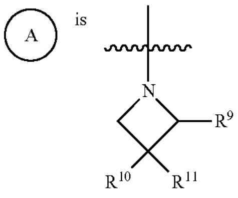

;

or a pharmaceutically acceptable salt thereof.

4. The compound of claim 1 wherein $R^1$ is selected from the group consisting of bromo, cyano, tetrazolyl, $CHF_2$, $CF_3$, $OCHF_2$ and $SO_2CH_3$; or a pharmaceutically acceptable salt thereof.

5. The compound of claim 1 wherein $R^4$ is selected from the group consisting of hydrogen, $CH_3$, $CHF_2$, $OCH_3$, $NH_2$, $N(CH_3)_2$, (C=O)OH and (C=O)$NH_2$, or a pharmaceutically acceptable salt thereof.

6. The compound of claim 1 wherein $R^5$ is hydrogen, $CH_3$, $CHF_2$ or $CH_2OH$; or a pharmaceutically acceptable salt thereof.

7. The compound of claim 1 wherein J is N; M is N; G is $CR^7$; L is $CR^7$; or a pharmaceutically acceptable salt thereof.

8. The compound of claim 1 wherein $X^1$ is N; $X^2$ is $CR^4$; $X^3$ is N; $X^4$ is CH; or a pharmaceutically acceptable salt thereof.

9. The compound of claim 1 selected from:

N-(1-((2-(Azetidin-1-yl)pyrimidin-5-yl)methyl)-1H-pyrazol-4-yl)-6-(3-chloro-6-(difluoromethyl)-2-fluorophenyl)-3-methoxypyrazine-2-carboxamide, N-(1-((2-(Azetidin-1-yl)-4-(hydroxymethyl)pyrimidin-5-yl)methyl)-1H-pyrazol-4-yl)-6-(3-chloro-6-(difluoromethyl)-2-fluorophenyl)pyrazine-2-carboxamide, 3-Amino-N-(1-((2-(azetidin-1-yl)pyrimidin-5-yl)methyl)-1H-pyrazol-4-yl)-6-(3-chloro-6-(difluoromethyl)-2-fluorophenyl)pyrazine-2-carboxamide, (R)—N-(1-(1-(2-(Azetidin-1-yl)pyrimidin-5-yl)ethyl)-1H-pyrazol-4-yl)-6-(3-chloro-6-(difluoromethyl)-2-fluorophenyl)pyrazine-2-carboxamide, (S)—N-(1-(1-(2-(Azetidin-1-yl)pyrimidin-5-yl)ethyl)-1H-pyrazol-4-yl)-6-(3-chloro-6-(difluoromethyl)-2-fluorophenyl)pyrazine-2-carboxamide, (R)—N-(1-(1-(2-(Azetidin-1-yl)pyrimidin-5-yl)-2-hydroxyethyl)-1H-pyrazol-4-yl)-6-(3-chloro-6-(difluoromethyl)-2-fluorophenyl)pyrazine-2-carboxamide, (S)—N-(1-(1-(2-(Azetidin-1-yl)pyrimidin-5-yl)-2-hydroxyethyl)-1H-pyrazol-4-yl)-6-(3-chloro-6-(difluoromethyl)-2-fluorophenyl)pyrazine-2-carboxamide, N-(1-((2-(Azetidin-1-yl)-4-methylpyrimidin-5-yl)methyl)-1H-pyrazol-4-yl)-6-(3-chloro-6-(difluoromethyl)-2-fluorophenyl)pyrazine-2-carboxamide, N-(1-((6-(Azetidin-1-yl)-2-methylpyridin-3-yl)methyl)-1H-pyrazol-4-yl)-6-(3-chloro-6-(difluoromethyl)-2-fluorophenyl)pyrazine-2-carboxamide, N-(1-4(5-(Azetidin-1-yl)-6-methylpyrazin-2-yl)methyl)-1H-pyrazol-4-yl)-6-(3-chloro-6-(difluoromethyl)-2-fluorophenyl)pyrazine-2-carboxamide, 6-(3-Chloro-6-(difluoromethyl)-2-fluorophenyl)-N-(1-((5-(3,3-difluoroazetidin-1-yl)-6-methylpyrazin-2-yl)methyl)-1H-pyrazol-4-yl)-3-methylpyrazine-2-carboxamide, N-(1-((6-(Azetidin-1-yl)-5-fluoropyridin-3-yl)methyl)-1H-pyrazol-4-yl)-6-(3-chloro-6-(difluoromethyl)-2-fluorophenyl)pyrazine-2-carboxamide, N-(1-((5-(Azetidin-1-yl)pyrazin-2-yl)methyl)-1H-pyrazol-4-yl)-6-(3-chloro-6-(difluoromethyl-2-fluorophenyl)pyrazine-2-carboxamide, N-(1-((2-(Azetidin-1-yl)pyrimidin-5-yl)methyl)-1H-pyrazol-4-yl)-6-(3-chloro-6-(difluoromethyl)-2-fluorophenyl)-3-ethylpyrazine-2-carboxamide, 6-(3-Chloro-6-(difluoromethyl)-2-fluorophenyl)-N-(1-((5-(3,3-difluoroazetidin-1-yl)-6-methylpyrazin-2-yl)methyl)-1H-pyrazol-4-yl)pyrazine-2-carboxamide, N-(1-((6-(Azetidin-1-yl)-4-cyanopyridin-3-yl)methyl)-1H-pyrazol-4-yl)-6-(3-chloro-6-(difluoromethyl)-2-fluorophenyl)pyrazine-2-carboxamide, N-(1-((6-(Azetidin-1-yl)-4-methylpyridin-3-yl)methyl)-1H-pyrazol-4-yl)-6-(3-chloro-6-(difluoromethyl)-2-fluorophenyl)pyrazine-2-carboxamide, N-(1-((6-(Azetidin-1-yl)pyridin-3-yl)methyl)-1H-pyrazol-4-yl)-6-(3-chloro-6-(difluoromethyl)-2-fluorophenyl)pyrazine-2-carboxamide, N-(1-((2-(Azetidin-1-yl)-4-(difluoromethyl)pyrimidin-5-yl)methyl)-1H-pyrazol-4-yl)-6-(3-chloro-6-(difluoromethyl)-2-fluorophenyl)pyrazine-2-carboxamide, N-(1-((2-(Azetidin-1-yl)pyrimidin-5-yl)methyl)-1H-pyrazol-4-yl)-6-(3-chloro-6-(difluoromethyl)-2-fluorophenyl)-3-hydroxypyrazine-2-carboxamide, N-(1-(1-(2-(Azetidin-1-yl)pyrimidin-5-yl)cyclopropyl)-1H-pyrazol-4-yl)-6-(3-chloro-6-(difluoromethyl)-2-fluorophenyl)pyrazine-2-carboxamide, N-(1-((2-(Azetidin-1-yl)-4-cyclopropylpyrimidin-5-yl)methyl)-1H-pyrazol-4-yl)-6-(3-chloro-6-(difluoromethyl)-2-fluorophenyl)pyrazine-2-carboxamide, N-(1-((2-(Azetidin-1-yl)-4-methoxypyrimidin-5-yl)methyl)-1H-pyrazol-4-yl)-6-(3-chloro-6-(difluoromethyl)-2-fluorophenyl)pyrazine-2-carboxamide, N-(1-((5-(Azetidin-1-yl)-3-methylpyrazin-2-yl)methyl)-1H-pyrazol-4-yl)-6-(3-chloro-6-(difluoromethyl)-2-fluorophenyl)pyrazine-2-carboxamide, N-(2-(2-(Azetidin-1-yl)pyrimidin-5-yl)methyl)-2H-1,2,3-triazol-4-yl)-6-(3-chloro-6-(difluoromethyl)-2-fluorophenyl)pyrazine-2-carboxamide, N-(1-((6-(Azetidin-1-yl)pyridin-3-yl)sulfonyl)-1H-pyrazol-4-yl)-6-(3-chloro-6-trifluoromethyl)-2-fluorophenyl)pyrazine-2-carboxamide, (S)—N-(1-(1-(2-(azetidin-1-yl)pyrimidin-5-yl)ethyl)-1H-pyrazol-4-yl)-6-(3-chloro-6-(difluoromethyl)-2-fluorophenyl)-3-methylpyrazine-2-carboxamide, (R)—N-(1-(1-(2-(azetidin-1-yl)pyrimidin-5-yl)ethyl-1H-pyrazol-4-yl)-6-(3-chloro-6-(difluoromethyl)-2-fluorophenyl-3-methylpyrazine-2-carboxamide, (S)—N-(1-(1-(5-(azetidin-1-yl)pyrazin-2-ylethyl)-1H-pyrazol-4-yl)-6-(3-chloro-6-(difluoromethyl)-2-fluorophenyl)pyrazine-2-carboxamide, (R)—N-(1-(1-(5-(azetidin-1-yl)pyrazin-2-yl)ethyl)-1H-pyrazol-4-yl)-6-(3-chloro-6-(difluoromethyl)-2-fluorophenyl)pyrazine-2-carboxamide, N-(1-((1S)-1-(2-(3-azabicyclo[3.1.0]hexan-3-yl)pyrimidin-5-yl)ethyl)-1H-pyrazol-4-yl)-6-(3-chloro-6-(difluoromethyl)-2-fluorophenyl)pyrazine-2-carboxamide, N-(1-((1R)-1-(2-(3-azabicyclo[3.1.0]hexan-3-yl)pyrimidin-5-yl)ethyl)-1H-pyrazol-4-yl)-6-(3-chloro-6-(difluoromethyl)-2-fluorophenyl)pyrazine-2-carboxamide, N-(1-((1S)-1-(2-(3-azabicyclo[3.1.0]hexan-3-yl)pyrimidin-5-yl)ethyl-1H-pyrazol-4-yl)-3-amino-6-(3-chloro-6-(difluoromethyl)-2-fluorophenyl)pyrazine-2-carboxamide, N-(1-(1R)-1-(2-(3-azabicyclo[3.1.0]hexan-3-yl)pyrimidin-5-yl)ethyl)-1H-pyrazol-4-yl)-3-amino-6-(3-chloro-6-(difluoromethyl)-2-fluorophenyl)pyrazine-2-carboxamide, (S)—N-(1-(2-(azetidin-1-yl)-6,7-dihydro-5H-cyclopenta[b]pyridin-5-yl)-1H-pyrazol-4-yl)-6-(3-chloro-6-(difluoromethyl)-2-fluorophenyl)pyrazine-2-carboxamide, (R)—N-(1-(-2-(azetidin-1-yl)-6,7-dihydro-5H-cyclopenta[b]pyridin-5-yl)-1H-pyrazol-4-yl)-6-(3-chloro-6-(difluoromethyl)-2-fluorophenyl)pyrazine-2-carboxamide, (S)—N-(1-(1-(2-(azetidin-1-yl)pyrimidin-5-yl)-2,2-difluoroethyl)-1H-pyrazol-4-yl)-6-(3-chloro-6-(difluoromethyl)-2-fluorophenyl)pyrazine-2-carboxamide, (R)—N-(1-(1-(2-(azetidin-1-yl)pyrimidin-5-yl)-2,2-difluoroethyl)-1H-pyrazol-4-yl)-6-(3-chloro-6-(difluoromethyl)-2-fluorophenyl)pyrazine-2-carboxamide, (S)—N-(1-(1-(6-(azetidin-1-yl)pyridin-3-yl)ethyl)-1H-pyrazol-4-yl)-6-(3-chloro-6-(difluoromethyl)-2-fluorophenyl)pyrazine-2-carboxamide, (R)—N-(1-(1-(6-(azetidin-1-yl)pyridin-3-yl)ethyl)-1H-pyrazol-4-yl)-6-(3-chloro-6-(difluoromethyl)-2-fluorophenyl)pyrazine-2-carboxamide, (S)—N-(1-(1-(5-(azetidin-1-yl)-6-methylpyrazin-2-yl)ethyl)-1H-pyrazol-4-yl)-6-(3-chloro-6-(difluoromethyl)-2-fluorophenyl)pyrazine-2-carboxamide, (R)—N-(1-(1-(5-(azetidin-1-yl)-6-methylpyrazin-2-yl)ethyl-1H-pyrazol-4-yl)-6-(3-chloro-6-(difluoromethyl)-2-fluorophenyl)pyrazine-2-carboxamide, (S)—N-(1-(1-(5-azetidin-1-yl)-3-methylpyrazin-2-yl)ethyl-1H-pyrazol-4-yl)-6-(3-chloro-6-(difluoromethyl)-2-fluorophenyl)pyrazine-2-carboxamide, (R)—N-(1-(1-(5-(azetidin-1-yl)-3-methylpyrazin-2-yl)ethyl)-1H-pyrazol-4-yl)-6-(3-chloro-6-(difluoromethyl)-2-fluorophenyl)pyrazine-2-carboxamide, (S)—N-(1-(1-(2-(azetidin-1-yl)pyrimidin-5-yl)ethyl-1-d)-1H-pyrazol-4-yl)-6-(3-chloro-6-(difluoromethyl)-2-fluorophenyl)pyrazine-2-carboxamide, (R)—N-(1-(1-(2-(azetidin-1-yl)pyrimidin-5-yl)ethyl-1-d)-1H-pyrazol-4-yl)-6-(3-chloro-6-(difluoromethyl)-2-fluorophenyl)pyrazine-2-carboxamide, N-(1-((S)-1-(2-(3-Azabicyclo[3.1.0]hexan-3-yl)pyrimidin-5-yl)-2-hydroxyethyl)-1-1H-pyrazol-4-yl)-6-(3-chloro-6-(difluoromethyl)-2-fluorophenyl)pyrazine-2-carboxamide, N-(1-((R)-1-(2-(3-Azabicyclo[3.1.0]hexan-3-yl)pyrimidin-5-yl)-2-hydroxyethyl)-1H-pyrazol-4-yl)-6-(3-chloro-6-(difluoromethyl)-2-fluorophenyl)pyrazine-2-carboxamide, (S)—N-(1-(1-(2-(Azetidin-1-yl)pyrimidin-5-yl-2-hydroxyethyl-1H-pyrazol-4-yl)-6-(3-chloro-6-(difluoromethyl)-2-fluorophenyl)-3-methylpyrazine-2-carboxamide, (R)—N-(1-(1-(2-(Azetidin-1-yl)pyrimidin-5-yl)-2-hydroxyethyl)-1H-pyrazol-4-yl)-6-(3-chloro-6-(difluoromethyl)-2-fluorophenyl)-3-methylpyrazine-2-carboxamide, 6-(3-Chloro-6-(difluoromethyl)-2-fluorophenyl)-N-(1-((S)-2-hydroxy-1(2-((1 S,2R,5R)-2-methyl-3-azabicyclo[3.1.0]hexan-3-yl)pyrimidin-5-yl)ethyl)-1H-pyrazol-4-yl)pyrazine-2-carboxamide, 6-(3-Chloro-6-(difluoromethyl)-2-fluorophenyl)-N-(1-((S)-2-hydroxy-1-(2-((1R,2S,5S)-2-methyl-3-azabicyclo[3.1.0]hexan-3-yl)pyrimidin-5-yl)ethyl)-1H-pyrazol-4-yl)pyrazine-2-carboxamide, 6-(3-Chloro-6-(difluoromethyl)-2-fluorophenyl)-N-(1-((R)-2-hydroxy-1-(2-(1(1S,2R,5R)-2-methyl-3-azabicyclo[3.1.0]hexan-3-yl)pyrimidin-5-yl)ethyl)-1H-pyrazol-4-yl)pyrazine-2-carboxamide, 6-(3-Chloro-6-(difluoromethyl)-2-fluorophenyl)-N-(1-((R)-2-hydroxy-1-(2-(1R,2S,5S)-2-methyl-3-azabicyclo[3.1.0]hexan-3-yl)pyrimidin-5-yl)ethyl)-1H-pyrazol-4-yl)pyrazine-2-carboxamide, N-(1-((6-(Azetidin-1-yl)pyridin-3-yl)methyl)-1H-pyrazol-4-yl)-6-(3-chloro-6-cyano-2-fluorophenyl)pyrazine-2-carboxamide, N-(1-((2-(Azetidin-1-yl)pyrimidin-5-yl)methyl)-1H-pyrazol-4-yl)-6-(3-chloro-6-cyano-2-fluorophenyl)pyrazine-2-carboxamide, (R)—N-(1-(1-(2-(Azetidin-1-yl)pyrimidin-5-yl)ethyl)-1H-pyrazol-4-yl)-6-(3-chloro-2-fluoro-6-trifluoromethyl)phenyl)pyrazine-2-carboxamide, (S)—N-(1-(1-(2-(Azetidin-1-yl)pyrimidin-5-yl)ethyl)-1H-pyrazol-4-yl)-6-(3-chloro-2-fluoro-6-(trifluoromethyl)phenyl)pyrazine-2-carboxamide, (R)—N-(1-(1-(2-(Azetidin-1-yl)pyrimidin-5-yl)ethyl)-1H-pyrazol-4-yl)-6-(3-chloro-6-(difluoromethoxy)-2-fluorophenyl)pyrazine-2-carboxamide, (S)—N-(1-(1-(2-(Azetidin-1-yl)pyrimidin-5-yl)ethyl)-1H-pyrazol-4-yl)-6-(3-chloro-6-(difluoromethoxy)-2-fluorophenyl)pyrazine-2-carboxamide, (S)—N-(1-(1-(2-(Azetidin-1-yl)pyrimidin-5-yl)ethyl-1H-pyrazol-4-yl)-6-(5-chloro-2-(1H-tetrazol-1-yl)phenyl)pyrazine-2-carboxamide, (R)—N-(1-(1-(2-(Azetidin-1-yl)pyrimidin-5-yl)ethyl-1H-pyrazol-4-yl)-6-(5-chloro-2-(1H-tetrazol-1-yl)phenyl)pyrazine-2-carboxamide, (S)—N-(1(1-(2-(Azetidin-1-yl)pyrimidin-5-yl)ethyl)-1H-pyrazol-4-yl)-6-(5-methoxy-2-(1H-tetrazol-1-yl)phenyl)pyrazine-2-carboxamide, (R)—N-(1-(1-(2-(Azetidin-1-yl)pyrimidin-5-yl)ethyl)-1H-pyrazol-4-yl)-6-(5-methoxy-2-(1H-tetrazol-1-1)phenyl)pyrazine-2-carboxamide, N-(1-(1-(2-(Azetidin-1-yl)pyrimidin-5-yl)ethyl)-1H-pyrazol-4-yl)-6-(6-bromo-3-chloro-2-fluorophenyl)pyrazine-2-carboxamide, N-(1-((6-(Azetidin-1-yl)pyridin-3-yl)methyl)-1H-pyrazol-4-yl)-6-(3-chloro-6-(difluoromethoxy)-2-fluorophenyl)pyrazine-2-carboxamide, N-(1-((2-(Azetidin-1-yl)pyrimidin-5-yl)methyl)-1H-pyrazol-4-yl)-6-(3-chloro-6-(difluoromethoxy)-2-fluorophenyl)pyrazine-2-carboxamide, N-(1-((2-(Azetidin-1-yl)pyrimidin-5-yl)methyl)-1H-pyrazol-4-yl)-6-(3-chloro-2-fluoro-6-(trifluoromethyl)phenyl)pyrazine-2-carboxamide, (S)—N-(1-(1-(6-(Azetidin-1-yl)-4-methylpyridin-3-yl)ethyl)-1H-pyrazol-4-yl)-6-(3-chloro-6-(difluoromethyl)-2-fluorophenyl)pyrazine-2-carboxamide, (R)—N-(1-(1-(6-(Azetidin-1-yl)-4-methylpyridin-3-yl)ethyl)-1H-pyrazol-4-yl)-6-(3-chloro-6-(difluoromethyl)-2-fluorophenyl)pyrazine-2-carboxamide, (R)-6-(3-Chloro-6-(difluoromethyl)-2-fluorophenyl)-N-(1-((6-(2-(hydroxymethyl)azetidin-1-yl)pyridin-3-yl)methyl)-1H-pyrazol-4-yl)pyrazine-2-carboxamide, (S)—N-(1-(1-(2-(Azetidin-1-yl)-4-methylpyrimidin-5-yl)ethyl)-1H-pyrazol-4-yl)-6-(3-chloro-6-(difluoromethyl)-2-fluorophenyl)pyrazine-2-carboxamide, (R)—N-(1-(1-(2-(Azetidin-1-yl)-4-methylpyrimidin-5-yl)ethyl)-1H-pyrazol-4-yl)-6-(3-chloro-6-(difluoromethyl)-2-fluorophenyl)pyrazine-2-carboxamide, 6-(3-Chloro-6-(difluoromethyl)-2-fluorophenyl)-N-(1-((S)-1-(2-((1S,2R,5R)-2-(hydroxymethyl)-3-azabicyclo[3.1.0]hexan-3-yl)pyrimidin-5-yl)ethyl)-1H-pyrazol-4-yl)pyrazine-2-carboxamide, 6-(3-chloro-6-(difluoromethyl)-2-fluorophenyl)-N-(1-((S)-1-(2-((1R,2S,5S)-2-(hydroxymethyl)-3-azabicyclo[3.1.0]hexan-3-yl)pyrimidin-5-yl)ethyl)-1H-pyrazol-4-yl)pyrazine-2-carboxamide, 6-(3-(Chloro-6-(difluoromethyl)-2-fluorophenyl)-N-(1-((R)-1-(2-((1S,2R,2R)-2-(hydroxymethyl)-3-azabicyclo[3.1.0]hexan-3-yl)pyrimidin-5-yl)ethyl)-1H-pyrazol-4-yl)pyrazine-2-carboxamide, 6-(3-Chloro-6-(difluoromethyl)-2-fluorophenyl)-N-(1-((1S)-1-(2-((1R,2S,5S)-2-(hydroxymethyl)-3-azabicyclo[3.1.0]hexan-3-yl)pyrimidin-5-yl)ethyl)-1H-pyrazol-4-yl)pyrazine-2-carboxamide, 6-(3-Chloro-6-(difluoromethyl)-2-fluorophenyl)-N-(1-(2-((2-(dimethylamino)-2-oxoethyl)methyl)amino)pyrimidin-5-yl ethyl)-1H-pyrazol-4-yl)pyrazine-2-carboxamide, 6-(3-Chloro-6-(difluoromethyl)-2-fluorophenyl)-N-(1-((2-((1R,2S,5S)-2-(hydroxymethyl)-3-azabicyclo[3.1.0]hexan-3-yl)pyrimidin-5-yl)methyl)-1H-pyrazol-4-yl)pyrazine-2-carboxamide, 6-(3-Chloro-6-(difluoromethyl)-2-fluorophenyl)-N-(1-((S)-1-(2-((1R,2S,2S)-2-(hydroxymethyl)-3-azabicyclo[3.1.0]hexan-3-yl)pyrimidin-5-yl)ethyl)-1H-pyrazol-4-yl)pyrazine-2-carboxamide, 6-(3-Chloro-6-(difluoromethyl)-2-fluorophenyl)-N-(1-(2-(hexahydro-4H-furo[3,2-b]pyrrol-4-yl)pyrimidin-5-yl)methyl)-1H-pyrazol-4-yl)pyrazine-2-carboxamide, 6-(3-Chloro-6-(difluoromethyl)-2-fluorophenyl)-N-(1-(1-((2-(1R,2S,5S)-2-(hydroxymethyl)-3-azabicyclo[3.1.0]hexan-3-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-((1S,2S,5R)-2-(hydroxymethyl)-3-azabicyclo[3.1.0]hexan-3-yl)pyrimidin-5-yl)methyl)-1H-pyrazol-4-yl)pyrazine-2-carboxamide, 6-(3-Chloro-6-(difluoromethyl)-2-fluorophenyl)-N-(1-(1-(2-(5,7-dihydro-6H-pyrrolo[3,4-d]pyrimidin-6-yl)pyrimidin-5-yl)ethyl-1H-pyrazol-4-yl pyrazine-2-carboxamide, 6-(3-Chloro-6-(difluoromethyl)-2-fluorophenyl)-N-(1-((2-((1R,2S,5S)-2-(hydroxymethyl)-3-azabicyclo[3.1.0]hexan-3-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-(1S,2R,5R)-2-(hydroxymethyl)-3-azabicyclo[3.1.0]hexan-3-yl)pyrimidin-5-yl)methyl)-1H-pyrazol-4-yl)pyrazine-2-carboxamide, N-(1-((2-(3-Azabicyclo[3.1.0]hexan-3-yl)pyrimidin-5-yl)methyl)-1H-pyrazol-4-yl)-6-(3-chloro-6-(difluoromethyl)-2-fluorophenyl)pyrazine-2-carboxamide, N-(1-((2-(2-(Aminomethyl)pyrrolidin-1-yl)pyrimidin-5-yl)methyl)-1H-pyrazol-4-yl)-6-(3-chloro-6-(difluoromethyl)-2-fluorophenyl)pyrazine-2-carboxamide, 6-(3-Chloro-6-(difluoromethyl)-2-fluorophenyl)-N-(1-(1-(2-(3,3-difluoroazetidin-1-yl)pyrimidin-5-yl)ethyl)-1H-pyrazol-4-yl)pyrazine-2-carboxamide, 6-(3-chloro-6-(difluoromethyl)-2-fluorophenyl)-N-(1-(1-(2-(5,7-dihydro-6H-pyrrolo[3,4-b]pyridin-6-yl)pyrimidin-5-yl)ethyl)-1H-pyrazol-4-yl)pyrazine-2-carboxamide, 6-(3-Chloro-6-(difluoromethyl)-2-fluorophenyl)-N-(1-((2-((1S,2R,5R)-2-((S)-1-hydroxyethyl)-3-azabicyclo[3.1.0]hexan-3-yl)pyrimidin-5-yl)methyl)-1H-pyrazol-4-yl)pyrazine-2-carboxamide, 6-(3-Chloro-6-(difluoromethyl)-2-fluorophenyl)-N-(1-(1-(2-((2-hydroxyethyl)(pyridin-2-ylmethyl)amino)pyrimidin-5-yl)ethyl)-1H-pyrazol-4-yl)pyrazine-2-carboxamide, 6-(3-Chloro-6-(difluoromethyl)-2-fluorophenyl)-N-(1-((2-((1S,2R,5R)-2-((R)-1-hydroxyethyl)-3-azabicyclo[3.1.0]hexan-3-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-((2-(dimethylamino)ethyl)(2-hydroxyethyl)amino)pyrimidin-5-yl)methyl)-1H-pyrazol-4-yl)pyrazine-2-carboxamide, 6-(3-Chloro-6-(difluoromethyl)-2-fluorophenyl)-N-(1-(1-(2-(1,3-dihydro-2H-pyrrolo[3,4-c]pyridin-2-yl)pyrimidin-5-yl)ethyl-1H-pyrazol-4-yl)pyrazine-2-carboxamide, 6-(3-Chloro-6-(difluoromethyl)-2-fluorophenyl)-N-(1-((2-(6,6-difluoro-3-azabicyclo[3.1.0]hexan-3-yl)pyrimidin-5-yl)methyl)-1H-pyrazol-4-yl)pyrazine-2-carboxamide, 6-(3-Chloro-6-(difluoromethyl)-2-fluorophenyl)-N-(1-(2-(2-propionyl-3-azabicyclo[3.1.0]hexan-3-yl)pyrimidin-5-yl)methyl)-1H-pyrazol-4-yl)pyrazine-2-carboxamide, (S)-6-(3-Chloro-6-(difluoromethyl)-2-fluorophenyl)-N-(1-(1-(3-fluoroazetidin-1-yl)pyrimidin-5-yl)ethyl)-1H-pyrazol-4-yl)pyrazine-2-carboxamide, (R)—N-(1-(1-(2-(5-Azaspiro[2.3]hexan-5-yl)pyrimidin-5-yl)ethyl)- 1H-pyrazol-4-yl)-6-(3chloro-6-(difluoromethyl)-2-fluorophenyl)pyrazine-2-carboxamide, (S)—N-(1-(1-(2-(5-Azaspiro[2.3]hexan-5-yl)pyrimidin-5-yl)ethyl)-1H-pyrazol-4-yl)-6-(3-chloro-6-(difluoromethyl)-2-fluorophenyl)pyrazine-2-carboxamide, 6-(3-Chloro-6-(difluoromethyl)-2-fluorophenyl)-N-(1-(1-(2-(1-methyl-4,6-dihydropyrrolo[3,4-c]pyrazol-5(1H)-yl)pyrimidin-5-yl)ethyl)-1H-pyrazol-4-yl)pyrazine-2-carboxamide, 6-(3-Chloro-6-(difluoromethyl)-2-fluorophenyl)-N-(1-(1-(2-(4-methyl-3-oxopiperazin-1-yl)pyrimidin-5-yl)ethyl)-1H-pyrazol-4-yl)pyrazine-2-carboxamide, 6-(3-Chloro-6-(difluoromethyl)-2-fluorophenyl)-N-(1-(R and S)-1-(2-((S)-3-hydroxypyrrolidin-1-yl)pyrimidin-5-yl)ethyl)-11H-pyrazol-4-yl)pyrazine-2-carboxamide, (R)—N-(1-((2-(2-Carbamoylpyrrolidin-1-yl)pyrimidin-5-yl)methyl)-1H-pyrazol-4-yl)-6-(3-chloro-6-(difluoromethyl)-2-fluorophenyl)pyrazine-2-carboxamide, 6-(3-Chloro-6-(difluoromethyl)-2-fluorophenyl)-N-(1-((2-((2-(dimethyl-amino)ethyl(methyl)amino) pyrimidin-5-yl)methyl)-1H-pyrazol-4-yl)pyrazine-2-carboxamide, N-(1-(1-(2-(5-Azaspiro 2.3 hexan-5-yl)pyrimidin-5-t) ethyl)-1H-pyrazol-4-yl)-6-(3-chloro-6-(difluoromethyl)-2-fluorophenyl)pyrazine-2-carboxamide, 6-(3-Chloro-6-(difluoromethyl)-2-fluorophenyl)-N-(1-((R and S)-1-(2-((R and S)-2-methylazetidin-1-yl)pyrimidin-5-yl)ethyl)-1H-pyrazol-4-yl)pyrazine-2-carboxamide, (S)-6-(3-Chloro-6-(difluoromethyl)-2-fluorophenyl)-N-(1-(1-(2-(3-fluoro-3-methylazetidin-1-yl)pyrimidin-5-yl)ethyl)-1H-pyrazol-4-yl)pyrazine-2-carboxamide, (S)-6-(3-Chloro-6-(difluoromethyl)-2-fluorophenyl)-N-(1-((2-(2-(2-hydroxyethyl)pyrrolidin-1-yl)pyrimidin-5-yl)methyl-1H-pyrazol-4-yl)pyrazine-2-carboxamide, (R)-6-(3-Chloro-6-(difluoromethyl)-2-fluorophenyl)-N-(1-((2-(2-(2-hydroxyethyl)pyrrolidin-1-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-((3aS,6aS)-hexahydro-4H-furo[3,2-b]pyrrol-4-yl) pyrimidin-5-yl)methyl)-1H-pyrazol-4-yl)pyrazine-2-carboxamide, 6-(3-(Chloro-6-(difluoromethyl)-2-fluorophenyl)-N-(1-((2-((3aR,6aR)-hexahydro-4H-furo[3,2-b]pyrrol-4-yl) pyrimidin-5-yl)methyl)-1H-pyrazol-4-yl pyrazine-2-carboxamide, N-(1-((R and S)-1-(2-((R)-2-Carbamoylpyrrolidin-1-yl) pyrimidin-5-yl)ethyl)-1H-pyrazol-4-yl)-6-(3-chloro-6-(difluoromethyl)-2-fluorophenyl)pyrazine-2-carboxamide, (S)-6-(3-Chloro-6-(difluoromethyl)-2-fluorophenyl)-N-(1-((2-(2-hydroxethyl)pyrrolidin-1-yl)pyrimidin-5-yl) methyl)-1H-pyrazol-4-yl)pyrazine-2-carboxamide, (R)-6-(3-Chloro-6-(difluoromethyl)-2-fluorophenyl)-N-(1-((2-(2-(2-hydroxyethyl)pyrrolidin-1-yl)pyrimidin-5-yl)methyl)-1H-pyrazol-4-yl)pyrazine-2-carboxamide, 6-(3-Chloro-6-(difluoromethyl)-2-fluorophenyl)-N-(1-(2-(2-(2-hydroxy-2-methylpropyl)pyrrolidin-1-yl)pyrimidin-5-yl)methyl-1H-pyrazol-4-yl)pyrazine-2-carboxamide, 6-(3-Chloro-6-(difluoromethyl)-2-fluorophenyl)-N-(1-((2-(2-(1-hydroxycyclopropyl)pyrrolidin-1-yl)pyrimidin-5-yl)methyl)-1H-pyrazol-4-yl)pyrazine-2-carboxamide, N-(1-((2-(2-Azabicyclo[3.1.0]hexan-2-yl)pyrimidin-5-yl) methyl)-1H-pyrazol-4-yl)-6-(3-chloro-6-(difluoromethyl)-2-fluorophenyl)pyrazine-2-carboxamide, N-(1-((2-(2-((1H-Imidazol-1-yl)methyl)pyrrolidin-1-yl) pyrimidin-5-yl)methyl)-1H-pyrazol-4-yl)-6-(3-chloro-6-(difluoromethyl)-2-fluorophenyl)pyrazine-2-carboxamide, (S)-6-(3-Chloro-6-(difluoromethyl)-2-fluorophenyl)-N-(1-((2-(2-(2-hydroxy-2-methylpropyl)pyrrolidin-1-yl) pyrimidin-5-yl)methyl)-1H-pyrazol-4-yl pyrazine-2-carboxamide, (R)-6-(3-Chloro-6-(difluoromethyl)-2-fluorophenyl-N-(1-((2-(2-(2-hydroxy-2-methylpropyl)pyrrolidin-1-yl) pyrimidin-5-yl)methyl)-1H-pyrazol-4-yl)pyrazine-2-carboxamide, (R)-6-(3-Chloro-6-(difluoromethyl)-2-fluorophenyl)-N-(1-((2-(2-(hydroxymethyl)azetidin-1-yl)pyrimidin-5-yl)methyl)-1H-pyrazol-4-yl)pyrazine-2-carboxamide, (S)-6-(3-Chloro-6-(difluoromethyl)-2-fluorophenyl)-N-(1-((2-(2-((1-hydroxycyclopropyl)methyl)pyrrolidin-1-yl)pyrimidin-5-yl)methyl)-1H-pyrazol-4-yl)pyrazine-2-carboxamide, (R)-6-(3-Chloro-6-(difluoromethyl)-2-fluorophenyl)-N-(1-((2-(2-((1-hydroxycyclopropyl methyl)pyrrolidin-1-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-(2-(hydroxymethyl)pyrrolidin-1-yl)pyrimidin-5-yl) methyl)-1H-pyrazol-4-yl)pyrazine-2-carboxamide, 6-(3-Chloro-6-(difluoromethyl)-2-fluorophenyl)-N-(1-((6-(methyl(2-(pyrrolidin-1-yl)ethyl)amino)pyridin-3-yl)methyl)-1H-pyrazol-4-yl)pyrazine-2-carboxamide, 6-(3-Chloro-6-(difluoromethyl)-2-fluorophenyl)-N-(1-((6-(2-(2-hydroxyethyl)pyrrolidin-1-yl)pyrimidin-3-yl) methyl)-1H-pyrazol-4-yl)pyrazine-2-carboxamide, (S)—N-(1-((6-(2-Carbamoylpyrrolidin-1-yl)pyridin-3-yl) methyl)-1H-pyrazol-4-yl)-6(3-chloro-6-(difluoromethyl)-2-fluorophenyl)pyrazine-2-carboxamide, 6-(3-Chloro-6-(difluoromethyl)-2-fluorophenyl)-N-(1-((6-(hexahydro-4H-furo[3,2-b]pyrrol-4-yl)pyridin-3-yl)methyl)-1H-pyrazol-4-yl)pyrazine-2-carboxamide, 6-(3-Chloro-6-(difluoromethyl)-2-fluorophenyl)-N-(1-((6-(2-(hydroxymethyl)pyrrolidin-1-yl)pyridin-3-yl) methyl)-1H-pyrazol-4-yl)pyrazine-2-carboxamide, (R)—N-(1(3-(Azetidin-1-yl)-6,7-dihydro-5H-cyclopenta [c]pyridin-7-yl)-1H-pyrazol-4-yl)-6-(3-chloro-6-(difluoromethyl)-2-fluorophenyl)pyrazine-2-carboxamide, (S)—N-(1-(3-(Azetidin-1-yl)-6,7-dihydro-5H-cyclopenta [c]pyridin-7-yl)-1H-pyrazol-4-yl)-6-(3-chloro-6-(difluoromethyl)-2-fluorophenyl)pyrazine-2-carboxamide, (S)-6-(3-Chloro-6-(difluoromethyl)-2-fluorophenyl)-N-(1-((6-(2-(methoxymethyl)pyrrolidin-1-yl)pyridin-3-yl)methyl)-1H-pyrazol-4-yl)pyrazine-2-carboxamide, 6-(3-(Chloro-6-(difluoromethyl)-2-fluorophenyl)-N-(1-((6-((2-hydroxyethyl)(methyl)amino)pyridin-3-yl) methyl)-1H-pyrazol-4-yl)pyrazine-2-carboxamide, 6-(3-Chloro-6-(difluoromethyl)-2-fluorophenyl)-N-(1-((6-((3aR,6aR)-hexahydro-4H-furo[3,2-b]pyrrol-4-yl) pyridin-3-yl)methyl)-1H-pyrazol-4-yl)pyrazine-2-carboxamide, 6-(3-Chloro-6-(difluoromethyl)-2-fluorophenyl)-N-(1-((6-((3aS,6aS)-hexahydro-4H-furo[3,2-b]pyrrol-4-yl) pyridin-3-yl)methyl)-1H-pyrazol-4-yl)pyrazine-2-carboxamide, 6-(3-Chloro-6-(difluoromethyl)-2-fluorophenyl)-N-(1-((6-(3-hydroxypyrrolidin-1-yl)pyridin-3-yl)methyl)-1H-pyrazol-4-yl)pyrazine-2-carboxamide, (S)-6-(3-Chloro-6-(difluoromethyl)-2-fluorophenyl)-N-(1-((6-(2-(dimethylcarbamoyl)pyrrolidin-1-yl)pyridin-3-yl)methyl)-1H-pyrazol-4-yl)pyrazine-2-carboxamide, (S)-6-(3-Chloro-6-(difluoromethyl)-2-fluorophenyl)-N-(1-((6-(2-(hydroxymethyl)azetidin-1-yl)pyridin-3-yl) methyl)-1H-pyrazol-4-yl)pyrazine-2-carboxamide, 6-(3-Chloro-6-(difluoromethyl)-2-fluorophenyl)-N-(14 (6-(6,-difluoro-3-azabicyclo[3.1.0]hexan-3-yl)pyridin-3-yl)methyl)-1H-pyrazol-4-yl)pyrazine-2-carboxamide, N-(1-((6-(4,7-Diazaspiro[2.5]octan-7-yl)pyridin-3-yl)methyl)-1H-pyrazol-4-yl)-6-(3-chloro-6-(difluoromethyl)-2-fluorophenyl)pyrazine-2-carboxamide, N-(1-((6-(3-Carbamoylpiperidin-1-yl)pyridin-3-yl)methyl)-1H-pyrazol-4-yl)-6-(3-chloro-6-(difluoromethyl)-2-fluorophenyl)pyrazine-2-carboxamide, 6-(3-Chloro-6-(difluoromethyl)-2-fluorophenyl)-N-(1-((6-(2-(1-methyl-1H-1,2,4-triazol-3-yl)pyrrolidin-1-yl)pyridin-3-ylmethyl)-1H-pyrazol-4-yl)pyrazine-2-carboxamide, N-(1-((6-((1R,6S)-3-Acetyl-3,8-diazabicyclo[4.2.0]octan-8-yl)pyridin-3-yl)methyl)-1H-pyrazol-4-yl)-6-(3-chloro-6-(difluoromethyl)-2-fluorophenyl)pyrazine-2-carboxamide, 6-(3-Chloro-6-(difluoromethyl)-2-fluorophenyl)-N-(1-((6-(3-(hydroxymethyl)pyrrolidin-1-yl)pyridin-3-yl)methyl)-1H-pyrazol-4-yl)pyrazine-2-carboxamide, N-(1-((6-((1S,6R)-3-Acetyl-3,8-diazabicyclo[4.2.0]octan-8-yl)pyridin-3-yl)methyl)-1H-pyrazol-4-yl)-6-(3-chloro-6-(difluoromethyl)-2-fluorophenyl)pyrazine-2-carboxamide, (S)—N-(1-((2-(Azetidin-1-yl)pyrimidin-5-yl)methyl)-1H-pyrazol-4-yl)-6-(3-chloro-6-(difluoromethyl)-2-fluorophenyl)-3-(1-hydroxyethyl)pyrazine-2-carboxamide, (R)—N-(1-((2-(Azetidin-1-yl)pyrimidin-5-yl)methyl)-1H-pyrazol-4-yl)-6-(3-chloro-6-(difluoromethyl)-2-fluorophenyl)-3-(1-hydroxyethyl)pyrazine-2-carboxamide, N-(1-((2-(Azetidin-1-yl)pyrimidin-5-yl)methyl)-1H-Pyrazol-4-yl)-6-(3-chloro-6-(difluoromethyl)-2-fluorophenyl)-3-(difluoromethyl)pyrazine-2-carboxamide, 3-((1-((2-(Azetidin-1-yl)pyrimidin-5-yl)methyl-1H-pyrazol-4-yl)carbamoyl)-5-(3-chloro-6-(difluoromethyl)-2-fluorophenyl)pyrazine-2-carboxylic acid, $N^2$-(1-((2-(Azetidin-1-yl)pyrimidin-5-yl)methyl)-1H-pyrazol-4-yl)-6-(3-chloro-6-(difluoromethyl)-2-fluorophenyl)pyrazine-2,3-dicarboxamide, 6-(3-Chloro-6-(difluoromethyl)-2-fluorophenyl)-N-(1-((2-((1R,2S,5S)-2-(((2-hydroxy-2-methylpropyl)amino)methy)-3-azabicyclo[3.1.0]hexan-3-yl)pyrimidin-5-yl)methyl)-1H-pyrazol-4-yl)pyrazine-2-carboxamide, (S)-6-(3-Chloro-6-(difluoromethyl)-2-fluorophenyl)-N-(1-((2-(2-((((1-hydroxycyclopropyl)methyl)(methyl)amino)methyl)pyrrolidin-1-yl)pyrimidin-5-yl)methyl)-1H-pyrazol-4-yl)pyrazine-2-carboxamide, (R)-6-(3-Chloro-6-(difluoromethyl)-2-fluorophenyl)-N-(1-(2-(2-((((1-hydroxycyclopropyl)methyl)(methyl)amino)methyl)pyrrolidin-1-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-((S)-2-(((R)-3-hydroxypyrrolidin-1-yl)methyl)pyrrolidin-1-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-((1R,2S,5S)-2-((((R)-1-hydroxypropan-2-yl)amino)methyl)-3-azabicyclo[3.1.0]hexan-3-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-((2S)-2-((3-hydroxy-3-methylpyrrolidin-1-yl)methyl)pyrrolidin-1-yl)pyrimidin-5-yl)methyl)-1H-pyrazol-4-yl)pyrazine-2-carboxamide, 6-(3-Chloro-6-(difluoromethyl)-2-fluorophenyl)-N-(1-((24(1R,2S,5S)-2-((3-hydroxy-3-methylazetidin-1-yl)methyl)-3-azabicyclo[3.1.0]hexan-3-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-((S)-2-(((2S,3S)-3-hydroxy-2-methylpyrrolidin-1-yl)methyl)pyrrolidin-1-yl)pyrimidin-5-yl)methyl)-1H-pyrazol-4-yl)pyrazine-2-carboxamide, 6-(3-(Chloro-6-(difluoromethyl)-2-fluorophenyl)-N-(1-((2-(2-((((S)-2-fluoropropyl)(methyl)amino)methyl)pyrrolidin-1-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-(2-(((S)-3-fluoropyrrolidin-1-yl)methyl)pyrrolidin-1-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-((R,2S,5S)-2-(((1 S,2S)-2-hydroxycyclopentyl)amino)methyl)-3-azabicyclo[3.1.0]hexan-3-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-((1R,2S,5S)-2-(((3,3-difluoro-2-hydroxypropy)amino)methyl)-3-azabicyclo[3.1.0]hexan-3-yl)pyrimidin-5-yl)ethyl)-1H-pyrazol-4-yl)pyrazine-2-carboxamide, 6-(3-Chloro-6-(difluoromethyl)-2-fluorophenyl)-N-(1-((2-(2-((((R)-2-fluoropropyl)(methyl)amino)methyl)pyrrolidin-1-yl)pyrimidin-5-yl)methyl)-1H-pyrazol-4-yl)pyrazine-2-carboxamide, (S)-6-(3-Chloro-6-(difluoromethyl)-2-fluorophenyl)-N-(1-((2-(2-((3-hydroxy-3-methylazetidin-1-yl)methyl)pyrimidin-1-yl)pyrimidin-5-yl)methyl)-1H-pyrazol-4-yl)pyrazine-2-carboxamide, 6-(3-chloro-6-(difluoromethyl)-2-fluorophenyl)-N-(1-((2-(2-(morpholinomethyl)pyrrolidin-1-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-(2-((((R)-2-hydroxypropyl)amino)methyl)pyrrolidin-1-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-((1R,2S,5S)-2-((3-hydroxy-3-(trifluoromethyl)azetidin-1-yl)methyl)-3-azabicyclo[3.1.0]hexan-3-yl)pyrimidin-5-yl)methyl)-1H-pyrazol-4-yl)pyrazine-2-carboxamide, N-(1-((2-(2-(1-Aminoethyl)pyrrolidin-1-yl)pyrimidin-5-yl)methyl)-1H-pyrazol-4-yl)-6-(3-chloro-6-(difluoromethyl)-2-fluorophenyl)pyrazine-2-carboxamide, 6-(3-Chloro-6-(difluoromethyl)-2-fluorophenyl)-N-(1-((2-(2-(((2,2-difluoroethyl)amino)methyl)pyrrolidin-1-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-(2-(((3S,4S)-3,4-difluoropyrrolidin-1-yl)methyl)pyrrolidin-1-yl)pyrimidin-5-yl)methyl)-1H-pyrazol-4-yl)pyrazine-2-carboxamide, 6-(3-Chloro-6-(difluoromethyl)-2-fluorophenyl)-N-(1-((2-((1R,2S,5S)-2-(((1S,2S)-2-hydroxy cyclopentyl)amino)methyl)-3-azabicyclo[3.1.0]hexan-3-yl)pyrimidin-5-yl)methyl)-1H-pyrazol-4-yl)pyrazine-2-carboxamide, 6-(3-Chloro-6-(difluoromethyl)-2-fluorophenyl)-N-(1-(1-(2-((S)-2-(((2S,3S)-3-hydroxy-2-methylpyrrolidin-1-yl)methyl)azetidin-1-yl)pyrimidin-5-yl)ethyl)-1H-pyrazol-4-yl)pyrazine-2-carboxamide, 6-(3-Chloro-6-(difluoromethyl)-2-fluorophenyl)-N-(1-(1-(2-((S)-2-(((S)-3-hydroxypyrrolidin-1-yl)methyl)azetidin-1-yl)pyrimidin-5-yl))ethyl)-1H-pyrazol-4-yl)pyrazine-2-carboxamide, 6-(3-Chloro-6-(difluoromethyl)-2-fluorophenyl)-N-(1-(1-(2-((S)-2-(((R)-3-hydroxypyrrolidin-1-yl)methyl)azetidin-1-yl)pyrimidin-5-yl)ethyl)-1H-pyrazol-4-yl)pyrazine-2-carboxamide, 6-(3-Chloro-6-(difluoromethyl)-2-fluorophenyl)-N-(1-(1-(2-((S)-2-((2R,4R)-4-hydroxy-2-methylpyrrolidin-1-yl)methyl)azetidin-1-yl)pyrimidin-5-yl)ethyl)-1H-pyrazol-4-yl)pyrazine-2-carboxamide, 6-(3-(Chloro-6-(difluoromethyl)-2-fluorophenyl)-N-(1-(1-(2-((S)-2-(((3S,4S)-3-hydroxy-4-methoxypyrrolidin-1-yl)methyl azetidin-1-yl)pyrimidin-5-yl)ethyl)-1H-pyrazol-4-yl)pyrazine-2-carboxamide, 6-(3-Chloro-6-(difluoromethyl)-2-fluorophenyl)-N-(1-(1-(2-((2S)-2-((3-hydroxy-3-methylpyrrolidin-1-yl) methyl azetidin-1-yl)pyrimidin-5-yl)ethyl)-1H-pyrazol-4-yl)pyrazine-2-carboxamide, 6-(3-Chloro-6-(difluoromethyl)-2-fluorophenyl)-N-(1-(1-(2-(S)-2-(((3R,4S)-3,4-dihydroxypyrrolidin-1-yl) methyl)azetidin-1-yl)pyrimidin-5-yl)ethyl)-1H-pyrazol-4-yl)pyrazine-2-carboxamide, and 6-(3-Chloro-6-(difluoromethyl)-2-fluorophenyl-N-(1-(1-(2-((S)-2-(((3R,4R)-3,4-dihydroxypyrrolidin-1-yl) methyl)azetidin-1-yl)pyrimidin-5-yl)ethyl)-1H-pyrazol-4-yl)pyrazine-2-carboxamide, or a pharmaceutically acceptable salt thereof.

10. A pharmaceutical composition comprising a compound of claim 1 or a pharmaceutically acceptable salt thereof and a pharmaceutically acceptable carrier.

11. A method for treating impaired visual activity, diabetic retinopathy, diabetic macular edema, retinal vein occlusion, hereditary angioedema, diabetes, pancreatitis, cerebral hemorrhage, nephropathy, cardiomyopathy, neuropathy, inflammatory bowel disease, arthritis, inflammation, septic shock, hypotension, cancer, adult respiratory distress syndrome, disseminated intravascular coagulation, blood coagulation during cardiopulmonary bypass surgery, or bleeding from postoperative surgery in a mammal, comprising administering a composition of claim 10 to a mammal in need of thereof.

12. A method for treating uveitis, posterior uveitis, wet age related macular edema, diabetic macular edema, diabetic retinopathy or retinal vein occlusion in a mammal comprising administering a composition of claim 10 to a mammal in need thereof.

13. A method of treating diabetic retinopathy or diabetic macular edema in a mammal comprising administering a composition of claim 10 to a mammal in need thereof.

14. A method of treating retinal vein occlusion in a mammal comprising administering a composition of claim 10 to a mammal in need thereof.

15. The composition of claim 10 further comprising another agent selected from the group consisting of anti-inflammatory agents, anti-VEGF agents, immunosuppressive agents, anticoagulants, antiplatelet agents, and thrombolytic agents.

16. The method of claim 11 further comprising another agent selected from the group consisting of anti-inflammatory agents, anti-VEGF agents, immunosuppressive agents, anticoagulants, antiplatelet agents, and thrombolytic agents.

* * * * *